(12) United States Patent
Vaccaro et al.

(10) Patent No.: US 6,995,181 B2
(45) Date of Patent: Feb. 7, 2006

(54) MODULATORS OF THE GLUCOCORTICOID RECEPTOR AND METHOD

(75) Inventors: Wayne Vaccaro, Yardley, PA (US); Bingwei Vera Yang, Belle Mead, NJ (US); Soong-Hoon Kim, Titusville, NJ (US); Tram Huynh, Pennington, NJ (US); David R. Tortolani, Skillman, NJ (US); Kenneth J. Leavitt, Lawrenceville, NJ (US); Wenying Li, Middletown, CT (US); Arthur M. Doweyko, Long Valley, NJ (US); Xiao-Tao Chen, Newark, DE (US); Lidia Doweyko, Long Valley, NJ (US)

(73) Assignee: Bristol-Myers Squibb Co., Princeton, NJ (US)

( * ) Notice: Subject to any disclaimer, the term of this patent is extended or adjusted under 35 U.S.C. 154(b) by 36 days.

(21) Appl. No.: 10/621,909

(22) Filed: Jul. 17, 2003

(65) Prior Publication Data

US 2004/0132758 A1 Jul. 8, 2004

Related U.S. Application Data

(60) Provisional application No. 60/396,877, filed on Jul. 18, 2002.

(51) Int. Cl.
*A61K 31/426* (2006.01)
*C07D 277/38* (2006.01)

(52) U.S. Cl. .................. 514/371; 548/195; 548/160; 548/222; 548/233; 548/332.5; 546/139; 546/152; 546/270.7; 546/285; 514/367; 514/377; 514/394; 514/398

(58) Field of Classification Search ............ 514/371, 514/367, 377, 394, 398; 548/195, 160, 222, 548/233, 332.5; 546/139, 152, 270.7, 285
See application file for complete search history.

(56) References Cited

U.S. PATENT DOCUMENTS

| | | |
|---|---|---|
| 4,786,646 A | 11/1988 | Guthrie et al. |
| 5,055,468 A | 10/1991 | Gray et al. |
| 5,332,820 A | 7/1994 | Duncia |
| 5,409,932 A | 4/1995 | Schwenner et al. |
| 5,411,960 A | 5/1995 | Schwenner et al. |
| 5,514,683 A | 5/1996 | Kalindjian et al. |
| 5,616,780 A | 4/1997 | Pitteloud et al. |
| 6,214,915 B1 | 4/2001 | Avakian et al. |
| 6,262,059 B1 | 7/2001 | Pamukcu et al. |

FOREIGN PATENT DOCUMENTS

| | | |
|---|---|---|
| CS | 198 678 | 11/1982 |
| DE | 197 42 014 | 3/1999 |
| EP | 0 405 436 | 11/1995 |
| WO | WO 93/16982 | 9/1993 |
| WO | WO 94/00421 | 1/1994 |
| WO | WO 95/05359 | 2/1995 |
| WO | WO 95/15947 | 6/1995 |
| WO | WO 99/15493 | 4/1999 |
| ZA | 681802 | 3/1968 |

OTHER PUBLICATIONS

Alibert, S. et al., "Synthesis and Effects on Chloroquine Susceptibility in *Plasmodim falciparum* of a Series of New Dihydroanthracene Derivatives," J. Med. Chem., vol. 45, pp. 3195–3209 (2002).

El–Zanfally, S. et al., "Reactions of Aminopyridines with some Inner Anhydrides", Egypt J. Pharm. Sci., vol. 17, No. 3, pp. 53–62 (1976).

Pradines, B. et al, "In Vitro Increase in Chloroquine Accumulation Induced by Dihydroethano– and Ethenoanthracene Derivatives in *Plasmodium falciparum*–Parasitized Erythrocytes", Anitmicrobial Agents and Chemotherapy, vol. 46, No. 7, pp. 2061–2068 (2002).

*Primary Examiner*—Charanjit S. Aulakh
(74) *Attorney, Agent, or Firm*—Burton Rodney; Laurelee A. Duncan

(57) ABSTRACT

Novel non-steroidal compounds are provided which are glucocorticoid receptor modulators which are useful in treating diseases requiring glucocorticoid receptor agonist or antagonist therapy such as obesity, diabetes, inflammatory and immune disorders, and have the structure

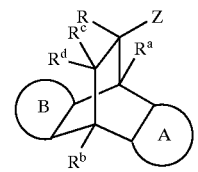

where Z is $CONR^1R^2$ or $CH^2NR^1R^2$ and where R, $R^a$, $R^b$, $R^c$, $R^d$, Z, A and B are defined herein.

28 Claims, No Drawings

MODULATORS OF THE GLUCOCORTICOID RECEPTOR AND METHOD

This application claims priority from U.S. Provisional Application 60/396,877 filed Jul. 18, 2002 which is incorporated herein by reference.

The present invention relates to new non-steroidal compounds which are glucocorticoid receptor (GR) modulators (that is agonists and antagonists) and thus are useful in treating diseases requiring glucocorticoid receptor agonist or antagonist therapy such as obesity, diabetes and inflammatory or immune associated diseases, and to a method for using such compounds to treat these and related diseases.

BACKGROUND OF THE INVENTION

The nuclear hormone receptor (NHR) family of transcription factors bind low molecular weight ligands and either stimulate or repress transcription (The Nuclear Receptor Facts Book, V. Laudet and H. Gronemeyer, Academic Press, p345, 2002). NHRs stimulate transcription by binding to DNA and inducing transcription of specific genes. NHRs may also stimulate transcription by not binding to DNA itself, rather they may modulate the activity of other DNA binding proteins (Stocklin, E., et al., Nature (1996) 383:726–8). The process of stimulation of transcription is called transactivation. NHRs repress transcription by interacting with other transcription factors or coactivators and inhibiting the ability of these other transcription factors or coactivators from inducing transcription of specific genes. This repression is called transrepression. (for a review see The Nuclear Receptor Factsbook, V. Laudet and H. Gronemeyer, Academic Press, p42, 2002).

The glucocorticoid receptor (GR) is a member of the nuclear hormone receptor family of transcription factors, and a member of the steroid hormone family of transcription factors. Affinity labeling of the glucocorticoid receptor protein allowed the production of antibodies against the receptor which facilitated cloning the human (Weinberger, et al. Science 228, p640–742, 1985, Weinberger, et al. Nature, 318, p670–672, 1986) and rat (Miesfeld, R. Nature, 312, p779–781, 1985) glucocorticoid receptors.

Glucocorticoids which interact with GR have been used for over 50 years to treat inflammatory diseases. It has been clearly shown that glucocorticoids exert their anti-inflammatory activity via the inhibition by GR of the transcription factors NF-kappaB and AP-1. This inhibition is termed transrepression. It has been shown that the primary mechanism for inhibition of these transcription factors by GR is via a direct physical interaction. This interaction alters the transcription factor complex and inhibits the ability of NF-kappaB and AP-1 to stimulate transcription (Jonat, C., et al. Cell, 62, p1189, 1990, Yang-Yen, H. F., et al. Cell 62, p1205, 1990, Diamond, M. I. et al. Science 249, p1266, 1990, Caldenhoven, E. et al., Mol. Endocrinol. 9, p401, 1995). Other mechanisms such as sequestration of co-activators by GR have also been proposed (Kamer Y, et al., Cell 85, p403, 1996, Chakravarti, D. et al., Nature 383, p99, 1996). NF-kappaB and AP-1 play key roles in the initiation and perpetuation of inflammatory and immunological disorders (Baldwin, AS, Journal of Clin. Investigation 107, p3, 2001, Firestein, G. S., and Manning, A. M. Arthritis and Rheumatism, 42, p609, 1999, Peltz, G., Curr. Opin, in Biotech. 8, p467, 1997). NF-kappaB and AP-1 are involved in regulating the expression of a number of important inflammatory and immunomodulatory genes including: TNF-alpha, IL-1, IL-2, IL-5, adhesion molecules (such as E-selectin), chemokines (such as Eoxtaxin and Rantes), Cox-2, and others.

In addition to causing transrepression, the interaction of a glucocorticoid with GR can cause GR to induce transcription of certain genes. This induction of transcription is termed transactivation. Transactivation requires dimerization of GR and binding to a glucocorticoid response element (GRE).

Recent studies using a transgenic GR dimerization defective mouse which cannot bind DNA have shown that the transactivation (DNA binding) activities of GR could be separated from the transrepressive (non-DNA binding) effect of GR. These studies also indicate that many of the side effects of glucocorticoid therapy are due to the ability of GR to induce transcription of various genes involved in metabolism, whereas, transrepression, which does not require DNA binding leads to suppression of inflammation (Tuckermann, J. et al. Cell 93, p531, 1998; Reichardt, HM. EMBO J., 20, p7168, 2001).

The art is in need of modulators of NHRs. A modulator of an NHR may be useful in treating NHR-associated diseases, that is diseases associated with the expression products of genes whose transcription is stimulated or repressed by NHRs. For instance, the art is in need of modulators of NHRs that inhibit AP-I and NFκB, as such compounds would be useful in the treatment of inflammatory and immune diseases and disorders such as osteoarthritis, rheumatoid arthritis, multiple sclerosis, asthma, inflammatory bowel disease, transplant rejection and graft vs. host disease.

Particularly concerning GR, although glucocorticoids are potent anti-inflammatory agents, their systemic use is limited by side effects. A compound that retained the anti-inflammatory efficacy of glucocorticoids while minimizing the side effects such as diabetes, osteoporosis and glaucoma would be of great benefit to a very large number of patients with inflammatory diseases.

Additionally concerning GR, the art is in need of compounds that antagonize transactivation. Such compounds may be useful in treating metabolic diseases associated with increased levels of glucocorticoid, such as diabetes, osteoporosis and glaucoma.

Additionally concerning GR, the art is in need of compounds that cause transactivation. Such compounds may be useful in treating metabolic diseases associated with a deficiency in glucocorticoid. Such diseases include Addison's disease.

It is believed that the compounds of the present invention as described below fill the above needs.

DESCRIPTION OF THE INVENTION

In accordance with the present invention, compounds are provided having the structure

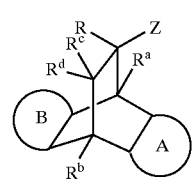

I including all stereoisomers thereof, or a prodrug ester thereof, or a pharmaceutically acceptable salt thereof, wherein R is hydrogen, alkyl, alkenyl, alkynyl, alkoxy, aryl, arylalkyl, aryloxy, heteroaryl, cycloheteroalkyl, heteroarylalkyl, cycloheteroalkylalkyl, cycloalkyl, cycloalkylalkyl, cyanoalkyl, aminoalkyl, hydroxyalkyl, aryloxyalkyl, or hydroxyaryl;

$R^a$ is hydrogen, alkyl, alkenyl, alkynyl, alkoxy, aryl, aryloxy, heteroaryl, cycloheteroalkyl, heteroarylalkyl, cycloheteroalkylalkyl, cyano, halogen, heteroarylaminocarbonyl, cycloheteroalkylcarbonyl, cyanoalkyl, alkylaminoalkyl, hydroxyalkyl, hydroxyaryl, aryloxyalkyl, nitro, amino, CHO, $CO_2$ alkyl, $CONR^eR^f$, $CH_2NR^gR^h$, $CO_2H$, $CH_2OH$, $CH_2NHR^g$, $NHCH_2R^g$, $NHCHR^gR^h$, $NHCOR^e$, $NHCONR^eR^f$ or $NHSO_2R^e$;

$R^b$ is hydrogen, alkyl, alkenyl, alkynyl, alkoxy, aryl, aryloxy, heteroaryl, cycloheteroalkyl, heteroarylalkyl, cycloheteroalkylalkyl, cyano, halogen, heteroarylaminocarbonyl, cycloheteroalkylcarbonyl, cyanoalkyl, alkylaminoalkyl, hydroxyalkyl, nitro, amino, CHO, $CO_2$ alkyl, hydroxyaryl, aryloxyalkyl, $CONR^iR^j$, $CH_2NR^kR^1$, $CO_2H$, $CH_2OH$, $CH_2NHR^k$, $NHCH_2R^k$, $NHCHR^kR^l$, $NHCOR^i$, $NHCONR^iR^j$ or $NHSO_2R^i$;

where $R^e$ and $R^f$ are the same or different and are independently selected from hydrogen, aryl, alkyl, alkenyl, alkynyl, alkoxy, amino, alkoxyalkyl, alkylaminoalkyl, dialkylaminoalkyl, heteroaryl, cycloheteroalkyl, heteroarylalkyl, cycloheteroalkylalkyl, cycloalkyl, or cycloalkylalkyl, and $R^e$ and $R^f$ can be taken together with the nitrogen to which they are attached to form a 5-, 6- or 7-membered heteroaryl ring or cycloheteroalkyl ring which contains 1, 2 or 3 hetero atoms which can be N, O or S;

$R^g$ and $R^h$ are the same or different and are independently selected from hydrogen, aryl, alkyl, alkenyl, alkynyl, alkoxy, amino, alkoxyalkyl, alkylaminoalkyl, dialkylaminoalkyl, heteroaryl, cycloheteroalkyl, heteroarylalkyl, cycloheteroalkylalkyl, cycloalkyl, or cycloalkylalkyl, and $R^g$ and $R^h$ can be taken together with the nitrogen to which they are attached to form a 5-, 6- or 7-membered heteroaryl ring or cycloheteroalkyl ring which contains 1, 2 or 3 hetero atoms which can be N, O or S;

$R^i$ and $R^j$ are the same or different and are independently selected from hydrogen, aryl, alkyl, alkenyl, alkynyl, alkoxy, amino, alkoxyalkyl, alkylaminoalkyl, dialkylaminoalkyl, heteroaryl, cycloheteroalkyl, heteroarylalkyl, cycloheteroalkylalkyl, cycloalkyl, or cycloalkylalkyl, and $R^i$ and $R^j$ can be taken together with the nitrogen to which they are attached to form a 5-, 6- or 7-membered heteroaryl ring or cycloheteroalkyl ring which contains 1, 2 or 3 hetero atoms which can be N, O or S;

$R^k$ and $R^l$ are the same or different and are independently selected from hydrogen, aryl, alkyl, alkenyl, alkynyl, alkoxy, amino, alkoxyalkyl, alkylaminoalkyl, dialkylaminoalkyl, heteroaryl, cycloheteroalkyl, heteroarylalkyl, cycloheteroalkylalkyl, cycloalkyl, or cycloalkylalkyl, and $R^k$ and $R^l$ can be taken together with the nitrogen to which they are attached to form a 5-, 6- or 7-membered heteroaryl ring or cycloheteroalkyl ring which contains 1, 2 or 3 hetero atoms which can be N, O or S;

$R^c$ and $R^d$ are the same or different and are independently selected from hydrogen, alkyl, alkenyl, alkynyl, alkoxy, aryl, hydroxy, aryloxy, heteroaryl, cycloheteroalkyl, heteroarylalkyl, cycloheteroalkylalkyl, hydroxyaryl, or aryloxyalkyl;

$R^c$ and $R^d$ can be taken together with the carbon to which they are attached to form a 3- to 7-membered ring which may include an O or N atom in the ring;

Z is $CONR^1R^2$ or $CH_2NR^1R^2$ wherein $R^1$ and $R^2$ are the same or different and are independently selected from hydrogen, alkyl, alkenyl, alkynyl, alkoxy, cycloalkyl, cycloalkylalkyl, aryl, heteroaryl, heteroarylalkyl, cycloheteroalkyl, cycloalkenyl, mono- or di-alkylaminoalkyl, cycloheteroalkylalkyl, hydroxyaryl, aryloxyalkyl, alkoxyalkyl or hydroxyalkyl;

the A ring represents a saturated, partially saturated or unsaturated 6-membered carbocyclic or heterocyclic ring; and the B ring represents a saturated, partially saturated or unsaturated 6-membered carbocyclic or heterocyclic ring;

with the following provisos;

I. provided that where Z is $CONR^1R^2$ and (a) R is $CH_3$ or H and $R^a$, $R^b$, $R^c$ and $R^d$ are each hydrogen, or (b) $R^a$ and $R^b$ are each hydrogen and one of $R^c$ and $R^d$ is alkyl, then (1) at least one of $R^1$ and $R^2$ is heteroaryl, heteroarylalkyl, cycloheteroalkyl or cycloheteroalkylalkyl, but where the heteroaryl is

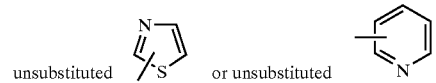

or the heteroarylalkyl is

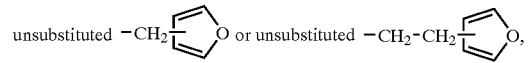

then the other of $R^1$ and $R^2$ is other than hydrogen, and/or the A ring and/or the B ring includes a hetero atom; or (2) where one of $R^1$ and $R^2$ is phenyl which is substituted with alkyl, hydroxy, halo, $C_1$–$C_2$-alkoxycarbonyl or nitro, then (a) the phenyl must be substituted with at least one other group other than hydrogen, alkyl, hydroxy, halo, $C_1$-$C_2$-alkoxycarbonyl or nitro, except that the phenyl may be substituted with two or more halo atoms, and/or two or more hydroxy groups, and/or (b) the other of $R^1$ and $R^2$ is other than hydrogen and/or (c) the A ring and/or the B ring includes a hetero atom;

(3) where one of $R^1$ and $R^2$ is phenyl substituted with $C_1$–$C_2$ alkoxy, the phenyl cannot be substituted with a second $C_1$–$C_2$ alkoxy or the other of $R^1$ and $R^2$ is other than hydrogen, or (4) where at least one of $R^1$ and $R^2$ is hydrogen, unsubstituted alkyl, alkenyl, cycloalkyl, alkylcycloalkyl, cycloalkenyl, alkylcycloalkenyl, alkylphenyl, monoalkylaminoalkyl, dialkylaminoalkyl, arylalkyl, aryl, alkoxyalkyl or hydroxyalkyl then (a) the other of $R^1$ and $R^2$ is other than hydrogen, unsubstituted alkyl, alkenyl, cycloaklyl, alkylcycloalkyl, cycloalkenyl, alkylcycloalkenyl, alkylphenyl, monoalkylaminoalkyl, dialkylaminoalkyl, arylalkyl, aryl, alkoxyalkyl or hydroxyalkyl; and/or (b) at least one of $R^a$, $R^b$, $R^c$ and/or $R^d$ is other than hydrogen and/or (c) R is other than hydrogen or $C_1$–$C_2$ alkyl and/or (d) the A ring and/or the B ring includes a hetero atom; and II. provided that where Z is $CH_2NR^1R^2$ and/or where at least one of $R^1$ and $R^2$ is hydrogen, alkyl, alkenyl, cycloalkyl, alkylcycloalkyl, phenyl, alkylphenyl, phenylalkyl, monoalkylaminoalkyl, dialkylaminoalkyl, arylalkyl, aryl, alkoxyalkyl, hydroxyalkyl, heteroaryl which is pyridinyl, pyrimidinyl, pyridazinyl, pyrazinyl or imidazolinyl, or cycloheteroalkyl which is 4,5-dihydro-imidazol-2-yl, piperidinyl or piperazinyl, then (a) the other of $R^1$ and $R^2$ is other than hydrogen, alkyl, alkenyl, cycloalkyl, alkylcycloalkyl, phenyl, alkylphenyl, phenylalkyl, monoalkylaminoalkyl, dialkylaminoalkyl, arylalkyl, aryl, alkoxyalkyl or hydroxyalkyl and/or (b) at least one of $R^a$, $R^b$, $R^c$ and/or $R^d$ is other than hydrogen or $C_{1-2}$ alkyl and/or (c) R is other than hydrogen or $C_1$–$C_2$ alkyl and/or (d) the A ring and/or the B ring includes a hetero atom and/or (e) one of $R^c$ or $R^d$ cannot be hydroxyalkyl.

In the compounds of formula I the A ring has the structure

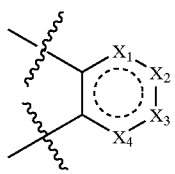

and the B ring has the structure

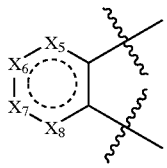

wherein $X_1$, $X_2$, $X_3$ and $X_4$ are the same or different and are independently selected from CH, $CH_2$, $CHR^{15}$, $CR^{16}$, $CR^{16}R^{17}$, N, NH, $NR^{18}$, O or S, and $X_5$, $X_6$, $X_7$ and $X_8$ are the same or different and are independently selected from CH, $CH_2$, $CHR^{19}$, $CR^{20}$, $CR^{20}R^{21}$, N, NH, $NR^{22}$, O or S, wherein $R^{15}$, $R^{16}$, $R^{17}$, $R^{18}$, $R^{19}$, $R^{20}$, $R^{21}$ and $R^{22}$ are the same or different and are independently selected from hydrogen, alkyl, aryl, cycloalkyl, heteroaryl, and cycloheteroalkyl, wherein each of said A ring and said B ring contains at most two nitrogen ring atoms, at most two oxygen ring atoms and at most one sulfur ring atom.

It is preferred that the A ring and B ring are each 6-membered rings which are aromatic carbocyclic rings, namely benzo rings, or are heterocyclic rings each of which includes one hetero atom, which is nitrogen, namely pyridyl rings preferably

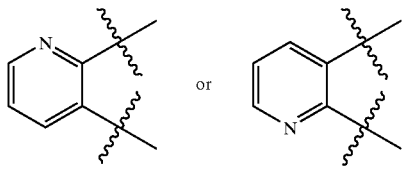

Preferred compounds of formula I of the invention which have glucocorticoid receptor (GR)/Dexamethasone (Dex) inhibition activity (>95% at 10 μM) are set out below:

1. compounds of formula I of the invention where A and B are fused phenyl rings, R is $CH^3$, $R^a$, $R^b$, $R^c$ and $R^d$ are each H, and Z is $CONR^1R^2$ where one of $R^1$ and $R^2$ is H and the other is heteroaryl, preferably imidazol-2-yl, that is

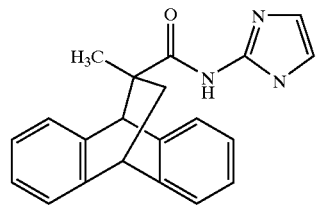

2. compounds of formula I of the invention where A and B are fused phenyl rings, R is $CH_3$, $R^a$, $R^b$, $R^c$ and $R^d$ are each H, and Z is $CONR^1R^2$ where one of $R^1$ and $R^2$ is H and the other is heteroaryl, other than benzothiazol-2-yl, and preferably heteroaryl is alkylbenzothiazol-2-yl, alkoxybenzothiazol-2-yl, and halobenzothiazol-2-yl, such as
6-methylbenzothiazol-2-yl
4-methoxybenzothiazol-2-yl
6-fluorobenzothiazol-2-yl
6-chlorobenzothiazol-2-yl for example, compounds of the structure

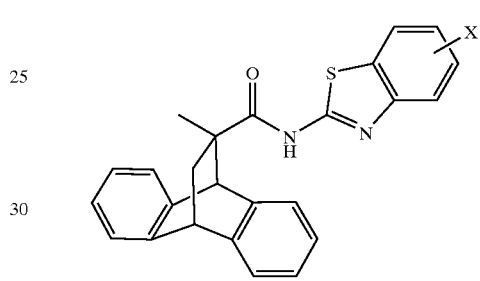

where X is 6-$CH_3$, 4-$CH_3O$, 6-Cl or 6-F.

3. compounds of formula I of the invention where A and B are fused phenyl rings, R is $CH_3$, $R^a$, $R^b$, $R^c$ and $R^d$ are each H, and Z is $CONR^1R^2$ where one of $R^1$ and $R^2$ is H and the other is a thiazole which preferably is substituted with dialkyl, alkyl, alkyl O—N

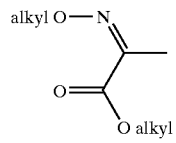

alkyl, aryl such as phenyl or naphthyl (where the aryl may be optionally substituted with halo, alkyl, nitro, hydroxy, alkoxy, dialkoxy, carboxy, alkylaminocarbonyl, arylaminocarbonyl, hydroxyalkylaminocarbonyl, cycloheteroalkylcarbonyl, alkoxyalkylaminocarbonyl, heteroarylaminocarbonyl), heteroarylthio or heteroaryl such as
4,5-dimethylthiazol-2-yl
5-chlorothiazol-2-yl
4-methylthiazol-2-yl
5-methylthiazol-2-yl
4-phenylthiazol-2-yl
4-(1-naphthyl)thiazol-2-yl
5-(1-naphthyl)thiazol-2-yl
4-[1-(4-fluoro)naphthyl]thiazol-2-yl
4-[1-(4-methyl)naphthyl]thiazol-2-yl
4-(3-nitrophenyl)thiazol-2-yl
4-[1-(6-hydroxy)naphthyl]thiazol-2-yl
4-[(1,2,4-triazol-5-yl)thio]methylthiazol-2-yl
4-(4-benzoic acid)thiazol-2-yl 4-[1-(4-bromo)naphthyl]thiazol-2-yl
4-[4-N-ethylbenzamide]thiazol-2-yl
4-[4-N-(2-methoxyphenyl)benzamide]thiazol-2-yl
4-[4-N-methy-N-(2-hydroxyethyl)benzamide]thiazol-2-yl
4-[4-N-(pyrrolidinyl)benzamide]thiazol-2-yl
4-[4-N-(mopholinyl)benzamide]thiazol-2-yl
4-[4-N-phenyl-N-methylbenzamide]thiazol-2-yl
4-[3-N-ethylbenzamide]thiazol-2-yl
4-[3-N-(2-methoxyphenyl)benzamide]thiazol-2-yl
4-[3-N-(2-methoxyethyl)benzamide]thiazol-2-yl
4-[3-N-methyl-N-2-hydroxyethyl)benzamide]thiazol-2-yl
4-[3-N-methyl-N-phenylbenzamide]thiazol-2-yl
4-[3-N-(4-acetylpiperaziny-1-yl)benzamide]thiazol-2-yl
4-[3-N-(3-methoxypropyl)benzamide]thiazol-2-yl
4-(6-carboxypyrid-2-yl)thiazol-2-yl
4-[3-N-(3-hydroxy-4-methoxyphenyl)benzamide]thiazol-2-yl
4-[3-N-(3-fluoro-4-methoxyphenyl)benzamide]thiazol-2-yl
4-[3-N-(2,3-dimethoxyphenyl)benzamide]thiazol-2-yl
4-[3-N-(3-dimethoxyphenyl)benzamide]thiazol-2-yl
4-[3-N-(5-trifluormethyl-1,3,4-thiadiazol-2-yl)benzamide]thiazol-2-yl
4-[3-N-(5-methyl-1,3.4-thiadiazol-2-yl)benzamide]thiazol-2-yl
4-[3-N-(5-chlorobenzoxazol-2-yl)benzamide]thiazol-2-yl
4-[3-N-(3-benzonitrile)benzamide]thiazol-2-yl
4-[3-N-(4-methoxypyrid-3-yl)benzamide]thiazol-2-yl
4-[5-(1,4-benzodioxane)]thiazol-2-yl
4-[4-(1,3-benzodioxole)]thiazol-2-yl,
for example, compounds of the structure

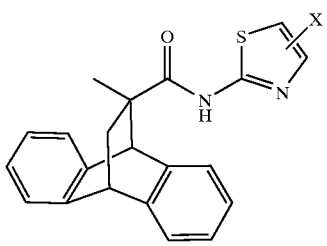

Ib

X=4,5-dimethyl, 5-chloro, 4-methyl, 5-methyl, 4-phenyl, 4-(1-naphthyl), 4-(2-naphthyl), 4-(4-fluoronaphth-1-yl), 4-(4-methylnaphth-1-yl), 4-(3-nitrophenyl), 4-(6-hydroxynaphth-1-yl), 4-[(1,2,4-triazol-5-yl)thio]methyl, 4-benzoic acid, 4-(4-bromonaphth-1-yl), 4-(N-ethyl)benzamide, 4-(N-2-methoxyphenyl)benzamide, 4-(N-deoxyspergualin methyl-N-2-hydroxyethyl)benzamide, 4-(N-(pyrrolidinyl)benzamide, 4-(N-morpholinyl)benzamide, 4-(N-phenyl-N-methyl)benzamide, 3-(N-ethyl)benzamide, 3-(N-2-methoxyphenyl)benzamide, 3-(N-2-methoxyethyl)benzamide, 3-(N-methyl-N-2-hydroxyethyl)benzamide, 3-(N-methyl-N-phenyl)benzamide, 3-(N-4-acetylpiperaziny-1-yl)benzamide, 3-(N-3-methoxypropyl)benzamide, 2-(6-carboxy)pyridine, 3-(N-3-hydroxy-4-methoxyphenyl)benzamide, 3-(N-3-fluoro-4-methoxyphenyl)benzamide, 3-(N-2,3-dimethoxyphenyl)benzamide, 3-(N-3-dimethoxyphenyl)benzamide, 3-(N-5-trifluormethyl-1,3,4-thiadiazol-2-yl)benzamide, 3-(N-5-methyl-1,3,4-thiadiazol-2-yl)benzamide, 3-(N-5-chlorobenzoxazol-2-yl)benzamide, 3-(N-3-benzonitrile)benzamide, 3-(N-4-methoxypyrid-3-yl)benzamide, 5-(1,4-benzodioxane), 4-(1,3-benzodioxole).

4. compounds of formula I of the invention where A and B are fused phenyl rings, R is $C_2H_5$, $R^a$, $R^b$, $R^c$ and $R^d$ are each H, and Z is $CONR^1R^2$ where one of $R^1$ and $R^2$ is H and the other is heteroaryl, preferably thiazol-2-yl or 4-(1-naphthyl)thiazol-2-yl.

5. compounds of formula I of the invention where A and B are fused phenyl rings, R is 2-hydroxyethyl, $R^a$, $R^b$, $R^c$ and $R^d$ are each H, and Z is $CONR^1R^2$ where one of $R^1$ and $R^2$ is H and the other is heteroaryl, preferably thiazol-2-yl.

6. compounds of the formula I of the invention where A and B are fused phenyl rings, R is $CH_3$, $R^a$, $R^b$, $R^c$ and $R^d$ are H, and Z is $CONR^1R^2$ where one of $R^1$ and $R^2$ is H and the other is a heteroaryl, preferably 2-quinolin-1-yl.

Preferred compounds of formula I of the invention which have AP-1 inhibitory activity (IC50<15 μM) are set out below:

1(a). compounds of formula I of the invention where A and B are fused phenyl rings, R is $CH_3$, $R^a$, $R^b$, $R^c$ and $R^d$ are each H, and Z is $CONR^1R^2$ where one of $R^1$ and $R^2$ is H and the other is heteroaryl, preferably imidazole which is preferably substituted with an aryl group, which preferably is naphthyl preferably substituted with alkyl, halo or alkoxy, such as 4-(1-naphthyl)imidazol-2-yl
4-[1-(4-methyl)naphthyl]imidazol-2-yl
4-[1-(4-fluoro)naphthyl]imidazol-2-yl
4-[1-(6-methoxynaphthyl)]imidazol-2-yl
4-phenylimidazol-2-yl
4-t-butylimidazol-2-yl for example, compounds of the structure

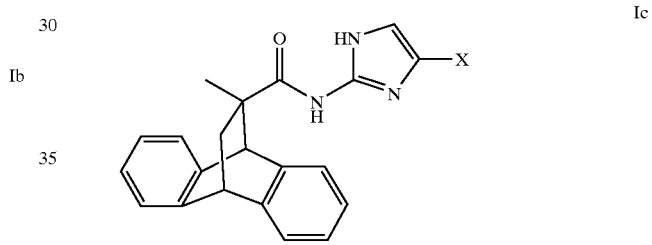

Ic

X is aryl or alkyl, such as 1-naphthyl, 1-[(4-methyl)naphthyl, 1-(4-fluoro)naphthyl, 1-(6-methoxynaphthyl), phenyl, t-butyl, or quinolinyl optionally substituted with alkyl such as methyl and/or alkoxy such as methoxy, or isoquinolinyl optionally substituted with alkyl such as methyl and/or alkoxy such as methoxy.

1(b). compounds of the structure

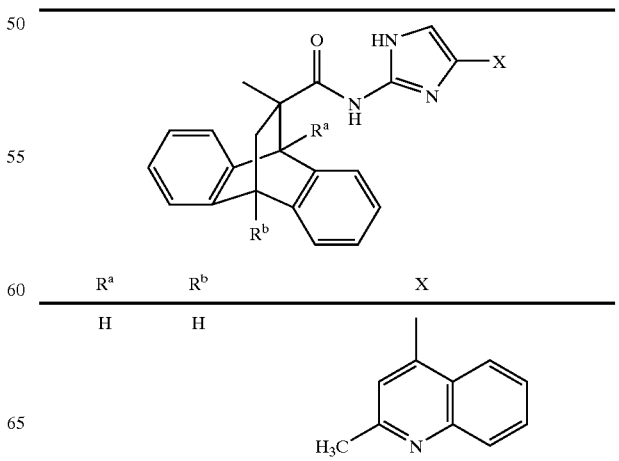

| $R^a$ | $R^b$ | X |
|---|---|---|
| H | H | (4-methylquinolin-2-yl) |

-continued

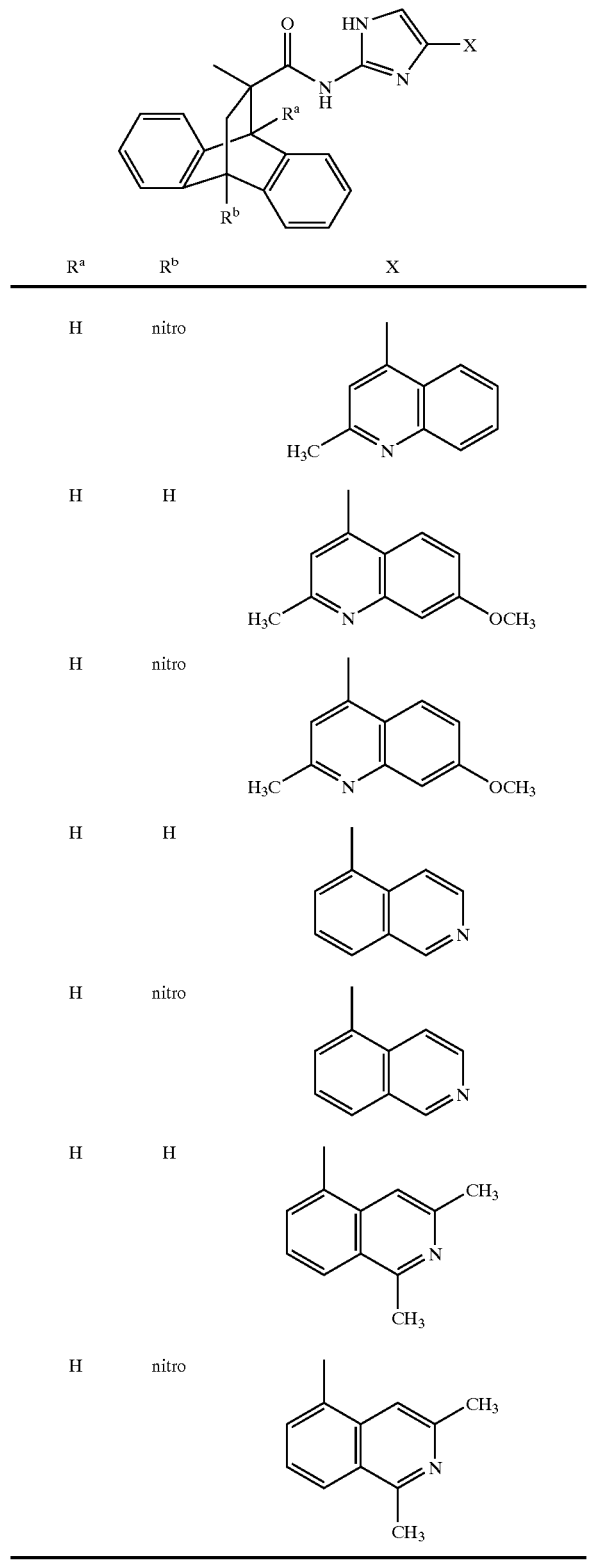

| $R^a$ | $R^b$ | X |
|---|---|---|
| H | nitro | 4-methylquinolin-2-yl (H$_3$C) |
| H | H | 4-methyl-7-methoxy-2-methylquinolinyl |
| H | nitro | 4-methyl-7-methoxy-2-methylquinolinyl |
| H | H | 5-methylisoquinolinyl |
| H | nitro | 5-methylisoquinolinyl |
| H | H | 5-methyl-1,3-dimethylisoquinolinyl |
| H | nitro | 5-methyl-1,3-dimethylisoquinolinyl |

2. compounds of formula I of the invention where A and B are fused phenyl rings, R is CH$_3$, $R^a$, $R^b$, $R^c$ and $R^d$ are each H, and Z is CONR$^1$R$^2$ where one of R$^1$ and R$^2$ is H and the other is heteroaryl, preferably an oxazole which is preferably substituted with an aryl group which preferably is naphthyl such as 4-(1-naphthyl)oxazol-2-yl, that is, a compound of the structure

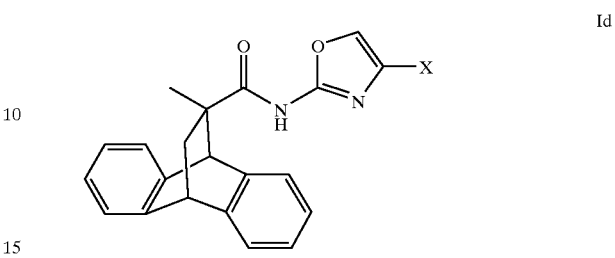

Id where X is aryl such as 1-naphthyl.

3. compounds of formula I of the invention where A and B are fused phenyl rings, R is CH$_3$, $R^a$, $R^b$, $R^c$ and $R^d$ are each H, and Z is CONR$^1$R$^2$ where one of R$^1$ and R$^2$ is H and the other is a pyridyl which is preferably substituted with an aryl group which preferably is naphthyl, such as 4-(1-naphthyl)pyrid-2-yl, that is a compound of the structure

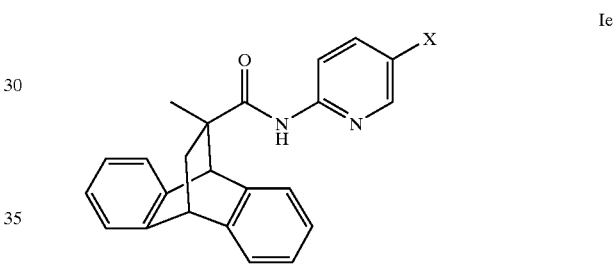

Ie where X is aryl such as 1-naphthyl.

4. compounds of formula I of the invention where A and B are fused phenyl rings, R is CH$_3$, $R^a$, $R^b$, $R^c$ and $R^d$ are each H, and Z is CONR$^1$R$^2$ where one of R$^1$ and R$^2$ is H and the other is a heteroaryl, preferably a thiazole substituted with alkyl, aryl, heteroaryl or alkoxy, and where the aryl is phenyl, naphthyl or anthracenyl, which preferably is substituted with halo, alkyl, alkoxy, aryl, or hydroxy, such as 4-(phenyl)thiazol-2-yl
4-(t-butyl)thiazol-2-yl
4-(1-naphthyl)thiazol-2-yl
4-[1-(4-fluoro)naphthyl]thiazol-2-yl
4-(benzthiophen-3-yl)thiazol-2-yl
4-[1-(4-methyl)naphthyl]thiazol-2-yl
4-[1-(2-methoxynaphthyl)]thiazol-2-yl
4-[1-(6-methoxynaphthyl)]thiazol-2-yl
4-(3-fluorophenyl)thiazol-2-yl
4-(4-fluorophenyl)thiazol-2-yl
4-(3-methylphenyl)thiazol-2-yl
4-(2-chlorophenyl)thiazol-2-yl
4-[1-(4-methoxynaphthyl)]thiazol-2-yl
4-[1-(4-bromonaphthyl)]thiazol-2-yl
4-[1-(4-iodonaphthyl)]thiazol-2-yl
4-[anthracen-5-yl)]thiazol-2-yl
4-[anthracen-1-yl)]thiazol-2-yl
4-[4-quinolin-1-yl)]thiazol-2-yl 4-[2-quinolin-1-yl)]thiazol-2-yl
4-[1-(4-cyano-naphthyl)]thiazol-2-yl
5-iodothiazol-2-yl
4-(benzthiophen-4-yl)thiazol-2-yl
4-[1-(2-hydroxynaphthyl)]thiazol-2-yl
4-[1-(6-hydroxynaphthyl)]thiazol-2-yl
4-[1-(4-hydroxynaphthyl)]thiazol-2-yl for example, compounds of the structure

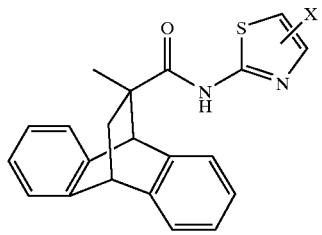

If where X is aryl, alkyl, heteroaryl or halo, such as phenyl, t-butyl, 1-naphthyl, 1-(4-fluoro)naphthyl, benzthiophen-3-yl, 1-(4-methyl)naphthyl, 1-(2-methoxy)naphthyl, 1-(6-methoxy)naphthyl, 3-fluorophenyl, 4-fluorophenyl, 3-methylphenyl, 2-chlorophenyl, 1-(4-methoxy)naphthyl, 1-(4-bromo)naphthyl, 1-(4-iodo)naphthyl, 5-anthracenyl, 1-anthracenyl, 4-quinolin-1-yl, 2-quinolin-1-yl, 1-(4-cyano)naphthyl, 5-iodo, 4-benzthiophenyl, 1-(2-hydroxy)naphthyl, 1-(6-hydroxy)naphthyl, 1-(4 hydroxy)naphthyl.

5. compounds of formula I of the invention where A and B are fused phenyl rings, R is $C_2H_5$, $R^a$, $R^b$, $R^c$ and $R^d$ are each H, and Z is $CONR^1R^2$ where one of $R^1$ and $R^2$ is H and the other is a heteroaryl, preferably thiazole which is substituted with aryl, preferably naphthyl, such as 4-(1-naphthyl)thiazol-2-yl, that is

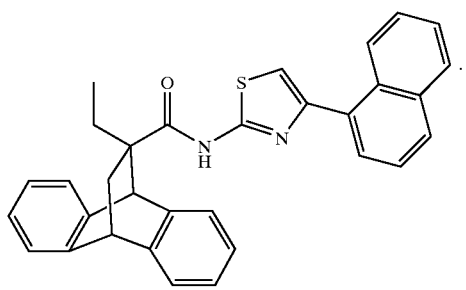

6. compounds of formula I of the invention where A and B are fused phenyl rings, R is $CH_3$, $R^a$, $R^b$, $R^c$ and $R^d$ are each H, and Z is $CONR^1R^2$ where one of $R^1$ and $R^2$ is H and the other is

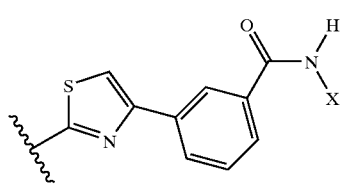

that is

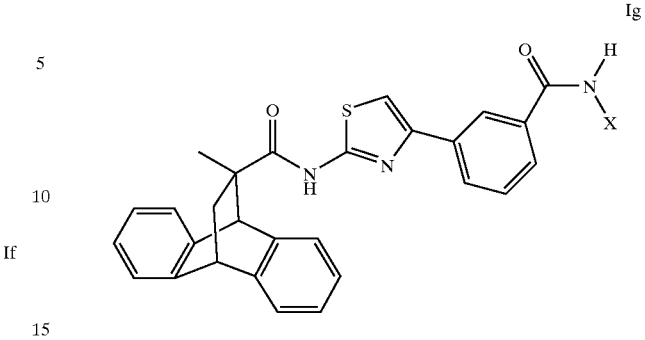

Ig where X is aryl, alkoxyaryl, dialkoxyaryl, heteroaryl, heteroarylalkyl, halo (alkoxy)-aryl, hydroxy (alkoxy)aryl, trialkoxyaryl, alkyl(alkoxy)aryl, haloaryl, dihaloaryl, heteroarylaryl, alkylthioaryl, alkenylaryl, alkoxyheteroaryl, cyanoaryl, where aryl is phenyl or naphthyl and heteroaryl by itself or part of another group is pyridyl, imidazolyl, azido, isothiazolyl, pyrazolyl or thiadiazolyl;

preferred examples of X include phenyl, 3-methoxyphenyl, 4-methoxyphenyl, 2,5-dimethoxyphenyl, 3,5-dimethoxyphenyl, 3-pyridyl, 2-(4-pyridyl)ethyl, 2-(4-imidazolyl)ethyl, 3-chloro-4-methoxyphenyl, 3-hydroxy-4-methoxyphenyl, 3-fluoro-4-methoxyphenyl, 3,4,5-trimethoxyphenyl, 3,4-dimethoxyphenyl, 4-methyl-3-methoxyphenyl, 3-methoxyphenyl, 3,5-dimethoxyphenyl, 2,3-dimethoxyphenyl, 4-chlorophenyl, 2-naphthyl, 3-chlorophenyl, 3,4-dichlorophenyl, 4-azidophenyl, 2,4-dimethoxyphenyl, 3-ethoxyphenyl, 3-(methylthio)phenyl, 4-(methylthio)phenyl, 3-(acetylenyl)phenyl, 4-methoxy-3-pyridyl, 3-cyanophenyl, 2-methyl-4-methoxyphenyl, 3-azidophenyl, 3-methyl-isothiazolyl, 1-methyl-pyrazol-5-yl or 5-trifluormethyl-1,3,4-thiadiazol-2-yl.

7. compounds of formula I of the invention of the structure (a)

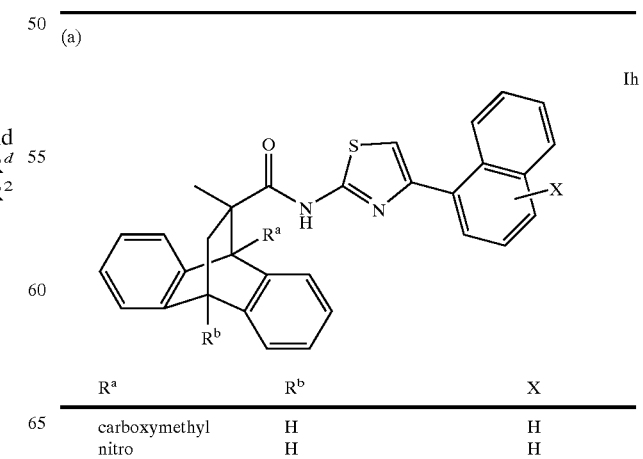

Ih

| $R^a$ | $R^b$ | X |
|---|---|---|
| carboxymethyl | H | H |
| nitro | H | H |

(a)

Ih

[Structure: tricyclic compound with thiazole-naphthyl carboxamide, substituents R^a, R^b, X]

| R^a | R^b | X |
|---|---|---|
| cyano | H | H |
| carboxymethyl | H | methyl |
| nitro | H | methyl |
| cyano | H | methyl |
| H | carboxymethyl | H |
| H | nitro | H |
| H | cyano | H |
| H | formyl | H |
| H | CO—(N-morpholine) | H |
| H | CH₂—NH—ethyl | H |
| H | CH₂—(N-morpholine) | H |
| H | nitro | methyl |
| H | cyano | methyl |
| H | NH₂ | methyl |
| H | nitro | F |
| H | cyano | F |
| H | Cl | H |
| H | Cl | F |
| H | Cl | Methyl |
| H | Br | F |
| H | Br | Methyl |
| H | CH3 | H |
| H | CH3 | F |
| H | CH3 | Methyl |

(b)

[Structure with hydroxyl and fluoro-naphthyl-thiazole carboxamide]

(c)

Ii

[Structure with Y, Q heteroatoms and fluoro-naphthyl-thiazole carboxamide]

(d)

[Structure: tricyclic compound with imidazole-naphthyl carboxamide, substituents R^a, R^b, X]

| R^a | R^b | X |
|---|---|---|
| CH₃OOC— | H | H |
| Nitro | H | H |
| Cyano | H | H |
| CH₃OOC— | H | Methyl |
| Nitro | H | Methyl |
| Cyano | H | Methyl |
| H | CH₃OOC— | H |
| H | Nitro | H |
| H | Cyano | H |
| H | formyl | H |
| H | CO—(N-morpholine) | H |
| H | —CH2—NH—Ethyl | H |
| H | —CH2—(N-morpholine) | H |
| H | Nitro | Methyl |
| H | Cyano | Methyl |
| H | NH2 | Methyl |
| H | Nitro | F |
| H | Cyano | F |
| H | Cl | H |
| H | Cl | F |
| H | Cl | Methyl |
| H | Br | F |
| H | Br | Methyl |
| H | CH3 | H |
| H | CH3 | F |
| H | CH3 | Methyl |

8. compounds of formula I of the structure

Ij

[Structure with R, NR¹R² amide group on tricyclic scaffold]

wherein one of $R^1$ and $R^2$ is heteroaryl, preferably wherein one of $R^1$ and $R^2$ is

[Heteroaryl structures: thiazole with R^m, imidazole (HN) with R^m, oxazole with R^m, pyrazole with R^m and NR^o, isoquinoline with R^m]

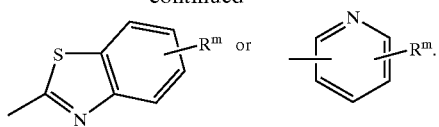

where $R^m$ is selected from H, alkyl, aryl, heteroaryl, halo, or alkoxy and $R^o$ is H or alkyl, and more preferably where one of $R^1$ and $R^2$ is

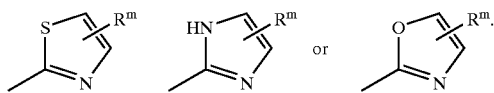

Other preferred compounds of the invention have the structure

Ik

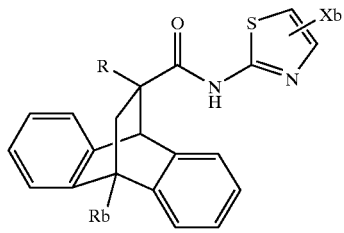

where R is $CH_3$, $C_2H_5$ or 2-hydroxyethyl, Rb is H, CN, $NO_2$, halogen, alkyl or amino, and Xb is H, arylalkoxycarbonyl, arylalkylaminocarbonyl, alkoxyalkylaminocarbonyl, heteroarylcarbonyl, aryl, alkoxyalkylamidocarbonyl, arylaminocarbonyl, heteroarylaminocarbonyl, arylaminocarbonylaryl or heteroaryl;

provided that where Xb is H, then R is $C_2H_5$ or 2-hydroxymethyl or Rb is CN or $NO_2$.

Examples of the above preferred compounds include the following:

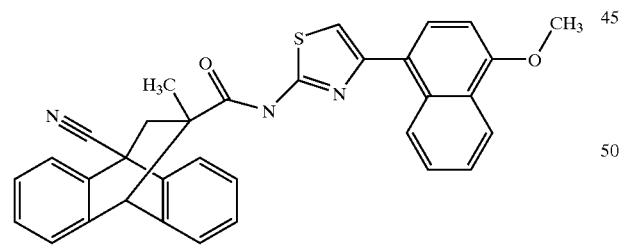

(Chiral (R))

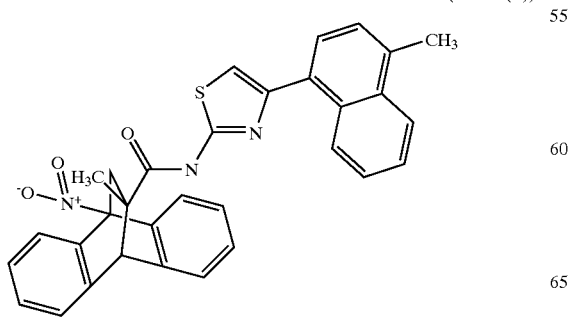

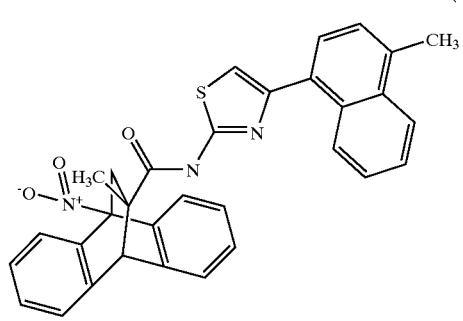

(Chiral (S))

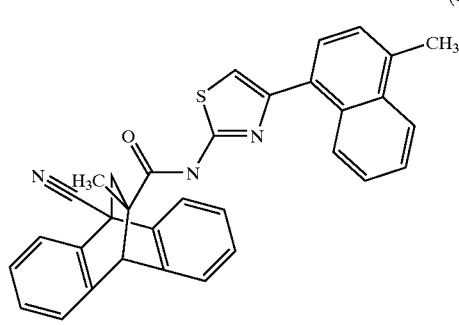

(Chiral (R))

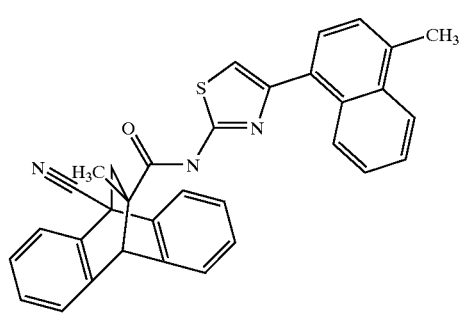

(Chiral (S))

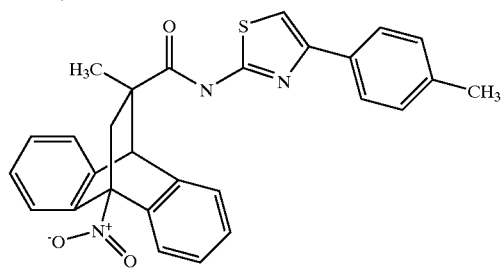

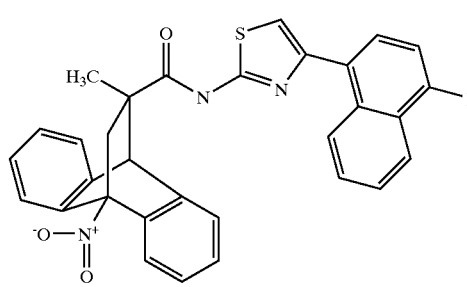

(Chiral (R))

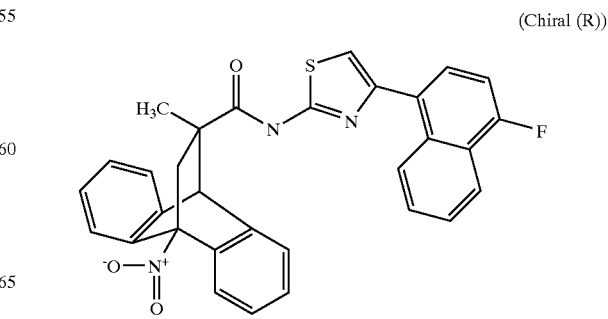

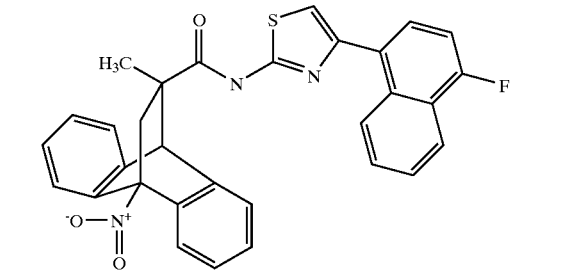
(Chiral (S))
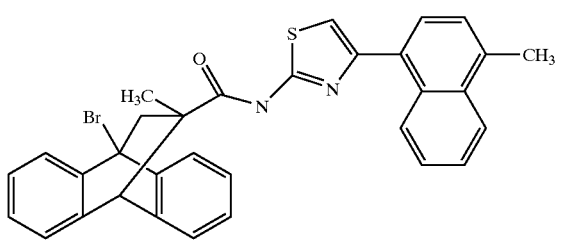
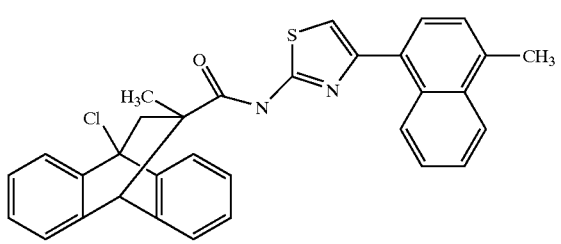
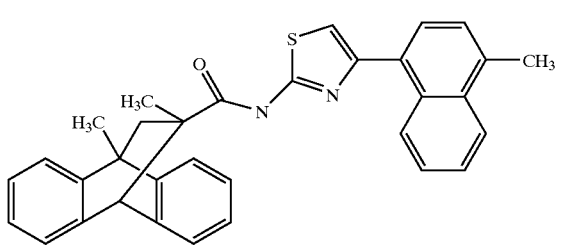
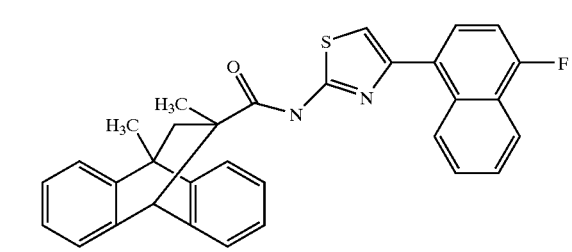
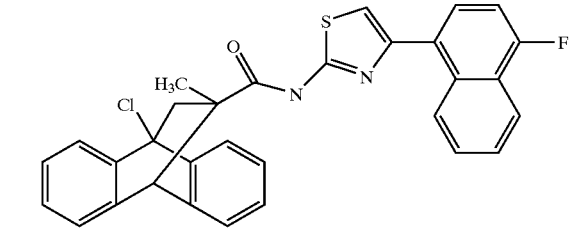
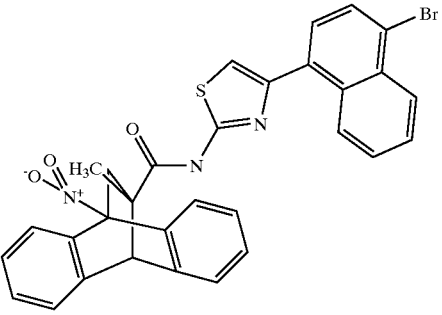
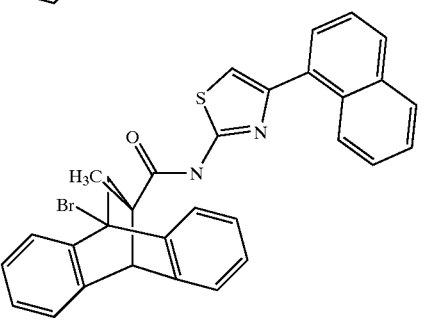
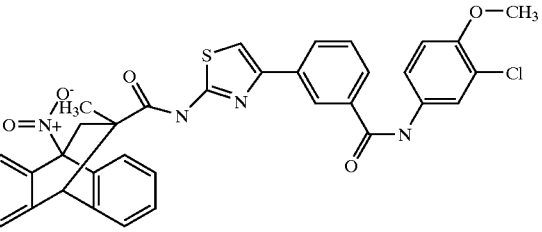
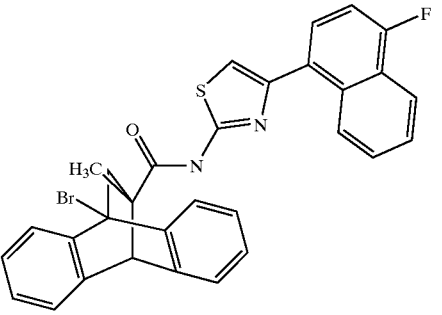
Still other preferred compounds of the invention have the structure
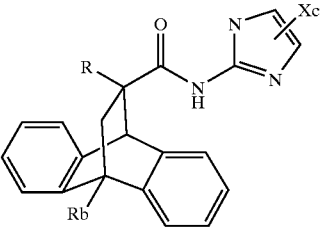
II
where R is CH₃, C₂H₅ or 2-hydroxyethyl, Rb is H, CN, NO₂, halogen, alkyl or amino, and Xc is aryl, quinolinyl or isoquinolinyl.
Examples of the above preferred compounds include the following:

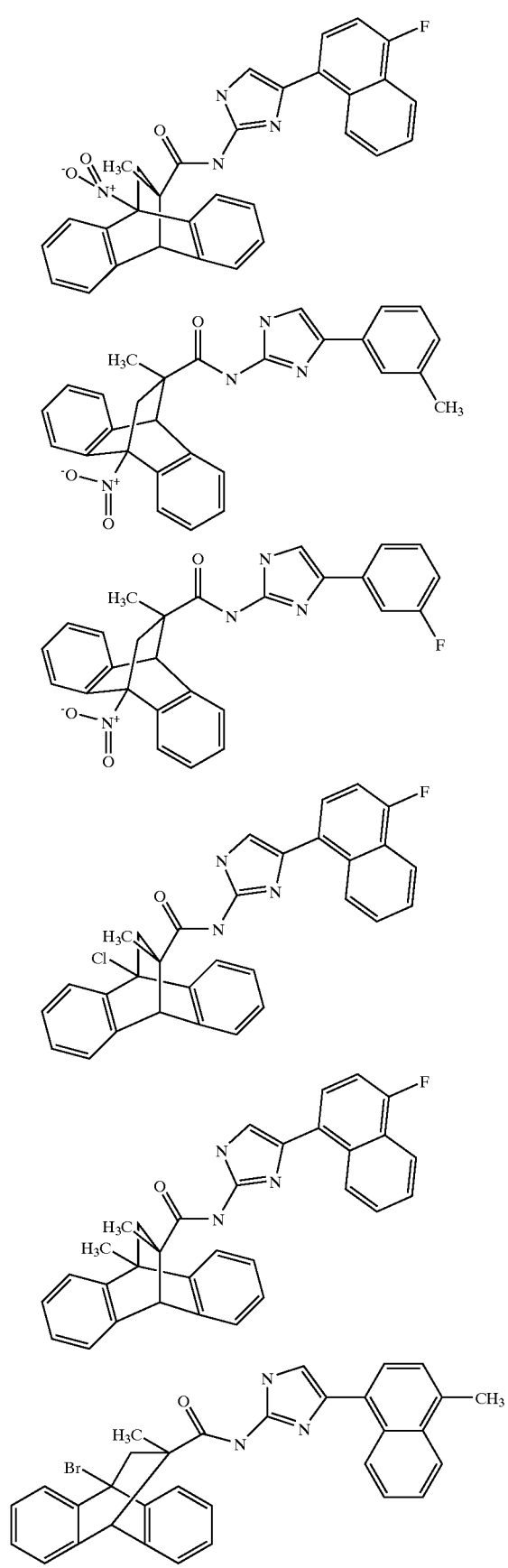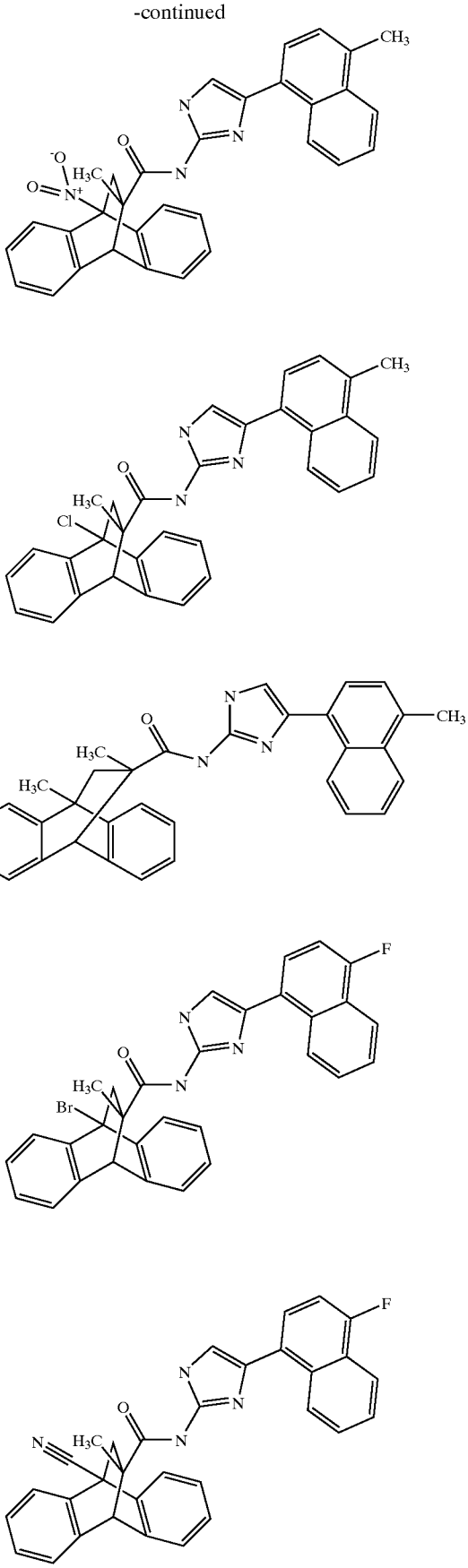

-continued

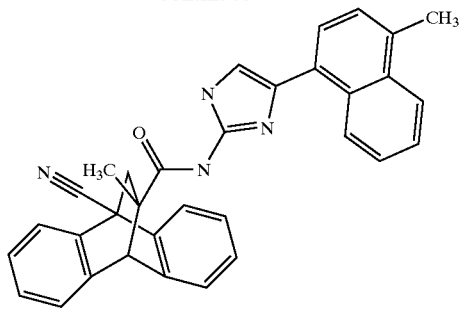

(Chiral (S))

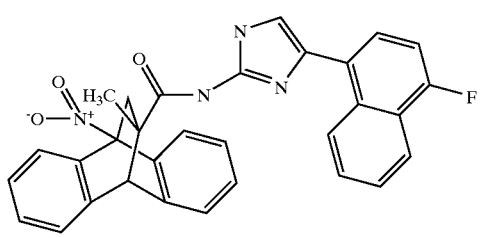

(Chiral (R))

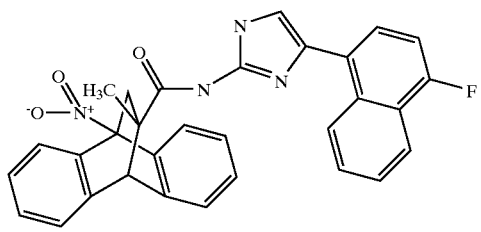

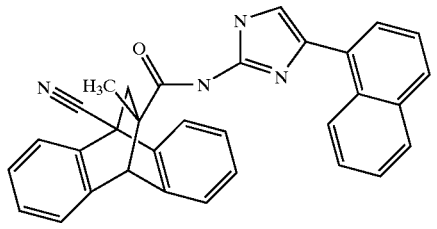

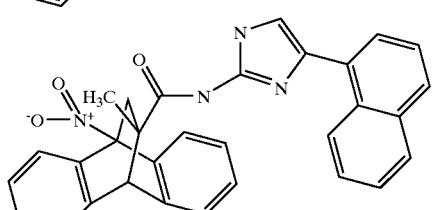

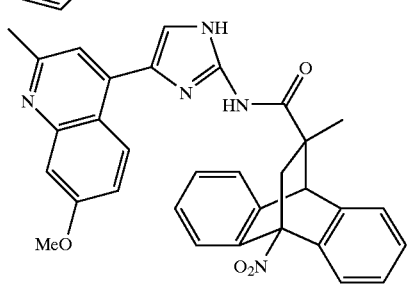

-continued

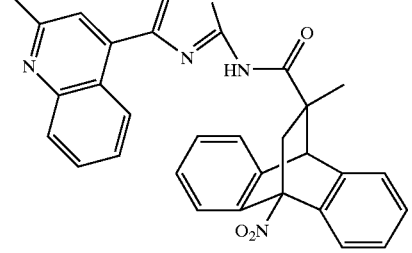

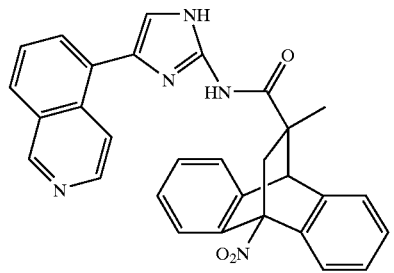

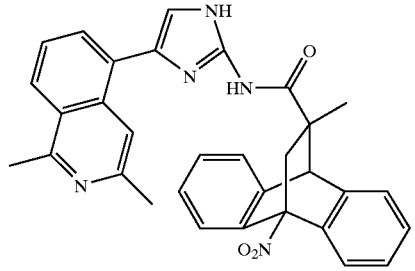

In another aspect of the present invention, there is provided pharmaceutical compositions useful in treating endocrine disorders, rheumatic disorders, collagen diseases, dermatologic disease, allergic disease, ophthalmic disease, respiratory disease, hematologic disease, gastrointestinal disease, inflammatory disease, autoimmune disease, diabetes, obesity, and neoplastic disease, as well as other uses as described herein, which includes a therapeutically effective amount (depending upon use) of a compound of formula I of the invention and a pharmaceutically acceptable carrier.

In still another aspect, the present invention provides a method of preventing, inhibiting onset of or treating endocrine disorders, rheumatic disorders, collagen diseases, dermatologic disease, allergic disease, ophthalmic disease, respiratory disease, hematologic disease, gastrointestinal disease, inflammatory disease, autoimmune disease, diabetes, obesity, and neoplastic disease, GR-associated diseases, that is a disease associated with the expression product of a gene whose transcription is stimulated or repressed by GR or a disease associated with GR transactivation, including inflammatory and immune diseases and disorders as described hereinafter, which includes the step of administering a therapeutically effective amount of a compound of formula I of the invention to a patient in need of treatment.

Another aspect of the present involves a method for preventing, inhibiting onset of or treating a disease associated with AP-1-dependent gene expression, that is a disease associated with the expression of a gene under the regulatory control of AP-1, such as inflammatory and immune disorders, cancer and tumor disorders, such as solid tumors, lymphomas and leukemia, and fungal infections such as mycosis fungoides.

The term "disease associated with GR transactivation," as used herein, refers to a disease associated with the transcription product of a gene whose transcription is transactivated by a GR. Such diseases include, but are not limited to: osteoporosis, diabetes, glaucoma, muscle loss, facial swelling, personality changes, hypertension, obesity, depression, and AIDS, the condition of wound healing, primary or secondary andrenocortical insufficiency, and Addison's disease.

The term "treat", "treating", or "treatment," in all grammatical forms, as used herein refers to the prevention, reduction, or amelioration, partial or complete alleviation, or cure of a disease, disorder, or condition.

The terms "glucocorticoid receptor" and "GR," as used herein, refer either to a member of the nuclear hormone receptor family of transcription factors which bind glucocorticoids and either stimulate or repress transcription, or to GR-beta. These terms, as used herein, refer to glucocorticoid receptor from any source, including but not limited to: human glucocorticoid receptor as disclosed in Weinberger, et al. Science 228, p640–742, 1985, and in Weinberger, et al. Nature, 318, p670–672, 1986; rat glucocorticoid receptor as disclosed in Miesfeld, R. Nature, 312, p779–781, 1985; mouse glucocortoid receptor as disclosed in Danielson, M. et al. EMBO J., 5, 2513; sheep glucocorticoid receptor as disclosed in Yang, K., et al. J. Mol. Endocrinol. 8, p173–180, 1992; marmoset glucocortoid receptor as disclosed in Brandon, D. D., et al, J. Mol. Endocrinol. 7, p89–96, 1991; and human GR-beta as disclosed in Hollenberg, S. M. et al. Nature, 318, p635, 1985, Bamberger, C. M. et al. J. Clin Invest. 95, p2435, 1995.

The term, "disease associated with AP-1-dependent gene expression," as used herein, refers to a disease associated with the expression product of a gene under the regulatory control of AP-1. Such diseases include, but are not limited to: inflammatory and immune diseases and disorders; cancer and tumor disorders, such as solid tumors, lymphomas and leukemia; and fungal infections such as mycosis fungoides.

The term "inflammatory or immune associated diseases or disorders" is used herein to encompass any condition, disease, or disorder that has an inflammatory or immune component, including, but not limited to, each of the following conditions: transplant rejection (e.g., kidney, liver, heart, lung, pancreas (e.g., islet cells), bone marrow, cornea, small bowel, skin allografts, skin homografts (such as employed in burn treatment), heart valve xenografts, serum sickness, and graft vs. host disease, autoimmune diseases, such as rheumatoid arthritis, psoriatic arthritis, multiple sclerosis, Type I and Type II diabetes, juvenile diabetes, obesity, asthma, inflammatory bowel disease (such as Crohn's disease and ulcerative colitis), pyoderma gangrenum, lupus (systemic lupus erythematosis), myasthenia gravis, psoriasis, dermatitis, dermatomyositis; eczema, seborrhoea, pulmonary inflammation, eye uveitis, hepatitis, Grave's disease, Hashimoto's thyroiditis, autoimmune thyroiditis, Behcet's or Sjorgen's syndrome (dry eyes/mouth), pernicious or immunohaemolytic anaemia, atherosclerosis, Addison's disease (autoimmune disease of the adrenal glands), idiopathic adrenal insufficiency, autoimmune polyglandular disease (also known as autoimmune polyglandular syndrome), glomerulonephritis, scleroderma, morphea, lichen planus, vitelgo (depigmentation of the skin), alopecia greata, autoimmune alopecia, autoimmune hypopituatarism, Guillain-Barre syndrome, and alveolitis; T-cell mediated hypersensitivity diseases, including contact hypersensitivity, delayed-type hypersensitivity, contact dermatitis (including that due to poison ivy), uticaria, skin allergies, respiratory allergies (hayfever, allergic rhinitis) and gluten-sensitive enteropathy (Celiac disease); inflammatory diseases such as osteoarthritis, acute pancreatitis, chronic pancreatitis, acute respiratory distress syndrome, Sezary's syndrome and vascular diseases which have an inflammatory and or a proliferatory component such as restenosis, stenosis and artherosclerosis. Inflammatory or immune associated diseases or disorders also includes, but is not limited to: endocrine disorders, rheumatic disorders, collagen diseases, dermatologic disease, allergic disease, ophthalmic disease, respiratory disease, hematologic disease, gastrointestinal disease, inflammatory disease, autoimmune disease, congenital adrenal hyperplasia, non-suppurative thyroiditis, hypercalcemia associated with cancer, juvenile rheumatoid arthritis, Ankylosing spondylitis, acute and subacute bursitis, acute nonspecific tenosynovitis, acute gouty arthritis, post-traumatic osteoarthritis, synovitis of osteoarthritis, epicondylitis, acute rheumatic carditis, pemphigus, bullous dermatitis herpetiformis, severe erythema multiforme, exfoliative dermatitis, seborrheic dermatitis, seasonal or perennial allergic rhinitis, bronchial asthma, contact dermatitis, atopic dermatitis, drug hypersensitivity reactions, allergic conjunctivitis, keratitis, herpes zoster ophthalmicus, iritis and iridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) hemolytic anemia, leukemias and lymphomas in adults, acute leukemia of childhood, regional enteritis, autoimmune vasculitis, multiple sclerosis, chronic obstructive pulmonary disease, solid organ transplant rejection, sepsis.

In addition, in accordance with the present invention a method of treating a disease associated with AP-1-induced or NFκB-induced transcription is provided wherein a compound of formula I of the invention is administered to a patient in need of treatment in a therapeutically effective amount to induce NHR transrepression of the AP-1-induced or NFκB-induced transcription, thereby treating the disease.

Other therapeutic agents, such as those described hereafter, may be employed with the compounds of the invention in the present methods. In the methods of the present invention, such other therapeutic agent(s) may be administered prior to, simultaneously with or following the administration of the compound(s) of the present invention.

In a particular embodiment, the compounds of the present invention are useful for the treatment of the aforementioned exemplary disorders irrespective of their etiology, for example, for the treatment of transplant rejection, rheumatoid arthritis, inflammatory bowel disease, and viral infections.

Methods of Preparation

The compounds of the present invention may be synthesized by many methods available to those skilled in the art of organic chemistry. General synthetic schemes, in accordance with the present invention, for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds. Examples of compounds of the present invention prepared by methods described in the general schemes are given in the preparations and examples section set out hereinafter.

Compounds of formula 1

Compounds of formula I of the invention are prepared as described in the Schemes and examples below. In the schemes the various groups A, B, Z, R, $R^a$, $R^b$, $R^c$, and $R^d$ correspond to those described above.

Scheme A

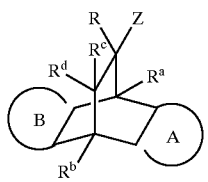

General methods for the synthesis of compounds of the invention of structure IA of the invention where A and B are each fused phenyl or pyridyl, and Z is

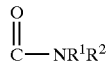

are well known in the literature. Compound IA is constructed by the cycloaddition of a compound of formula 1 with an unsaturated compound of formula 2 neat or in an appropriate solvent such as xylenes or benzene, at temperatures ranging from 50 to 200° C. to form compound 3 (which is a novel intermediate). It is well known that the cycloaddition may be facilitated by the use of a catalysts such as diethylaluminium chloride or boron trifluoride diethyl etherate. The cycloaddition may also be carried out at higher pressures as when the reactions are performed in sealed vessels.

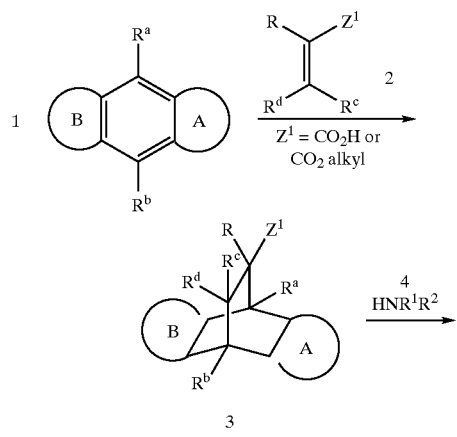

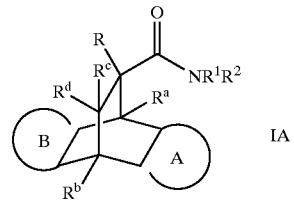

Compound 3 is reacted with an amine of formula 4 by one of the many methods of amidation well known to those skilled in the art (preferably treatment of 3 in a suitable solvent such as acetonitrile with diethylaminoethyl chloride hydrochloride (DEC), 1-hydroxy-7-azabenzotriazole, triethylamine and amine 4) to provide compounds of the invention of structure IA.

The starting compound 1 is known in the art and may be commercially available or prepared employing procedures known in the art.

Scheme B

Compounds of formula I of the invention where R is other than H and Z is

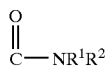

(that is IA) may be prepared preferably starting with compound 3 where R is H which is treated with a suitable base such as lithium diisopropylamide (LDA) in a suitable solvent such as tetrahydrofuran or dethyl ether and at a temperature ranging from −100° C. to 100° C. and with a compound 5 ($R^x$-LG, where LG is a leaving group, such as methyl iodide and $R^x$ is R other than H) affords compounds of structure 6. Compound 6 may be subjected to amidation as described in Scheme A to form compounds of the invention IA (where R is other than H).

Scheme C

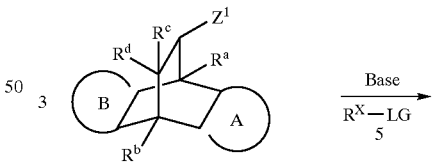

($Z^1$ = $CO_2H$ or $CO_2$—alkyl)

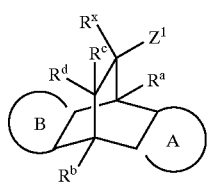

($R^x$ is an R group other than H)

Compounds of formula I of the invention where Z is

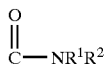

where each of $R^1$ and $R^2$ is other than H may be prepared starting with compound of formula IA where $R^{1a}$ is $R^1$ other than H and $R^2$ is H which is treated with base such as sodium hydride and compound 5a $R^{2a}$-LG, where LG is a leaving group, such as methyl iodide, and $R^{2a}$ is $R^2$ other than H, to provide compounds of structure IB of the invention where $R^1$ and $R^2$ are other than H.

Scheme D

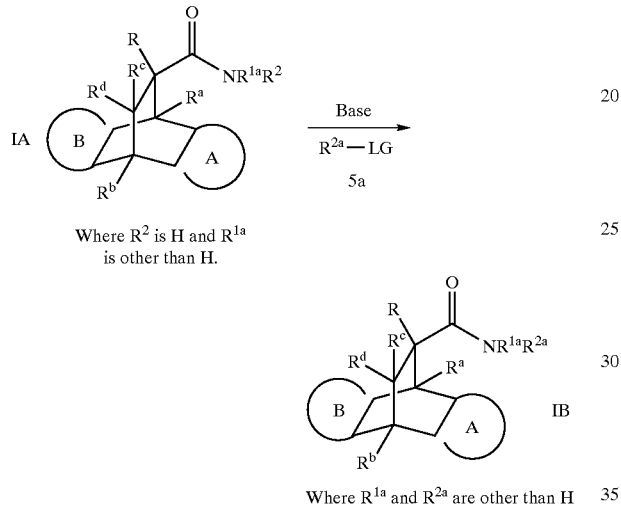

Scheme D

Compounds of formula I of the invention where Z is —$CH_2NR^1R^2$ (that is IC) may be prepared starting with compounds of formula IA which when treated with a reducing agent such as lithium aluminum hydride (LAH) provides compounds IC of the invention.

Scheme E

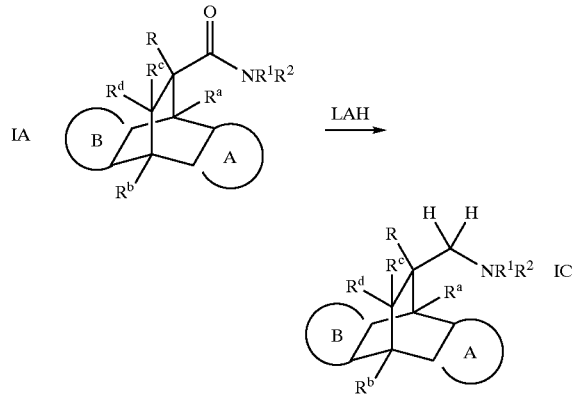

Compounds of formula I of the invention where one or more of A, B, Z, R, $R^a$, $R^b$, $R^c$ and $R^d$ includes a hydroxyaryl group may be prepared as follows.

A compound of formula IA of the invention that contains one or more aryloxyalkyl groups located in A, B, Z, R, $R^a$, $R^b$, $R^c$, and $R^d$ when treated with dealkylating agent such as boron tribromide, sodium methyl sulfide or other known dealkylating agents provides phenols of formula ID of the invention.

Scheme F

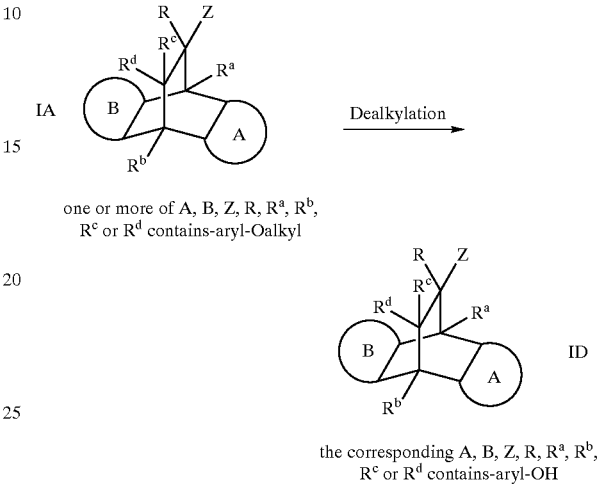

Scheme F

A compound of formula IE where $R^a$ or $R^b$ is a functional group such as CHO, $NH_2$, $CO_2H$ or $NO_2$ may be further elaborated by various methods well known to those skilled in the art to give compounds of structure IF. A few illustrative examples are shown below. The newly introduced groups may also be further elaborated,

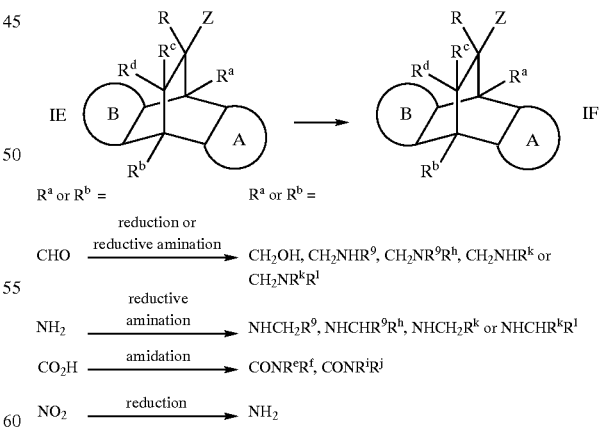

The following compounds are new intermediates and may be prepared employing procedures set out hereinbefore and/or known in the art:

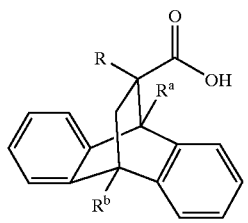

or an alkyl ester thereof, where R is $CH_3$, $C_2H_5$; $R^a$ is nitro, cyano, Cl, Br, CH3, —COOCH3, formyl and Rb is H; $R^b$ is nitro, cyano, Cl, Br, CH3, —COOCH3, formyl and $R^a$ is H; and

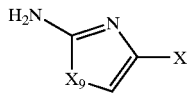

where $X_9$ is S or NH; X is:

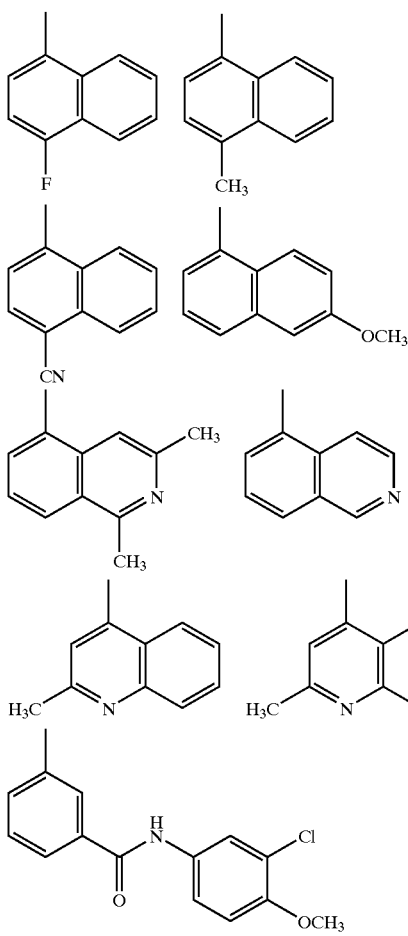

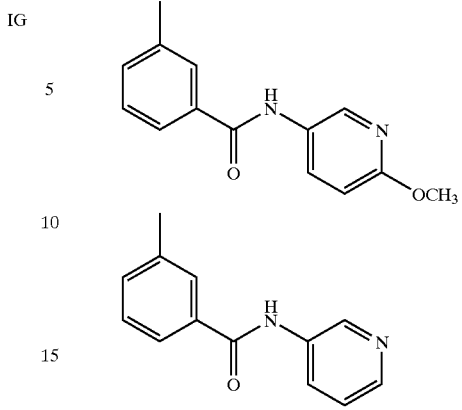

Definition of Terms

Unless otherwise indicated, the term "lower alkyl", "alkyl" or "alk" as employed herein alone or as part of another group includes both straight and branched chain hydrocarbons, containing 1 to 20 carbons, preferably 1 to 10 carbons, more preferably 1 to 8 carbons, in the normal chain, and may optionally include an oxygen or nitrogen in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 4 substituents such as halo, for example F, Br, Cl or I or $CF_3$, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, HO—N═, cycloheteroalkyl, alkyloxycarbonyl, alkoxyoximyl, arylheteroaryl, arylalkoxycarbonyl, heteroarylalkyl, heteroarylalkoxy, aryloxyalkyl, aryloxyaryl, alkylamido, alkanoylamino, hydroxyalkyl (alkyl)amino carbonyl, arylcarbonylamino, nitro, cyano, thiol, haloalkyl, trihaloalkyl and/or alkylthio and/or any of the substituents for aryl.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

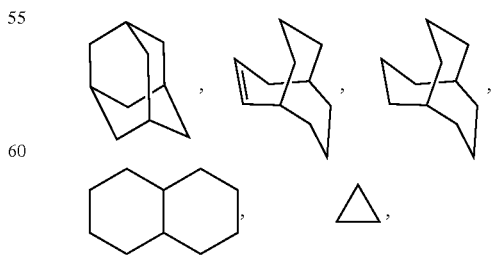

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio and/or any of the substituents for alkyl.

The term "cycloalkenyl" as employed herein alone or as part of another group refers to cyclic hydrocarbons containing 3 to 12 carbons, preferably 5 to 10 carbons and 1 or 2 double bonds. Exemplary cycloalkenyl groups include cyclopentenyl, cyclohexenyl, cycloheptenyl, cyclooctenyl, cyclohexadienyl, and cycloheptadienyl, which may be optionally substituted as defined for cycloalkyl.

The term "cycloalkylene" as employed herein refers to a "cycloalkyl" group which includes free bonds and thus is a linking group such as

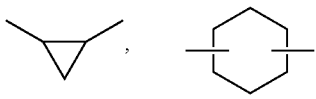

and the like, and may optionally be substituted as defined above for "cycloalkyl".

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, and may optionally include an oxygen or nitrogen in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio and/or any of the substituents for alkyl set out herein.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, and may optionally include an oxygen or nitrogen in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the substituents for alkyl set out herein.

The terms "arylalkenyl" and "arylalkynyl" as used alone or as part of another group refer to alkenyl and alkynyl groups as described above having an aryl substituent.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

$(CH_2)_p$ and $(CH_2)_q$, includes alkylene, allenyl, alkenylene or alkynylene groups, as defined herein, each of which may optionally include an oxygen or nitrogen in the normal chain, which may optionally include 1, 2, or 3 substituents which include alkyl, alkenyl, halogen, cyano, hydroxy, alkoxy, amino, thioalkyl, keto, $C_3$–$C_6$ cycloalkyl, alkylcarbonylamino or alkylcarbonyloxy; the alkyl substituent may be an alkylene moiety of 1 to 4 carbons which may be attached to one or two carbons in the $(CH_2)_p$ or $(CH_2)_q$ group to form a cycloalkyl group therewith.

Examples of $(CH_2)_p$, $(CH_2)_q$, alkylene, alkenylene and alkynylene include

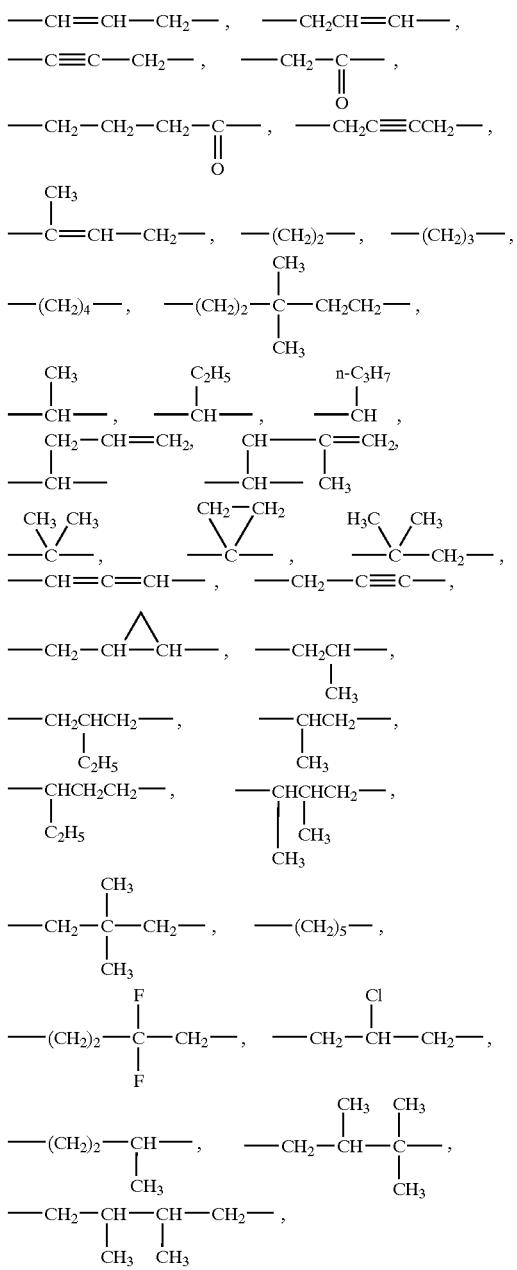

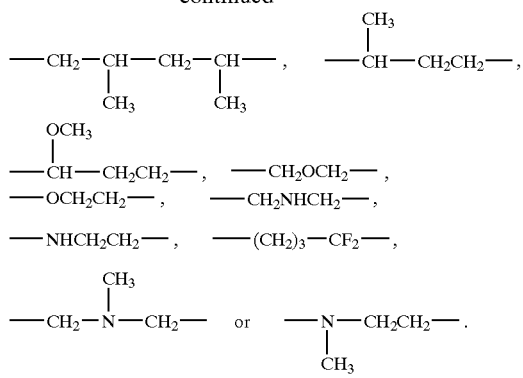

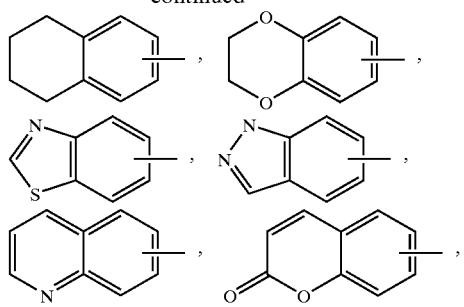

and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl, carboxy, cycloalkyl, arylalkoxy, aryloxycarbonyl, cycloalkylaminocarbonyl, cycloalkylalkylaminocarbonyl, alkoxycarbonylalkyl, alkoxyalkylaminocarbonyl, heteroarylaminocarbonyl, heteroarylalkylaminocarbonyl, arylalkylaminocarbonyl, N-hydroxyalkyl(N-alkyl)aminocarbonyl, cycloheteroalkylaminocarbonyl, cycloheteroalkylalkylaminocarbonyl, N-aryl(N-alkyl) aminocarbonyl, N-arylalkyl(N-cyanoalkyl)aminocarbonyl, dialkylaminoalkylaminocarbonyl, dialkylaminocarbonyl, alkyl-, arylalkyl- or aryl-cycloheteroalkylaminocarbonyl, N-dialkylaminoalkyl(N-alkyl or N-arylalkyl) aminocarbonyl, N-heteroarylalkyl(N-alkyl)aminocarbonyl, N-arylalkyl(N-alkyl)aminocarbonyl, N-dialkylamino(N-arylalkyl)aminocarbonyl, N-hydroxyalkyl(N-arylalkyl) aminocarbonyl, aminoalkyloxycarbonyl, cycloheteroalkylcarbonyl, N=N=N, alkylsulfonyl, aminosulfonyl, heteroarylaminosulfonyl, and/or any of the substituents for alkyl set out herein.

The term "halogen" or "halo" as used herein alone or as part of another group refers to chlorine, bromine, fluorine, and iodine as well as $CF_3$, with chlorine or fluorine being preferred.

The term "metal ion" refers to alkali metal ions such as sodium, potassium or lithium and alkaline earth metal ions such as magnesium and calcium, as well as zinc and aluminum.

Unless otherwise indicated, the term "aryl", as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings for example Unless otherwise indicated, the term "lower alkoxy", "alkoxy", "aryloxy" or "aralkoxy" as employed herein alone or as part of another group includes any of the above alkyl, aralkyl or aryl groups linked to an oxygen atom.

Unless otherwise indicated, the term "substituted amino" as employed herein alone or as part of another group refers to amino substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl or thioalkyl. These substituents may be further substituted with a carboxylic acid and/or any of the substituents for alkyl as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl or hydroxy.

Unless otherwise indicated, the term "lower alkylthio", "alkylthio", "arylthio" or "aralkylthio" as employed herein alone or as part of another group includes any of the above alkyl, aralkyl or aryl groups linked to a sulfur atom.

Unless otherwise indicated, the term "lower alkylamino", "alkylamino", "arylamino", or "arylalkylamino" as employed herein alone or as part of another group includes any of the above alkyl, aryl or arylalkyl groups linked to a nitrogen atom.

Unless otherwise indicated, the term "acyl" as employed herein by itself or part of another group, as defined herein, refers to an organic radical linked to a carbonyl

group; examples of acyl groups include any of the R groups attached to a carbonyl, such as alkanoyl, alkenoyl, aroyl, aralkanoyl, heteroaroyl, cycloalkanoyl, cycloheteroalkanoyl and the like.

Unless otherwise indicated, the term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_p$ (where p is 0, 1, 2 or 3), such as

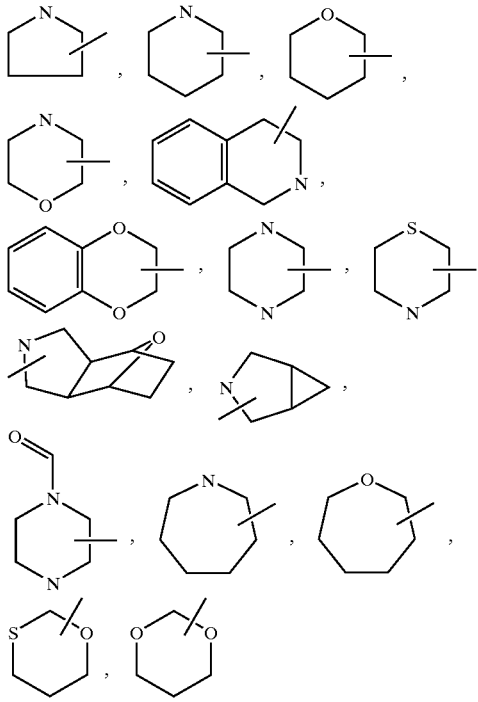

and the like. The above groups may include 1 to 4 substituents such as alkyl, halo, oxo and/or any of of the substituents for alkyl or aryl set out herein. In addition, any of the cycloheteroalkyl rings can be fused to a cycloalkyl, aryl, heteroaryl or cycloheteroalkyl ring.

Unless otherwise indicated, the term "heteroaryl" as used herein alone or as part of another group refers to a 5-, 6- or 7-membered aromatic ring which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), and includes possible N-oxides, The heteroaryl group may optionally include 1 to 4 substituents such as any of the substituents for alkyl or aryl set out above. Examples of heteroaryl groups include the following:

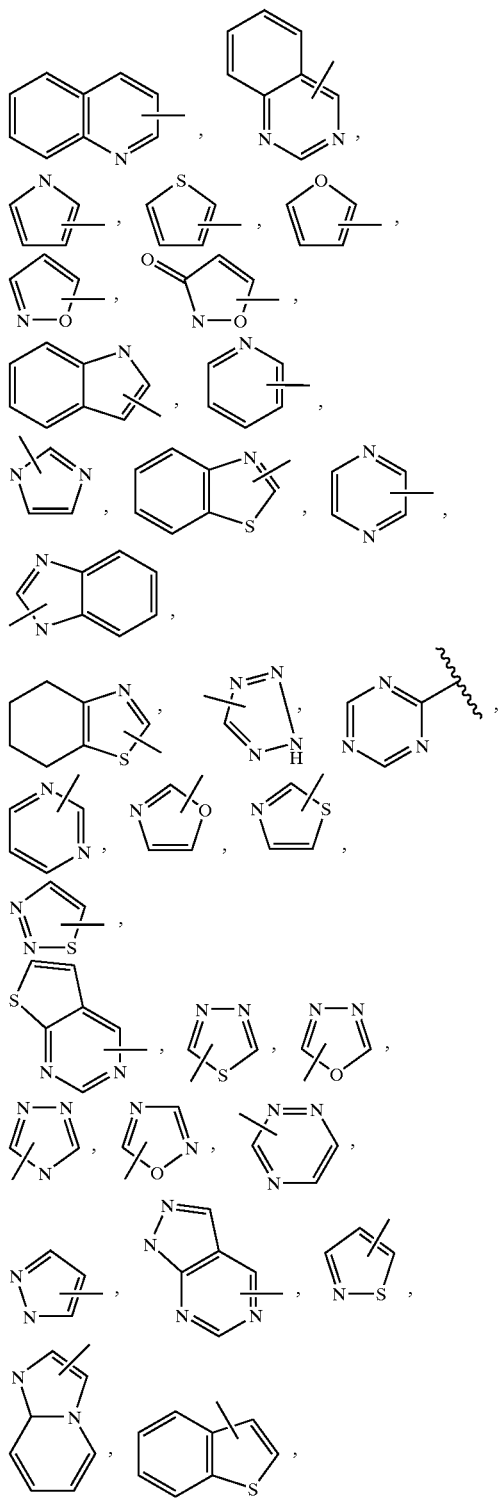

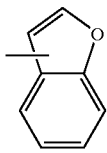

and the like.

Examples of A rings and B rings include, but are not limited to any of the 6-membered heteroaryl groups as defined above, 6-membered cycloheteroalkyl groups as defined above, and 6-membered aryl groups as defined above.

The term "cycloheteroalkylalkyl" as used herein alone or as part of another group refers to cycloheteroalkyl groups as defined above linked through a C atom or heteroatom to a $(CH_2)_p$ chain.

The term "heteroarylalkyl" or "heteroarylalkenyl" as used herein alone or as part of another group refers to a heteroaryl group as defined above linked through a C atom or heteroatom to a —$(CH_2)_q$— chain, alkylene or alkenylene as defined above.

The term "polyhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "polyhaloalkyloxy" as used herein refers to an "alkoxy" or "alkyloxy" group as defined above which includes from 2 to 9, preferably from 2 to 5, halo substituents, such as F or Cl, preferably F, such as $CF_3CH_2O$, $CF_3O$ or $CF_3CF_2CH_2O$.

The term "prodrug esters" as employed herein includes prodrug esters which are known in the art for carboxylic and phosphorus acid esters such as methyl, ethyl, benzyl and the like. Other prodrug ester examples include the following groups: (1-alkanoyloxy)alkyl such as,

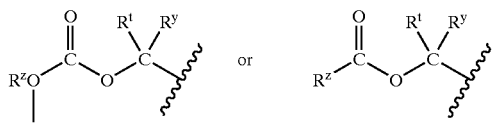

wherein $R^z$, $R^t$ and $R^y$ are H, alkyl, aryl or arylalkyl; however, $R^zO$ cannot be HO.

Examples of such prodrug esters include

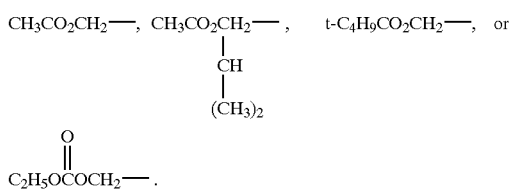

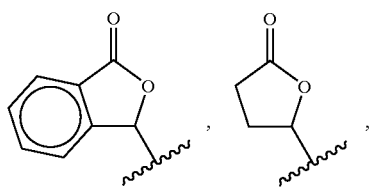

Other examples of suitable prodrug esters include

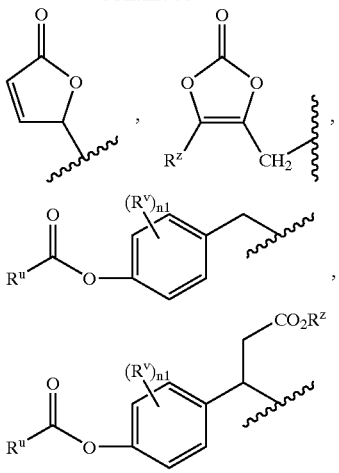

wherein $R^z$ can be H, alkyl (such as methyl or t-butyl), arylalkyl (such as benzyl) or aryl (such as phenyl); $R^v$ is H, alkyl, halogen or alkoxy, $R''$ is alkyl, aryl, arylalkyl or alkoxyl, and $n_1$ is 0, 1 or 2.

The terms pharmaceutically acceptable "salt" and "salts" refer to basic salts formed with inorganic and organic bases. Such salts include ammonium salts; alkali metal salts, such as lithium, sodium and potassium salts (which are preferred); alkaline earth metal salts, such as calcium and magnesium salts; salts with organic bases, such as amine like salts (e.g., dicyclohexylamine salt, benzathine, N-methyl-D-glucamine, and hydrabamine salts); and salts with amino acids like arginine, lysine and the like; and zwitterions, the so-called "inner salts". Nontoxic, pharmaceutically acceptable salts are preferred, although other salts are also useful, e.g., in isolating or purifying the product.

The term pharmaceutically acceptable "salt" and "salts" also includes acid addition salts. These are formed, for example, with strong inorganic acids, such as mineral acids, for example sulfuric acid, phosphoric acid or a hydrohalic acid such as HCl or HBr, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$–$C_4$) alkyl or arylsulfonic acids which are unsubstituted or substituted, for example by halogen, for example methanesulfonic acid or p-toluenesulfonic acid.

All stereoisomers of the compounds of the instant invention are contemplated, either in admixture or in pure or substantially pure form. The compounds of the present invention can have asymmetric centers at any of the carbon atoms including any one or the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

Combinations

Where desired, the compounds of structure I may be used in combination with one or more other types of therapeutic agents such as immunosuppressants, anticancer agents, antiviral agents, anti-inflammatory agents, anti-fungal agents, antibiotics, anti-vascular hyperproliferation agents, anti-depressive agents, hypolipidemic agents or lipid-lowering agents or lipid modulating agents, antidiabetic agents, anti-obesity agents, antihypertensive agents, platelet aggregation inhibitors, and/or anti-osteoporosis agents, which may be administered orally in the same dosage form, in a separate oral dosage form or by injection.

The immunosuppressants which may be optionally employed in combination with compounds of formula I of the invention include cyclosporins, for example cyclosporin A, mycophenolate, interferon-beta, deoxyspergolin, FK-506 or Ant.—IL-2.

The anti-cancer agents which may be optionally employed in combination with compounds of formula I of the invention include azathiprine, 5-fluorouracil, cyclophosphamide, cisplatin, methotrexate, thiotepa, carboplatin, and the like.

The anti-viral agents which may be optionally employed in combination with compounds of formula I of the invention include abacavir, aciclovir, ganciclovir, zidanocin, vidarabine, and the like.

The anti-inflammatory agents which may be optionally employed in combination with compounds of formula I of the invention include non-steroidal anti-inflammatory drugs (NSAIDs) such as ibuprofen, cox-2 inhibitors such as celecoxib, rofecoxib, aspirin, naproxen, ketoprofen, diclofenac sodium, indomethacin, piroxicam, steroids such as prednisone, dexamethasone, hydrocortisone, triamcinolone diacetate, gold compounds, such as gold sodium thiomalate, TNF-αinhibitors such as tenidap, anti-TNF antibodies or soluble TNF receptor, and rapamycin (sirolimus or Rapamune) or derivatives thereof, infliximab (Remicade® Centocor, Inc.). CTLA4Ig, LEA29Y, antibodies such as anti-ICAM-3, anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and CD 154 (a.k.a. "gp39"), such as antibodies specific for CD40 and/or CD154, fusion proteins such as etanercept, fusion proteins constructed from CD40 and/or CD154gp39 (e.g. CD40Ig and CD8gp39), inhibitors, such as nuclear translocation inhibitors, of NF-kappa B function, such as deoxyspergualin (DSG).

The anti-fungal agents which may be optionally employed in combination with compounds of formula I of the invention include fluconazole, miconazole, amphotericin B, and the like.

The antibiotics which may be optionally employed in combination with compounds of formula I of the invention include penicillin, tetracycline, amoxicillin, ampicillin, erythromycin, doxycycline, vancomycin, minocycline, clindamycin or cefalexin.

The anti-vascular hyperproliferation agents which may be optionally employed with compounds of formula I of the invention include methotrexate, leflunomide, FK506 (tacrolimus, Prograf).

The hypolipidemic agent or lipid-lowering agent or lipid modulating agents which may be optionally employed in combination with the compounds of formula I of the invention may include 1, 2, 3 or more MTP inhibitors, HMG CoA reductase inhibitors, squalene synthetase inhibitors, fibric acid derivatives, ACAT inhibitors, lipoxygenase inhibitors, cholesterol absorption inhibitors, ileal Na$^+$/bile acid cotransporter inhibitors, upregulators of LDL receptor activity, bile acid sequestrants, and/or nicotinic acid and derivatives thereof.

MTP inhibitors employed herein include MTP inhibitors disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. application Ser. No. 09/175,180 filed Oct. 20, 1998, now U.S. Pat. No. 5,962,440. Preferred are each of the preferred MTP inhibitors disclosed in each of the above patents and applications.

All of the above U.S. Patents and applications are incorporated herein by reference.

Most preferred MTP inhibitors to be employed in accordance with the present invention include preferred MTP inhibitors as set out in U.S. Pat. Nos. 5,739,135 and 5,712,279, and U.S. Pat. No. 5,760,246.

The most preferred MTP inhibitor is 9-[4-[4-[[2-(2,2,2-trifluoroethoxy)benzoyl]amino]-1-piperidinyl]butyl]-N-(2,2,2-trifluoroethyl)-9H-fluorene-9-carboxamide

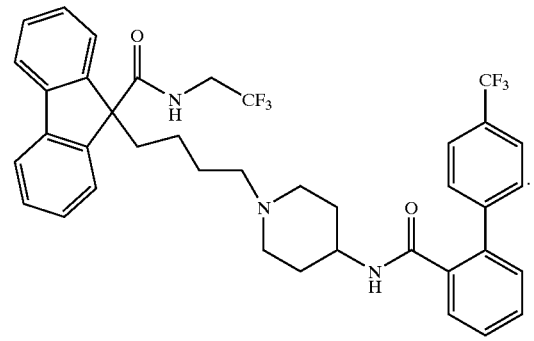

The hypolipidemic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, itavastatin (Nissan/Sankyo's nisvastatin (NK-104)) disclosed in U.S. Pat. No. 5,011,930, Shionogi-Astra/Zeneca visastatin (ZD-4522) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No.0,142,146 A2, and quinoline and pyridine derivatives disclosed in U.S. Pat. Nos. 5,506,219 and 5,691,322.

In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp 1869–1871, including isoprenoid (phosphinyl-methyl) phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 140 (1996).

In addition, other squalene synthetase inhibitors suitable for use herein include the terpenoid pyrophosphates disclosed by P. Ortiz de Montellano et al, J. Med. Chem., 1977, 20, 243–249, the farnesyl diphosphate analog A and presqualene pyrophosphate (PSQ-PP) analogs as disclosed by Corey and Volante, J. Am. Chem. Soc., 1976, 98, 1291–1293, phosphinylphosphonates reported by McClard, R. W. et al, J.A.C.S., 1987, 109, 5544 and cyclopropanes reported by Capson, T. L, PhD dissertation, June, 1987, Dept. Med. Chem. U of Utah, Abstract, Table of Contents, pp 16, 17,40–43,48–51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Policexide®) and cholestagel (Sankyo/Geltex), as well as lipostabil (Rhone-Poulenc), Eisai E-5050 (an N-substituted ethanolamine derivative), imanixil (HOE402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly(diallyldimethylammonium chloride) and ionenes such as disclosed in U.S. Pat. No. 4,027,009, and other known serum cholesterol lowering agents.

The hypolipidemic agent may be an ACAT inhibitor such as disclosed in, Drugs of the Future 24, 9–15 (1999), (Avasimibe); "The ACAT inhibitor, C1-1011 is effective in the prevention and regression of aortic fatty streak area in hamsters", Nicolosi et al, Atherosclerosis (Shannon, Irel). (1998), 137(1), 77–85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16–30; "RP 73163: a bioavailable alkylsulfinyl-diphenylimidazole ACAT inhibitor", Smith, C., et al, Bioorg. Med. Chem. Lett. (1996), 6(1), 47–50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173–98, Publisher: CRC, Boca Raton, Fla.; "ACAT inhibitors: potential anti-atherosclerotic agents", Sliskovic et al, Curr. Med. Chem. (1994), 1(3), 204–25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359–62, or TS-962 (Taisho Pharmaceutical Co. Ltd).

The hypolipidemic agent may be an upregulator of LD2 receptor activity such as MD-700 (Taisho Pharmaceutical Co. Ltd) and LY295427 (Eli Lilly).

The hypolipidemic agent may be a cholesterol absorption inhibitor preferably Schering-Plough's ezetimibe (SCH58235) and SCH48461 as well as those disclosed in Atherosclerosis 115, 45–63 (1995) and J. Med. Chem. 41, 973 (1998).

The hypolipidemic agent may be an ileal $Na^+$/bile acid cotransporter inhibitor such as disclosed in Drugs of the Future, 24,425430 (1999).

The lipid-modulating agent may be a cholesteryl ester transfer protein (CETP) inhibitor such as Pfizer's CP 529, 414 (WO/0038722 and EP 818448) and Pharmacia's SC-744 and SC-795.

The ATP citrate lyase inhibitor which may be employed in the combination of the invention may include, for example, those disclosed in U.S. Pat. No. 5,447,954.

Preferred hypolipidemic agents are pravastatin, lovastatin, simvastatin, atorvastatin, fluvastatin, cerivastatin, itavastatin and visastatin and ZD-4522.

The above-mentioned U.S. patents are incorporated herein by reference. The amounts and dosages employed will be as indicated in the Physician's Desk Reference and/or in the patents set out above.

The compounds of formula I of the invention will be employed in a weight ratio to the hypolipidemic agent (were present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent will be as disclosed in the various patents and applications discussed above.

The dosages and formulations for the other hypolipidemic agent to be employed, where applicable, will be as set out in the latest edition of the Physicians' Desk Reference.

For oral administration, a satisfactory result may be obtained employing the MTP inhibitor in an amount within the range of from about 0.01 mg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor, for example, pravastatin, lovastatin, simvastatin, atorvastatin, fluvastatin or cerivastatin in dosages employed as indicated in the Physician's Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 0.5 to about 80 mg, and more preferably from about 1 to about 40 mg.

A preferred oral dosage form, such as tablets or capsules will contain the squalene synthetase inhibitor in an amount of from about 10 to about 500 mg, preferably from about 25 to about 200 mg.

The hypolipidemic agent may also be a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al "Attenuation of diet-induced atherosclerosis in rabbits with a highly selective 15-lipoxygenase inhibitor lacking significant antioxidant properties", Brit. J. Pharmacology (1997) 120, 1199–1206, and Cornicelli et al, "15-Lipoxygenase and its Inhibition: A Novel Therapeutic Target for Vascular Disease", Current Pharmaceutical Design, 1999, 5, 11–20.

The compounds of formula I and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The preferred hypolipidemic agent is pravastatin, simvastatin, lovastatin, atorvastatin, fluvastatin or cerivastatin as well as niacin and/or cholestagel.

The other antidiabetic agent which may be optionally employed in combination with the compound of formula I may be 1, 2, 3 or more antidiabetic agents or antihyperglycemic agents including insulin secretagogues or insulin sensitizers, or other antidiabetic agents preferably having a mechanism of action different from the compounds of formula I of the invention, which may include biguanides, sulfonyl ureas, glucosidase inhibitors, PPAR Y agonists, such as thiazolidinediones, aP2 inhibitors, dipeptidyl peptidase IV (DP4) inhibitors, SGLT2 inhibitors, and/or meglitinides, as well as insulin, and/or glucagon-like peptide-1 (GLP-1).

The other antidiabetic agent may be an oral antihyperglycemic agent preferably a biguanide such as metformin or phenformin or salts thereof, preferably metformin HCl.

Where the antidiabetic agent is a biguanide, the compounds of structure I will be employed in a weight ratio to biguanide within the range from about 0.001:1 to about 10:1, preferably from about 0.01:1 to about 5:1.

The other antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the □-cells, with glyburide and glipizide being preferred, which may be administered in the same or in separate oral dosage forms.

The compounds of structure I will be employed in a weight ratio to the sulfonyl urea in the range from about 0.01:1 to about 100:1, preferably from about 0.02:1 to about 5:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of structure I will be employed in a weight ratio to the glucosidase inhibitor within the range from about 0.01:1 to about 100:1, preferably from about 0.05:1 to about 10:1.

The compounds of structure I may be employed in combination with a PPAR y agonist such as a thiazolidinedione oral anti-diabetic agent or other insulin sensitizers (which has an insulin sensitivity effect in NIDDM patients) such as troglitazone (Warner-Lambert's Rezulin®, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM440 (Yamanouchi), preferably rosiglitazone and pioglitazone.

The compounds of structure I will be employed in a weight ratio to the thiazolidinedione in an amount within the range from about 0.01:1 to about 100:1, preferably from about 0.05 to about 10:1.

The sulfonyl urea and thiazolidinedione in amounts of less than about 150 mg oral antidiabetic agent may be incorporated in a single tablet with the compounds of structure I.

The compounds of structure I may also be employed in combination with a antihyperglycemic agent such as insulin or with glucagon-like peptide-1 (GLP-1) such as GLP-1 (1–36) amide, GLP-1(7–36) amide, GLP-1(7–37) (as disclosed in U.S. Pat. No. 5,614,492 to Habener, the disclosure of which is incorporated herein by reference), as well as AC2993 (Amylin) and LY-315902 (Lilly), which may be administered via injection, intranasal, inhalation or by transdermal or buccal devices.

Where present, metfommin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the Physician's Desk Reference (PDR).

Where present, metformin or salt thereof may be employed in amounts within the range from about 500 to about 2000 mg per day which may be administered in single or divided doses one to four times daily.

Where present, the thiazolidinedione anti-diabetic agent may be employed in amounts within the range from about 0.01 to about 2000 mg/day which may be administered in single or divided doses one to four times per day.

Where present insulin may be employed in formulations, amounts and dosing as indicated by the Physician's Desk Reference.

Where present GLP-1 peptides may be administered in oral buccal formulations, by nasal administration or parenterally as described in U.S. Pat. Nos. 5,346,701 (TheraTech), 5,614,492 and 5,631,224 which are incorporated herein by reference.

The other antidiabetic agent may also be a PPAR α/γ dual agonist such as AR-H039242 (Astra/Zeneca), GW409544 (Glaxo-Wellcome), KRP297 (Kyorin Merck) as well as those disclosed by Murakami et al, "A Novel Insulin Sensitizer Acts As a Coligand for Peroxisome Proliferation- Activated Receptor Alpha (PPAR alpha) and PPAR gamma. Effect on PPAR alpha Activation on Abnormal Lipid Metabolism in Liver of Zucker Fatty Rats", Diabetes 47, 1841–1847 (1998).

The antidiabetic agent may be an SGLT2 inhibitor such as disclosed in U.S. application Ser. No. 09/679,027, filed Oct. 4, 2000, employing dosages as set out therein. Preferred are the compounds designated as preferred in the above application.

The antidiabetic agent may be an aP2 inhibitor such as disclosed in U.S. application Ser. No. 09/391,053, filed Sep. 7, 1999, and in U.S. application Ser. No. 09/519,079, filed Mar. 6, 2000, employing dosages as set out herein. Preferred are the compounds designated as preferred in the above application.

The antidiabetic agent may be a DP4 inhibitor such as disclosed in U.S. application Ser. No. 09/788,173 filed Feb. 16, 2001, WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S) pyrrolidine) (Novartis) (preferred) as disclosed by Hughes et al, Biochemistry, 38(36), 11597–11603, 1999, TSL-225 (tryptophyl-1,2,3,4-tetrahydro-isoquinoline-3-carboxylic acid (disclosed by Yamada et al, Bioorg. & Med. Chem. Lett. 8 (1998) 1537–1540, 2-cyanopyrrolidides and 4-cyanopyrrolidides as disclosed by Ashworth et al, Bioorg. & Med. Chem. Lett., Vol. 6, No. 22, pp 1163–1166 and 2745–2748 (1996) employing dosages as set out in the above references.

The meglitinide which may optionally be employed in combination with the compound of formula I of the invention may be repaglinide, nateglinide (Novartis) or KAD1229 (PF/Kissei), with repaglinide being preferred.

The compound of formula I will be employed in a weight ratio to the meglitinide, PPAR γ agonist, PPAR α/γ dual agonist, aP2 inhibitor, DP4 inhibitor or SGLT2 inhibitor within the range from about 0.01:1 to about 100:1, preferably from about 0.05 to about 10:1.

The other type of therapeutic agent which may be optionally employed with a compound of formula I may be 1, 2, 3 or more of an anti-obesity agent including a beta 3 adrenergic agonist, a lipase inhibitor, a serotonin (and dopamine) reuptake inhibitor, an aP2 inhibitor, a thyroid receptor agonist and/or an anorectic agent.

The beta 3 adrenergic agonist which may be optionally employed in combination with a compound of formula I may be AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, with AJ9677, L750,355 and CP331648 being preferred.

The lipase inhibitor which may be optionally employed in combination with a compound of formula I may be orlistat or ATL-962 (Alizyme), with orlistat being preferred.

The serotonin (and dopoamine) reuptake inhibitor which may be optionally employed in combination with a compound of formula I may be sibutramine, topiramate (Johnson & Johnson) or axokine (Regeneron), with sibutramine and topiramate being preferred.

The thyroid receptor agonist which may be optionally employed in combination with a compound of formula I may be a thyroid receptor ligand as disclosed in WO97/21993 (U. Cal SF), WO99/00353 (KaroBio), GB98/284425 (KaroBio), and U.S. Provisional Application 60/183,223 filed Feb. 17, 2000, with compounds of the KaroBio applications and the above U.S. provisional application being preferred.

The anorectic agent which may be optionally employed in combination with a compound of formula I may be dexamphetamine, phentermine, phenylpropanolamine or mazindol, with dexamphetamine being preferred.

The various anti-obesity agents described above may be employed in the same dosage form with the compound of formula I or in different dosage forms, in dosages and regimens as generally known in the art or in the PDR.

The antihypertensive agents which may be employed in combination with the compound of formula I of the invention include ACE inhibitors, angiotensin II receptor antagonists, NEP/ACE inhibitors, as well as calcium channel blockers, β-adrenergic blockers and other types of antihypertensive agents including diuretics.

The angiotensin converting enzyme inhibitor which may be employed herein includes those containing a mercapto (—S—) moiety such as substituted proline derivatives, such as any of those disclosed in U.S. Pat. No. 4,046,889 to Ondetti et al mentioned above, with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in Clin. Exp. Pharmacol. Physiol. 10:131 (1983); as well as pivopril and YS980.

Other examples of angiotensin converting enzyme inhibitors which may be employed herein include any of those disclosed in U.S. Pat. No. 4,374,829 mentioned above, with N-(1-ethoxycarbonyl-3-phenylpropyl)-L-alanyl-L-proline, that is, enalapril, being preferred, any of the phosphonate substituted amino or imino acids or salts disclosed in U.S. Pat. No. 4,452,790 with (S)-1-[6-amino-2-[[(hydroxy-(4-phenylbutyl)phosphinyl]oxy]-1-oxohexyl]-L-proline or (ceronapril) being preferred, phosphinylalkanoyl prolines disclosed in U.S. Pat. No. 4,168,267 mentioned above with fosinopril being preferred, any of the phosphinylalkanoyl substituted prolines disclosed in U.S. Pat. No. 4,337,201, and the phosphonamidates disclosed in U.S. Pat. No. 4,432,971 discussed above.

Other examples of ACE inhibitors that may be employed herein include Beecham's BRL 36,378 as disclosed in European Patent Application Nos. 80822 and 60668; Chugai's MC-838 disclosed in C.A. 102:72588v and Jap. J. Pharmacol. 40:373 (1986); Ciba-Geigy's CGS 14824 (3-([1-ethoxycarbonyl-3-phenyl-(1S)-propyl]amino)-2,3,4,5-tetrahydro-2-oxo-1-(3S)-benzazepine-1 acetic acid HCl) disclosed in U.K. Patent No.2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Eur. Therap. Res. 39:671 (1986); 40:543 (1986); ramipril (Hoechsst) disclosed in Euro. Patent No. 79-022 and Curr. Ther. Res. 40:74 (1986); Ru 44570 (Hoechst) disclosed in Arzneimittelforschung 34:1254 (1985), cilazapril (Hoffman-LaRoche) disclosed in J. Cardiovasc. Pharmacol. 9:39 (1987); R 31–2201 (Hoffman-LaRoche) disclosed in FEBS Lett. 165:201 (1984); lisinopril (Merck), indalapril (delapril) disclosed in U.S. Pat. No. 4,385,051; indolapril (Schering) disclosed in J. Cardiovasc. Pharmacol. 5:643, 655 (1983), spirapril (Schering) disclosed in Acta. Pharmacol. Toxicol. 59 (Supp. 5):173 (1986);

perindopril (Servier) disclosed in Eur. J. clin. Pharmacol. 31:519 (1987); quinapril (Warner-Lambert) disclosed in U.S. Pat. No. 4,344,949 and CI925 (Warner-Lambert) ([3S-[2[R(*)R(*)]]3R(*)]-2-[2-[[1-(ethoxy-carbonyl)-3-phenylpropyl]amino]-1-oxopropyl]-1,2,3,4-tetrahydro-6,7-dimethoxy-3-isoquinolinecarboxylic acid HCl) disclosed in Pharmacologist 26:243, 266 (1984), WY-44221 (Wyeth) disclosed in J. Med. Chem. 26:394 (1983).

Preferred ACE inhibitors are captopril, fosinopril, enalapril, lisinopril, quinapril, benazepril, fentiapril, ramipril and moexipril.

NEP/ACE inhibitors may also be employed herein in that they possess neutral endopeptidase (NEP) inhibitory activity and angiotensin converting enzyme (ACE) inhibitory activity. Examples of NEP/ACE inhibitors suitable for use herein include those disclosed in U.S. Pat. Nos. 5,362,727, 5,366,973, 5,225,401,4,722,810, 5,223,516,4,749,688, U.S. Pat. No. 5,552,397, U.S. Pat. No. 5,504,080, U.S. Pat. No. 5,612,359,U.S. Pat. No. 5,525,723, European Patent Application 0599,444, 0481,522,0599,444, 0595,610, European Patent Application 0534363A2, 534,396 and 534,492, and European Patent Application 0629627 A2.

Preferred are those NEP/ACE inhibitors and dosages thereof which are designated as preferred in the above patents/applications which U.S. patents are incorporated herein by reference; most preferred are omapatrilat, BMS 189,921 ([S—(R*,R*)]-hexahydro-6-[(2-mercapto-1-oxo-3-phenylpropyl)amino]-2,2-dimethyl-7-oxo-1H-azepine-1-acetic acid (gemopatrilat)) and CGS 30440.

The angiotensin U receptor antagonist (also referred to herein as angiotensin II antagonist or AII antagonist) suitable for use herein includes, but is not limited to, irbesartan, losartan, valsartan, candesartan, telmisartan, tasosartan or eprosartan, with irbesartan, losartan or valsartan being preferred.

A preferred oral dosage form, such as tablets or capsules, will contain the ACE inhibitor or AII antagonist in an amount within the range from abut 0.1 to about 500 mg, preferably from about 5 to about 200 mg and more preferably from about 10 to about 150 mg.

For parenteral administration, the ACE inhibitor, angiotensin II antagonist or NEP/ACE inhibitor will be employed in an amount within the range from about 0.005 mg/kg to about 10 mg/kg and preferably from about 0.01 mg/kg to about 1 mg/kg.

Where a drug is to be administered intravenously, it will be formulated in conventional vehicles, such as distilled water, saline, Ringer's solution or other conventional carriers.

It will be appreciated that preferred dosages of ACE inhibitor and AII antagonist as well as other antihypertensives disclosed herein will be as set out in the latest edition of the Physician's Desk Reference (PDR).

Other examples of preferred antihypertensive agents suitable for use herein include omapatrilat (Vanlev®) amlodipine besylate (Norvasc®), prazosin HCl (Minipress®), verapamil, nifedipine, nadolol, diltiazem, felodipine, nisoldipine, isradipine, nicardipine, atenolol, carvedilol, sotalol, terazosin, doxazosin, propranolol, and clonidine HCl (Catapres®).

Diuretics which may be employed in combination with compounds of formula I include hydrochlorothiazide, torasemide, furosemide, spironolactono, and indapamide.

Antiplatelet agents which may be employed in combination with compounds of formula I of the invention include aspirin, clopidogrel, ticlopidine, dipyridamole, abciximab, tirofiban, eptifibatide, anagrelide, and ifetroban, with clopidogrel and aspirin being preferred.

The antiplatelet drugs may be employed in amounts as indicated in the PDR. Ifetroban may be employed in amounts as set out in U.S. Pat. No. 5,100,889.

Antiosteoporosis agents suitable for use herein in combination with the compounds of formula I of the invention include parathyroid hormone or bisphosphonates, such as MK-217 (alendronate) (Fosamax®).

Dosages employed for the above drugs will be as set out in the Physician's Desk Reference.

Pharmaceutical Formulations

The pharmaceutical composition of the invention includes a pharmaceutically acceptable carrier, adjuvant or vehicle that may be administered to a subject, together with a compound of the present invention, and which does not destroy the pharmacological activity thereof. Pharmaceutically acceptable carriers, adjuvants and vehicles that may be used in the pharmaceutical compositions of the present invention include, but are not limited to, the following: ion exchangers, alumina, aluminum stearate, lecithin, self-emulsifying drug delivery systems ("SEDDS") such as d(-tocopherol polyethyleneglycol 1000 succinate), surfactants used in pharmaceutical dosage forms such as Tweens or other similar polymeric delivery matrices, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β- and γ-cyclodextrin, or chemically modified derivatives such as hydroxyalkylcyclodextrins, including 2- and 3-hydroxypropyl-β-cyclodextrins, or other solubilized derivatives may also be used to enhance delivery of the modulators of the present invention.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the invention may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The compounds of the invention may, for example, be administered in a form suitable for immediate release or extended release. Immediate release or extended release may be achieved by the use of suitable pharmaceutical compositions including the compounds of the invention, or, particularly in the case of extended release, by the use of devices such as subcutaneous implants or osmotic pumps. The compounds of the invention may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compunds may also be delivered through the oral cavity by sublingual and/or buccal administration. Molded tablets, compressed tablets or freeze-dried tablets are exemplary forms which may be used. Exemplary compositions include those formulating the compound(s) of the invention with fast dissolving diluents such as mannitol, lactose, sucrose and/or cyclodextrins. Also included in such formulations may be high molecular weight excipients such as celluloses (Avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.1 to 500 mg/kg of body weight of active compound per day, or between 5 and 2000 mg per day which may be administered in a single dose or in the form of individual divided doses, such as from 1 to 5 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like.

A typical capsule for oral administration contains compounds of structure I (250 mg), lactose (75 mg) and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

The compounds of formula I of the invention are glucocorticoid receptor modulators as shown by their ability to bind glucocorticoid receptors in GR binding assays.

Compounds of formula I of the invention may also inhibit AP-1 activity as indicated in cellular transrepressional assays, and cause none to minimal transactivation as indicated in cellular transcriptional assays.

The GR binding assay, cellular transrepressional assay and cellular transcriptional assay employed are described in copending provisional application No. 60/396,907, filed Jul. 18, 2002, which is incorporated herein by reference.

The following abbreviations are employed in the Examples:
Ph=phenyl
Bn=benzyl
t-Bu=tertiary butyl
Me=methyl
Et=ethyl
TMS=trimethylsilyl
TMSN$_3$=trimethylsilyl azide
TBS=tert-butyldimethylsilyl
FMOC=fluorenylmethoxycarbonyl
Boc=tert-butoxycarbonyl
Cbz=carbobenzyloxy or carbobenzoxy or benzyloxycarbonyl
THF=tetrahydrofuran
Et$_2$O=diethyl ether
hex=hexanes
EtOAc=ethyl acetate
DMF=dimethyl formamide
MeOH=methanol
EtOH=ethanol
i-PrOH=isopropanol
DMSO=dimethyl sulfoxide
DME=1,2 dimethoxyethane
DCE=1,2 dichloroethane
HMPA=hexamethyl phosphoric triamide
HOAc or AcOH=acetic acid
TFA=trifluoroacetic acid
TFAA=trifluoroacetic anhydride
i-Pr$_2$NEt=diisopropylethylamine
Et$_3$N=triethylamine
NMM=N-methyl morpholine
DMAP=4-dimethylaminopyridine
NaBH$_4$=sodium borohydride
NaBH(OAc)$_3$=sodium triacetoxyborohydride DIBALH=diisobutyl aluminum hydride
LAH or LiAlH$_4$=lithium aluminum hydride
n-BuLi=n-butyllithium
LDA=lithium diisopropylamide
Pd/C=palladium on carbon
PtO$_2$=platinum oxide
KOH=potassium hydroxide
NaOH=sodium hydroxide
LiOH=lithium hydroxide
K$_2$CO$_3$=potassium carbonate
NaHCO$_3$=sodium bicarbonate
DBU=1,8-diazabicyclo[5.4.0]undec-7-ene
EDC (or EDC.HCl) or EDCI (or EDCI.HCl) or EDAC=3-ethyl-3'-(dimethylamino)propyl-carbodiimide hydrochloride (or 1-(3-dimethylaminopropyl)-3-ethylcarbodiimide hydrochloride)
HOBT or HOBT.H$_2$O=1-hydroxybenzotriazole hydrate
HOAT=1-Hydroxy-7-azabenzotriazole
BOP reagent=benzotriazol-1-yloxy-tris (dimethylamino) phosphonium hexafluorophosphate
NaN(TMS)$_2$=sodium hexamethyldisilazide or sodium bis(trimethylsilyl)amide
Ph$_3$P=triphenylphosphine
Pd(OAc)$_2$=Palladium acetate
(Ph$_3$P)$_4$Pd$^o$=tetrakis triphenylphosphine palladium
DEAD=diethyl azodicarboxylate
DIAD=diisopropyl azodicarboxylate
Cbz-Cl=benzyl chloroformate
CAN=ceric ammonium nitrate
SAX=Strong Anion Exchanger
SCX=Strong Cation Exchanger
Ar=argon
N$_2$=nitrogen
min=minute(s)
h or hr=hour(s)
L=liter
mL=milliliter
µL=microliter
g=gram(s)
mg=milligram(s)
mol=moles
mmol=millimole(s)
meq=milliequivalent
RT=room temperature
sat or sat'd=saturated
aq.=aqueous
TLC=thin layer chromatography
HPLC=high performance liquid chromatography
LC/MS=high performance liquid chromatography/mass spectrometry
MS or Mass Spec=mass spectrometry
NMR=nuclear magnetic resonance
NMR spectral data: s=singlet; d=doublet; m=multiplet; br=broad; t=triplet
mp=melting point Preparations The preparations set out below are for the synthesis of reagents that were not obtained from commercial sources and were employed for the preparation of compounds of formula I of the invention. All chemical structures in the tables and schemes are racemic unless specified otherwise.

Preparation 1
2-Amino-4-[1-(4-fluoro)naphthyl]thiazole 1a

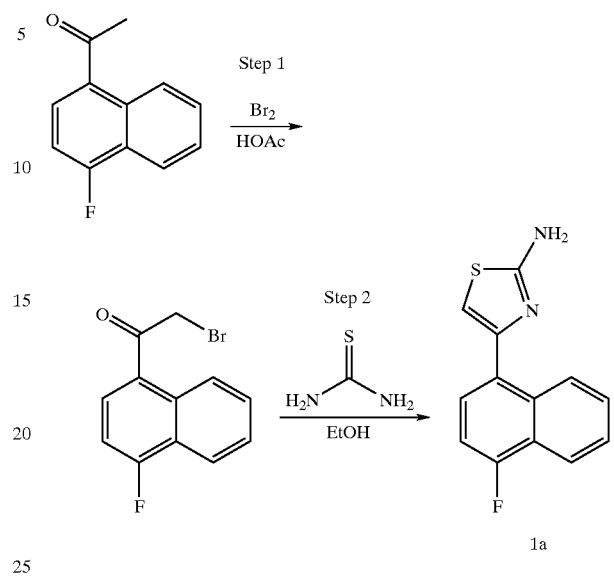

Step 1

To a solution of 4'-fluoro-1'-acetonaphthone (28.69 mmol, 5.4 g) in 1,4-dioxane (18.0 mL) at 0° C. was added bromine (35.13 mmol, 5.61 g). After 3 hours at room temperature the reaction mixture was concentrated in vacuo to give 7.66 g (Y: 100%) of the product of step 1.

Step 2

To a solution of the product of step 1 (28.69 mmol, 7.66 g) in ethyl alcohol (20 mL) at room temperature was added thiourea (36.13 mmol, 2.75 g). After 1 hour at room temperature a precipitate formed. To the reaction mixture was added water (100 mL) and the solid was collected by vacuum filtration. The solid was then washed with water (3×100 mL) and dichloromethane (3×100 mL). The solid was then dried in vacuo to give 5.5 g (Y: 75%) of the title compound 1a. MS (E+) m/z: 245 (MH$^+$).

In a similar manner the following compounds were prepared from the corresponding ketone.

| Preparation | Structure |
|---|---|
| 1b | 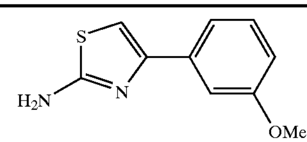 |
| 1c | 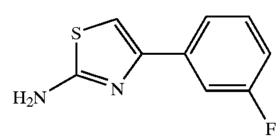 |
| 1d | 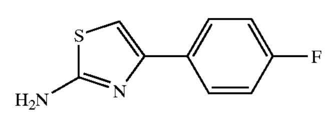 |

| Preparation | Structure |
|---|---|
| 1e | 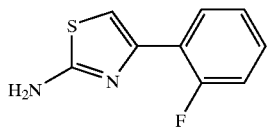 |
| 1f | 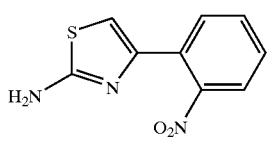 |
| 1g | 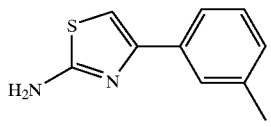 |
| 1h | 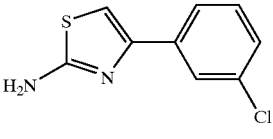 |
| 1i | 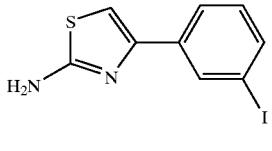 |
| 1j | 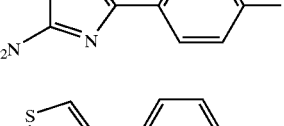 |
| 1k | 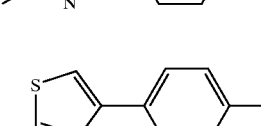 |
| 1l | 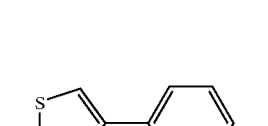 |
| 1m | 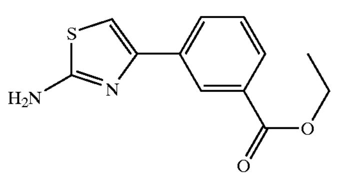 |
| 1n | 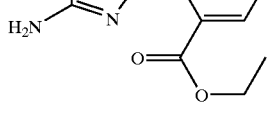 |
| 1o | 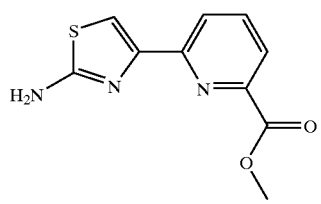 |
| 1p | 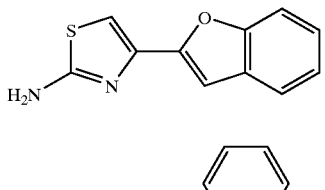 |
| 1q | 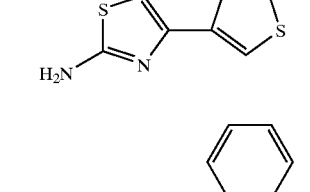 |
| 1r | 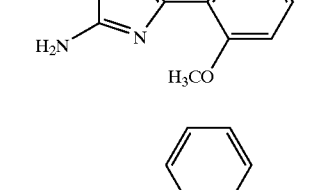 |
| 1s | 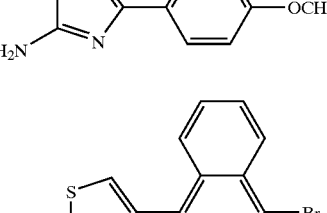 |
| 1t | 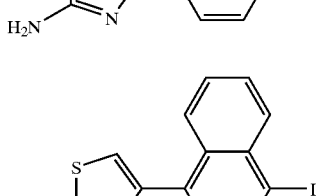 |
| 1u | 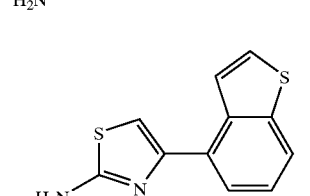 |
| 1v | 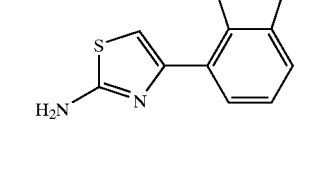 |

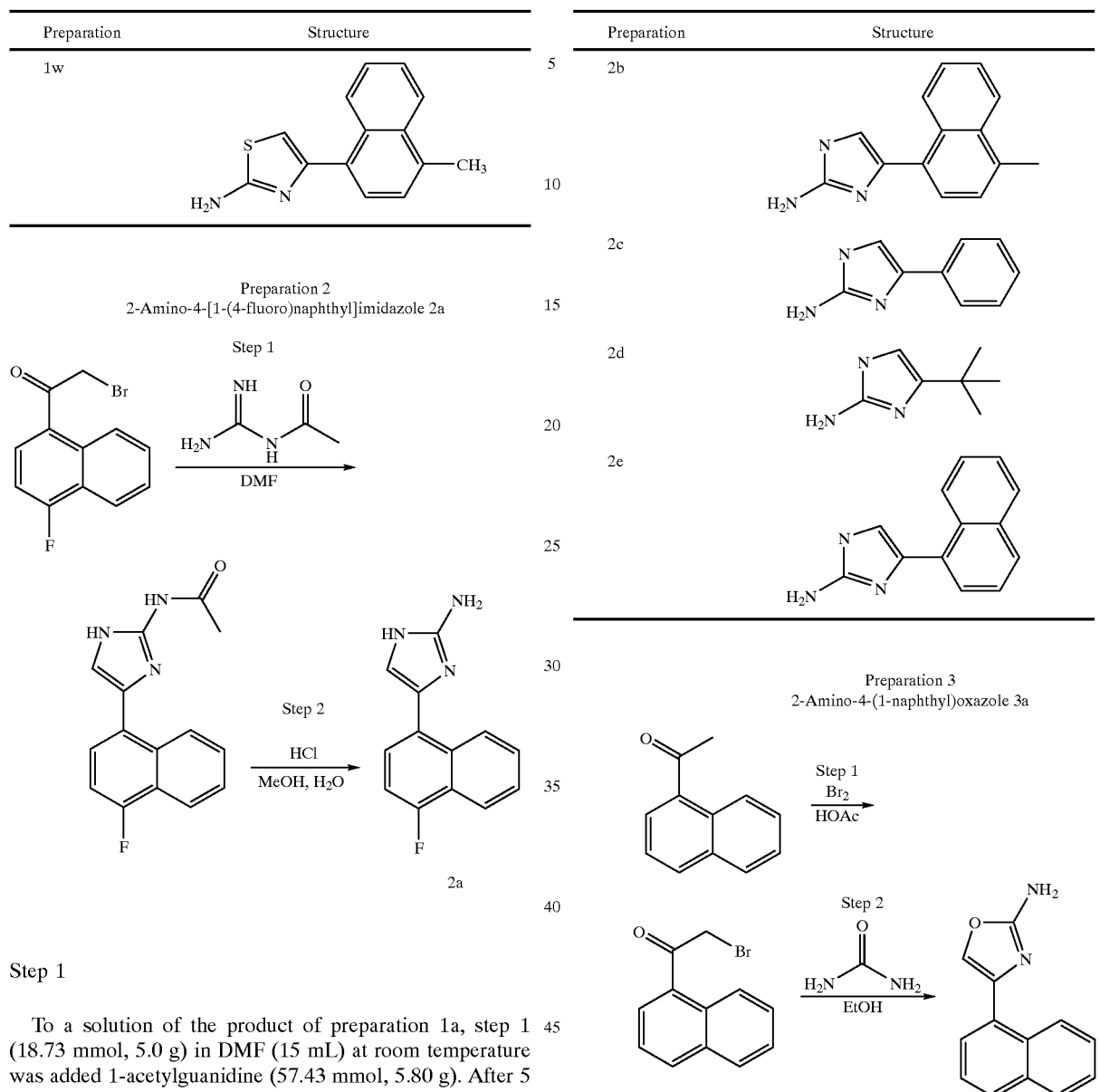

Step 1

To a solution of the product of preparation 1a, step 1 (18.73 mmol, 5.0 g) in DMF (15 mL) at room temperature was added 1-acetylguanidine (57.43 mmol, 5.80 g). After 5 hours at room temperature, the reaction mixture was diluted with water (100 mL) and extracted with ethyl acetate (3×100 mL). The organic phases were concentrated in vacuo and the residue chromatographed on silica gel (eluted with 5% methanol in dichloromethane) to give 2.0 g (Y: 39%) of the product of step 1. MS (E+) m/z: 270 (MH+).

Step 2

To a solution of the product of step 1 (7.43 mmol, 2.0 g) in methanol (17 mL) was added water (8.5 mL) and 12 N HCl (12.0 mL). After 1 hour at reflux the reaction mixture was concentrated in vacuo to approximately 15 mL. The resulting solution was then purified and neutralized by cation exchange SPE to give 1.66 g (Y: 99%) of the title compound 2a. MS (E+) m/z: 228 (MH+).

In a similar manner the following compounds were prepared from the corresponding ketones.

Step 1

To a solution of 1-acetonaphthone (29.38 mmol, 5.0 g) in glacial acetic acid (10.0 mL) at RT was added bromine (30.06 mmol, 4.80 g) in glacial acetic acid (5.0 mL). After 5 minutes the reaction mixture was poured onto crushed ice and extracted with dichloromethane to give 7.31 g (Y: 100%) of the product of step 1. MS (E+) m/z: 250 (MH+).

Step 2

To a solution of the product of step 1 (5.50 mmol, 1.37 g) in ethyl alcohol (10 mL) was added urea (27.50 mmol, 1.65 g). After 2 hours at reflux the reaction mixture was concentrated in vacuo and the residue chromatographed on silica gel (eluted with 30% ethyl acetate in hexane) to give 100 mg (Y: 9%) of the title compound 3a. MS (E+) m/z: 211 (MH+).

Preparation 4
5-(1-Naphthyl)-3-aminoisoxazole 4a

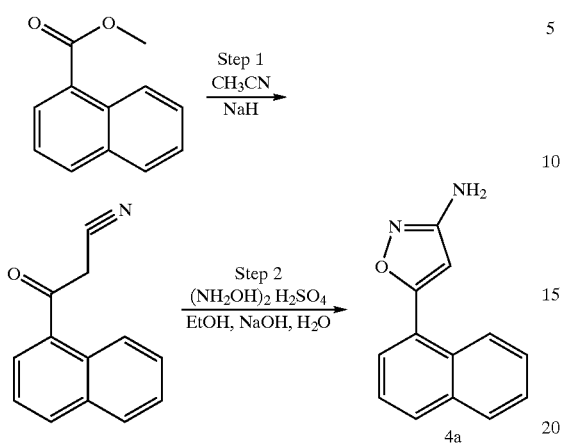

Step 1

To a solution of acetonitrile (12.18 mmol, 0.50 g) in THF (10.0 mL) was added 60% sodium hydride (24.36 mmol, 0.975 g), followed by 1-naphthoic acid methyl ester (12.18 mmol, 2.27 g). After 2 hours at 70° C. the reaction mixture was quenched with an excess of 1N HCl and extracted with dichloromethane (3×30 mL). The organic phases were concentrated in vacuo and the residue was chromatographed on silica gel (eluted with 33% ethyl acetate in hexane) to give 1.80 g (Y: 76%) of the product of step 1. MS (E+) m/z: 196 (MH$^+$).

Step 2

Hydroxylamine sulfate (1.61 mmol, 264 mg) was added to a stirred solution of the product of step 1 (2.94 mmol, 573 mg) and NaOH (3.53 mmol, 141 mg) in 50% aq. EtOH (6.0 mL). The mixture was heated at 80° C. for 5 hours and then stirred at RT for 14 hours. The reaction mixture was quenched with an excess of 1N HCl, washed with dichloromethane (3×50 mL), neutralized with saturated sodium bicarbonate solution and extracted with dichloromethane (3×50 mL). The organic extracts were combined, dried over Na$_2$SO$_4$ and concentrated under vacuo to give 237 mg (Y: 38%) of the title compound 4a. MS (E+) m/z: 211 (MH$^+$).

Preparation 5
3-(1-Naphthyl)-5-aminopyrazole 5a

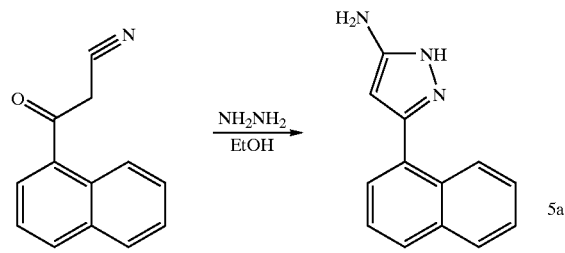

To a solution of the product of preparation 4, step 1 (2.70 mmol, 527 mg) in EtOH (5.0 mL) was added hydrazine (2.70 mmol, 85 mg). The resulting mixture was refluxed for 2 h, cooled, diluted with 1N HCl, washed with dichloromethane (3×50 mL), neutralized with saturated sodium bicarbonate solution and extracted with dichloromethane (3×50 mL). The organic extracts were combined, dried over Na$_2$SO$_4$ and concentrated under vacuum to give 280 mg (Y: 51%) of the title compound 5a. MS (E+) m/z: 210 (MH$^+$).

Preparation 6
4-[1-(6-Methoxy)naphthyl]-2-aminothiazole 6a

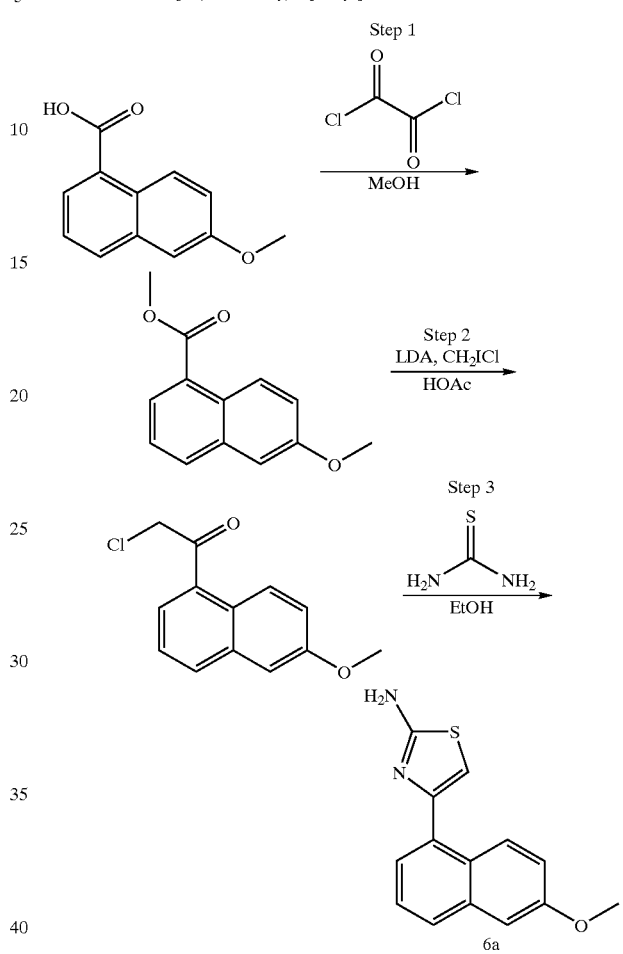

Step 1

To a solution of 6-methoxy-1-naphthoic acid (0.5 g, 2.47 mmol, 1.0 equi.) in dichloromethane (10 mL) at room temperature was added a solution of oxalyl chloride (2M in dichloromethane, 2.5 mL, 5.0 mmol, 2 equi.). The solution was stirred at room temperature for 2 hours, and the excess oxalyl chloride removed in vacuo. The residue was dissolved in methanol and stirred at room temperature for 18 hours. The solvent was removed in vacuo, yielding 0.45 g (84%) of the product of step 1: LC/MS (m/z 217, (M–H)$^+$); $^1$H NMR (CDCl$_3$) δ 8.82 (d, 1H), 8.03 (dd, 1H), 7.90 (d, 1H), 7.44 (t, 1H), 7.26 (dd, 1H), 7.16 (s, 1H), 4.02 (s, 3H), 3.95 (s, 3H).

Step 2

Reference: P. Chen, P. T. Cheng, S. H. Spergel, R. Zahler, X. Wang, J. Thottathil, J. C. Barrish, R. P. Polniaszek, Tetrahedron Letters, 38, 3175 (1997).

To a solution of the product of step 1 (0.238 g, 1.1 mmol, 1.0 equi.) and chloroiodomethane (0.32 mL, 4.4 mmol, 4 equi.) in THF (5 mL) was added a solution of LDA (2M, 2.2 mL, 4.0 equi.) in THF (10 mL) dropwise in 30 minutes, while keeping the solution temperature at –78° C. The reaction solution was stirred at –78° C. for 10 minutes. A solution of acetic acid (1.5 mL) in THF (10 mL) was added in dropwise in 10 minutes. After stirring for an additional 10 minutes at −78° C., the solution was quenched with ethyl acetate and saturated sodium chloride solution. The organic phase was washed with saturated sodium bisulfite, saturated sodium chloride, dried with sodium sulfate and concentrated in vacuo. The residue was purified by flash chromatography (10% ethyl acetate in hexane) to yield 0.23 g (90%) of the product of step 2: LC/MS (m/z 235, (M+H)+); 1H NMR (CDCl3) δ 8.82 (d, 1H), 8.03 (dd, 1H), 7.90 (d, 1H), 7.44 (t, 1H), 7.26 (dd, 1H), 7.16 (s, 1H), 4.80 (s, 2H), 3.95 (s, 3H).

Step 3

To a solution of the product of step 2 (0.23 g, 1.0 mmol, 1.0 equi.) in ethanol (5 mL) at room temperature was added thiourea (90 mg, 1.2 mmol, 1.2 equi.). The reaction solution was stirred at room temperature for 2 hours, after which a yellow precipitate was formed. The reaction was quenched by addition of water and ethyl acetate. The aqueous phase was extracted with ethyl acetate (3×). The combined organic phases were dried with sodium sulfate and concentrated in vacuo to yield 200 mg (78%) of the title compound 6a: LC/MS (m/z 235, (M+H)+); 1H NMR (CDCl3) δ 8.1 (d, 1H), 7.9 (m, 1H), 7.43 (m, 2H), 7.25 (m, 1H), 7.10 (dd, 1H), 6.65 (s, 1H), 3.95 (s, 3H).

In a similar manner the following compounds were prepared.

| Preparation | Structure |
|---|---|
| 6b | 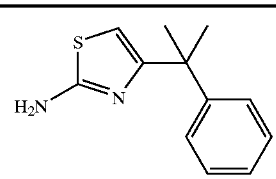 |
| 6c | 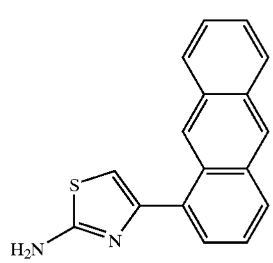 |

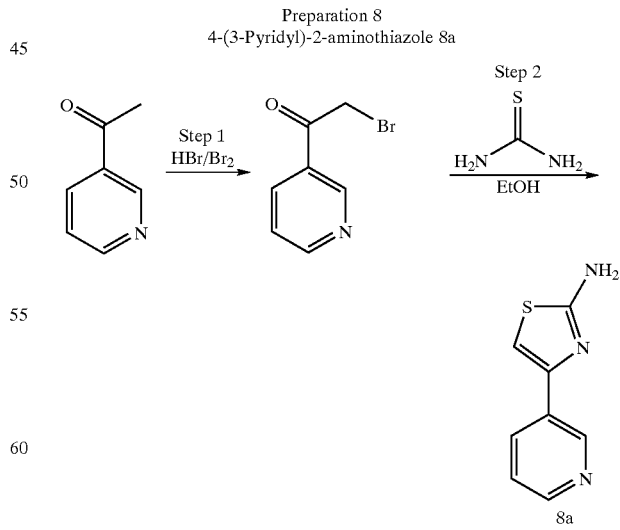

Preparation 7
4-[1-(6-Methoxy)naphthyl]-2-aminoimidazole 7a

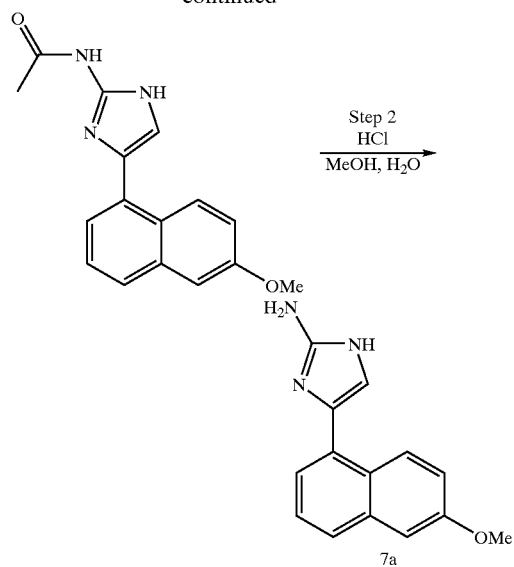

Step 1
To a solution of the product of preparation 6, step 2 (0.5 g, 2.14 mmol, 1.0 equi.), in ethanol (5 mL) at room temperature was added 1-acetylguanidine (650 mg, 6.42 mmol, 3.0 equi.). The reaction solution was stirred at room temperature for 24 hours. The reaction was quenched by addition of water and ethyl acetate. The aqueous phase was extracted with ethyl acetate (3×). The combined organic phases were dried with sodium sulfate and concentrated in vacuo to yield 0.2 g (35%) of the product of step 1: LC/MS (m/z 282, (M+H)+).

Step 2
To a solution of the product of step 1 (0.2 g, 0.7 mmol, 1.0 equi.) in methanol (5 mL) was added water (1.0 mL) and hydrochloric acid (12N, 1.0 mL). The reaction solution was heated to reflux for 1 hour, after which the solvent was removed in vacuo. The crude mixture was purified by cation exchange SPE to give 0.12 g (70%) of the title compound 7a: LC/MS (m/z 240, (M+H)+).

Preparation 8
4-(3-Pyridyl)-2-aminothiazole 8a

Step 1
To a solution of 3-acetylpyridine (20.0 mmol, 2.42 g) in 48% HBr (10.0 mL) was added bromine (20.0 mmol, 3.2 g)

in 48% HBr (4.0 mL). The reaction mixture was heated to 65° C. for one hour and stirred at RT for an additional hour. The reaction mixture was quenched with ice and filtered. The solid was washed with acetone (2×10 mL) and diethyl ether (2×10 mL). The solid was then dried in vacuo to give 3.70 g (Y: 83%) of the product of step 1.

Step 2

To a solution of the product of step 1 (6.10 mmol, 1.22 g) in ethyl alcohol (10 mL) at room temperature was added thiourea (7.32 mmol, 560 mg). After 1 hour at room temperature the reaction mixture was quenched with water (30 mL) and washed with dichloromethane (3×100 mL). The aqueous layer was then purified by cation exchange chromatography to give 600 mg (Y: 56%) of the title compound 8a. MS (E+) m/z: 178 (MH+).

In a similar manner the following compounds were prepared.

| Preparation | Structure |
|---|---|
| 8b | 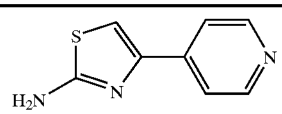 |
| 8c | 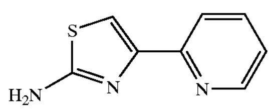 |
| 8d | 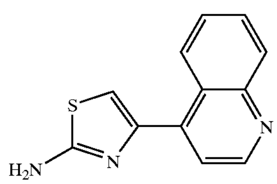 |

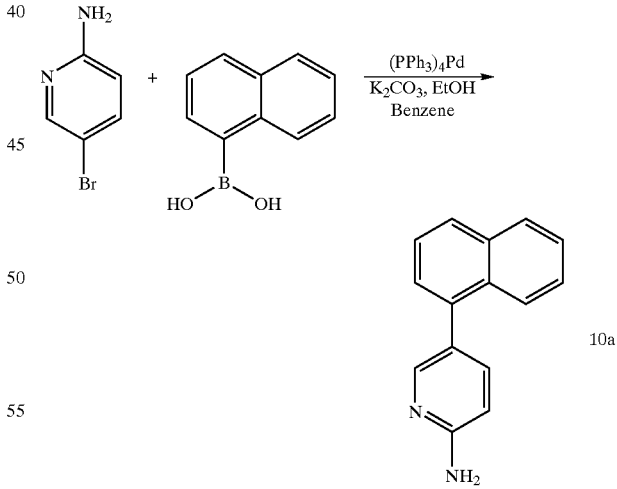

Preparation 9
4-(1-Isoquinolinyl)-2-aminothiazole 9a

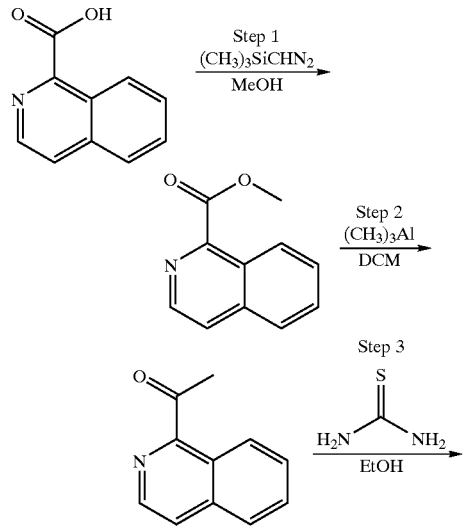

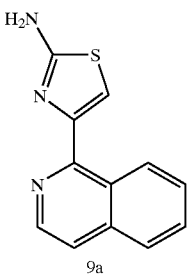

9a

Step 1

To a solution of 1-isoquinolinecarboxylic acid (11.55 mmol, 2.0 g) in THF (20.0 mL) and methanol (10.0 mL) is added trimethylsilyldiazomethane (69.3 mmol, 32.0 mL of a 2 M solution in hexanes). After 2 h at RT the reaction mixture was concentrated in vacuo to give 1.17 g (Y: 99%) of the product of step 1. MS (E+) m/z: 188 (MH+).

Step 2

To a solution of the product of step 1 (10.69 mmol, 2.0 g) in dichloromethane (100.0 mL) was added trimethylaluminum (32.88 mmol, 16.44 mL of a 2.0 M solution in toluene) at −78° C. After the addition was complete the reaction was allowed to warm to 0° C. The reaction mixture was then quenched with water (30 mL) and extracted with dichloromethane (3×30 mL). The organic phases were concentrated in vacuo and the residue chromatographed on silica gel (eluted with 10% ethyl acetate in hexanes) to give 930 mg (Y: 51%) of the product of step 2. MS (E+) m/z: 172 (MH+).

Step 3

The product of step 2 was converted to the title compound 9a as described in preparation 8, step 2. MS (E+) m/z: 228 (MH+).

Preparation 10
5-(1-naphthyl)-2-aminopyridine 10a

Potassium carbonate (5.19 mmol, 717 mg) in water (2.5 mL) and tetrakis(triphenylphosphine)palladium(0) (0.04 mol %, 80 mg) in ethyl alcohol (2.5 mL) were added to 2-amino-5-bromopyridine (1.73 mmol, 299 mg) and 1-naphthaleneboronic acid (2.60 mmol, 446 mg) in benzene (10.0 mL). After 2 hours at 90° C. the reaction mixture was quenched with water (30 mL) and extracted with dichloromethane (3×30 mL). The organic phases were concentrated in vacuo and the residue chromatographed on silica gel (eluted with 50% ethyl acetate in hexanes) to give 260 mg (Y: 68%) of the title compound 10a. MS (E+) m/z: 381 (MH+).

In a similar manner the following compounds were prepared.

| Preparation | Structure |
|---|---|
| 10b | 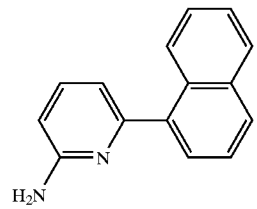 |
| 10c | 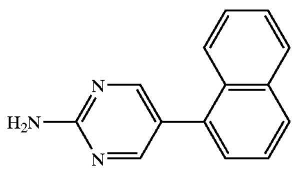 |

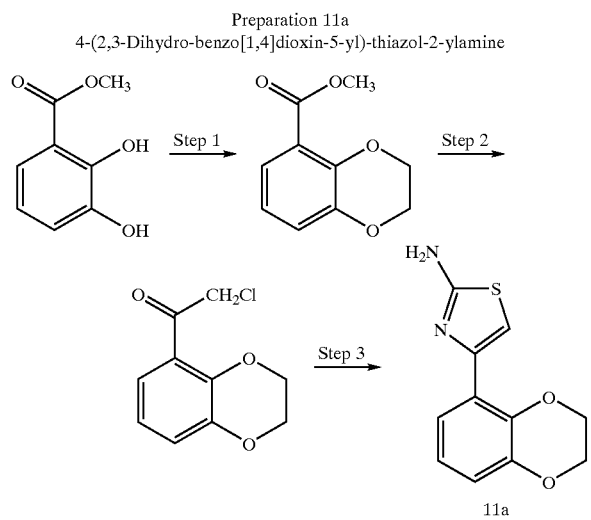

Preparation 11a
4-(2,3-Dihydro-benzo[1,4]dioxin-5-yl)-thiazol-2-ylamine

Step 1

A suspension of 2,3-dihydroxy-benzoic acid methyl ester (336 mg, 2 mmol) and cesium carbonate (1.56 g, 4.8 mmol) in DMF was stirred at room temperature for 0.5 h. 1,2-Dibromoethane (0.224 ml, 2.6 mmol) was added to the DMF solution.

The mixture was stirred at 80° C. for 4 h, and then diluted with ethyl acetate. The organic layer was washed with water and brine, dried over anhydrous MgSO$_4$, filtered and concentrated in vacuo to give the crude product. It was chromatographed on silica gel with EtOAc/hexane (20%–40%) as eluent to afford 2,3-dihydro-benzo[1,4]dioxine-5-carboxylic acid methyl ester as a white solid. (223 mg, 1.14 mmol, 57.4% yield).

Step 2

Reference: *Tetrahedron Lett,* 1997, 3173–78

To a mixture of 2,3-dihydro-benzo[1,4]dioxine-5-carboxylic acid methyl ester (100 mg, 0.515 mmol) and chloroiodomethane (0.075 ml, 1.03 mmol) in 1 ml of THF was added a solution of LDA in THF (2M, 0.57 ml, 1.13 mmol) dropwise at −78° C. over 15 min. The reaction mixture was stirred at −78° C. for 10 min. A solution of acetic acid (0.75 ml) in THF (5 ml) was added dropwise over 5 min at −78° C. The resulting solution was stirred at the same temperature for additional 10 min. and was then partitioned between ethyl acetate and water. The organic layer was washed with aqueous sodium bicarbonate, brine, dried over MgSO4 and concentrated in vacuo to give the crude 2-chloro-1-(2,3-dihydro-benzo[1,4]dioxin-5-yl)-ethanone as a light brown liquid.

Step 3

The crude product of step 2 was dissolved in EtOH (1.5 ml). Thiourea (76 mg, 1 mmol) was added followed by addition of TEA (0.14 ml, 1 mmol). The solution was heated at 80° C. for 6 h. After removal of ethanol, the reaction mixture was taken into ethyl acetate and aqueous sodium bicarbonate. The organic layer was washed with 0.5 N HCl. After separation, the aqueous layer was adjusted to pH 9 with sodium carbonate, and extracted with ethyl acetate. The ethyl acetate solution was washed with brine, dried over MgSO4 and concentrated to give 4-(2,3-dihydro-benzo[1,4]dioxin-5-yl)-thiazol-2-ylamine 11 a as a brown solid, 37 mg (0.16 mmol, 31% yield). $^1$H NMR (CDCl$_3$) δ 7.46 (dd, 1H), 7.04 (s, 1H), 6.75–6.83 (m, 2H), 5.33 (br s, 2H), 4.23–4.34 (m, 4H); LC/MS m/z 235 (M+H)+.

| Compound | Structure |
|---|---|
| 11b | 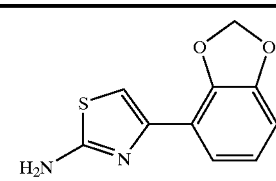 |

Preparation 12a

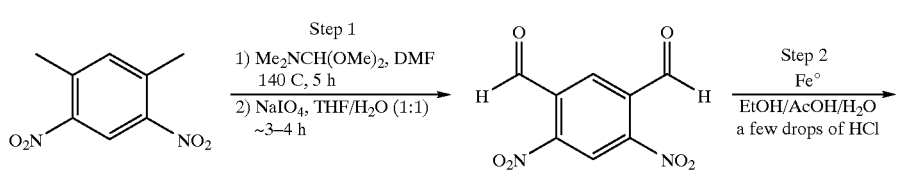

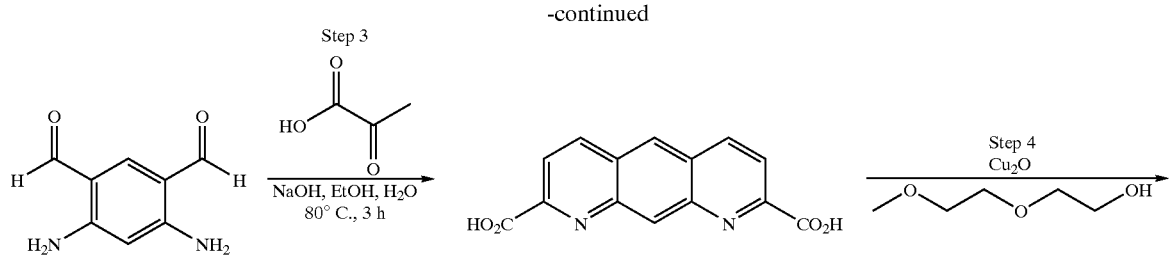

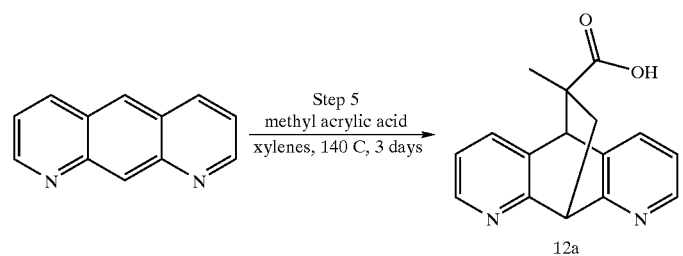

Step 1

To 1,3-dimethyl-4,6-dinitrobenzene (5.0 g, 25.489 mmol) under nitrogen in 50.0 mL DMF was added 10.16 mL N,N-dimethylformamide dimethyl acetal (76.468 mmol, 9.112 g, 3.0 eq). The mixture was stirred under nitrogen at 140° C. for 5 h, allowed to cool to room temperature and the solvent was removed under vacuum to afford a dark, black solid. To this solid was added 330 mL of 50% aqueous THF, followed by sodium periodate (32.7 g, 152.9 mmol, 6 eq). The solution turned red and produced a slight exotherm. The mixture was allowed to stir at room temperature for 5 h. This mixture was then filtered through a scintered glass funnel to remove excess solid material and rinsed with ethyl acetate until colorless. (Total volume of eluent was 750 mL after rinsing). The filtrate was washed with 100 mL saturated NaHCO$_{3(aq)}$. The aqueous was extracted again with 200 mL ethyl acetate. The organic layers were combined and dried over sodium sulfate. The solution was concentrated under vacuum. The remaining crude oil was chromatographed using silica gel eluted with 30% ethyl acetate in hexanes to yield 2.77 g of the product of step 1 as a yellow solid (48%).

Step 2

The product of step 1 (1.93 g, 8.62 mmol) and powdered iron (3.85 g, 68.93 mmol, 8 eq) were placed into a flask containing 100 mL of a 2:2:1 mixture of ethanol/acetic acid/water, respectively. The flask was placed into a 0° C. ice bath and allowed to equilibrate for 20 minutes. 8 drops of concentrated HCl were added. The reaction began to change color (yellow to green to red/brown). After 1 hour, the cooling bath was removed and allowed to warm to room temperature. After stirring for an additional 1 hour at room temperature, the mixture was filtered through a thin pad of celite. The filtrate was concentrated under vacuum to afford a yellow/green solid. This crude material was chromatographed using silica gel eluted with 30% hexanes in ethyl acetate. Removal of the solvent under vacuum yielded 1.165 g of the product of step 2 as a yellow/orange solid (82%).

Step 3

To the product of step 2 (901 mg, 5.49 mmol) under nitrogen in 30.0 mL ethanol was added 0.92 mL pyruvic acid (1.160 g, 13.173 mmol) followed by 13.0 mL of 2N aqueous sodium hydroxide. The mixture was stirred at 80° C. for 5 hours. 0.6 N Aqueous ammonia (~100 mL) was added and the mixture was gently heated to 74° C. A 0.6N HCl/0.3N AcOH solution was added until pH was ~4 to precipitate the product. The mixture was filtered to collect solid which was dried under vacuum to obtain 1.303 g of the product of step 3 as a yellow solid (88%).

Step 4

The product of step 3 (99 mg, 0.369 mmol) and ~3 mg Cu$_2$O (~0.018 mmol, 0.05 eq) were placed under nitrogen in 3.0 mL di(ethylene glycol) methyl ether. The mixture was stirred at 165° C. for 6 h and ~30 mL concentrated aqueous ammonia was added. The mixture was extracted with 2×100 mL methylene chloride and dried over sodium sulfate, concentrated under vacuum and chromatographed using silica gel eluted with 1% triethylamine, 7% methanol in chloroform. The eluent was removed under vacuum to obtain 44 mg of the product of step 4 as a brown crystalline solid (67%) M+H=181.28.

Step 5

The product of step 4 (21 mg, 0.117 mmol), 49 μL methyl acrylic acid (50 mg, 0.583 mmol, 5 eq), and ~3 mg hydroquinone were placed in a tube under nitrogen in 1.0 mL xylenes. The tube was sealed with a teflon lined cap and heated at 140° C. for 3 days. LC/MS shows reaction is complete. The solvent was removed under vacuum and the crude material was chromatographed using silica gel eluted with 1% triethylamine, 10% methanol in chloroform to afford 21 mg of the title compound 12a as a clear oil (68%). M+H=267.14

Preparation 13

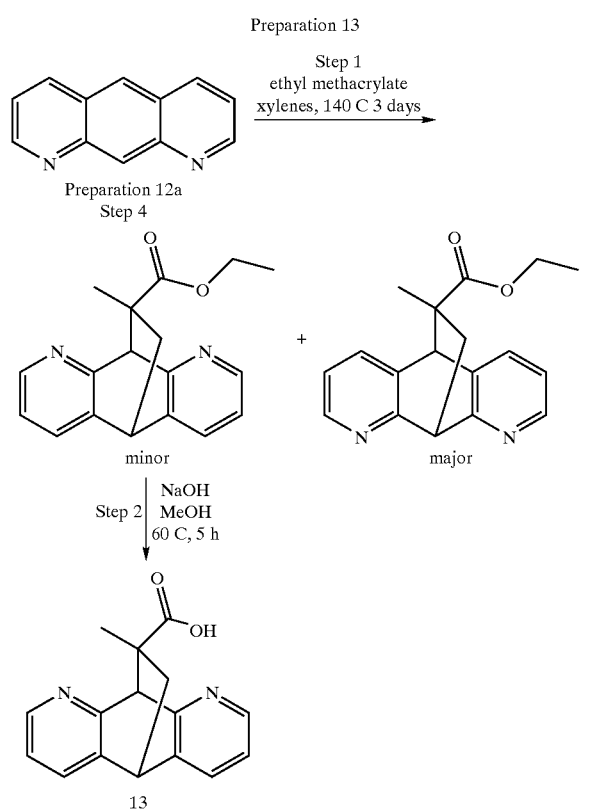

Step 1

The product of preparation 12a, step 4 (128 mg, 0.710 mmol), ethyl methacrylate (442 μL, 3.551 mmol, 5 eq), and ~20 mg hydroquinone into 5.0 mL xylenes were placed in a tube under nitrogen. The tube was sealed with a teflon lined cap and stirred at 140° C. for 3 days. Solvent was removed under vacuum and the crude material was directly purified on prep HPLC. The retention times on the HPLC (both analytical and prep) for the two isomeric products are very similar. 24 mgs of the pure minor isomer and 28 mg of a mixture of both the major and minor isomers was isolated.

Step 2

The minor product of step 1 (24 mg, 0.082 mmol) was placed under nitrogen in 1.5 mL methanol. 0.3 mL of 1N NaOH were added and the mixture stirred at 60° C. for 2 hours. An additional 0.1 μL of saturated aqueous NaOH were added and the mixture stirred an additional 5 h at 60° C. The mixture was allowed to cool, then 50 μL TFA were added. The mixture was purified directly on prep HPLC. Solvent was removed under vacuum to afford 21 mg of the title compound 13 as a clear oil (~95%). M+H=267

Preparation 14

Step 1

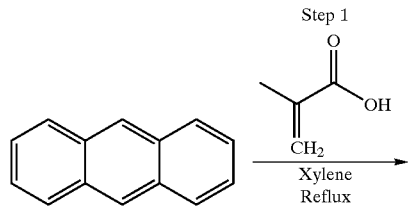

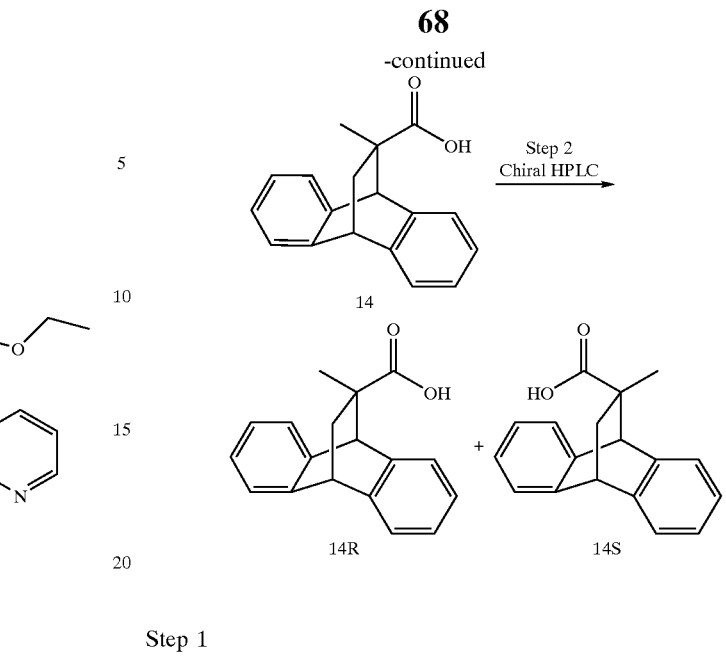

Step 1

Reference: B. Bacle and G. Levesque, *Polymer Communications*, 28, 36 (1987).

A 1 L flask was charged with anthracene (14 g, 0.078 mol, 1.0 equi.), hydroquinone (0.8 g, 0.008 mol, 0.1 equi.), methacrylic acid (14 mL, 0.156 mol, 2.0 equi.) and xylene (500 mL). The solution was heated to reflux for 1 day. The solution was cooled and concentrated in vacuo. The residue was dissolved in ethyl acetate and extracted with 1N NaOH (3×). The aqueous phase was acidified with 1N HCl, and the product was extracted with ethyl acetate (3×). The combined organic phases were concentrated in vacuo to give the crude product mixture. Recrystallization with hexane and ethyl acetate to yield 8 g (40%) of the product of step 1, 14:LC/MS (m/z 263 (M−H)$^+$); $^1$H NMR (CDCl$_3$) δ 7.08–7.25 (m, 8H), 4.37 (s, 1H), 4.25(t, 1H), 2.61 (dd, 1H), 1.39 (dd, 1H), 1.07 (s, 3H).

Step 2

The product of step 1, 14 was resolved into its corresponding enantiomers, 14(R) and 14(S) by chiral preparative HPLC with the following conditions, Column: Chiracel®-OJ, 5×50 cm, Mobile phase: trifluroacetic acid/acetonitrile: ¹⁄₁₀₀₀ (vol/vol), Temperature: ambient, Flowrate: 70 mL/min, Injection: 1.5 grams in 50 mL solvent, Detection: UV (250 nm). Retention times for R-enantiomer, 30 min, S-enantiomer, 52 min. Analytical HPLC conditions, Column: Chiracel®-OJ, 4.6×250 cm, Mobile phase: trifluroacetic acid/acetonitrile: ¹⁄₁₀₀₀ (vol/vol), Temperature: ambient, Flowrate: 1.5 mL/min, Detection: UV (250 nm). Retention times: R-enantiomer, 6.5 min, S-enantiomer, 15 min.

Preparation 15

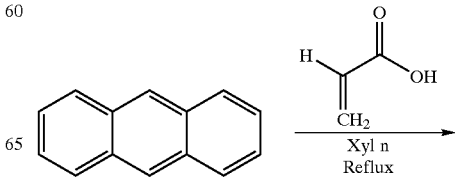

-continued

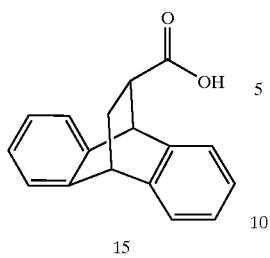

15

Acrylic acid and anthracene were reacted as described in preparation 14 to provide compound 15.

Preparation 16a

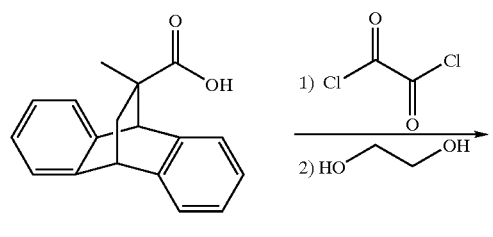

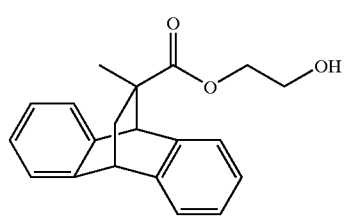

16a

To a solution of the product of step 1 preparation 14 (5.0 g, 18.9 mmol, 1.0 equi.) in dichloromethane (20 mL) was added an oxalyl chloride solution in dichloromethane (2M, 11.4 mL, 22.8 mmol, 1.2 equi.) dropwise. The solution was stirred at RT for 2 hours, after which the solvent was removed in vacuo. The residue was dissolved in acetonitrile (20 mL) and added dropwise to a solution of ethylene glycol (1.27 ml, 22.8 mmol, 1.2 equi.) in acetonitrile (20 mL). The reaction solution was stirred at RT for 4 hours and then the solution was concentrated in vacuo. Purification by flash chromatography (10% ethyl acetate in hexane) yielded 2.0 g (34%) of compound 16a: $^1$H NMR (CDCl$_3$) δ 7.52 (d, 1H), 7.09–7.27 (m, 8H), 4.40 (s, 1H), 4.31 (t, 1H), 4.11 (m, 1H), 4.0 (m, 1H), 3.63 (m, 2H), 2.72 (dd, 1H), 1.42 (dd, 1H), 1.16(s, 3H).

In a similar manner the following compounds were prepared from the corresponding acids and alcohols.

| Preparation Number | Chiral Compounds | Structure |
|---|---|---|
| 16b | | 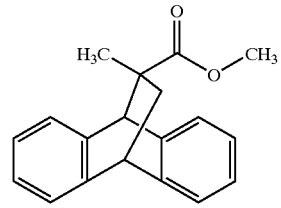 |
| 16c | | 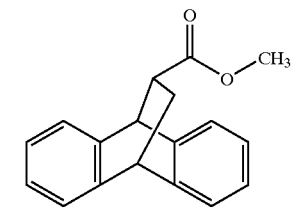 |
| 16d | | 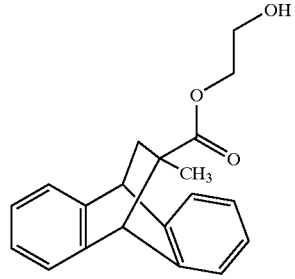 |
| 16e | Chiral (S) | 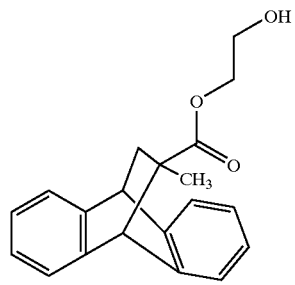 |
| 16f | Chiral (R) | 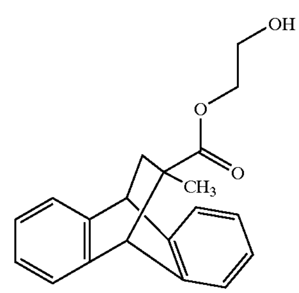 |
| 16g | Chiral (S) | 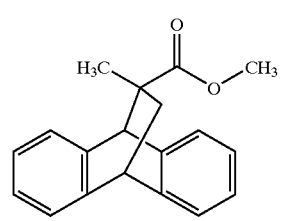 |

-continued

| Preparation Number | Chiral Compounds | Structure |
|---|---|---|
| 16h | Chiral (R) | 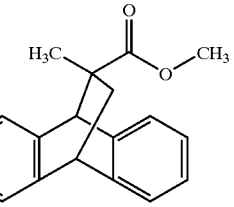 |

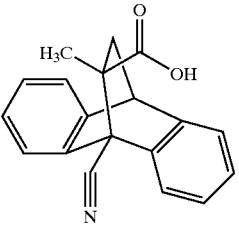

Ortho (17a)        Meta (17b)

Reference: P. V. Alston, R. M. Ottenbrite, J. Newby, *J. Org. Chem.*, 44, 4939 (1979).

9-Anthracenecarboxylic acid (4 g, 0.017 mol, 1.0 equi.) was added to a mixture of methacrylic acid (20 mL, 0.23 mol, 14.0 equi.), benzene (20 mL) and hydroquinone (0.2 g, 0.0017 mol, 0.1 equi.). The solution was heated to reflux for 7 days. The solution was cooled and the precipitate formed was filtered and washed with benzene. The precipitate was recrystallized with hexane and ethyl acetate to yield 0.4 g (7.2%) of the ortho product 17a: MS (m/z 321(M−H)$^+$); $^1$H NMR (CDCl$_3$) δ7.1–7.28 (m, 8H), 4.25 (t, 1H), 4.06 (s, 3H), 2.25 (dd, 1H), 1.69 (dd, 1H), 1.08 (s, 3H). The filtrate was extracted with 1N NaOH (3×). The aqueous phase was acidified with 1N HCl, and the product was extracted with ethyl acetate (3×). The organic phases were concentrated in vacuo. Recrystallization of the residue with hexane and ethyl acetate yielded 0.2 g (4%) of the meta product 17b MS (m/z 321 (M−H)$^+$); $^1$H NMR (CDCl$_3$) δ7.16–7.27 (m, 8H), 4.36 (s, 1H), 4.08 (s, 3H), 2.90 (d, 1H), 1.67 (d, 1H), 1.06 (s, 3H).

In a similar manner the following compounds were prepared from methacrylic acid and the appropriate anthracene.

| Preparation Number | Structure |
|---|---|
| 17C | 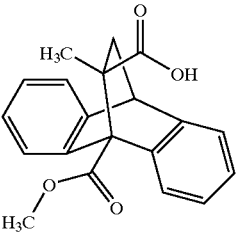 |
| 17D | 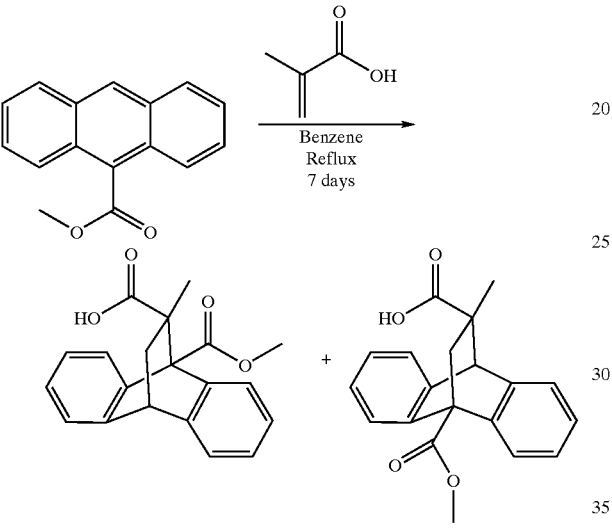 |
| 17E | 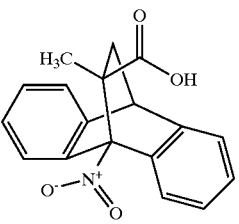 |
| 17F | 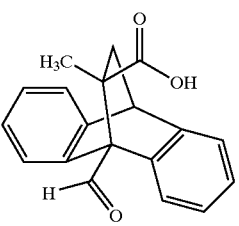 |
| 17G | 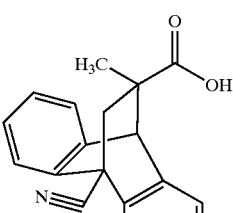 |

-continued

| Preparation Number | Structure |
|---|---|
| 17H | (structure: methyl carboxylic acid dibenzobicyclic with Cl) |
| 17I | (structure: methyl carboxylic acid dibenzobicyclic with Br) |
| 17J | (structure: methyl carboxylic acid dibenzobicyclic) |

EXAMPLES

The following Examples represent preferred embodiments of the invention.

Example 1

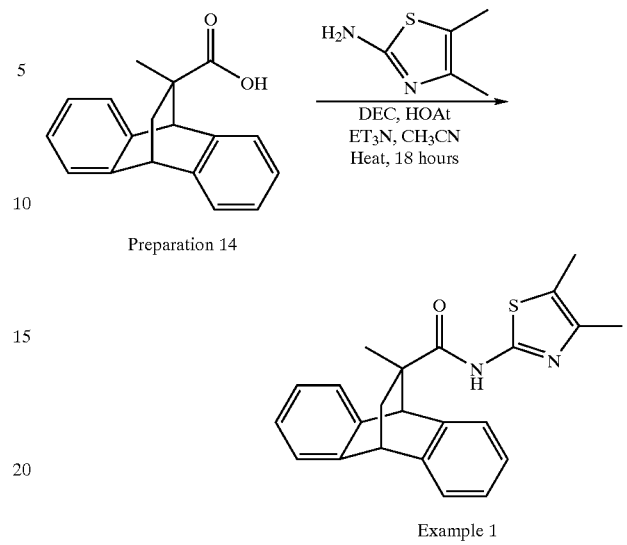

Preparation 14

Example 1

To a solution of the product of Preparation 14, step 1 (20 mg, 0.075 mmol, 1.0 equi.) in acetonitrile (2 mL) was added 1-[3-(dimethylamino) propyl]-3-ethylcarbodiimide hydrochloride (DEC) (17 mg, 0.09 mmol, 1.2 equi.), 1-hydroxy-7-azabenzotriazole (HOAt) (12 mg. 0.09 mmol, 1.2 equi.), triethyl amine (0.025 mL, 0.18 mmol, 2.5 equi.), and 2-amino-4,5-dimethylthiazole hydrochloride salt (14.8 mg, 0.09 mmol, 1.2 equi.). The reaction solution was heated to 80° C. for 18 hours. The reaction was then concentrated in vacuo. The product mixture was purified by flash chromatography (20% ethyl acetate in hexane) to yield 19.8 mg (70%) of Example 1. LC/MS (m/z 375, (M+H)+).

Examples 2 to 339

In a similar manner Examples 2–339 were prepared from the coupling of the appropriate acids and amines. Preparations of amines or acids not commercially available are described in the preceding preparations section of this document. All examples in the tables are racemic unless specified otherwise. Examples in the table where one enantiomer predominates or is the sole component, are designated as either R or S.

| Example | Chiral Compounds | Structure | MS: (M + H = MW +1) |
|---|---|---|---|
| 2 | | (structure showing isoxazole-sulfonamide-phenyl-amide linked to dibenzobicyclic with CH3) | 513.6 |

-continued

| Example | Chiral Compounds | Structure | MS: (M + H = MW +1) |
|---------|------------------|-----------|---------------------|
| 3 | | 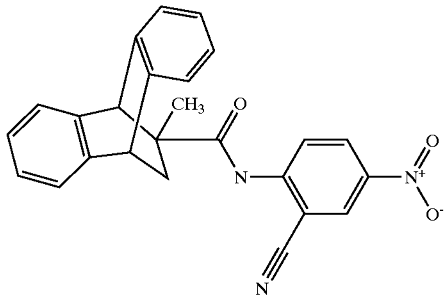 | 409.5 |
| 4 | | 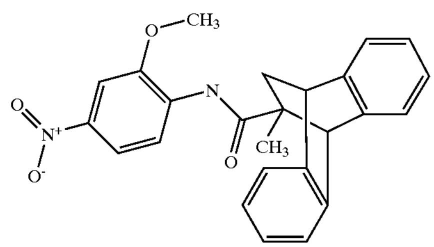 | 414.5 |
| 5 | | 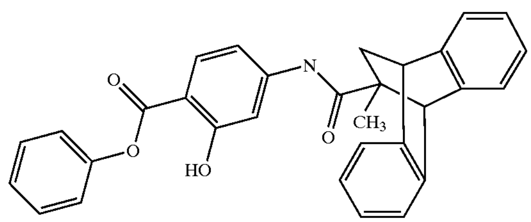 | 475.5 |
| 6 | | 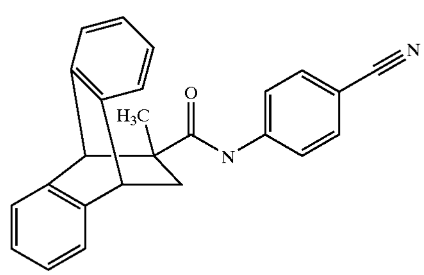 | 364.5 |
| 7 | | 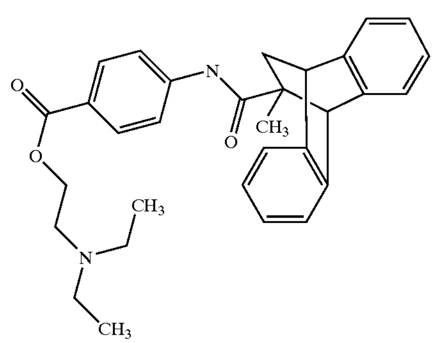 | 482.6 |

-continued

| Example | Chiral Compounds | Structure | MS: (M + H = MW +1) |
|---------|------------------|-----------|----------------------|
| 8 | | 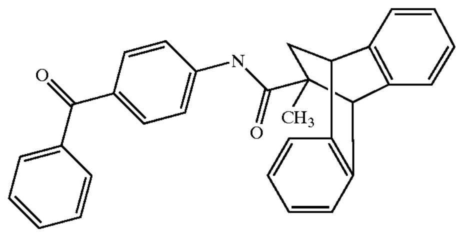 | 443.6 |
| 9 | | 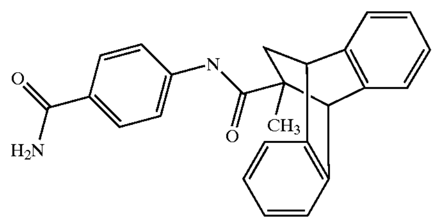 | 382.5 |
| 10 | | 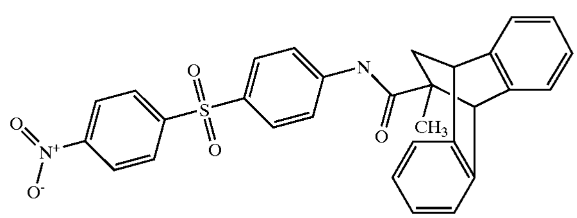 | 524.6 |
| 11 | | 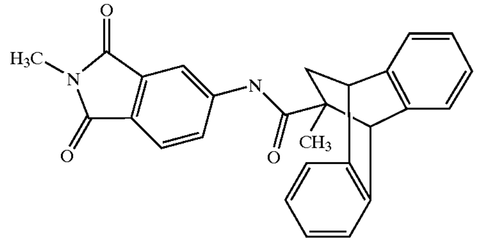 | 422.5 |
| 12 | | 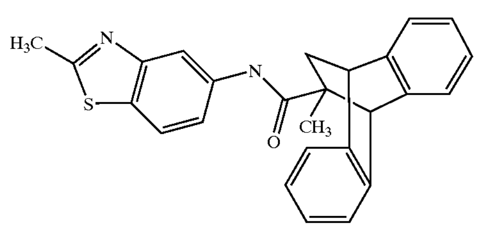 | 410.5 |

-continued

| Example | Chiral Compounds | Structure | MS: (M + H = MW +1) |
|---|---|---|---|
| 13 | | 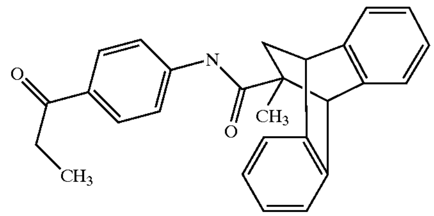 | 395.5 |
| 14 | | 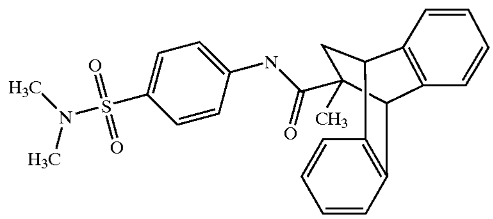 | 446.6 |
| 15 | | 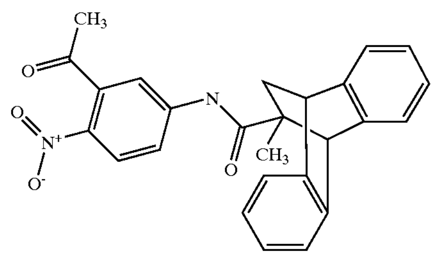 | 426.5 |
| 16 | | 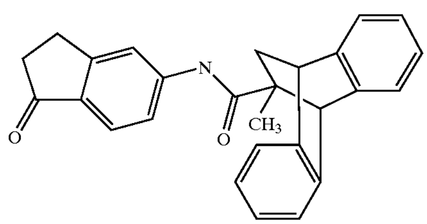 | 393.5 |
| 17 | | 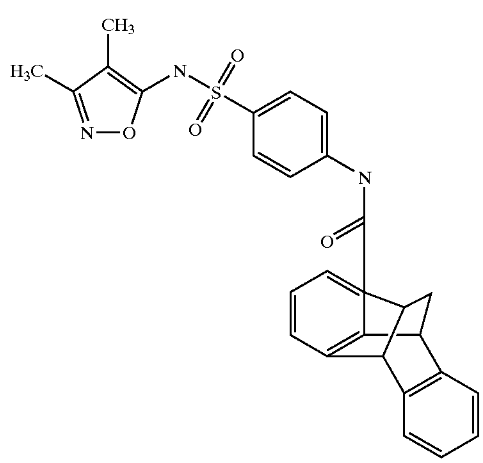 | 499.6 |

-continued

| Example | Chiral Compounds | Structure | MS: (M + H = MW +1) |
|---|---|---|---|
| 18 | | 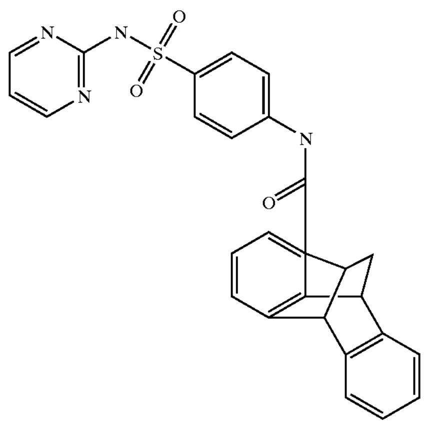 | 482.6 |
| 19 | | 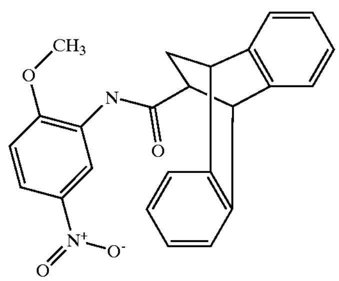 | 400.4 |
| 20 | | 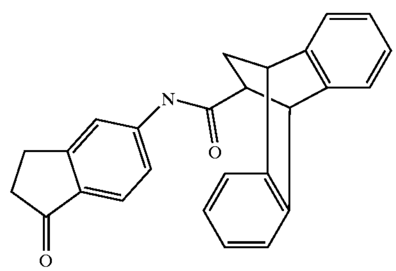 | 379.5 |
| 21 | | 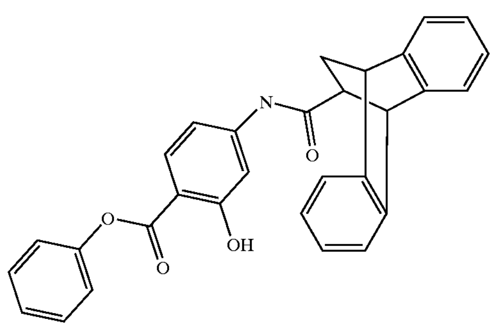 | 461.5 |
| 22 | | 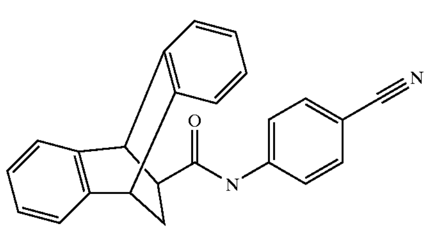 | 350.4 |

-continued
| Example | Chiral Compounds | Structure | MS: (M + H = MW +1) |
|---|---|---|---|
| 23 | | 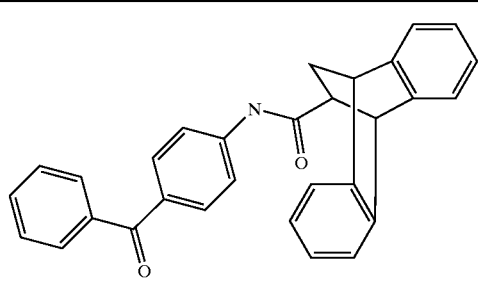 | 429.5 |
| 24 | | 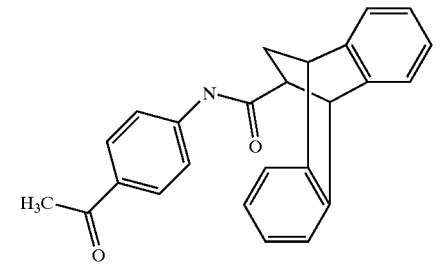 | 367.5 |
| 25 | | 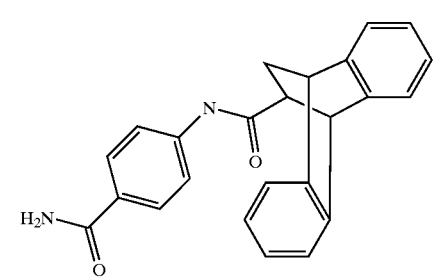 | 368.4 |
| 26 | | 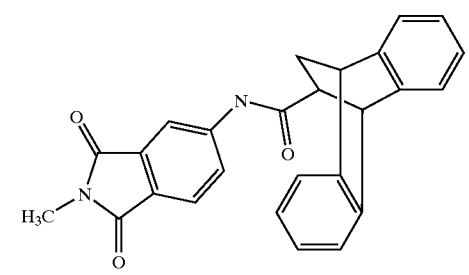 | 408.5 |
| 27 | | 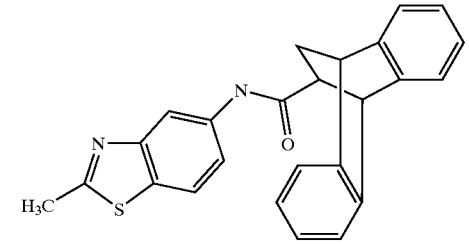 | 396.5 |

-continued

| Example | Chiral Compounds | Structure | MS: (M + H = MW +1) |
|---|---|---|---|
| 28 | | 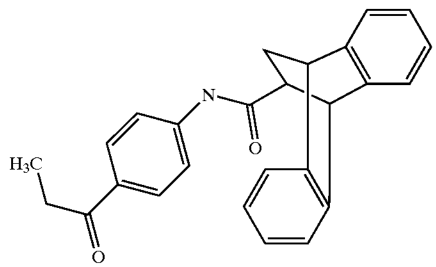 | 381.5 |
| 29 | | 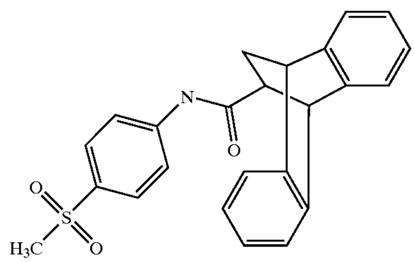 | 403.5 |
| 30 | | 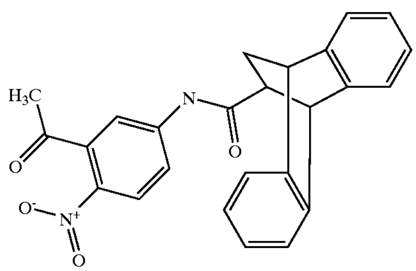 | 412.5 |
| 31 | | 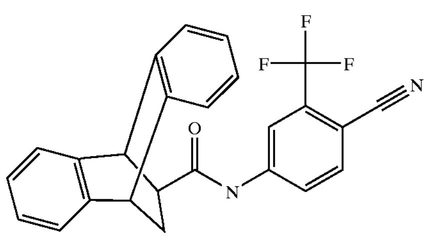 | 418.4 |
| 32 | | 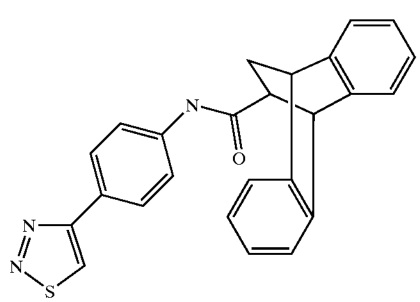 | 409.5 |

-continued
| Example | Chiral Compounds | Structure | MS: (M + H = MW +1) |
|---|---|---|---|
| 33 | | 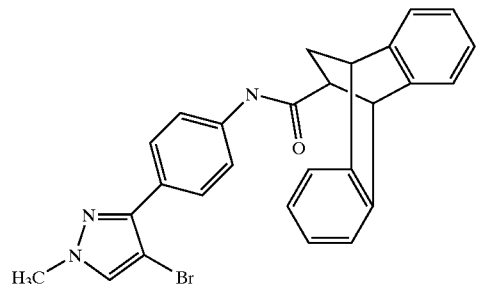 | 484.4 |
| 34 | | 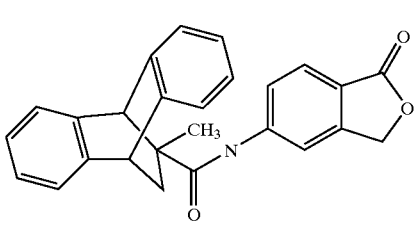 | 395.46 |
| 35 | | 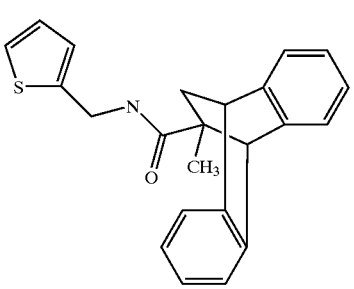 | 359.5 |
| 36 | | 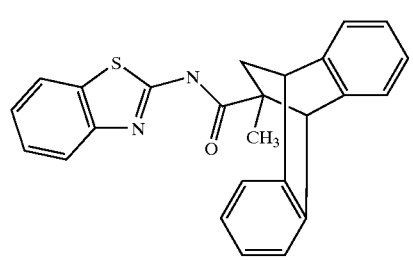 | 396.5 |
| 37 | | 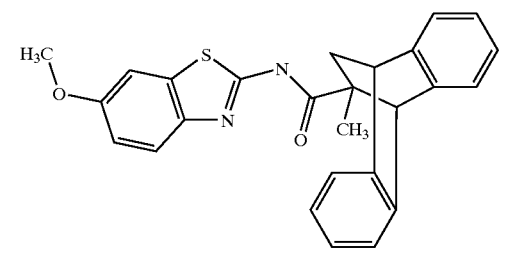 | 426.5 |
| 38 | | 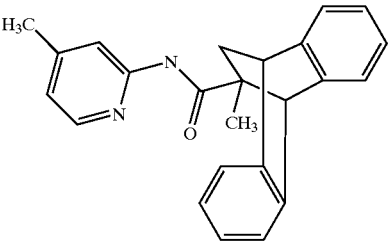 | 354.5 |

-continued

| Example | Chiral Compounds | Structure | MS: (M + H = MW +1) |
|---------|------------------|-----------|---------------------|
| 39 | | 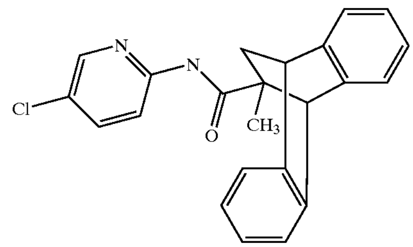 | 374.9 |
| 40–41 | | 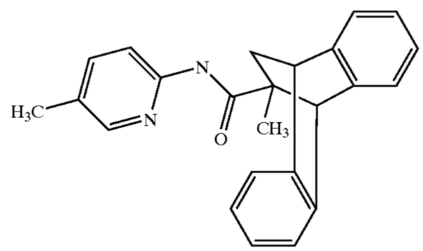 | 354.5 |
| 42 | | 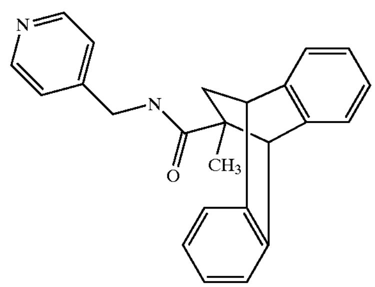 | 354.5 |
| 43 | | 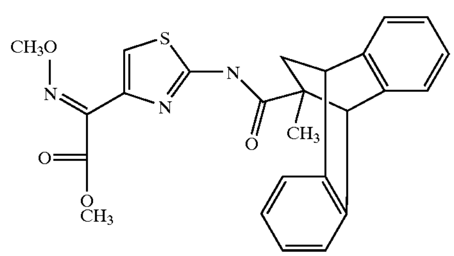 | 475.6 |
| 44 | | 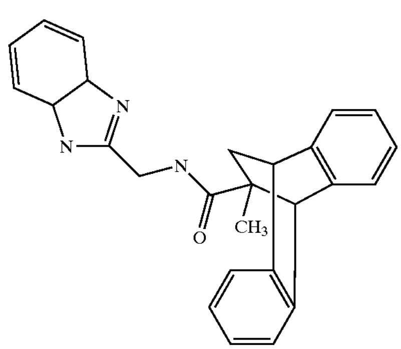 | 393.5 |

-continued

| Example | Chiral Compounds | Structure | MS: (M + H = MW +1) |
|---|---|---|---|
| 45 | | 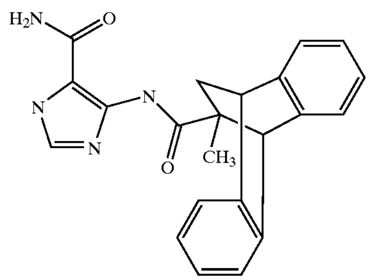 | 372.4 |
| 46 | | 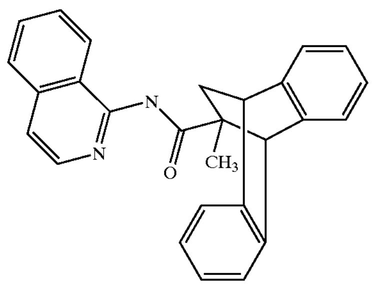 | 390.5 |
| 47 | | 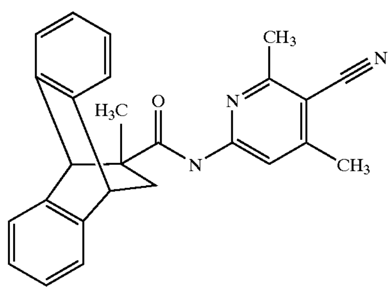 | 393.5 |
| 48 | | 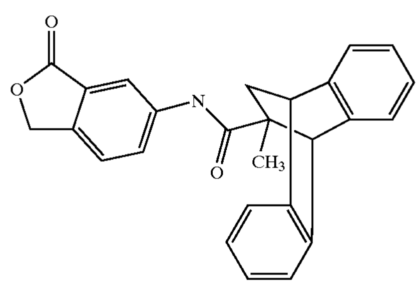 | 395.5 |
| 49 | | 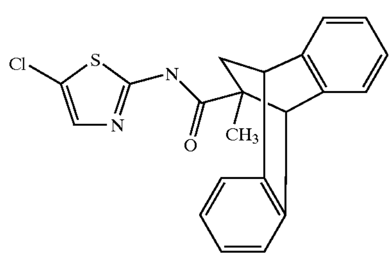 | 380.9 |

-continued
| Example | Chiral Compounds | Structure | MS: (M + H = MW +1) |
|---|---|---|---|
| 50 | | 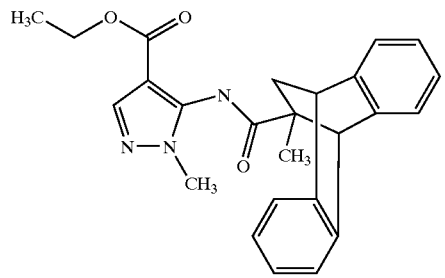 | 415.5 |
| 51 | | 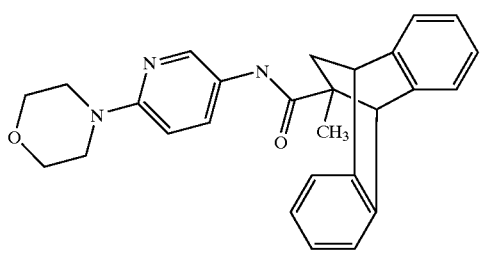 | 425.5 |
| 52 | | 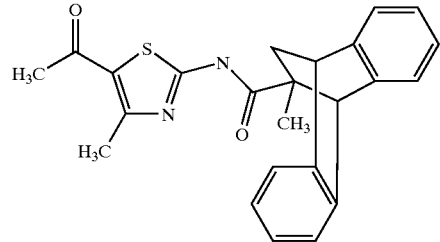 | 402.5 |
| 53 | | 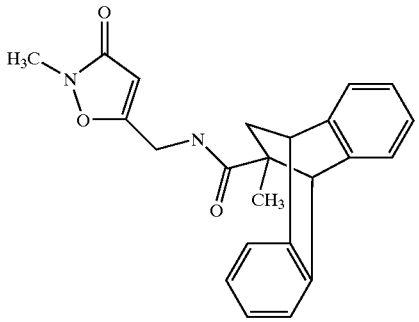 | 374.4 |
| 54 | | 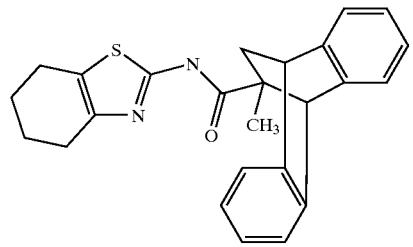 | 400.5 |

-continued

| Example | Chiral Compounds | Structure | MS: (M + H = MW +1) |
|---|---|---|---|
| 55 | | 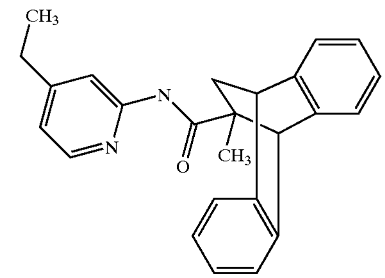 | 368.5 |
| 56 | | 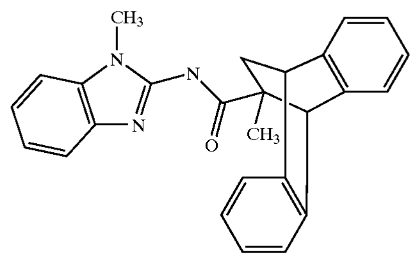 | 393.5 |
| 57 | | 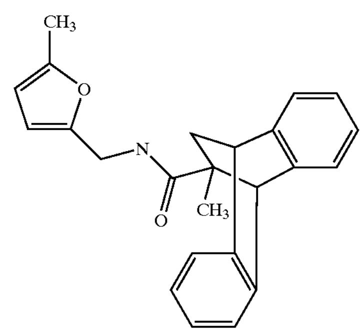 | 357.5 |
| 58 | | 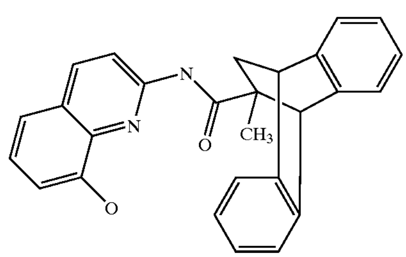 | |
| 59 | | 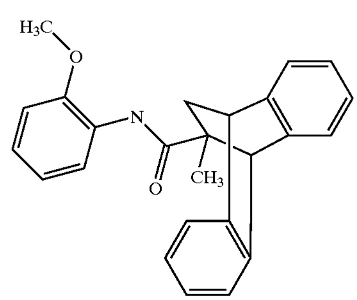 | 369.5 |

-continued
| Example | Chiral Compounds | Structure | MS: (M + H = MW +1) |
|---|---|---|---|
| 60 | | 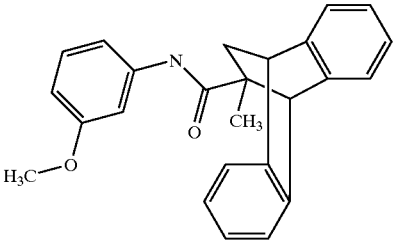 | 369.5 |
| 61 | | 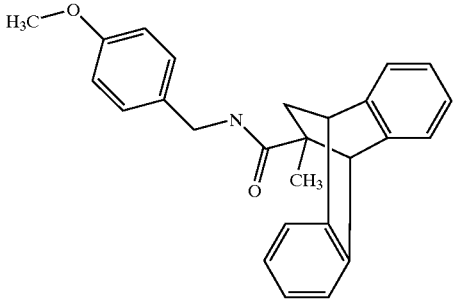 | 383.5 |
| 62 | | 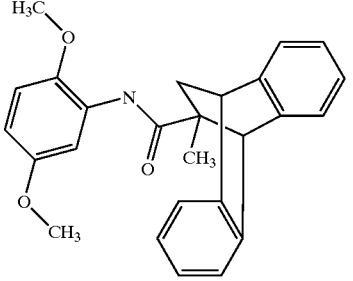 | 399.5 |
| 63 | | 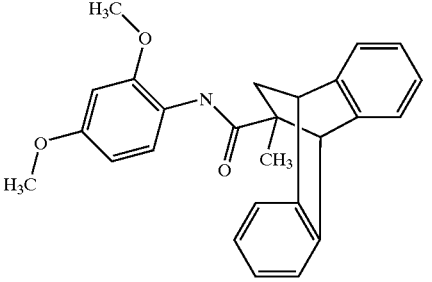 | 399.5 |
| 64 | | 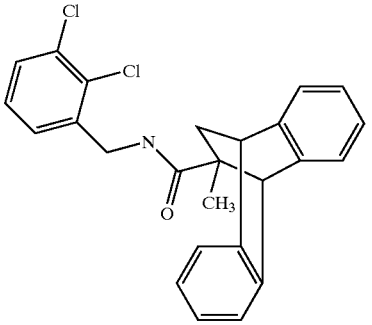 | 422.4 |

-continued

| Example | Chiral Compounds | Structure | MS: (M + H = MW +1) |
|---|---|---|---|
| 65 | | 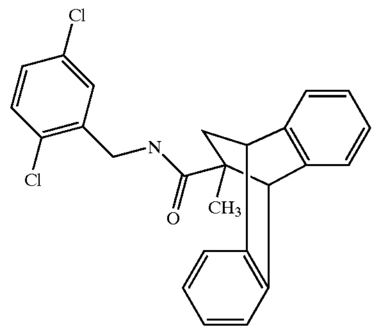 | 422.4 |
| 66 | | 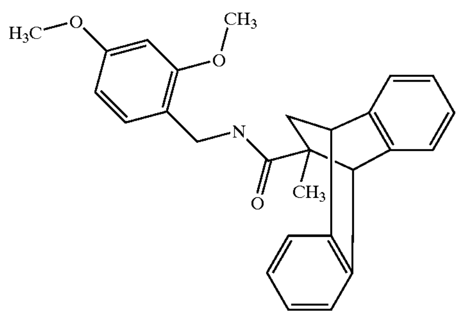 | 413.5 |
| 67 | | 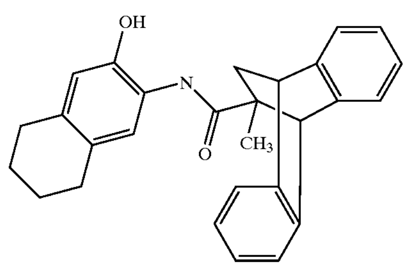 | 409.5 |
| 68 | | 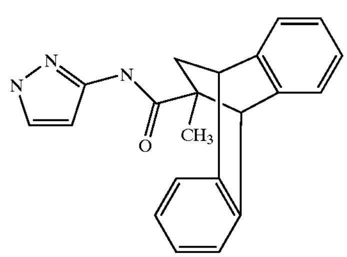 | 329.4 |
| 69 | | 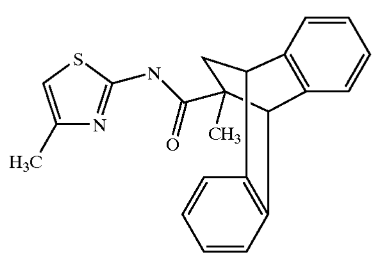 | 360.5 |

-continued

| Example | Chiral Compounds | Structure | MS: (M + H = MW +1) |
|---|---|---|---|
| 70 | | 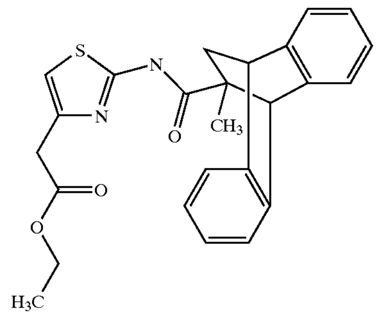 | 432.5 |
| 71 | | 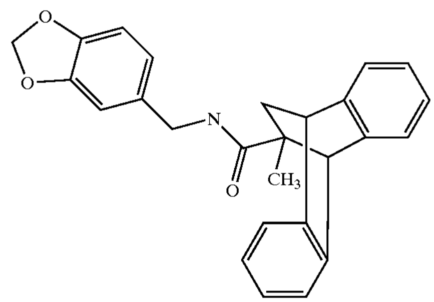 | 397.5 |
| 72 | | 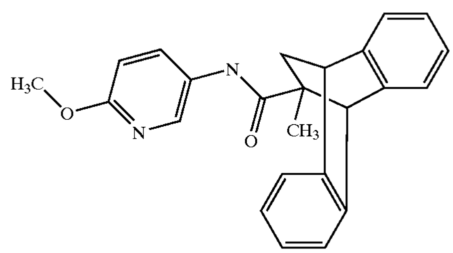 | 370.5 |
| 73 | | 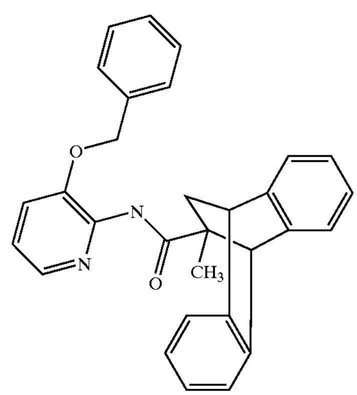 | 446.6 |
| 74 | | 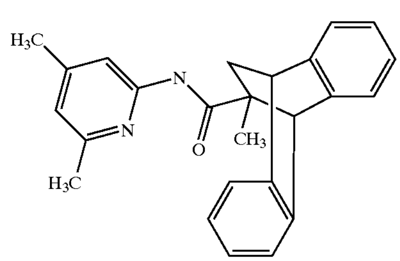 | 368.5 |

-continued
| Example | Chiral Compounds | Structure | MS: (M + H = MW +1) |
|---|---|---|---|
| 75 | | 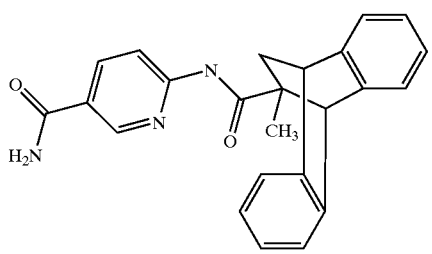 | 383.5 |
| 76 | | 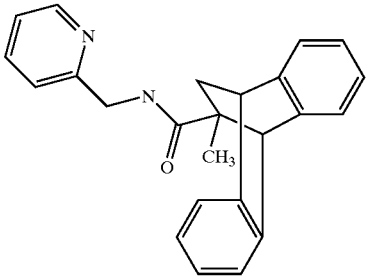 | 354.5 |
| 77–78 | | 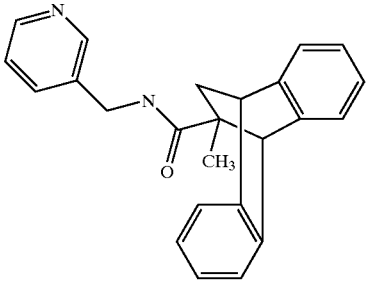 | 354.5 |
| 79 | | 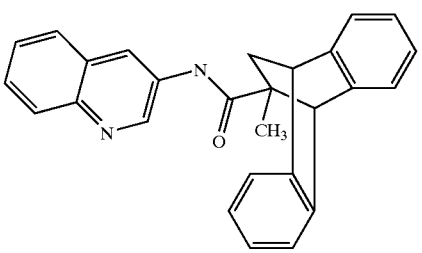 | 390.5 |
| 80 | | 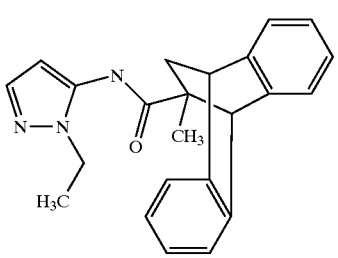 | 357.5 |

-continued

| Example | Chiral Compounds | Structure | MS: (M + H = MW +1) |
|---|---|---|---|
| 81 | | 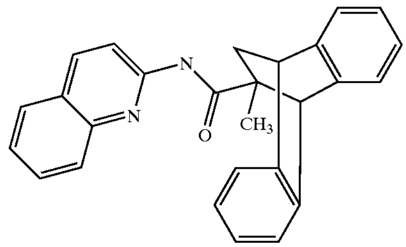 | 390.5 |
| 82 | | 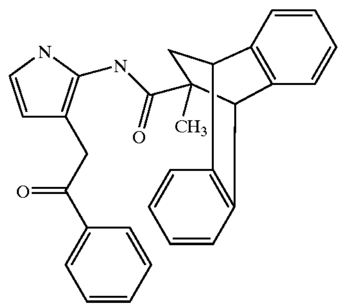 | 446.6 |
| 83 | | 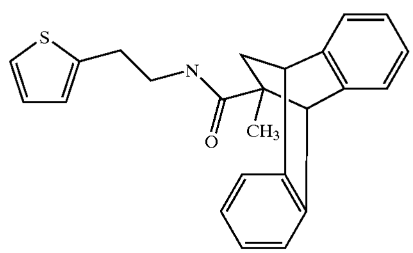 | 373.5 |
| 84 | | 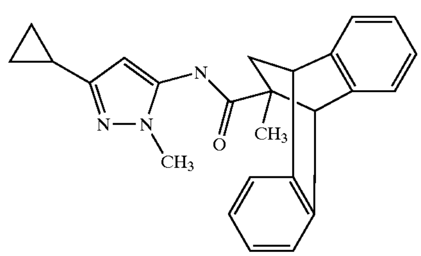 | 383.5 |
| 85 | | 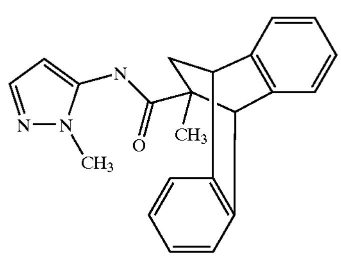 | 343.4 |

-continued
| Example | Chiral Compounds | Structure | MS: (M + H = MW +1) |
|---|---|---|---|
| 86 | | 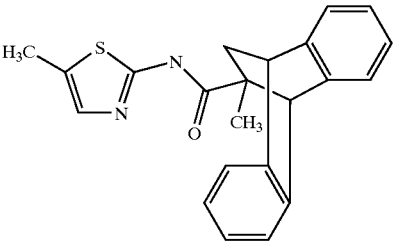 | 360.5 |
| 87 | | 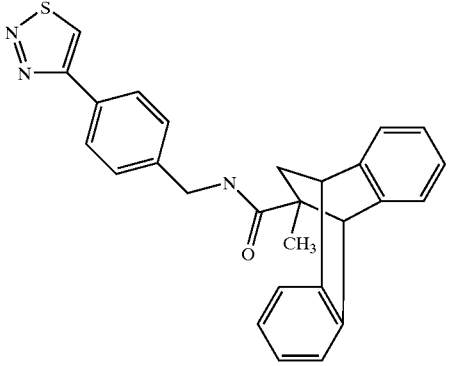 | 437.6 |
| 88 | | 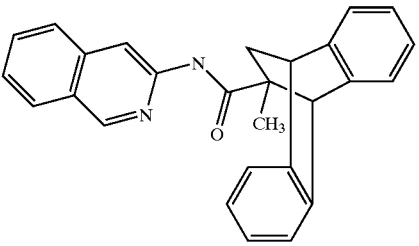 | 390.5 |
| 89 | | 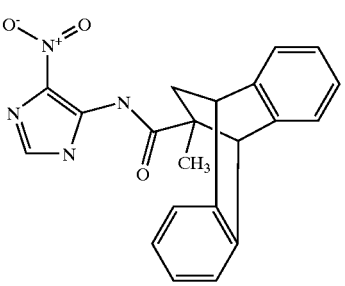 | 374.4 |
| 90 | | 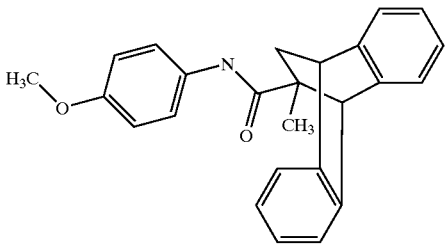 | 369.5 |

-continued

| Example | Chiral Compounds | Structure | MS: (M + H = MW +1) |
|---|---|---|---|
| 91 | | 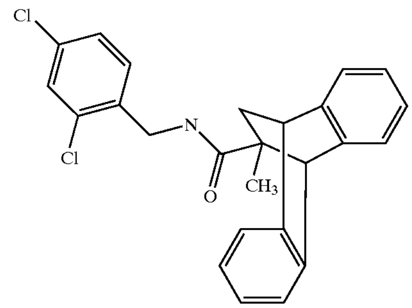 | 422.4 |
| 92 | | 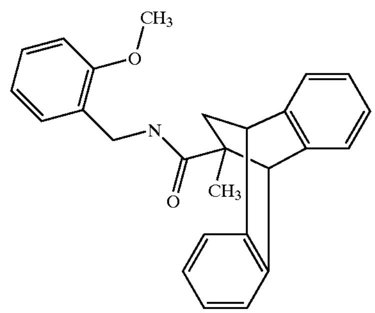 | 383.5 |
| 93 | | 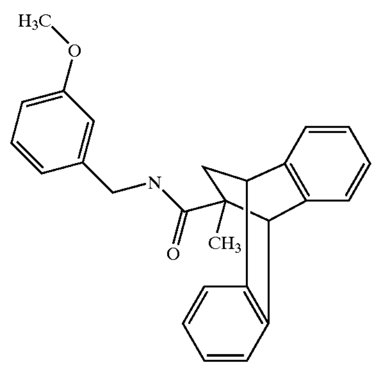 | 383.5 |
| 94 | | 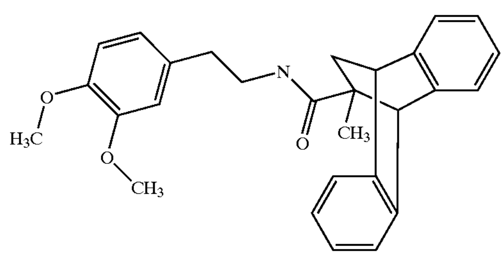 | 427.5 |
| 95 | | 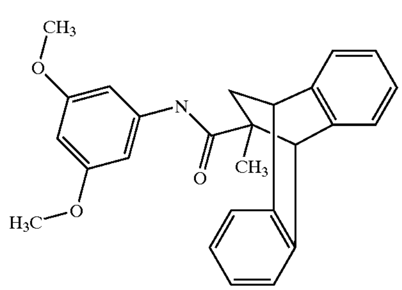 | 399.5 |

-continued

| Example | Chiral Compounds | Structure | MS: (M + H = MW +1) |
|---------|------------------|-----------|---------------------|
| 96 | | 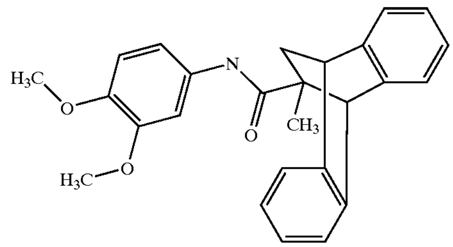 | 399.5 |
| 97 | | 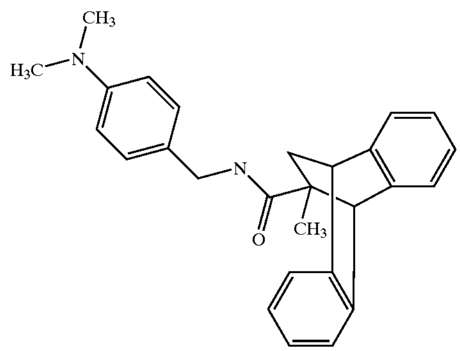 | 396.5 |
| 98 | | 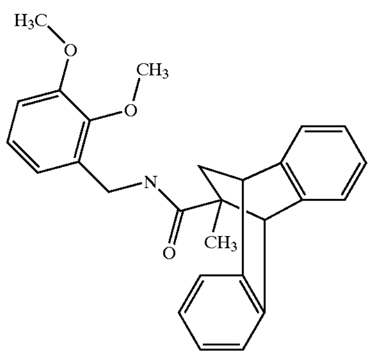 | 413.5 |
| 99 | | 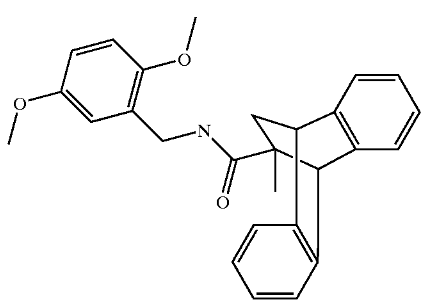 | 413.5 |
| 100 | | 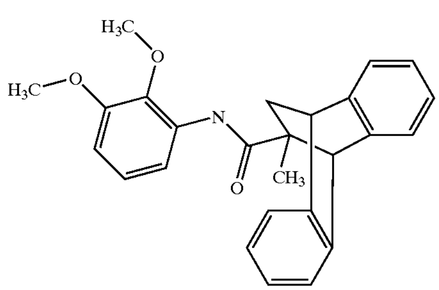 | 399.5 |

-continued
| Example | Chiral Compounds | Structure | MS: (M + H = MW +1) |
|---|---|---|---|
| 101 | | 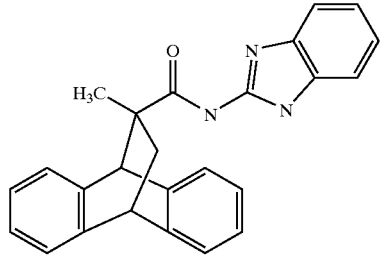 | 379.47 |
| 102 | | 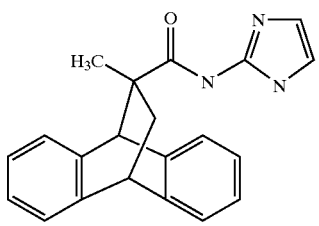 | 329.41 |
| 103 | | 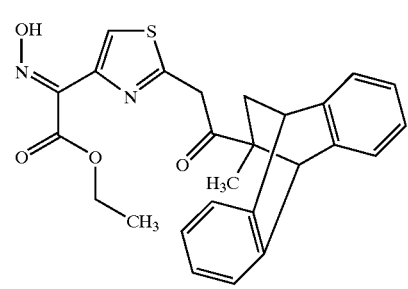 | 461.5 |
| 104 | | 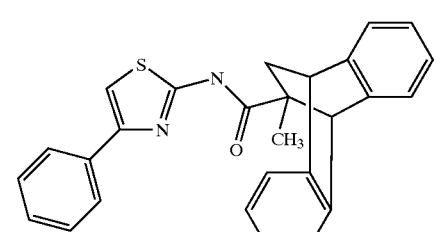 | 422.6 |
| 105 | | 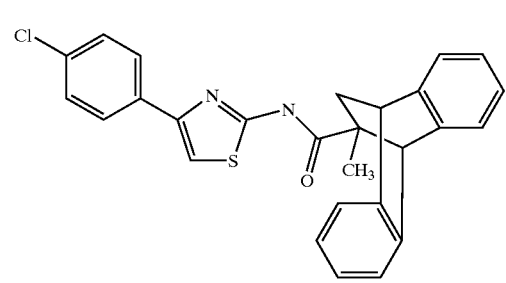 | 457 |
| 106 | | 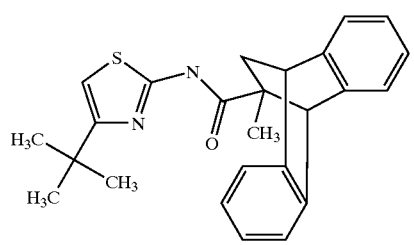 | 402.6 |

-continued

| Example | Chiral Compounds | Structure | MS: (M + H = MW +1) |
|---|---|---|---|
| 107 | | 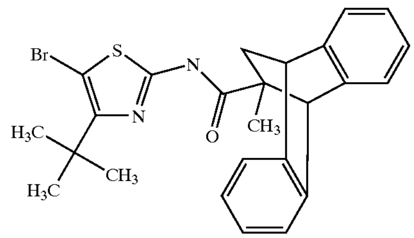 | 481.5 |
| 108 | | 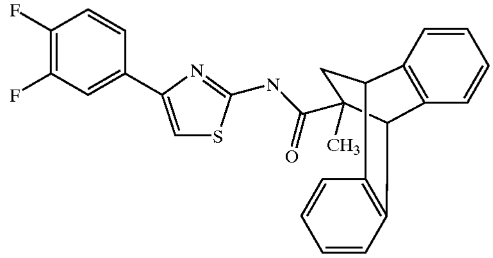 | 458.5 |
| 109 | | 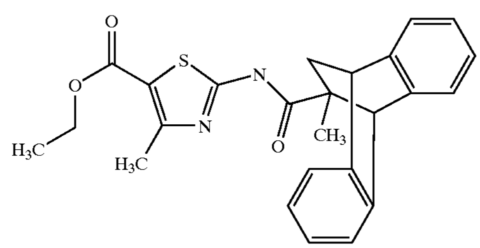 | 432.5 |
| 110 | | 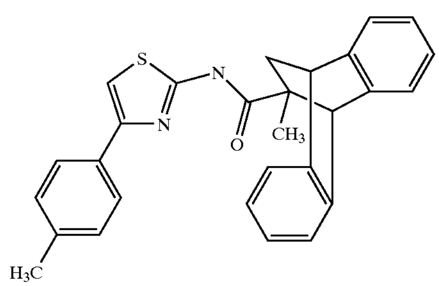 | 436.6 |
| 111 | | 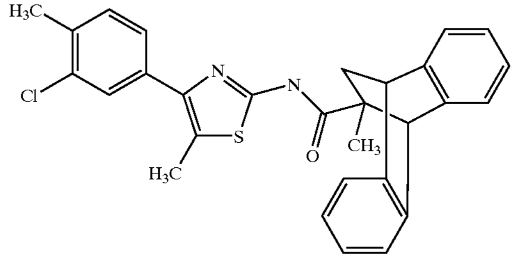 | 485 |

-continued

| Example | Chiral Compounds | Structure | MS: (M + H = MW +1) |
|---|---|---|---|
| 112 | | 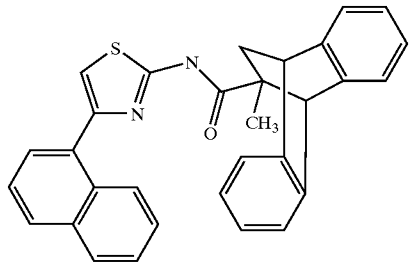 | 472.6 |
| 113 | | 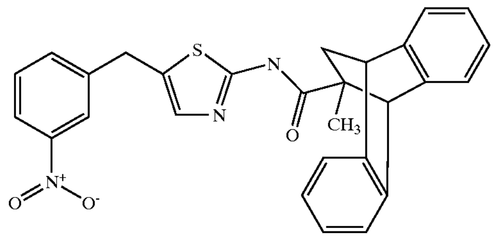 | 481.6 |
| 114 | | 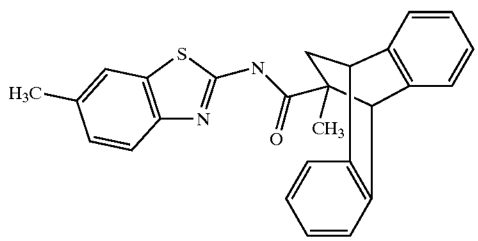 | 410.5 |
| 115 | | 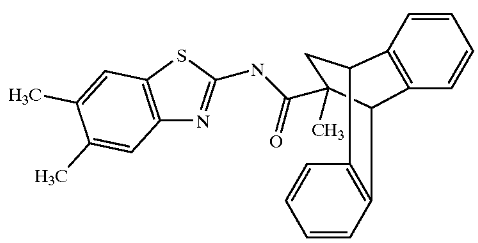 | 424.6 |
| 116 | | 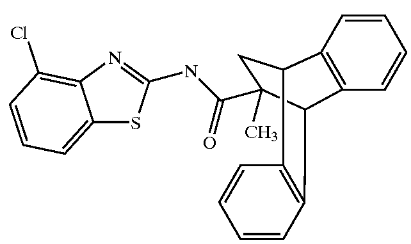 | 431 |
| 117 | | 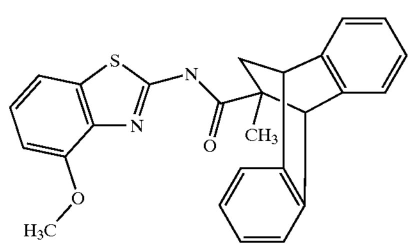 | 426.5 |

-continued

| Example | Chiral Compounds | Structure | MS: (M + H = MW +1) |
|---|---|---|---|
| 118 | | 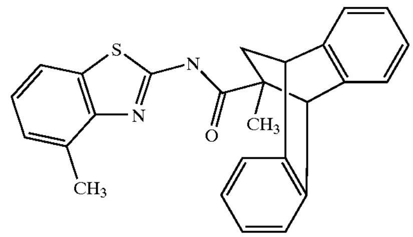 | 410.5 |
| 119 | | 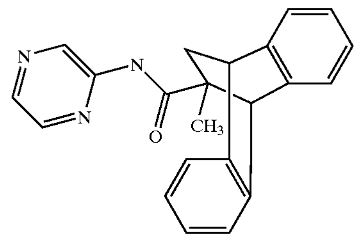 | 341.4 |
| 120 | | 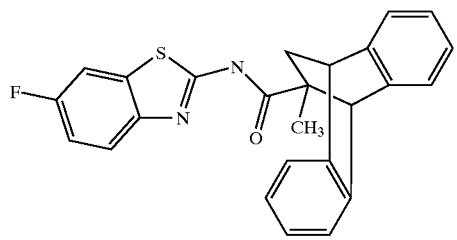 | 414.5 |
| 121 | | 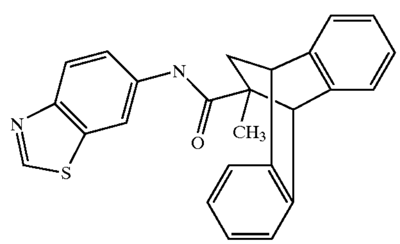 | 396.5 |
| 122 | | 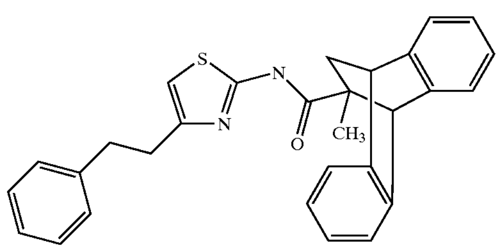 | 450.6 |
| 123–124 | | 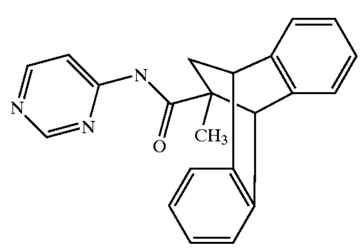 | 341.4 |

-continued

| Example | Chiral Compounds | Structure | MS: (M + H = MW +1) |
|---|---|---|---|
| 125 | | 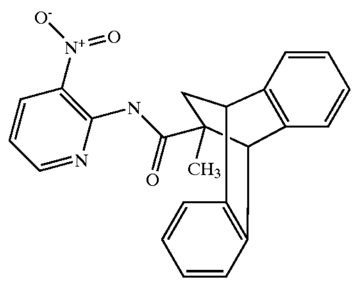 | 385.4 |
| 126 | | 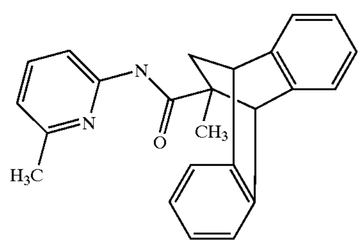 | 354.5 |
| 127 | | 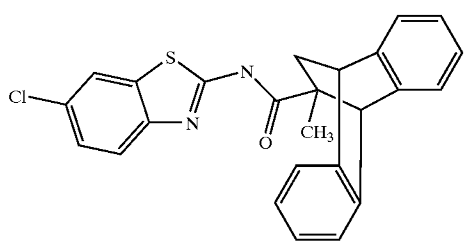 | 431 |
| 128 | | 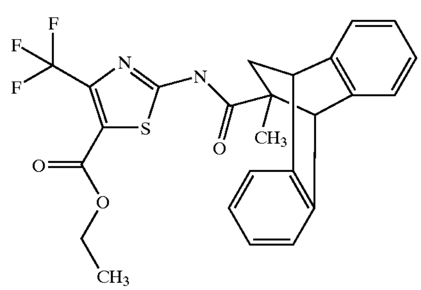 | 486.52 |
| 129 | | 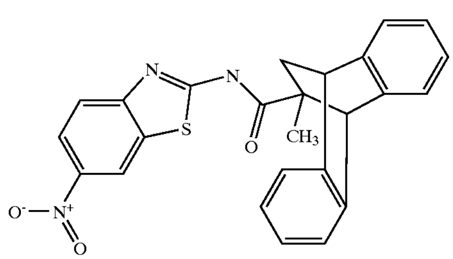 | 441.51 |

-continued
| Example | Chiral Compounds | Structure | MS: (M + H = MW +1) |
|---|---|---|---|
| 130 | | 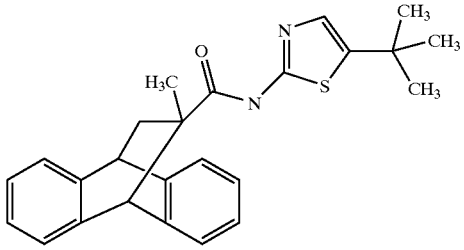 | 402.56 |
| 131 | Chiral (R) | 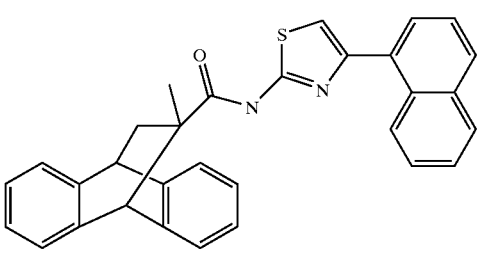 | 472.61 |
| 132 | Chiral (S) | 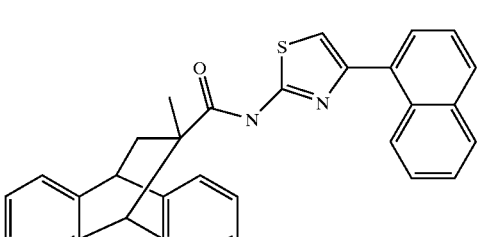 | 472.61 |
| 133 | | 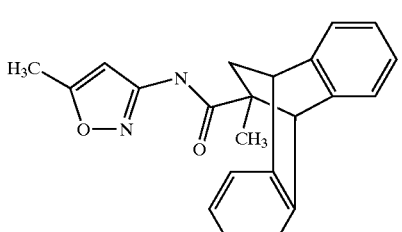 | 344.4 |
| 134 | | 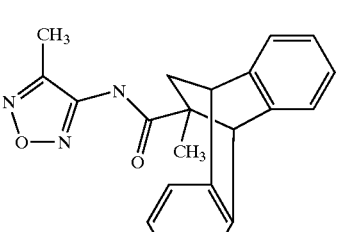 | 345.4 |
| 135 | | 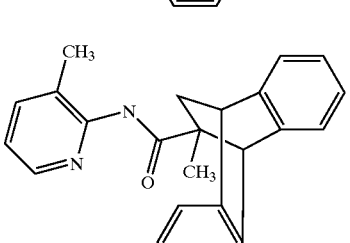 | 354.5 |

-continued

| Example | Chiral Compounds | Structure | MS: (M + H = MW +1) |
|---|---|---|---|
| 136 | | 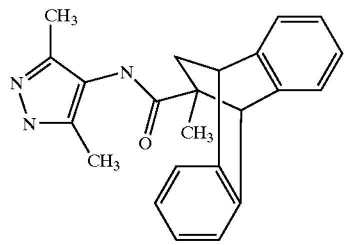 | 357.5 |
| 137 | | 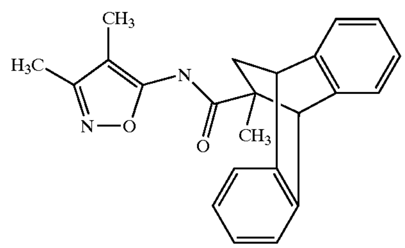 | 358.4 |
| 138 | | 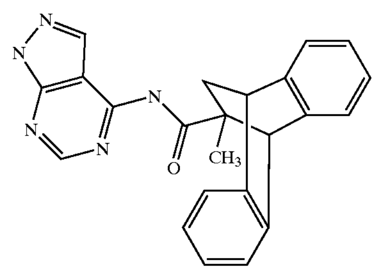 | 381.4 |
| 139 | | 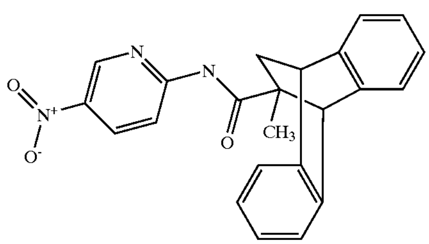 | 385.4 |
| 140 | | 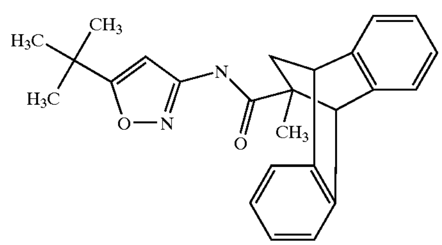 | 386.5 |
| 141 | | 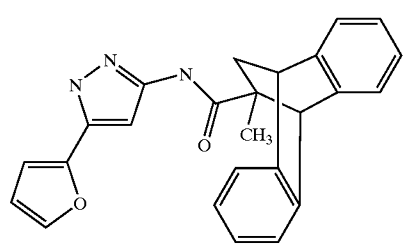 | 395.5 |

-continued

| Example | Chiral Compounds | Structure | MS: (M + H = MW +1) |
|---|---|---|---|
| 142 | | 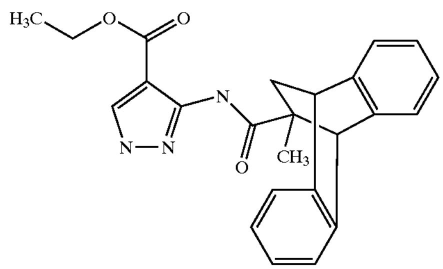 | 401.5 |
| 143 | | 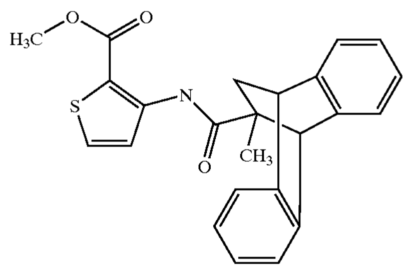 | 403.5 |
| 144 | | 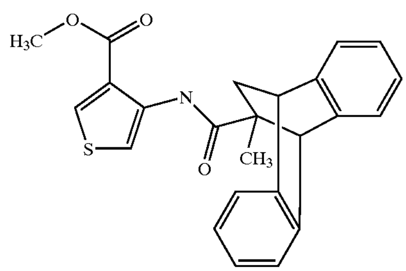 | 403.5 |
| 145 | | 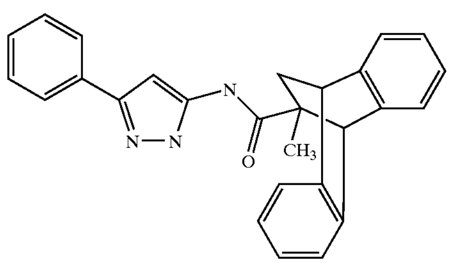 | 405.5 |
| 146 | | 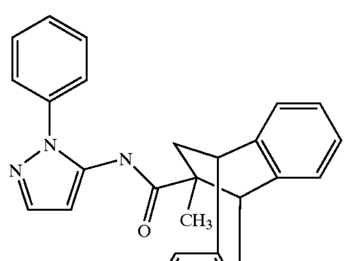 | 405.5 |

-continued

| Example | Chiral Compounds | Structure | MS: (M + H = MW +1) |
|---|---|---|---|
| 147 | | 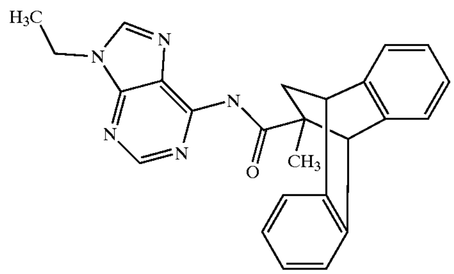 | 409.5 |
| 148 | | 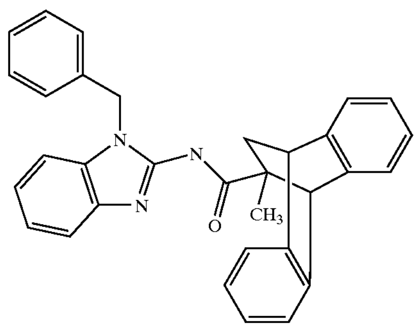 | 469.6 |
| 149 | | 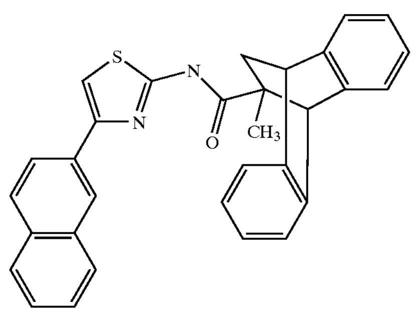 | 472.6 |
| 150 | | 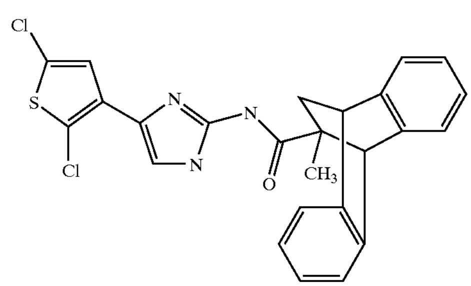 | 497.5 |
| 151 | | 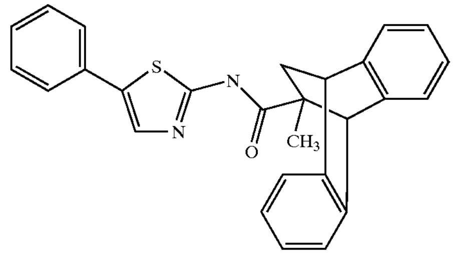 | 422.55 |

-continued
| Example | Chiral Compounds | Structure | MS: (M + H = MW +1) |
|---|---|---|---|
| 152 | | 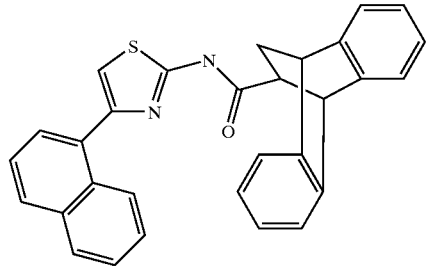 | 458.59 |
| 153 | | 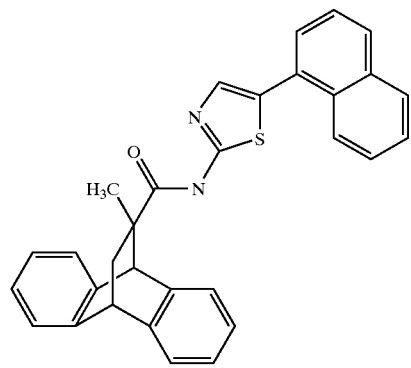 | 472.61 |
| 154 | | 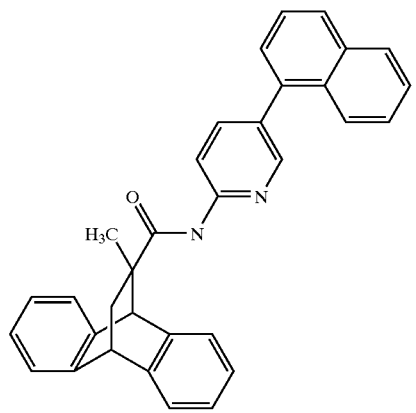 | 466.59 |
| 155 | | 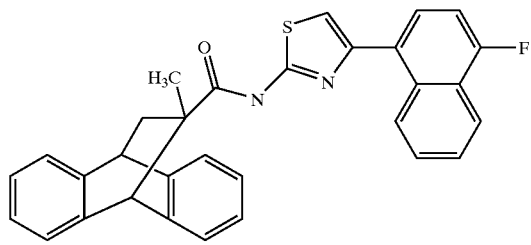 | 490.6 |

-continued
| Example | Chiral Compounds | Structure | MS: (M + H = MW +1) |
|---|---|---|---|
| 156 | | 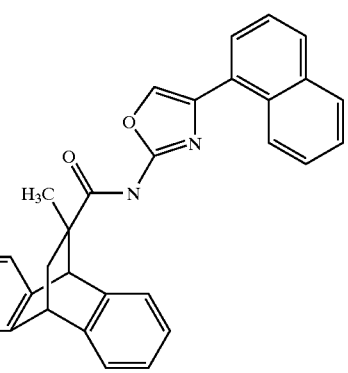 | 456.55 |
| 157 | | 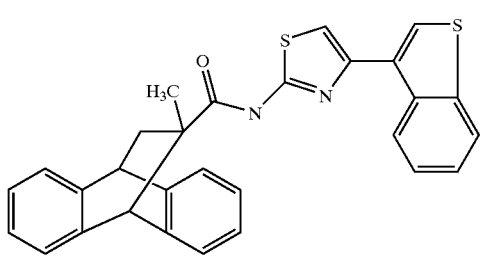 | 478.64 |
| 158 | | 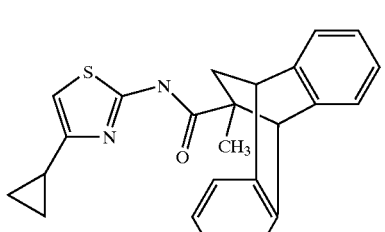 | 386.5 |
| 159 | | 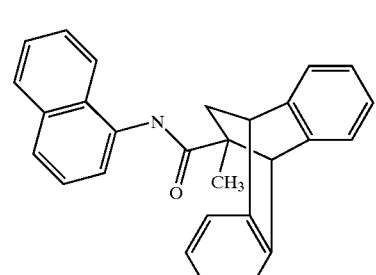 | 389.5 |
| 160 | | 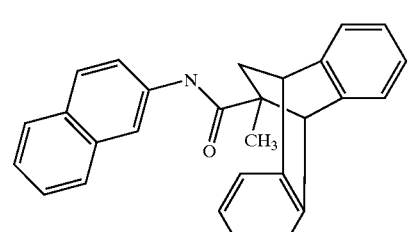 | 389.5 |

-continued

| Example | Chiral Compounds | Structure | MS: (M + H = MW +1) |
|---|---|---|---|
| 161 | | 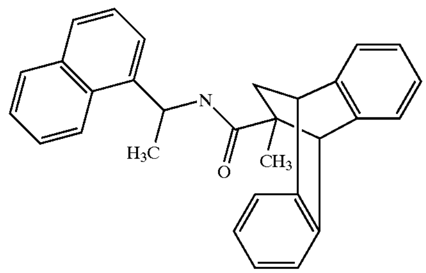 | 417.6 |
| 162 | | 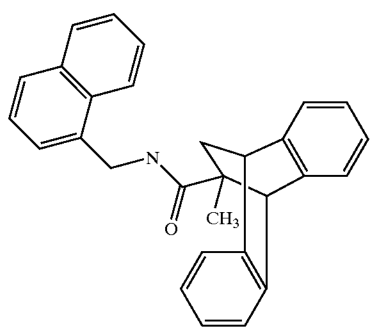 | 403.5 |
| 163 | | 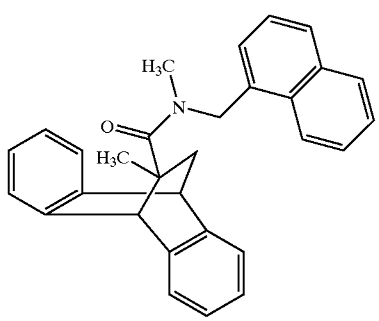 | 417.6 |
| 164 | | 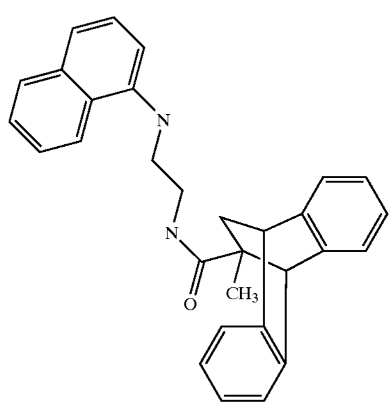 | 432.57 |

-continued

| Example | Chiral Compounds | Structure | MS: (M + H = MW +1) |
|---|---|---|---|
| 165 | | 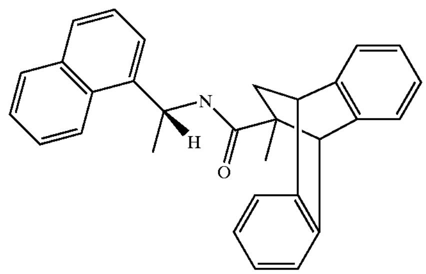 | 417.6 |
| 166 | | 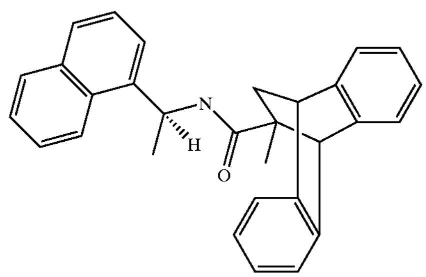 | 417.6 |
| 167 | | 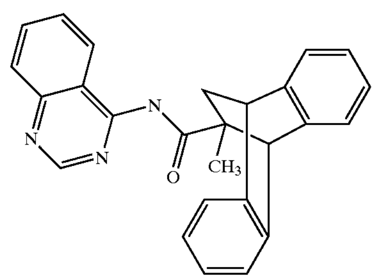 | 391.5 |
| 168 | | 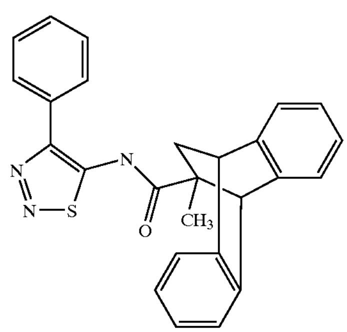 | 423.5 |
| 169 | | 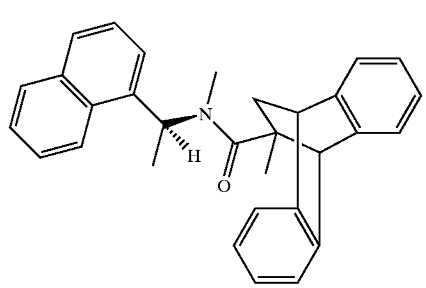 | 431.6 |

-continued

| Example | Chiral Compounds | Structure | MS: (M + H = MW +1) |
|---|---|---|---|
| 170 | | 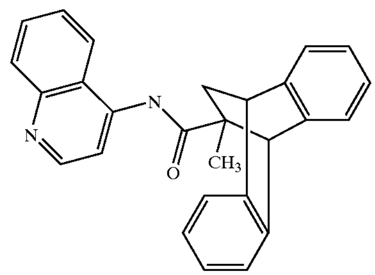 | 390.5 |
| 171 | | 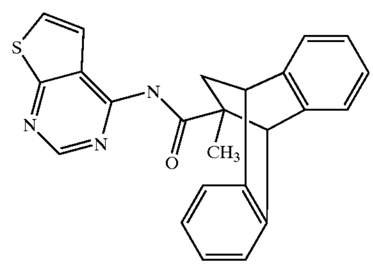 | 397.5 |
| 172 | | 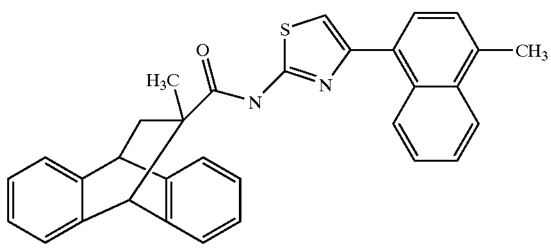 | 486.64 |
| 173 | | 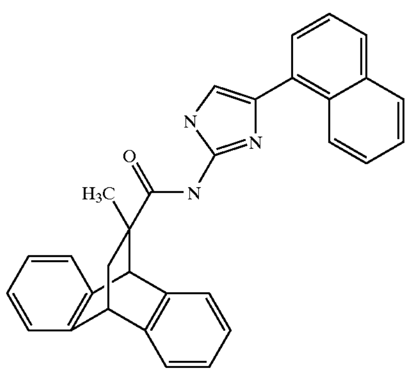 | 455.56 |
| 174 | | 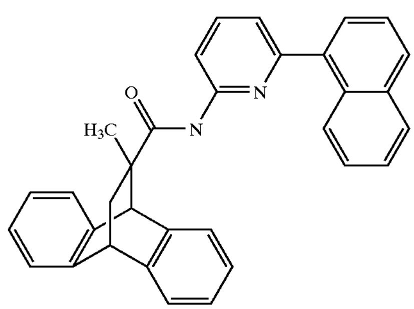 | 466.59 |

-continued
| Example | Chiral Compounds | Structure | MS: (M + H = MW +1) |
|---|---|---|---|
| 175 | | 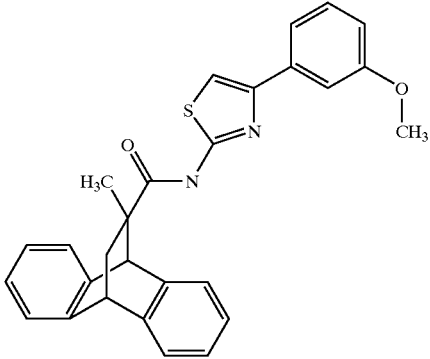 | 452.58 |
| 176 | | 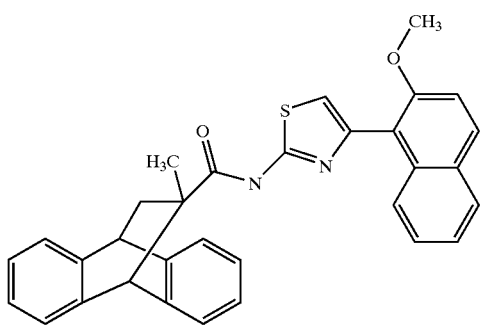 | 502.64 |
| 177 | | 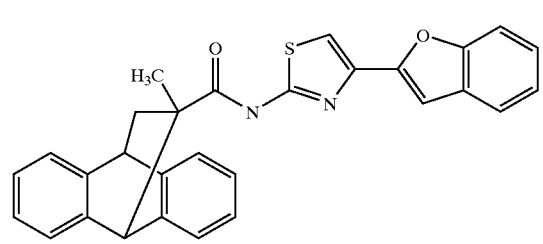 | 462.57 |
| 178 | | 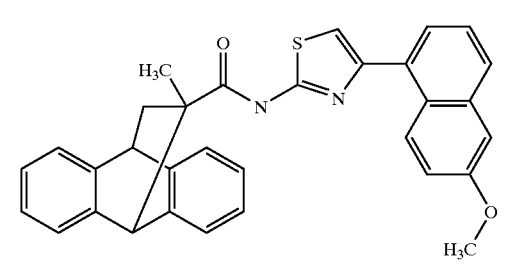 | 502.64 |
| 179 | | 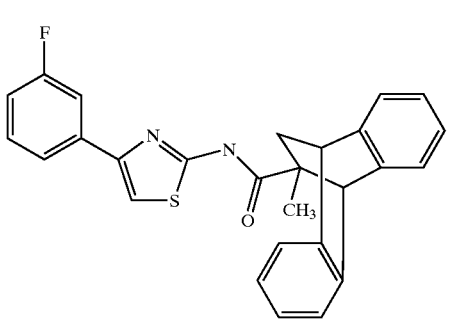 | 440.5 |

-continued

| Example | Chiral Compounds | Structure | MS: (M + H = MW +1) |
|---|---|---|---|
| 180 | | 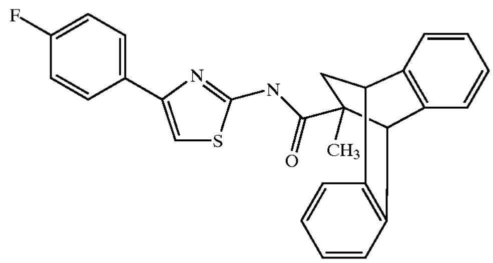 | 440.5 |
| 181 | | 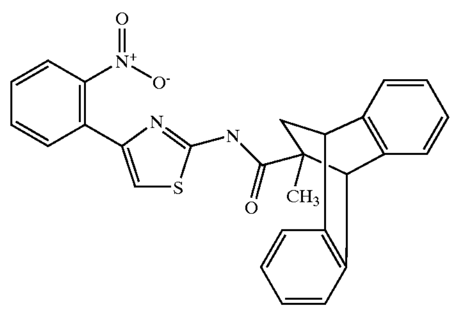 | 467.6 |
| 182 | | 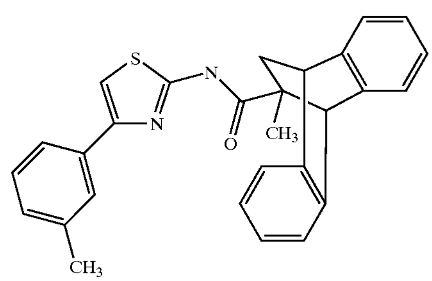 | 436.6 |
| 183 | | 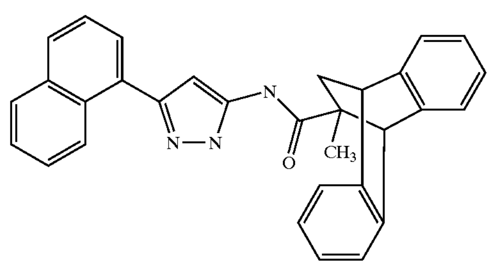 | 455.6 |
| 184 | | 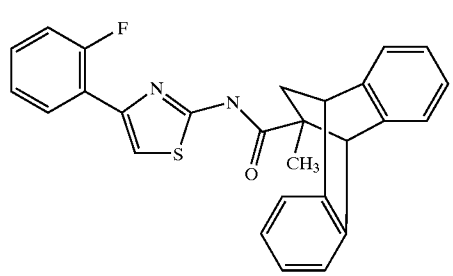 | 440.5 |

-continued
| Example | Chiral Compounds | Structure | MS: (M + H = MW +1) |
|---|---|---|---|
| 185 | | 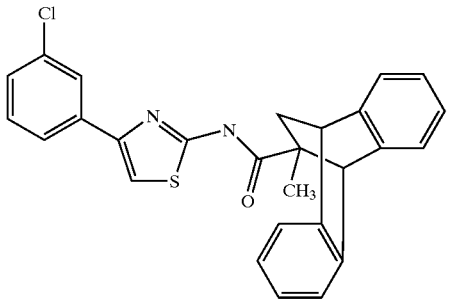 | 457 |
| 186 | | 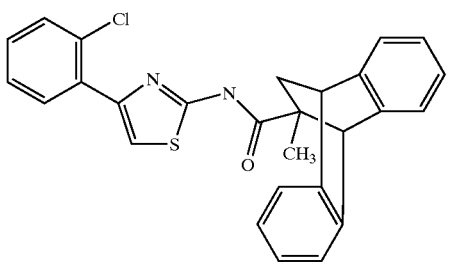 | 457 |
| 187 | | 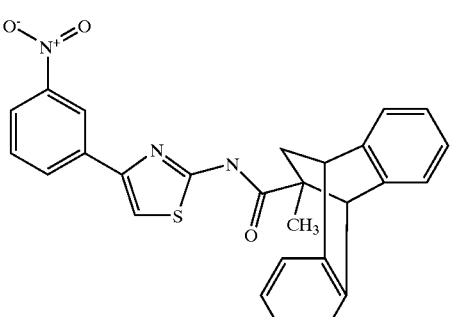 | 467.6 |
| 188 | Chiral (R) | 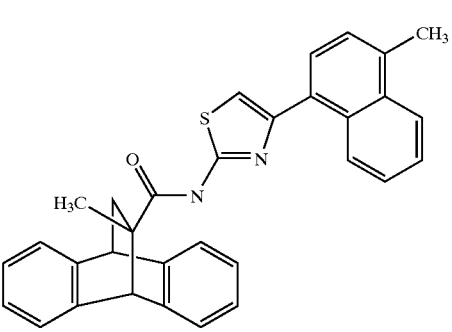 | 486.64 |
| 189 | Chiral (S) | 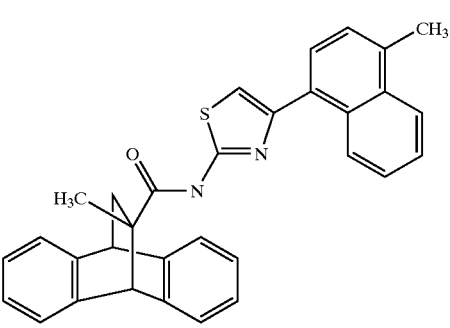 | 486.64 |

| Example | Chiral Compounds | Structure | MS: (M + H = MW +1) |
|---|---|---|---|
| 190 | | 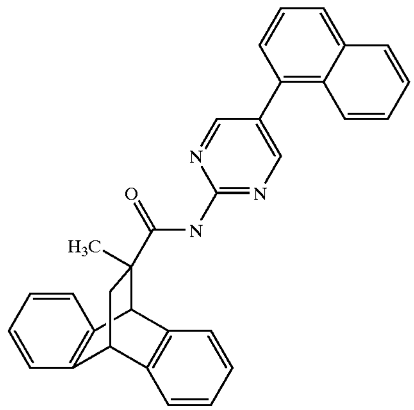 | 467.58 |
| 191 | | 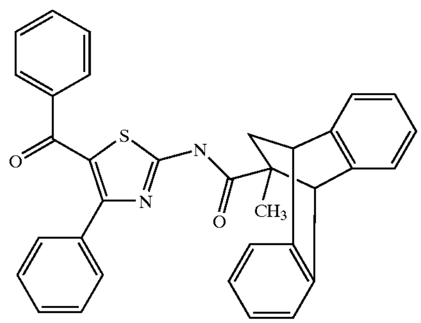 | 526.7 |
| 192 | | 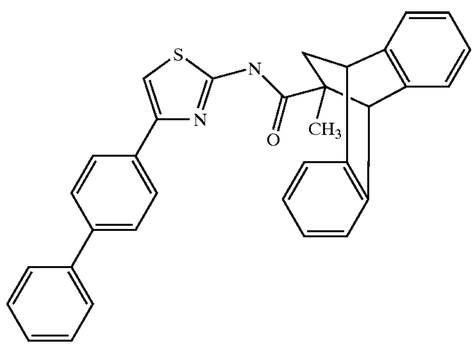 | 498.7 |
| 193 | | 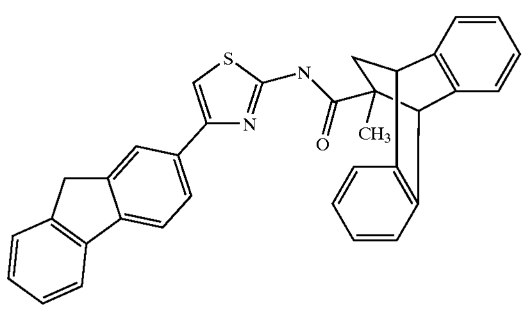 | 510.7 |

-continued
| Example | Chiral Compounds | Structure | MS: (M + H = MW +1) |
|---|---|---|---|
| 194 | | 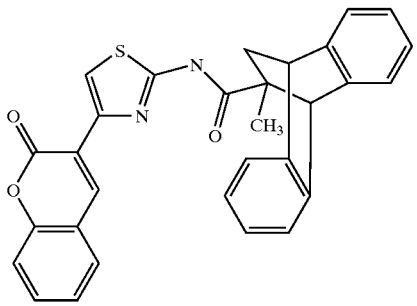 | 490.6 |
| 195 | | 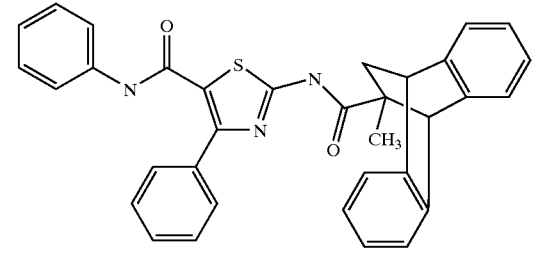 | 541.7 |
| 196 | | 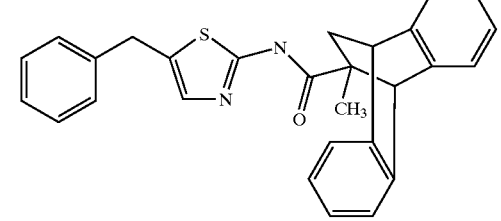 | 436.6 |
| 197 | | 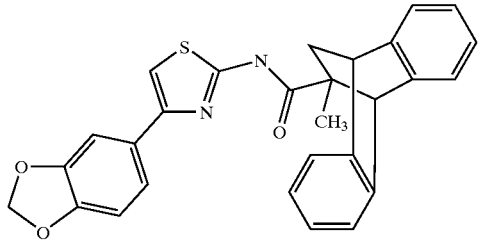 | 466.6 |
| 198 | | 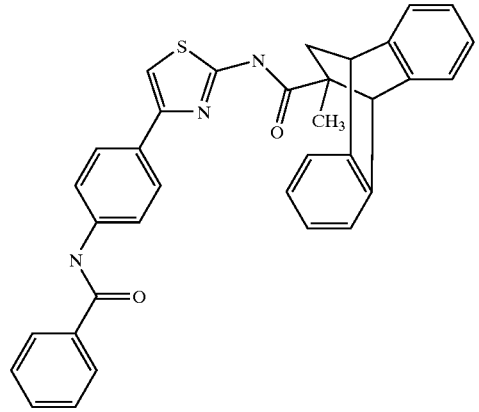 | 541.7 |

-continued
| Example | Chiral Compounds | Structure | MS: (M + H = MW +1) |
|---|---|---|---|
| 199 | | 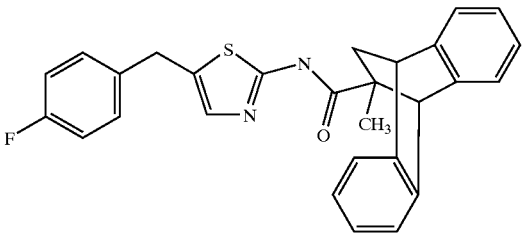 | 454.6 |
| 200 | | 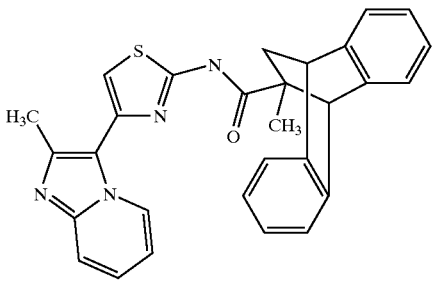 | 476.6 |
| 201 | | 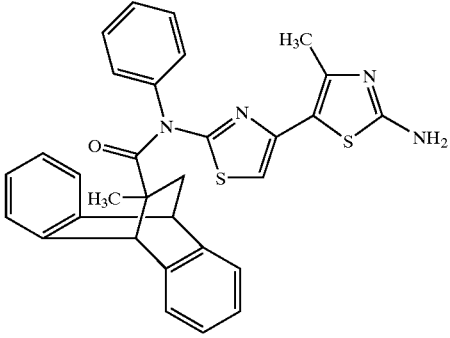 | 534.7 |
| 202 | | 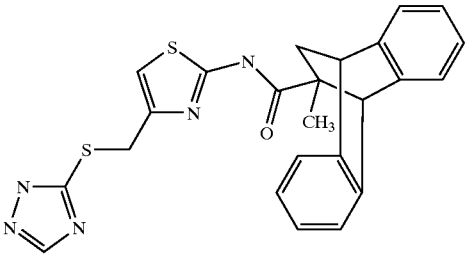 | 459.6 |
| 203 | | 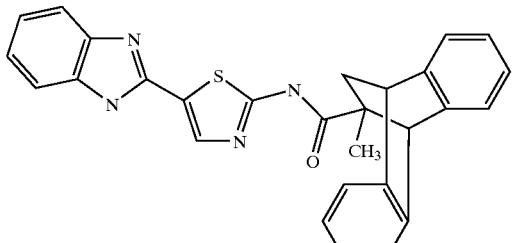 | 462.6 |

-continued
| Example | Chiral Compounds | Structure | MS: (M + H = MW +1) |
|---|---|---|---|
| 204 | | 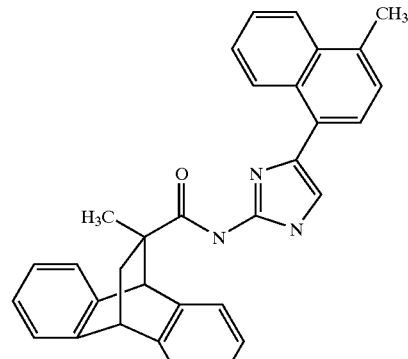 | 469.59 |
| 205 | | 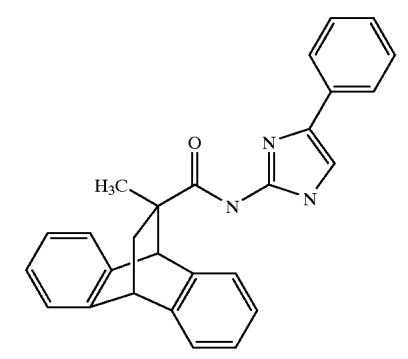 | 405.5 |
| 206 | | 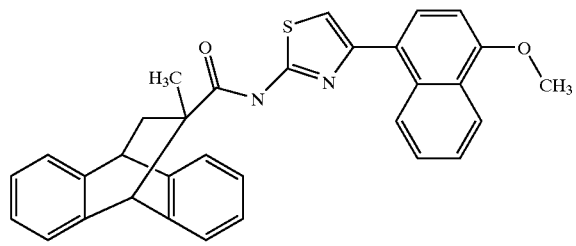 | 502.64 |
| 207 | Chiral (R) | 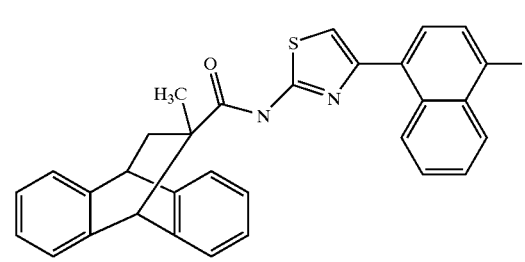 | 490.6 |
| 208 | Chiral (S) | 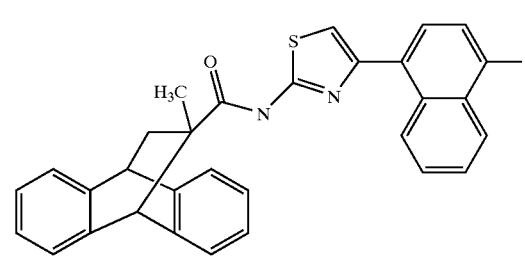 | 490.6 |

-continued
| Example | Chiral Compounds | Structure | MS: (M + H = MW +1) |
|---|---|---|---|
| 209 | | 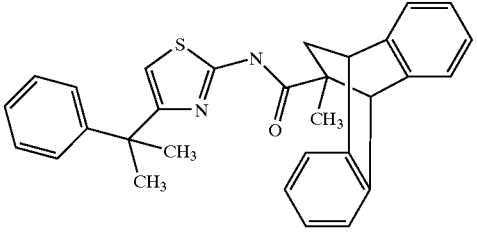 | 464.63 |
| 210 | | 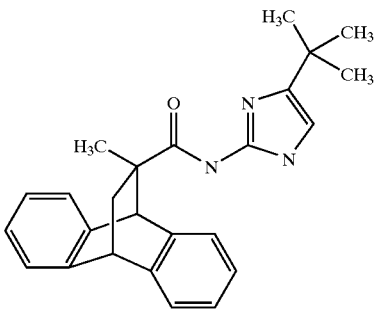 | 385.51 |
| 211 | | 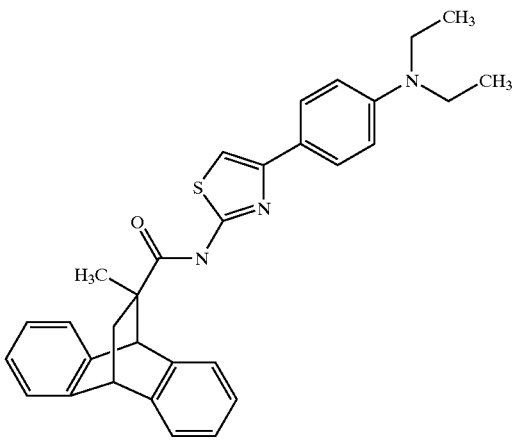 | 493.68 |
| 212 | | 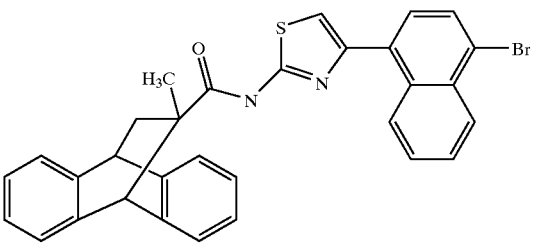 | 551.51 |
| 213 | Chiral (S) | 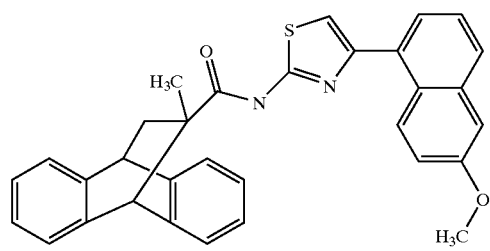 | 502.64 |

-continued
| Example | Chiral Compounds | Structure | MS: (M + H = MW +1) |
|---|---|---|---|
| 214 | Chiral (R) | 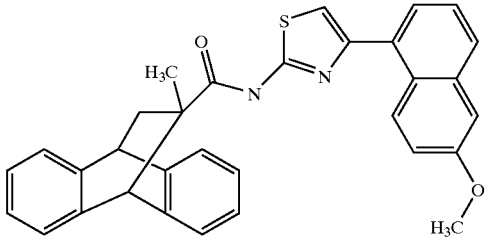 | 502.64 |
| 215 | | 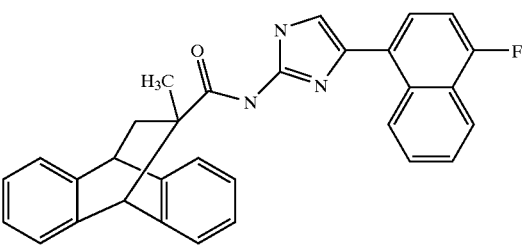 | 473.55 |
| 216 | Chiral (S) | 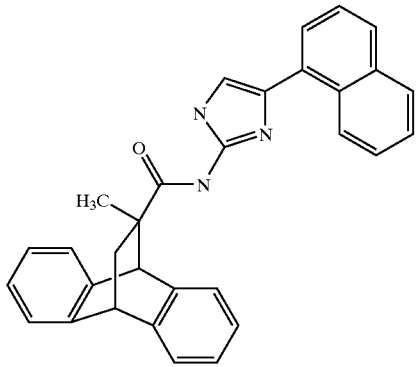 | 455.56 |
| 217 | Chiral (R) | 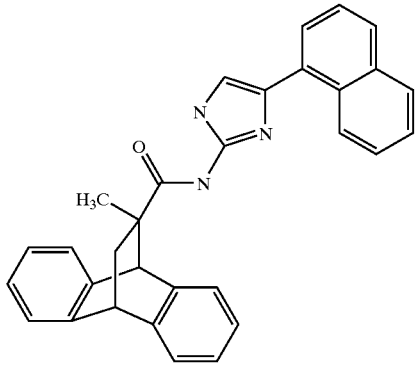 | 455.56 |

-continued
| Example | Chiral Compounds | Structure | MS: (M + H = MW +1) |
|---|---|---|---|
| 218 | Chiral (S) | 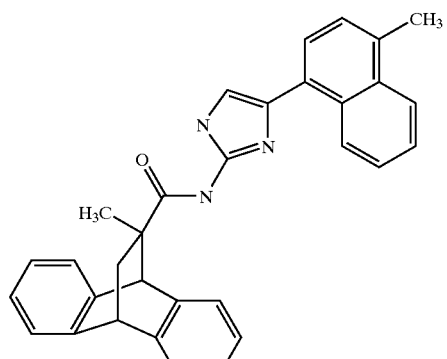 | 469.59 |
| 219 | Chiral (R) | 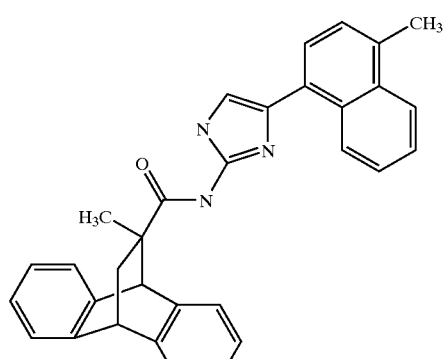 | 469.59 |
| 220 | | 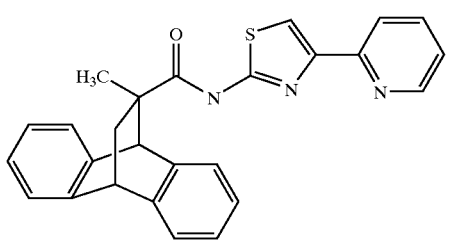 | 423.54 |
| 221 | | 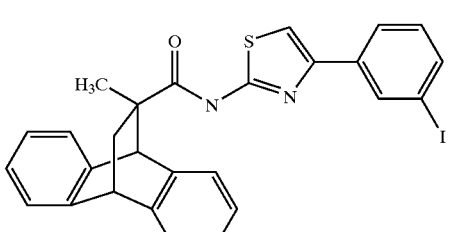 | 548.45 |
| 222 | | 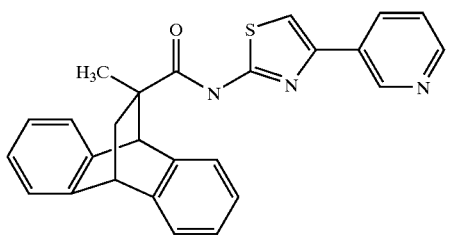 | 423.54 |

-continued
| Example | Chiral Compounds | Structure | MS: (M + H = MW +1) |
|---|---|---|---|
| 223 | | 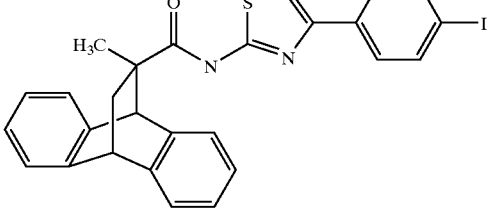 | 548.45 |
| 224 | | 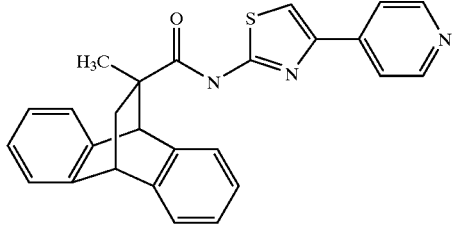 | 423.54 |
| 225 | | 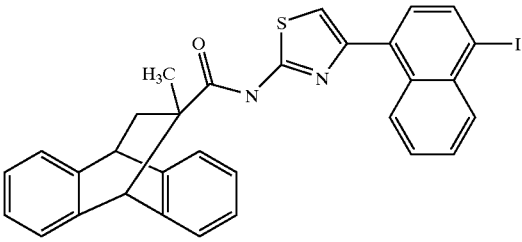 | 598.51 |
| 226 | | 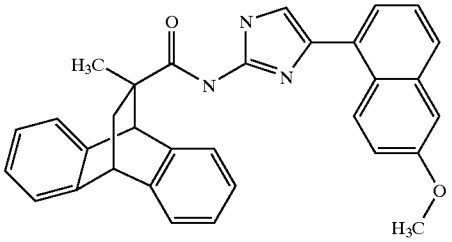 | 485,59 |
| 227 | Chiral (S) | 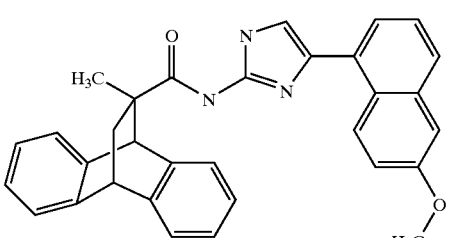 | 485.59 |
| 228 | Chiral (R) | 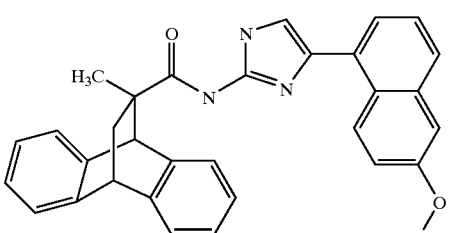 | 485.59 |

-continued
| Example | Chiral Compounds | Structure | MS: (M + H = MW +1) |
|---|---|---|---|
| 229 | Chiral (S) | 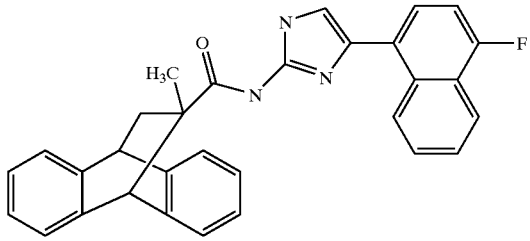 | 473.55 |
| 230 | Chiral (R) | 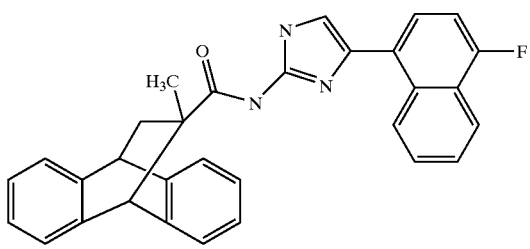 | 473.55 |
| 231 | | 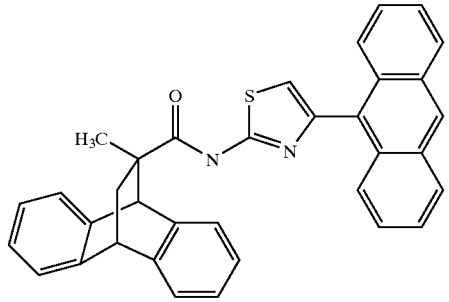 | 522.67 |
| 232 | Chiral (S) | 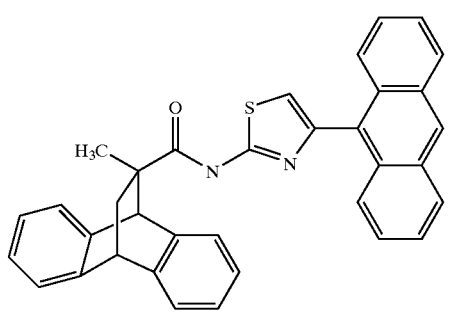 | 522.67 |
| 233 | Chiral (R) | 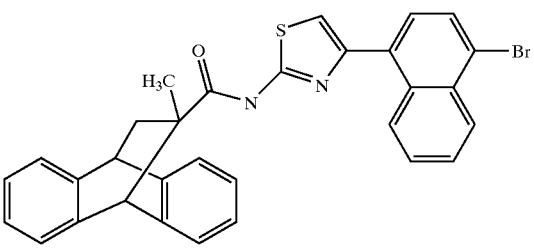 | 551.51 |

-continued

| Example | Chiral Compounds | Structure | MS: (M + H = MW +1) |
|---|---|---|---|
| 234 | Chiral (S) | 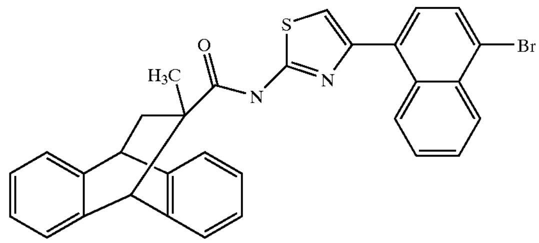 | 551.51 |
| 235 | Chiral (S) | 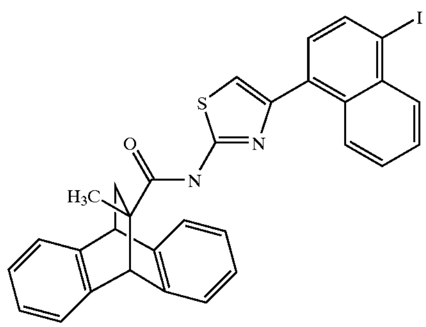 | 598.51 |
| 236 | Chiral (R) | 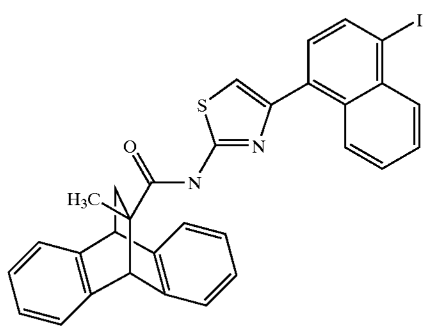 | 598.51 |
| 237 | | 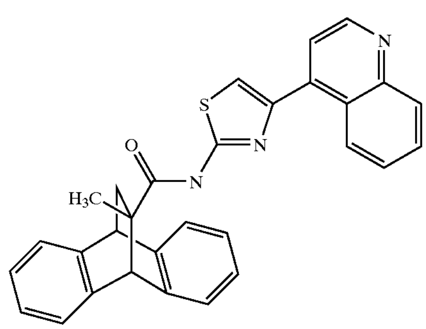 | 473.6 |
| 238 | | 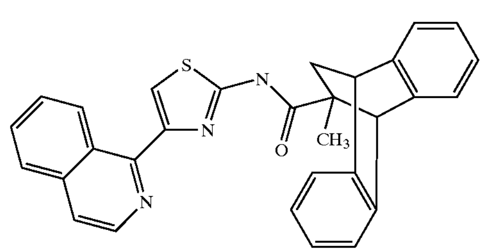 | 473.6 |

-continued
| Example | Chiral Compounds | Structure | MS: (M + H = MW +1) |
|---|---|---|---|
| 239 | Chiral (S) | 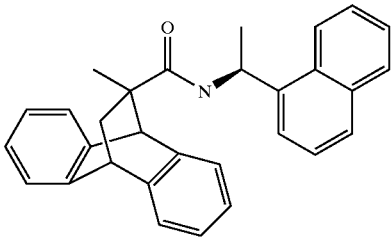 | 417.56 |
| 240 | | 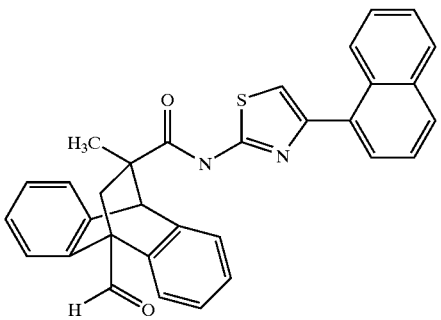 | 500.62 |
| 241 | | 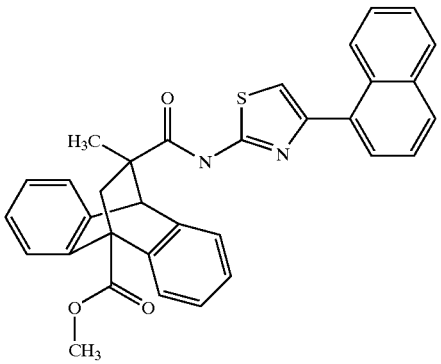 | 530.65 |
| 242 | | 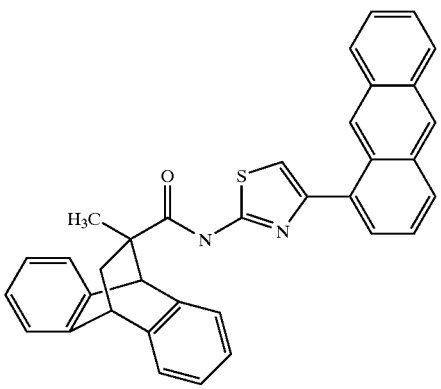 | 522.67 |

-continued

| Example | Chiral Compounds | Structure | MS: (M + H = MW +1) |
|---|---|---|---|
| 243 | Chiral (S) | 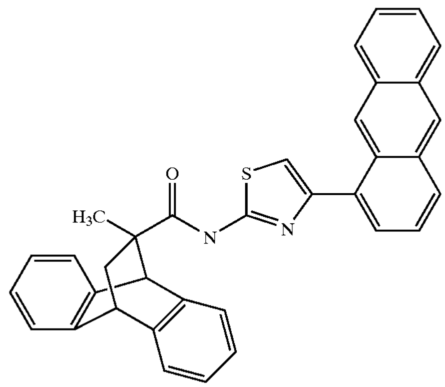 | 522.67 |
| 244 | | 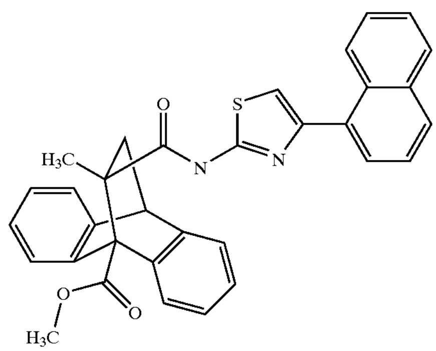 | 530.65 |
| 245 | | 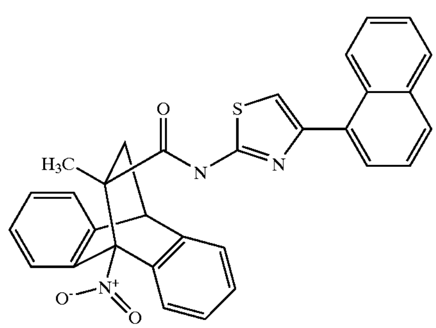 | 517.61 |
| 246 | | 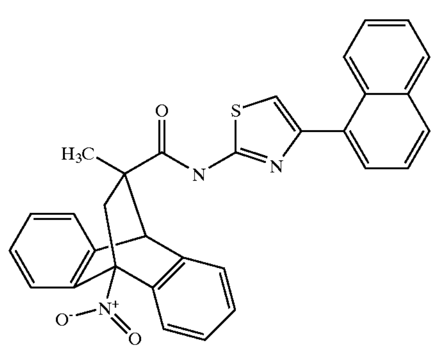 | 517.61 |

-continued
| Example | Chiral Compounds | Structure | MS: (M + H = MW +1) |
|---|---|---|---|
| 247 | | 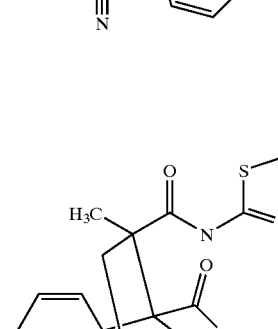 | 497.62 |
| 248 | | 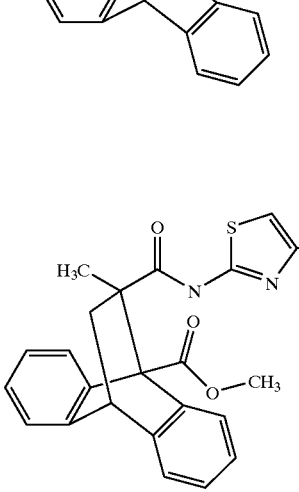 | 500.62 |
| 249 | | 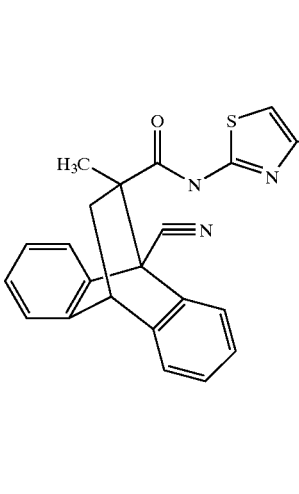 | 544.68 |
| 250 | | 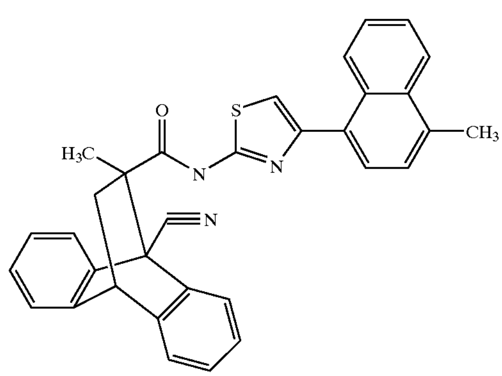 | 511.65 |

-continued
| Example | Chiral Compounds | Structure | MS: (M + H = MW +1) |
|---|---|---|---|
| 251 | | 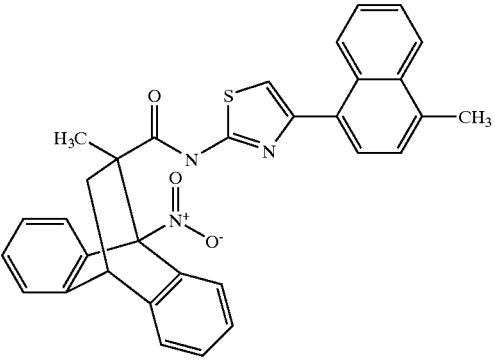 | 531.64 |
| 252 | | 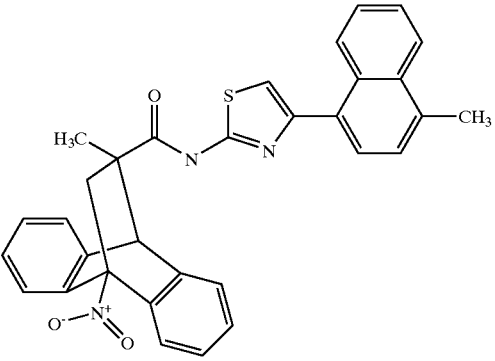 | 531.64 |
| 253 | | 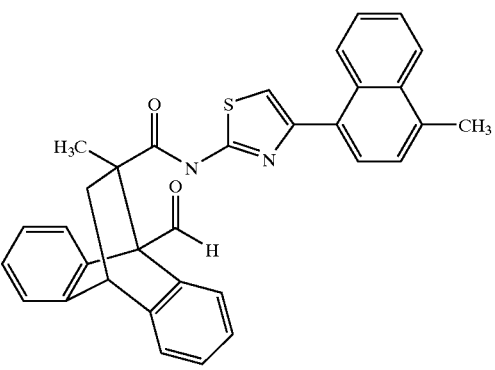 | 514.65 |
| 254 | | 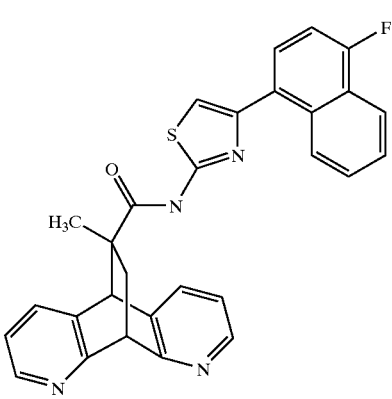 | 492.58 |

-continued

| Example | Chiral Compounds | Structure | MS: (M + H = MW +1) |
|---|---|---|---|
| 255 | | 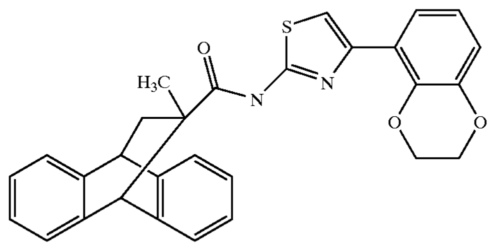 | 480.59 |
| 256 | | 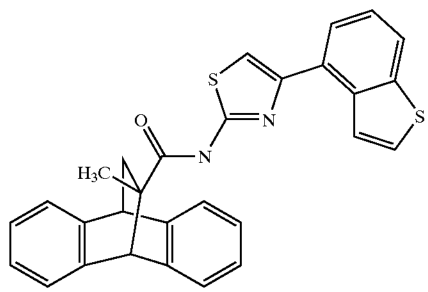 | 478.64 |
| 257 | | 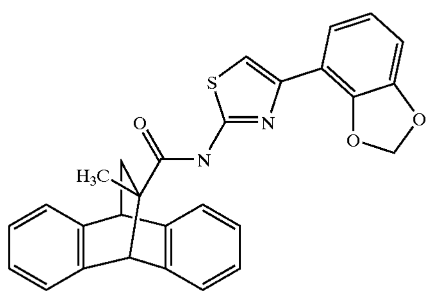 | 466.56 |
| 258 | | 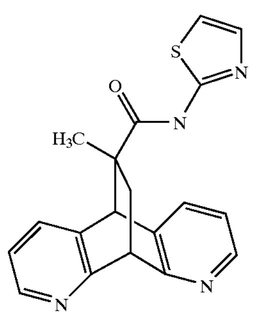 | 348.43 |
| 259 | | 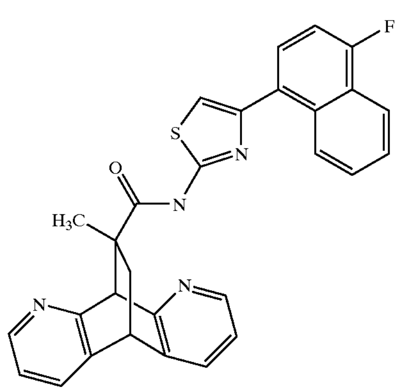 | 492.58 |

-continued

| Example | Chiral Compounds | Structure | MS: (M + H = MW +1) |
|---|---|---|---|
| 260 | | 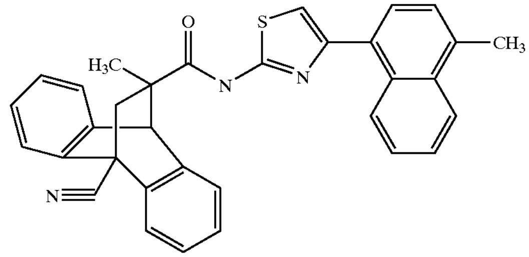 | 511.65 |
| 261 | | 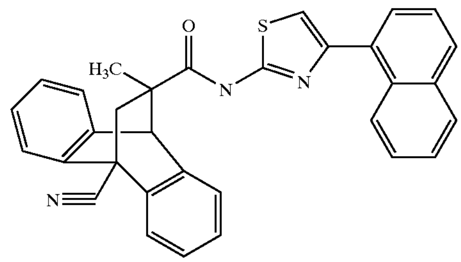 | 497.62 |
| 262 | | 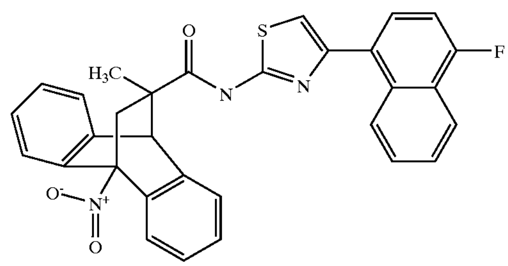 | 535.6 |
| 263 | | 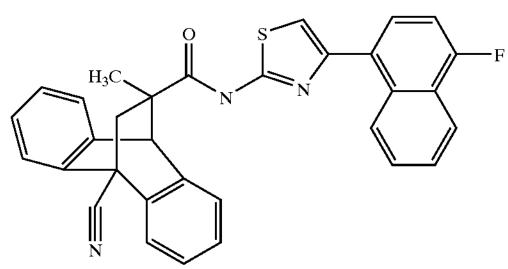 | 515.61 |
| 264 | Chiral (S) | 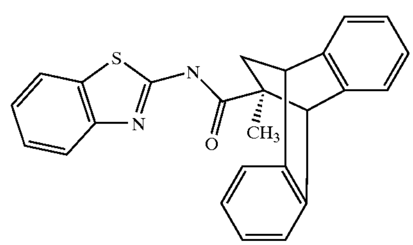 | 396.5 |
| 265 | Chiral (S) | 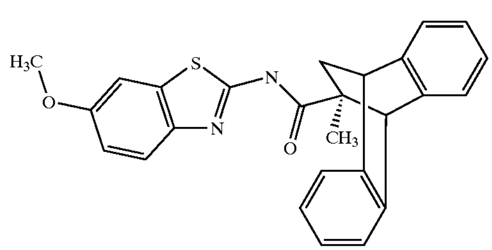 | 426.5 |

-continued

| Example | Chiral Compounds | Structure | MS: (M + H = MW +1) |
|---|---|---|---|
| 266 | Chiral (S) | 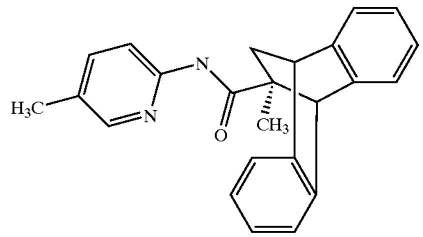 | 354.5 |
| 267 | Chiral (S) | 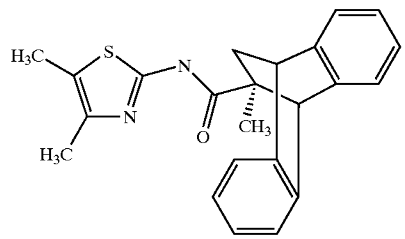 | 374.5 |
| 268 | Chiral (S) | 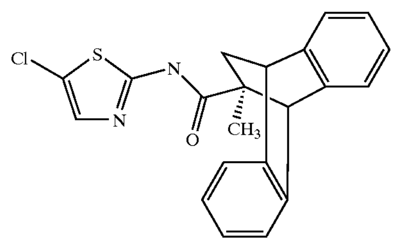 | 380.9 |
| 269 | Chiral (S) | 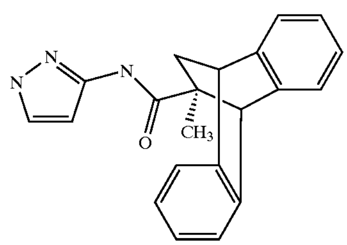 | 329.4 |
| 270 | Chiral (S) | 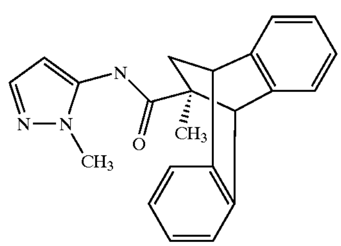 | 343.4 |
| 271 | Chiral (S) | 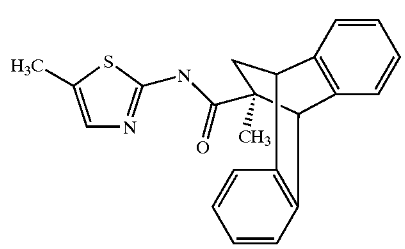 | 360.5 |

-continued

| Example | Chiral Compounds | Structure | MS: (M + H = MW +1) |
|---|---|---|---|
| 272 | Chiral (S) | 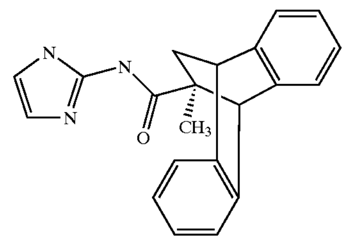 | 329.4 |
| 273 | Chiral (S) | 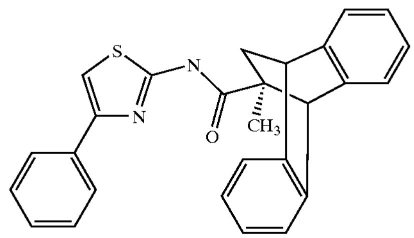 | 422.6 |
| 274 | Chiral (S) | 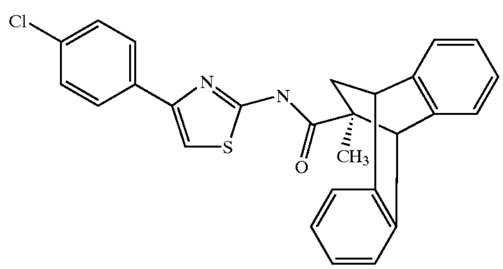 | 457 |
| 275 | Chiral (S) | 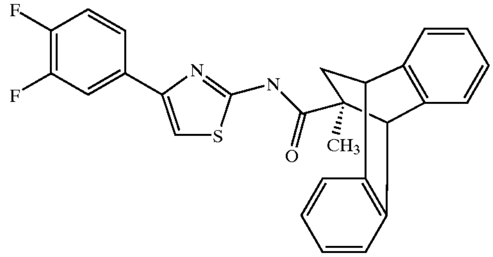 | 458.5 |
| 276 | Chiral (S) | 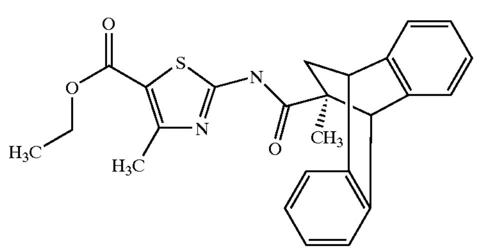 | 432.5 |
| 277 | Chiral (S) | 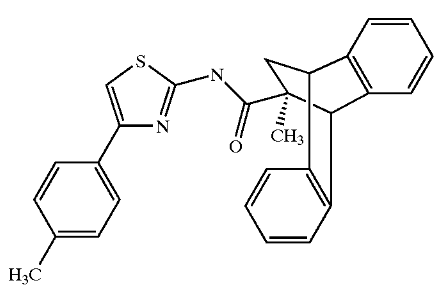 | 436.6 |

-continued

| Example | Chiral Compounds | Structure | MS: (M + H = MW +1) |
|---|---|---|---|
| 278 | Chiral (S) | 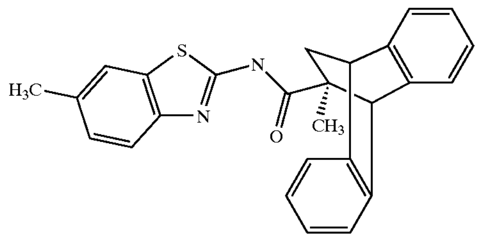 | 410.5 |
| 279 | Chiral (S) | 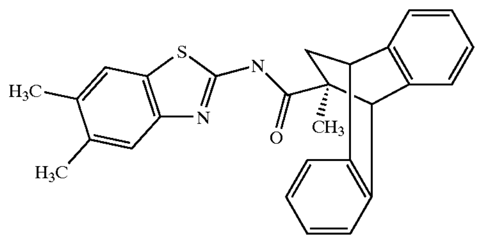 | 424.6 |
| 280 | Chiral (S) | 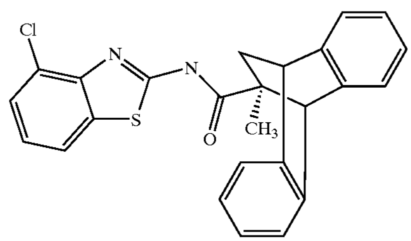 | 431 |
| 281 | Chiral (S) | 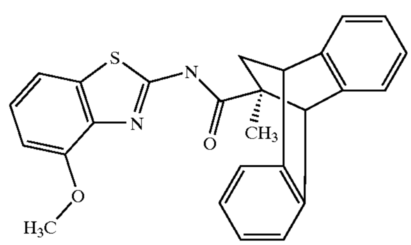 | 426.5 |
| 282 | Chiral (S) | 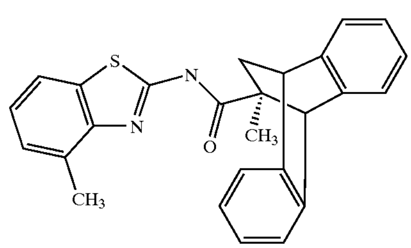 | 410.5 |
| 283 | Chiral (S) | 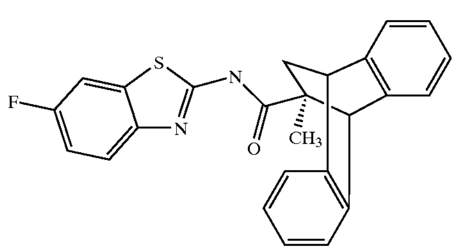 | 414.5 |

-continued

| Example | Chiral Compounds | Structure | MS: (M + H = MW +1) |
|---|---|---|---|
| 284 | Chiral (S) | 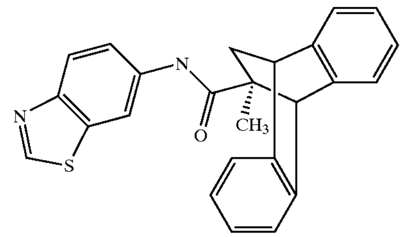 | 396.5 |
| 285 | Chiral (S) | 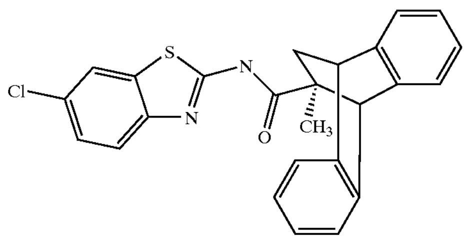 | 431 |
| 286 | Chiral (S) | 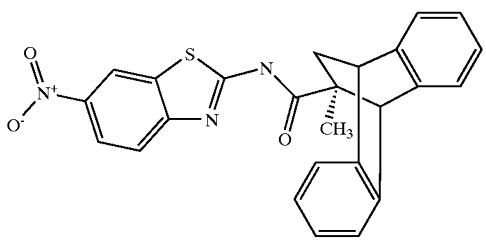 | 441.5 |
| 287 | Chiral (S) | 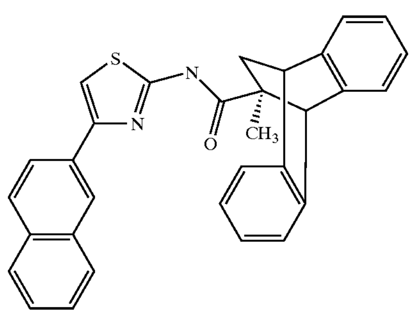 | 472.6 |
| 288 | Chiral (S) | 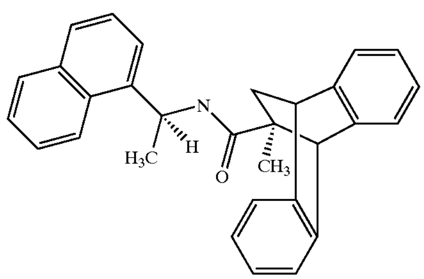 | 417.6 |

-continued
| Example | Chiral Compounds | Structure | MS: (M + H = MW +1) |
|---|---|---|---|
| 289 | Chiral (S) | 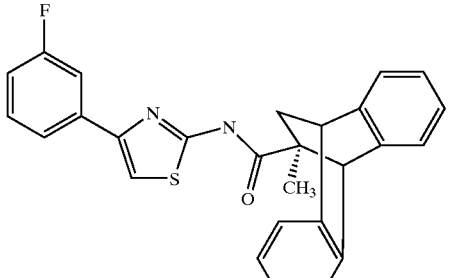 | 440.5 |
| 290 | Chiral (S) | 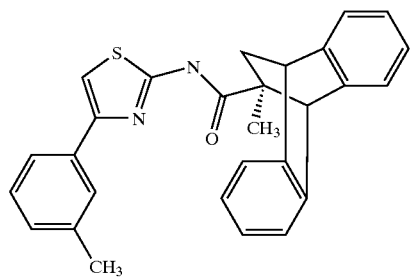 | 436.6 |
| 291 | Chiral (S) | 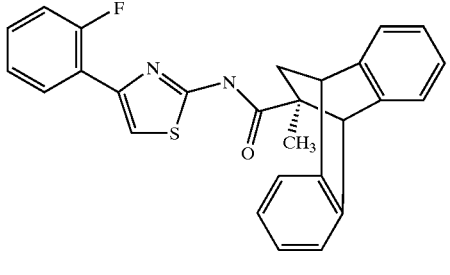 | 440.5 |
| 292 | Chiral (S) | 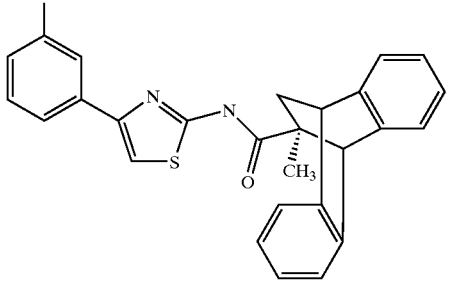 | 457 |
| 293 | Chiral (S) | 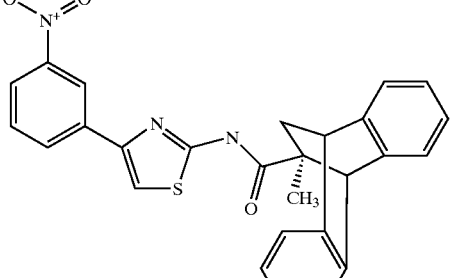 | 467.6 |

-continued

| Example | Chiral Compounds | Structure | MS: (M + H = MW +1) |
|---|---|---|---|
| 294 | Chiral (S) | 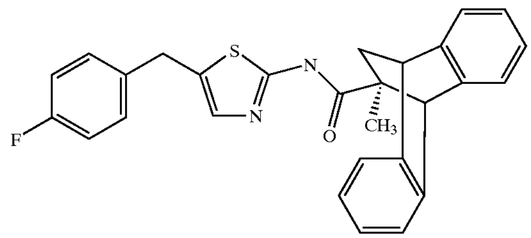 | 454.6 |
| 295 | Chiral (S) | 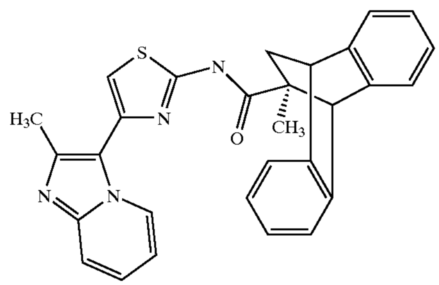 | 476.6 |
| 296 | Chiral (S) | 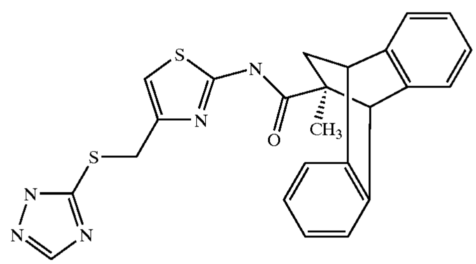 | 459.6 |
| 297 | Chiral (S) | 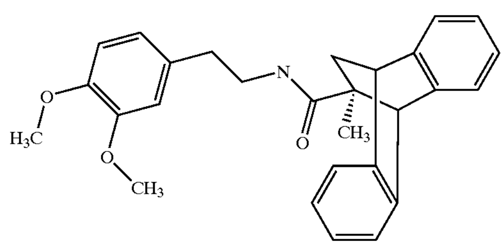 | 427.5 |
| 298 | Chiral (S) | 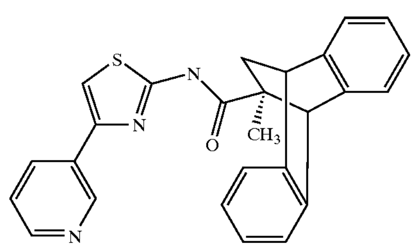 | 423.5 |
| 299–300 | Chiral (S) | 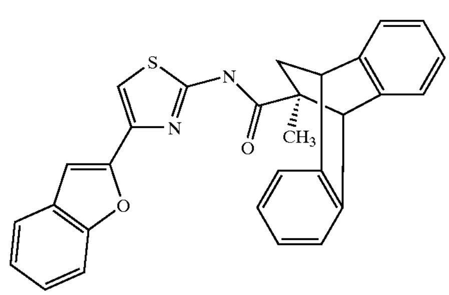 | 462.6 |

-continued

| Example | Chiral Compounds | Structure | MS: (M + H = MW +1) |
|---|---|---|---|
| 301 | Chiral (S) | 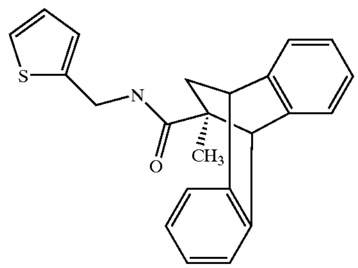 | 359.5 |
| 302 | Chiral (S) | 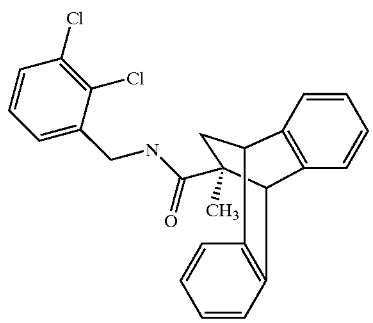 | 422.4 |
| 303 | Chiral (R) | 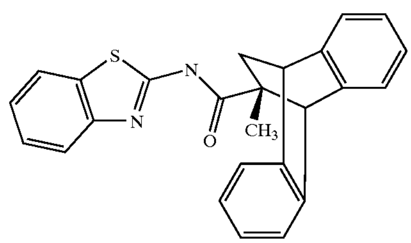 | 396.5 |
| 304 | Chiral (R) | 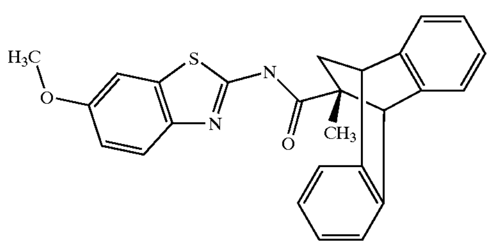 | 426.5 |
| 305 | Chiral (R) | 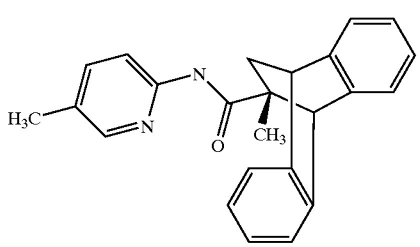 | 354.5 |

-continued
| Example | Chiral Compounds | Structure | MS: (M + H = MW +1) |
|---------|------------------|-----------|---------------------|
| 306 | Chiral (R) | 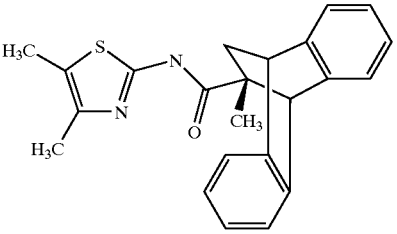 | 374.5 |
| 307 | Chiral (R) | 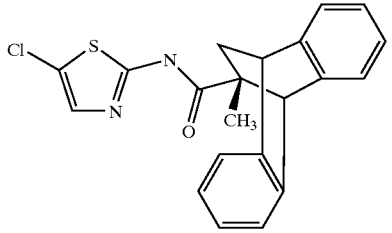 | 380.9 |
| 308 | Chiral (R) | 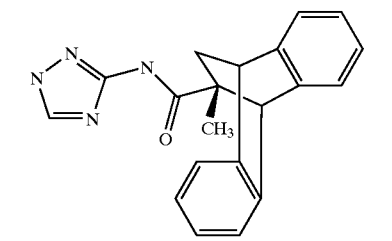 | 329.4 |
| 309 | Chiral (R) | 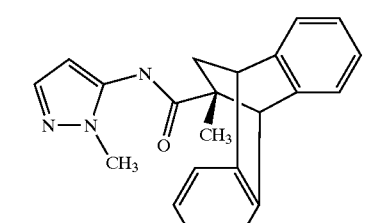 | 343.4 |
| 310 | Chiral (R) | 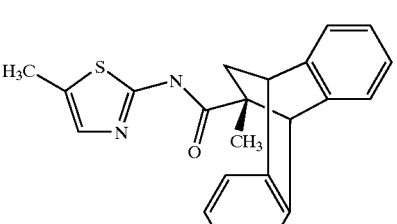 | 360.5 |
| 311 | Chiral (R) | 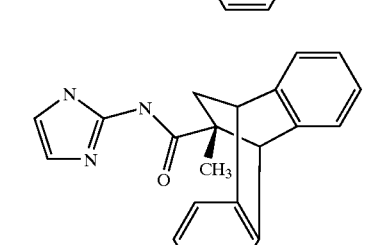 | 329.4 |

-continued

| Example | Chiral Compounds | Structure | MS: (M + H = MW +1) |
|---|---|---|---|
| 312 | Chiral (R) | 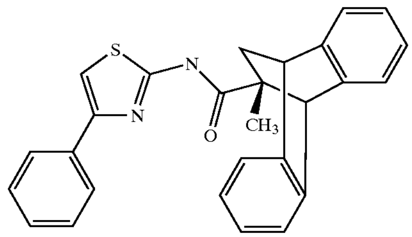 | 422.6 |
| 313 | Chiral (R) | 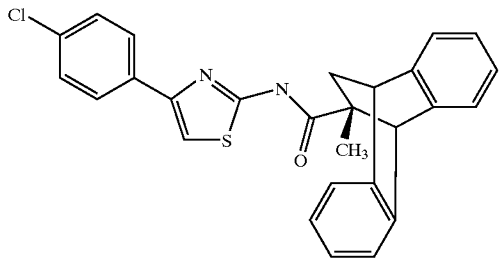 | 457 |
| 314 | Chiral (R) | 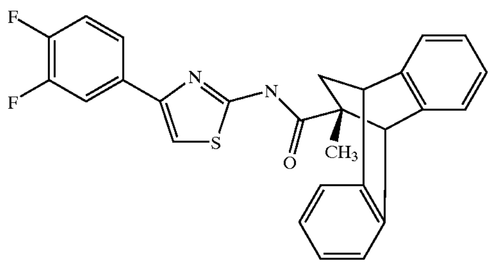 | 458.5 |
| 315 | Chiral (R) | 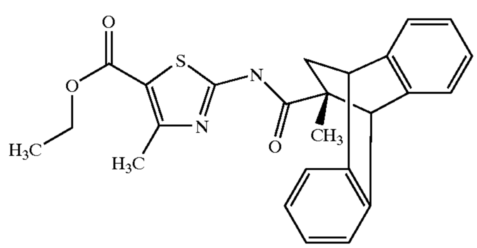 | 432.5 |
| 316 | Chiral (R) | 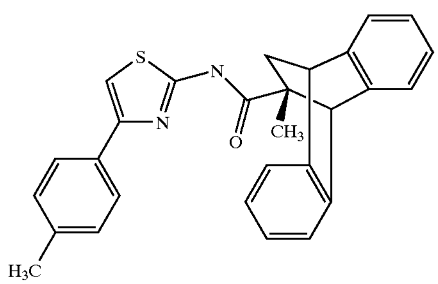 | 436.6 |
| 317 | Chiral (R) | 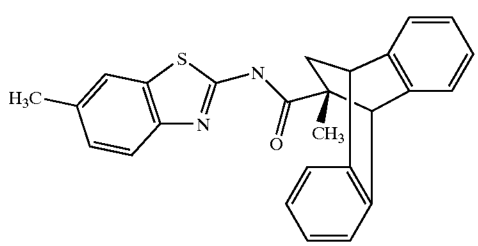 | 410.5 |

-continued

| Example | Chiral Compounds | Structure | MS: (M + H = MW +1) |
|---|---|---|---|
| 318 | Chiral (R) | 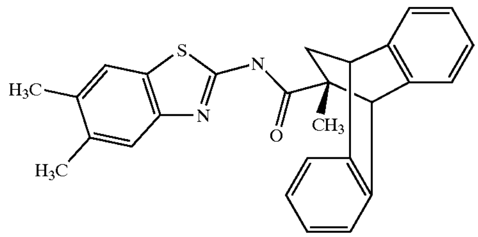 | 424.6 |
| 319 | Chiral (R) | 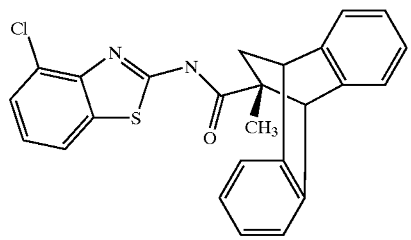 | 431 |
| 320 | Chiral (R) | 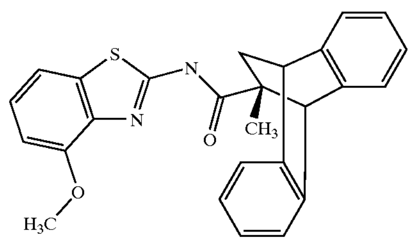 | 426.5 |
| 321 | Chiral (R) | 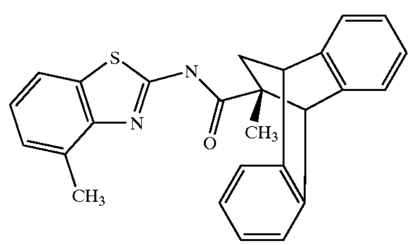 | 410.5 |
| 322 | Chiral (R) | 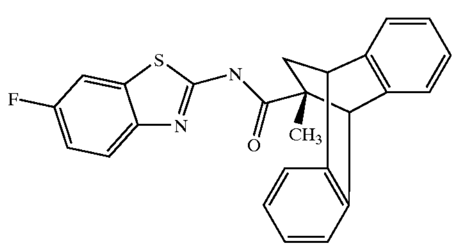 | 414.5 |
| 323 | Chiral (R) | 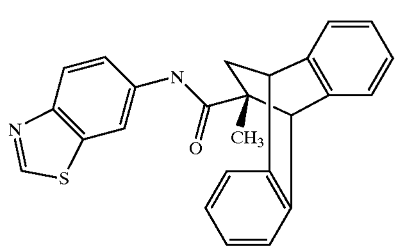 | 396.5 |

-continued

| Example | Chiral Compounds | Structure | MS: (M + H = MW +1) |
|---|---|---|---|
| 324 | Chiral (R) | 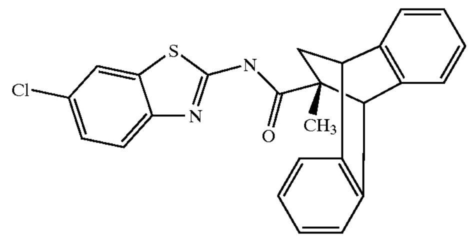 | 431 |
| 325 | Chiral (R) | 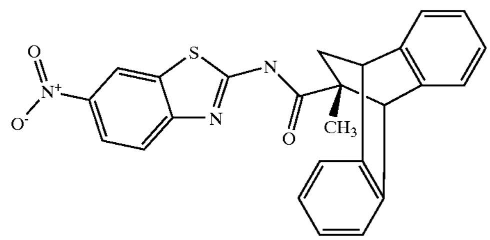 | 441.5 |
| 326 | Chiral (R) | 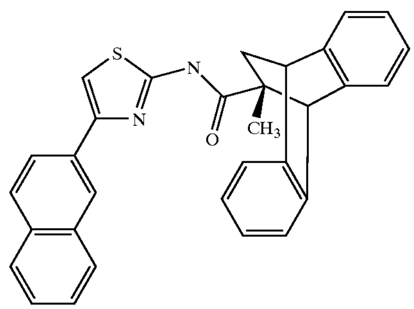 | 472.6 |
| 327 | Chiral (R) | 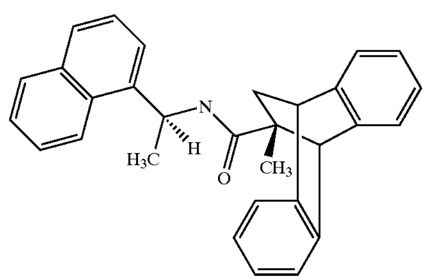 | 417.6 |
| 328 | Chiral (R) | 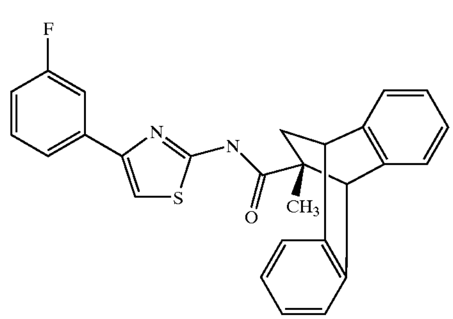 | 440.5 |

-continued

| Example | Chiral Compounds | Structure | MS: (M + H = MW +1) |
|---|---|---|---|
| 329 | Chiral (R) | 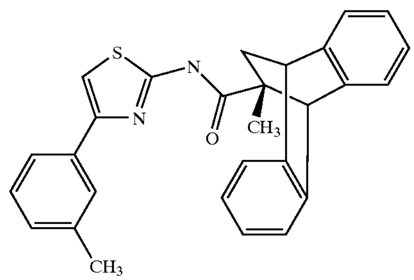 | 436.6 |
| 330 | Chiral (R) | 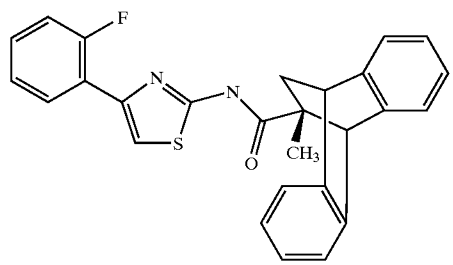 | 440.5 |
| 331 | Chiral (R) | 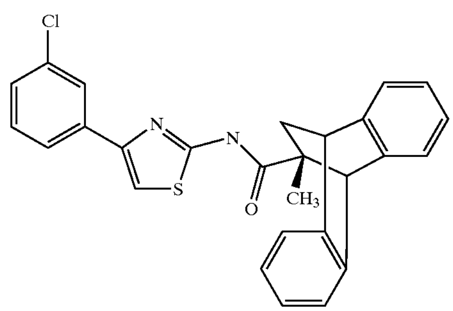 | 457 |
| 332 | Chiral (R) | 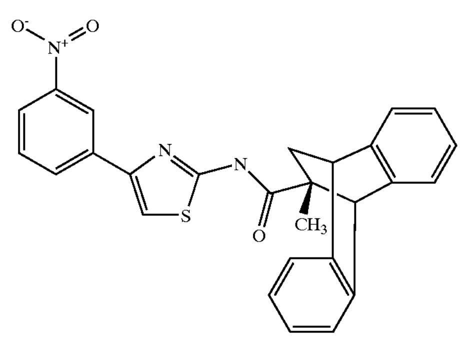 | 467.6 |
| 333 | Chiral (R) | 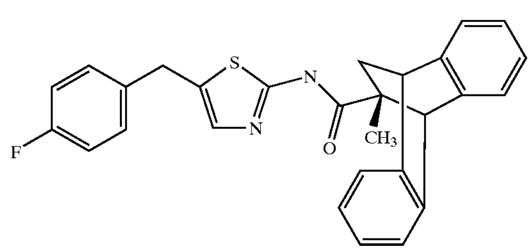 | 454.6 |

-continued

| Example | Chiral Compounds | Structure | MS: (M + H = MW +1) |
|---|---|---|---|
| 334 | Chiral (R) | 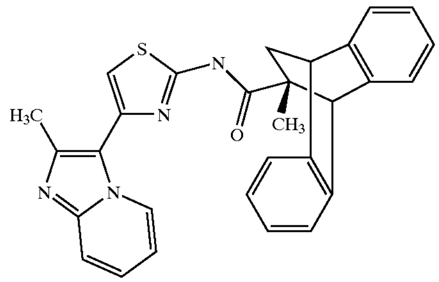 | 476.6 |
| 335 | Chiral (R) | 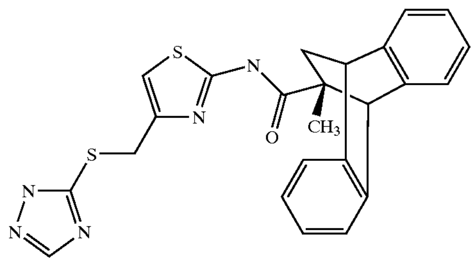 | 459.6 |
| 336 | Chiral (R) | 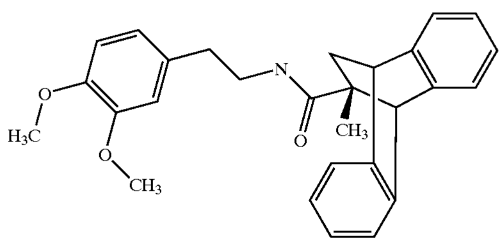 | 427.5 |
| 337 | Chiral (R) | 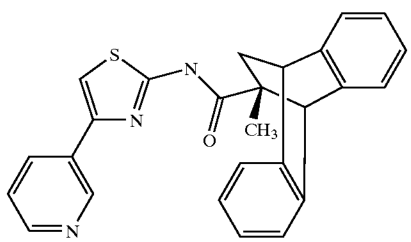 | 423.5 |
| 338 | Chiral (R) | 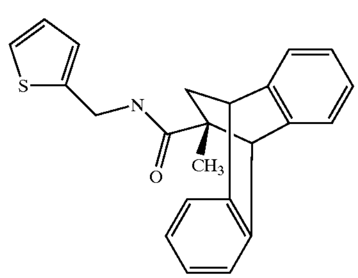 | 359.5 |

-continued

| Example | Chiral Compounds | Structure | MS: (M + H = MW +1) |
|---|---|---|---|
| 339 | Chiral (R) | 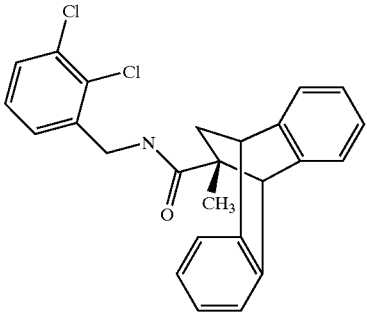 | 422.4 |

Example 340

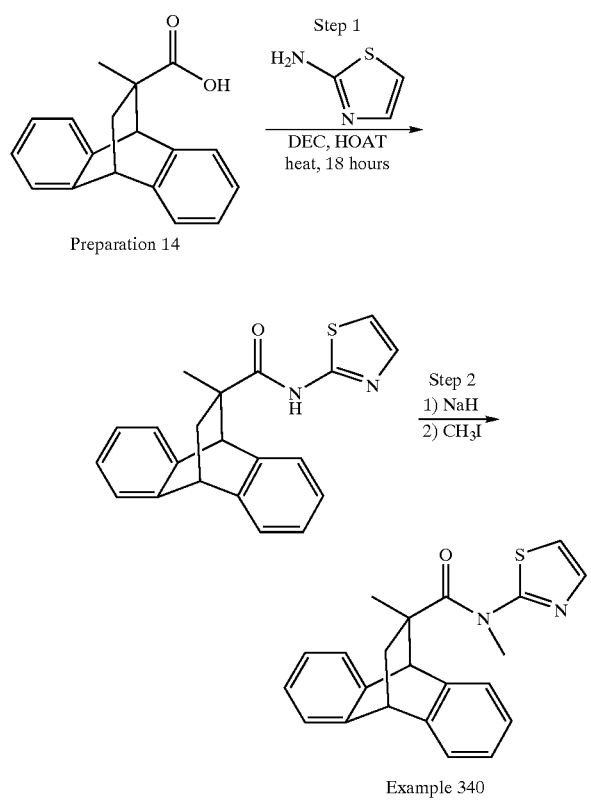

Example 340

Step 1

To a solution of the product of preparation 14 (100 mg, 0.38 mmol, 1.0 equi.) in acetonitrile (5 mL) was added 1-[3-(dimethylamino) propyl]-3-ethylcarbodiimide hydrochloride (DEC) (87 mg, 0.45 mmol, 1.2 equi.), 1-hydroxy-7-azabenzotriazole (HOAt) (62 mg. 0.45 mmol, 1.2 equi.), triethyl amine (0.13 mL, 0.94 mmol, 2.5 equi.), and 2-aminothiazole (45.5 mg, 0.45 mmol, 1.2 equi.). The reaction solution was heated to 80° C. for 18 hours. The reaction was then concentrated in vacuo. The product mixture was purified by flash chromatography (20% ethyl acetate in hexane) to yield 112.4 mg (86%) of the product of step 1: LC/MS (m/z 347, (M+H)$^+$); $^1$H NMR (CDCl$_3$) δ 7.52 (d, 1H), 6.98–7.27 (m, 9H), 4.42 (s, 1H), 4.32 (t, 1H), 2.69 (dd, 1H), 1.52 (dd, 1H), 1.16(s, 3H).

Step 2

To a solution of the product of step 1 (175 mg, 0.5 mmol, 1.0 equi.) in THF (5 mL) was added sodium hydride (18 mg, 0.75 mmol, 1.5 equi.) and the solution stirred at RT for 1 hour. A solution of methyl iodide (0.047 mL, 0.75 mmol, 1.5 equi.) in THF (1 mL) was added and the reaction solution was stirred at RT for 3 hours. The solution was quenched with ethyl acetate. The organic layer was washed with water, saturated sodium chloride, dried with magnesium sulfate and concentrated in vacuo. Purification of the crude product mixture by flash chromatography (10% ethyl acetate in hexane) yielded 141.7 mg (78%) of Example 340: LC/MS (m/z 361 (M+H)$^+$); $^1$H NMR (CDCl$_3$) δ 6.41–7.12 (m, 8H), 4.67 (s, 1H), 4.3 (t, 1H), 3.63 (s, 3H), 3.0 (dd, 1H), 1.49 (dd, 1H), 1.07 (s, 3H).

Examples 341 TO 343

In a similar manner the following compounds were prepared.

| Example | Structure | MS: (M + H = MW +1) |
|---|---|---|
| 341 | 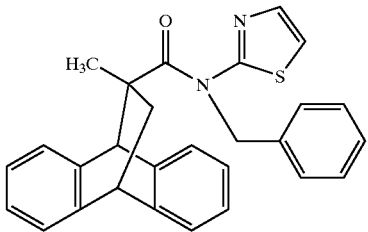 | 436.58 |

-continued
| Example | Structure | MS: (M + H = MW +1) |
|---|---|---|
| 342 | 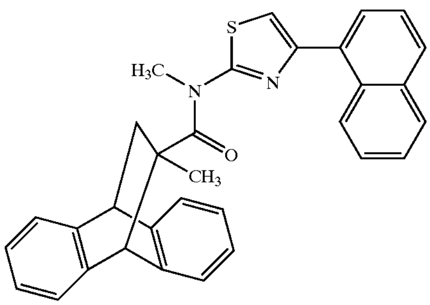 | 486.64 |
| 343 | 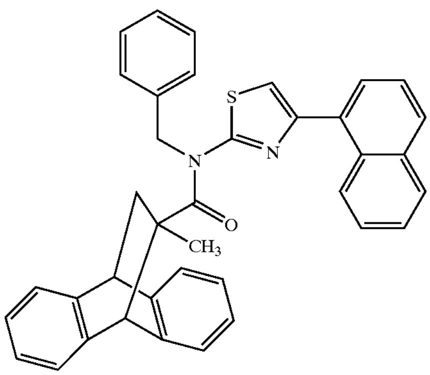 | 562.74 |
Examples 344 TO 346
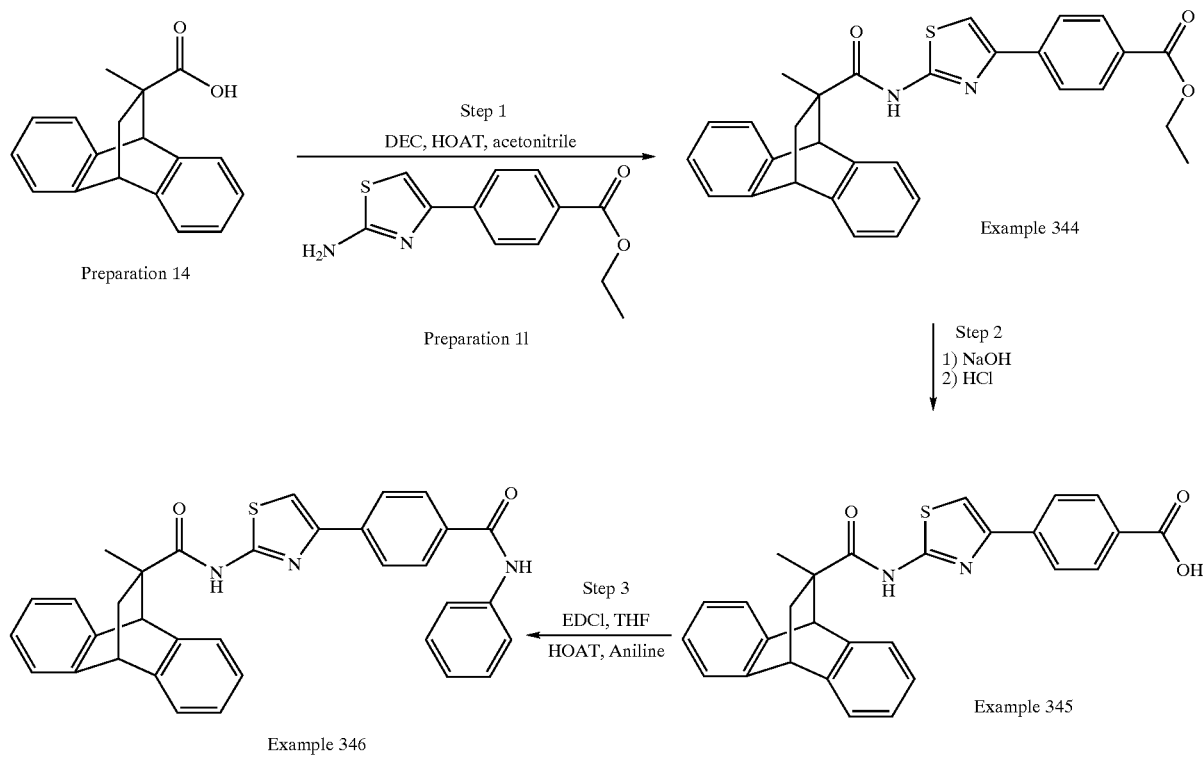

Step 1

To a solution of the product of Preparation 14, (4.72 mmol, 1.25 g) in acetonitrile (20 mL) was added 1-[3-(dimethylamino)propyl-3-ethylcarbodiimide hydrochloride (EDCI), (5.66 mmol, 1.09 g), 1-hydroxy-7-azabenzotriazole (HOAt), (5.66 mmol, 0.77 g), triethylamine (11.8 mmol, 1.20 g) and the product of preparation 11(5.66 mmol, 1.41 g). The resulting mixture was heated to 80° C. for 20 h, cooled and concentrated in vacuo. The residue was chromatographed on silica gel (eluted with 15% ethyl acetate in hexane) to give 1.80 g (Y: 77%) of Example 344. MS (E+) m/z: 494 (MH$^+$).

Step 2

To a solution of Example 344 (3.44 mmol, 1.70 g) in EtOH (30 mL) was added 10 N NaOH (2.0 mL). The resulting mixture was heated to 75° C. for 2.5 h, cooled and diluted with an excess of 1 N HCl. The mixture was then extracted with dichloromethane (3×100 mL), dried over Na$_2$SO$_4$ and concentrated under vacuo to give 1.40 g (Y: 88%) of Example 345. MS (E+) m/z: 467 (MH$^+$).

Step 3

To a solution of Example 345 (0.038 mmol, 18.0 mg) in tetrahydrofuran (1.0 mL) was added 1-[3-(dimethylamino)propyl-3-ethylcarbodiimide hydrochloride (EDCI), (0.046 mmol, 8.9 mg), 1-hydroxy-7-azabenzotriazole (HOAt), (0.046 mmol, 6.3 mg), triethylamine (0.046 mmol, 5.6 mg) and aniline (0.046 mmol, 4.3 mg). After 20 h at room temperature the product was purified using solid phase extraction cartridges (500 mg l/l high load, SCX strong cation exchanger/SAX strong anion exchanger) from United Chemical Technologies, Inc. After conditioning the cartridge with MeOH (2×1.5 mL) the crude reaction mixture was loaded on to the cartridge. The cartridge was then washed with MeOH (2×1.5 mL) to afford two fractions of the title compound. These fractions were combined & concentrated and then purified a second time using solid phase extraction cartridges (500 mg SAX strong anion exchanger) to remove any HOAt that was still present. After conditioning the cartridge with MeOH (2×1.5 mL) the crude product was loaded on to the cartridge. The cartridge was then washed with MeOH (1×1.5 mL) and the eluent was collected. The resultant eluent was evaporated in vacuo to afford 7.70 mg (37%) of Example 346. MS (E+) m/z: 542 (MH$^+$).

Examples 347 to 563

In a similar manner the Examples 347–563 were prepared.

| Example | Chiral Compounds | Structure | MS: (M + H = MW +1) |
|---|---|---|---|
| 347 | | 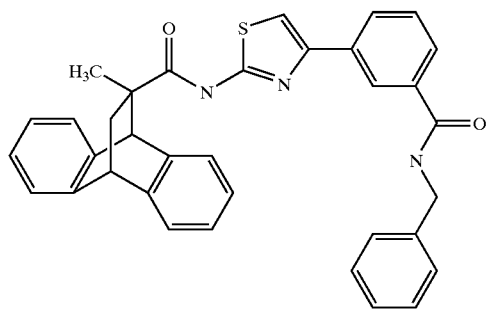 | 555.7 |
| 348 | | 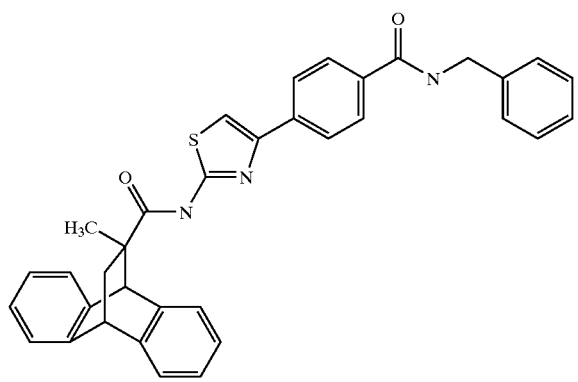 | 555.7 |

-continued
| Example | Chiral Compounds | Structure | MS: (M + H = MW +1) |
|---|---|---|---|
| 349 | | 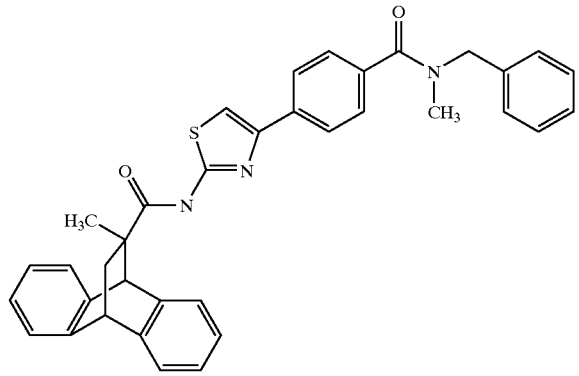 | 569.73 |
| 350 | | 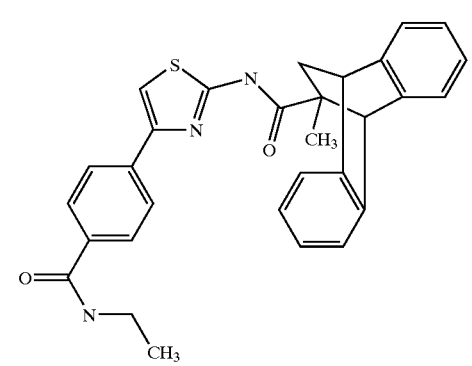 | 493.6 |
| 351 | | 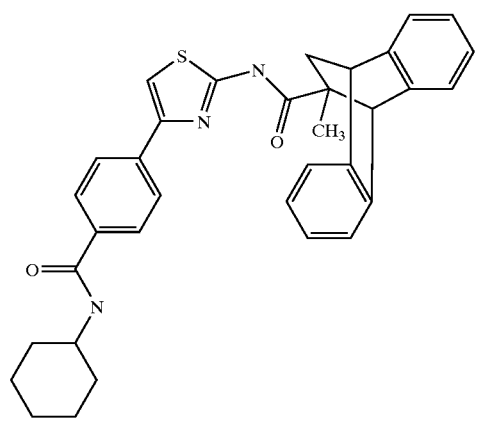 | 547.7 |
| 352 | | 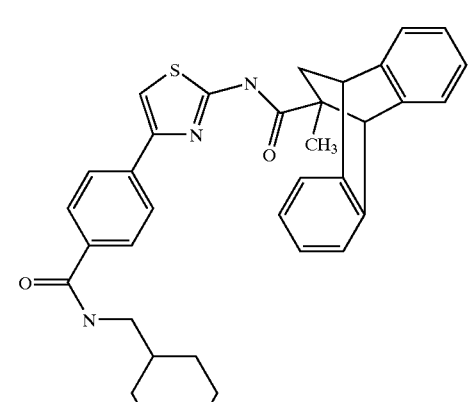 | 561.8 |

-continued
| Example | Chiral Compounds | Structure | MS: (M + H = MW +1) |
|---|---|---|---|
| 353 | | 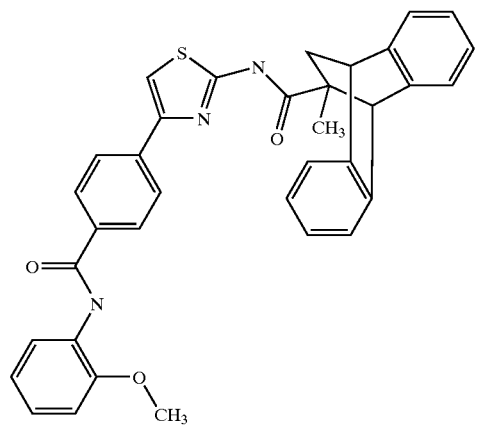 | 571.7 |
| 354 | | 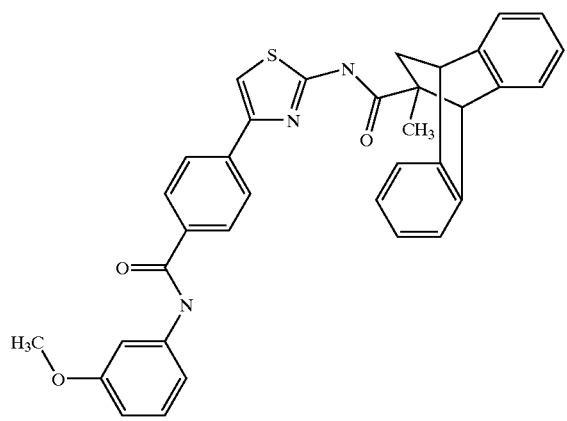 | 571.7 |
| 355 | | 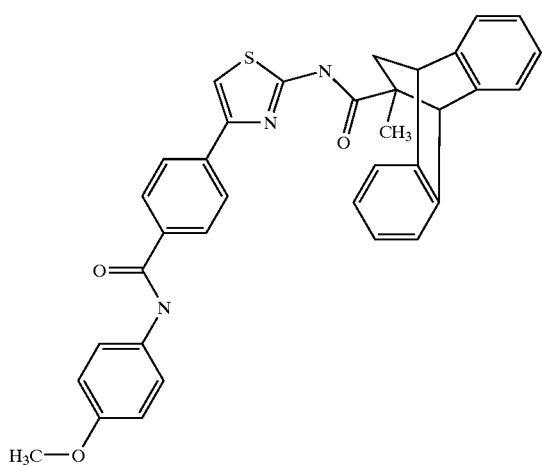 | 571.7 |

-continued

| Example | Chiral Compounds | Structure | MS: (M + H = MW +1) |
|---|---|---|---|
| 356 | | 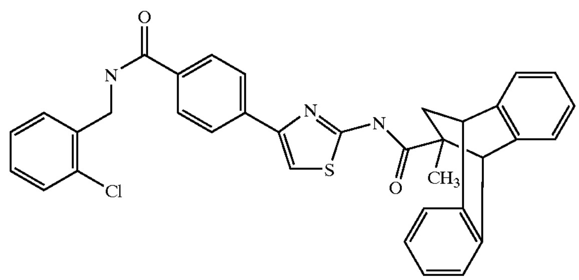 | 590.2 |
| 357 | | 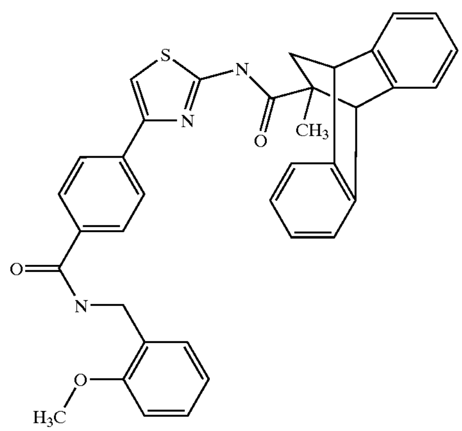 | 585.7 |
| 358 | | 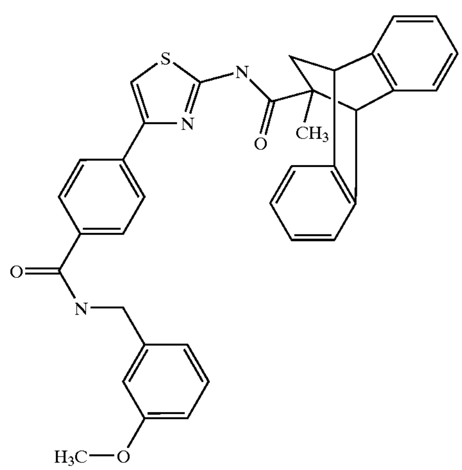 | 585.7 |
| 359 | | 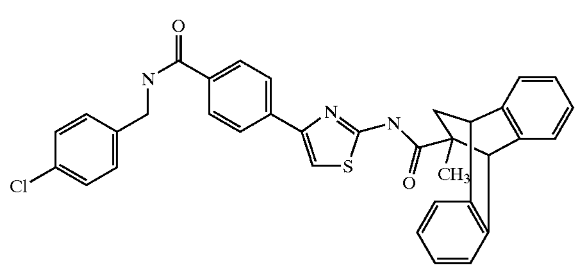 | 590.2 |

-continued
| Example | Chiral Compounds | Structure | MS: (M + H = MW +1) |
|---|---|---|---|
| 360 | | 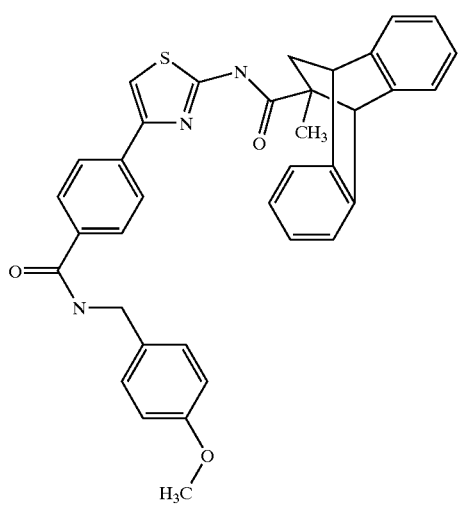 | 585.7 |
| 361 | | 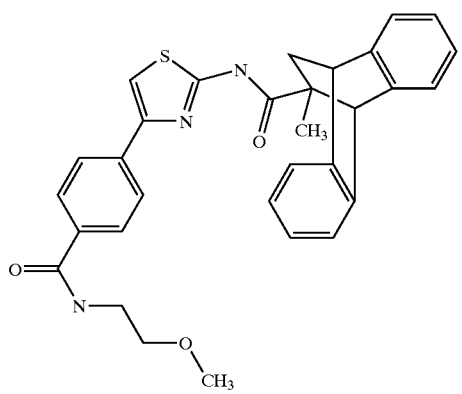 | 523.7 |
| 362 | | 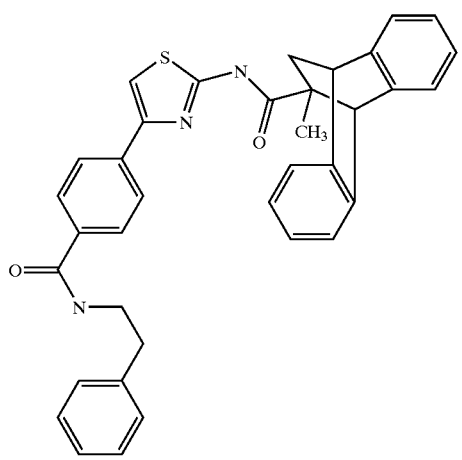 | 569.7 |

-continued

| Example | Chiral Compounds | Structure | MS: (M + H = MW +1) |
|---|---|---|---|
| 363 | | 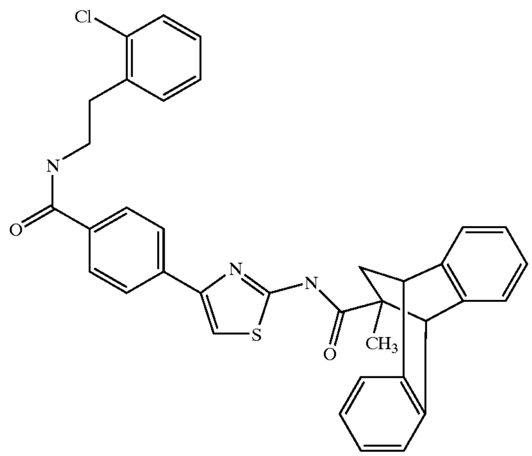 | 604.2 |
| 364 | | 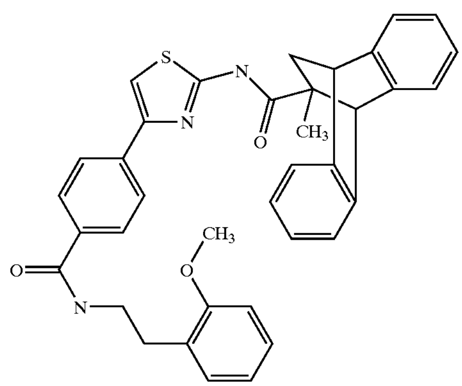 | 599.8 |
| 365 | | 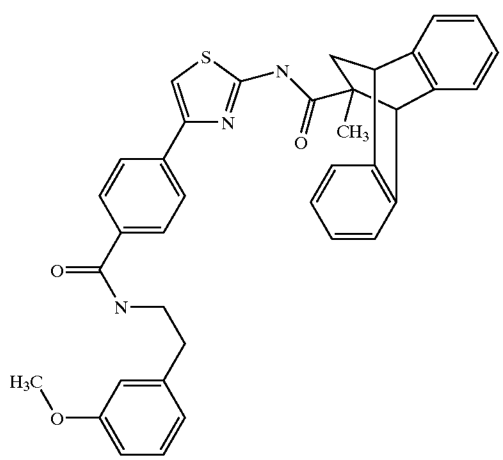 | 599.8 |

-continued
| Example | Chiral Compounds | Structure | MS: (M + H = MW +1) |
|---|---|---|---|
| 366 | | 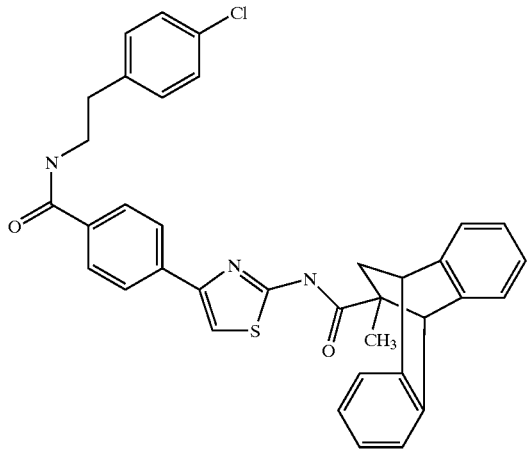 | 604.2 |
| 367 | | 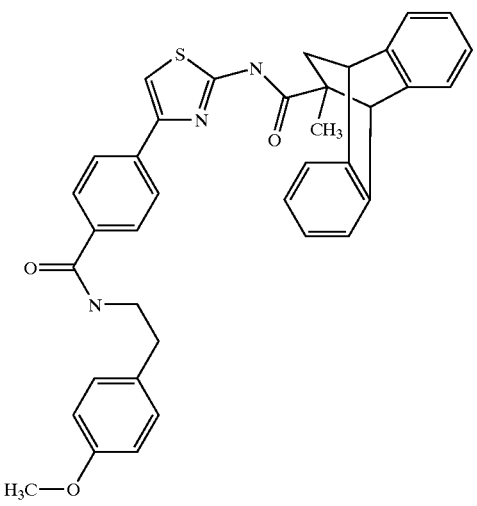 | 599.8 |
| 368 | | 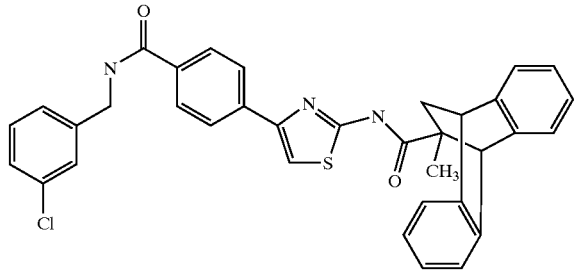 | 590.2 |

-continued

| Example | Chiral Compounds | Structure | MS: (M + H = MW +1) |
|---|---|---|---|
| 369 | | 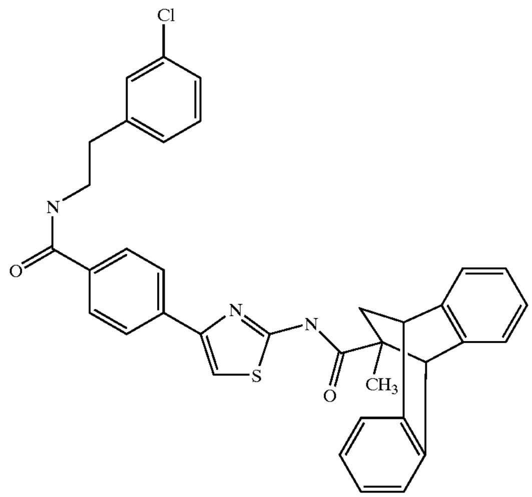 | 604.2 |
| 370 | | 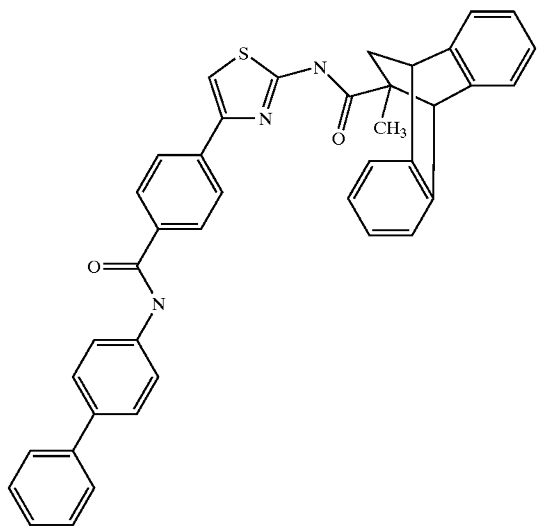 | 617.8 |
| 371 | | 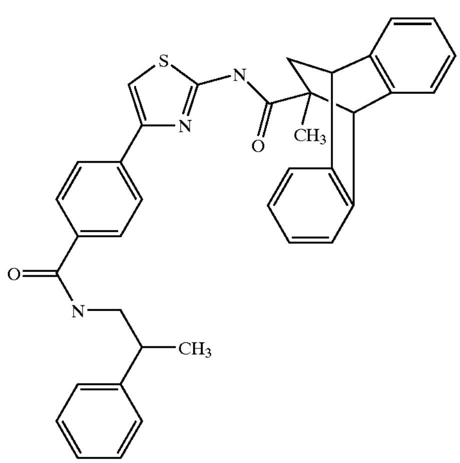 | 583.8 |

-continued

| Example | Chiral Compounds | Structure | MS: (M + H = MW +1) |
|---------|------------------|-----------|---------------------|
| 372 | | 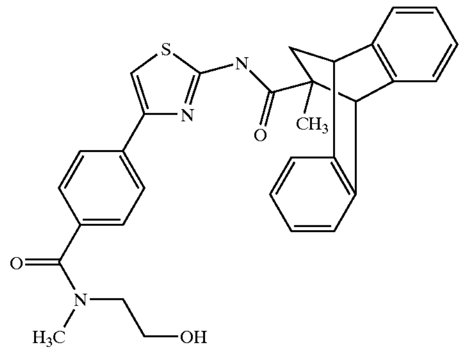 | 523.7 |
| 373 | | 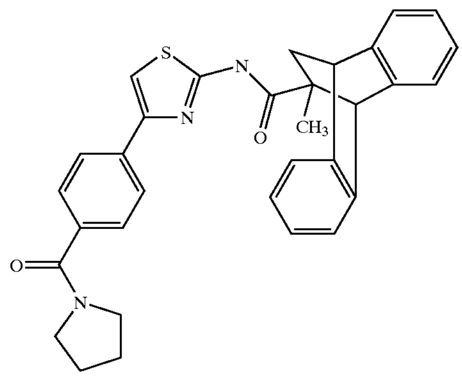 | 519.7 |
| 374 | | 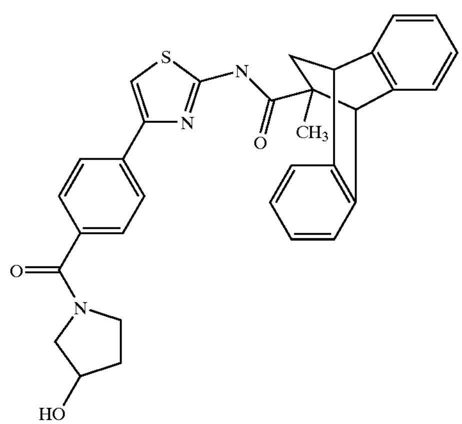 | 535.7 |
| 375 | | 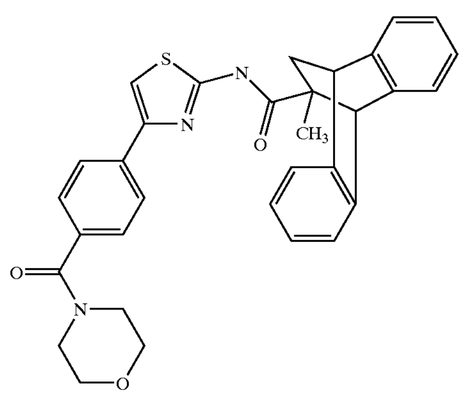 | 535.7 |

-continued

| Example | Chiral Compounds Structure | MS: (M + H = MW +1) |
|---|---|---|
| 376 | | 581.7 |
| 377 | | 555.7 |
| 378 | | 576.7 |

-continued

| Example | Chiral Compounds | Structure | MS: (M + H = MW +1) |
|---|---|---|---|
| 379 | | 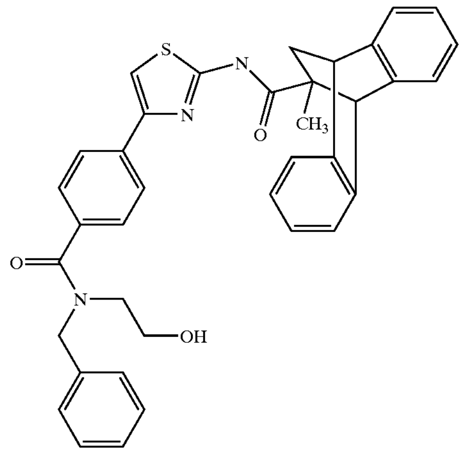 | 599.8 |
| 380 | | 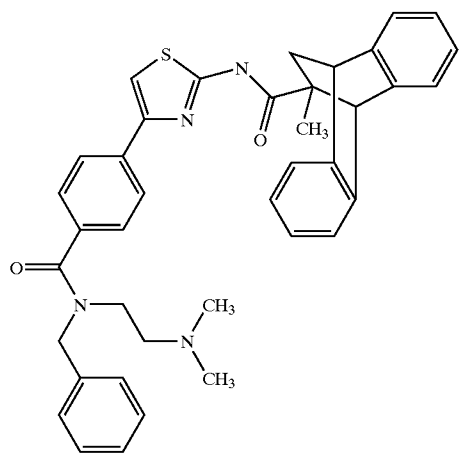 | 626.8 |
| 381 | | 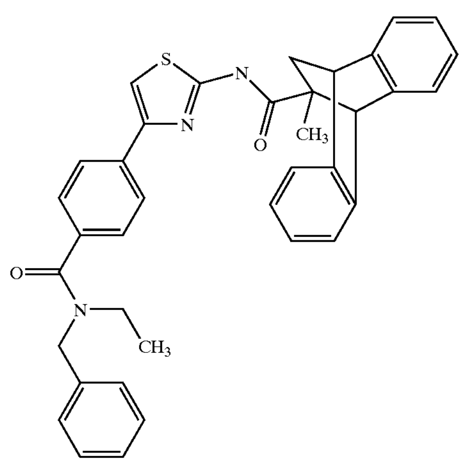 | 583.8 |

-continued

| Example | Chiral Compounds | Structure | MS: (M + H = MW +1) |
|---|---|---|---|
| 382 | | 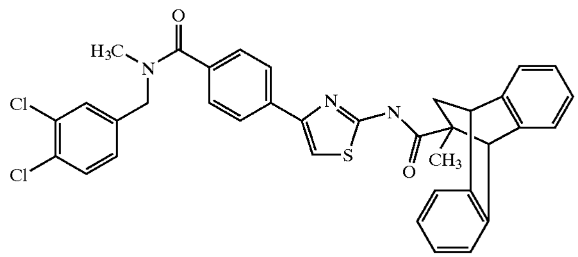 | 638.6 |
| 383 | | 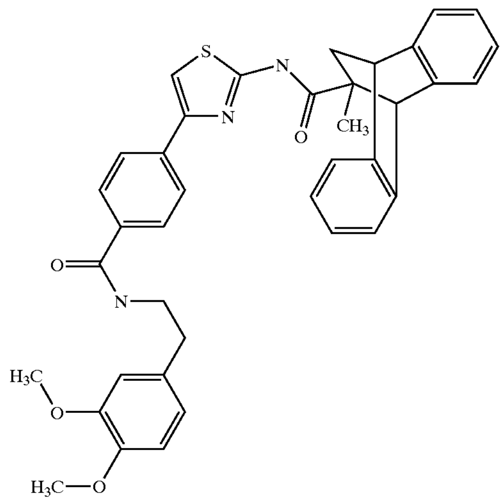 | 629.8 |
| 384 | | 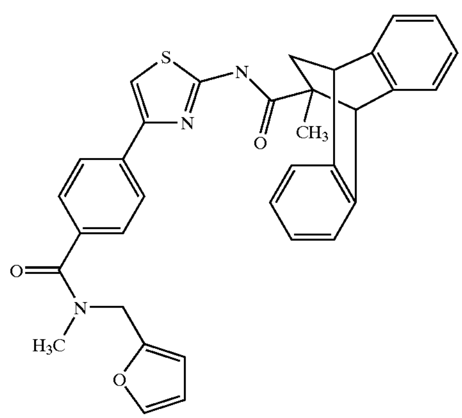 | 559.7 |
| 385 | | 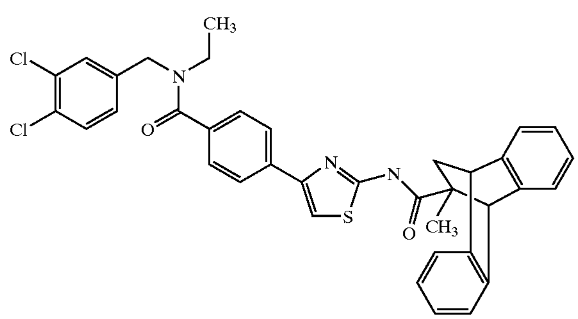 | 652.6 |

-continued

| Example | Chiral Compounds | Structure | MS: (M + H = MW +1) |
|---------|------------------|-----------|---------------------|
| 386 | | 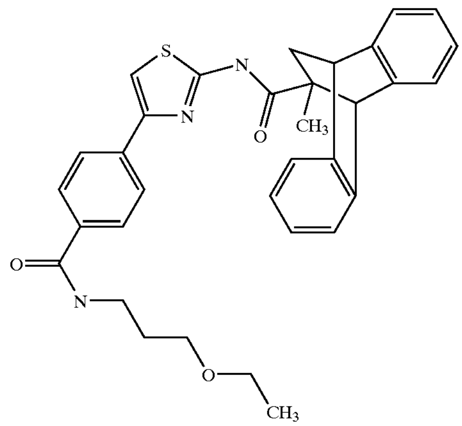 | 551.7 |
| 387 | | 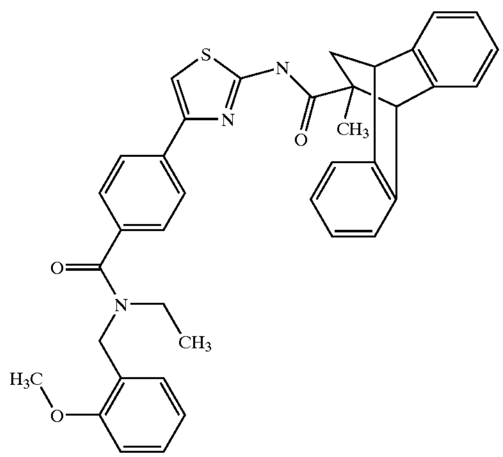 | 613.8 |
| 388 | | 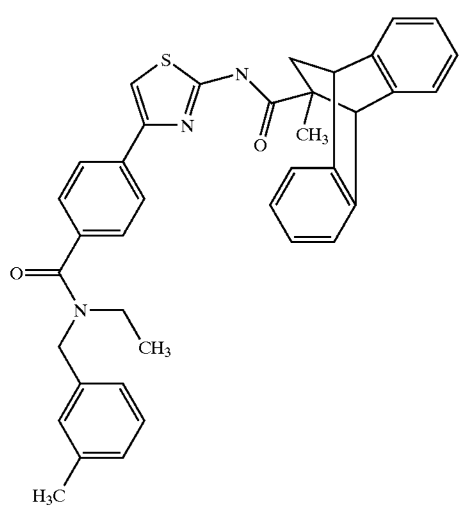 | 597.8 |

-continued

| Example | Chiral Compounds | Structure | MS: (M + H = MW +1) |
|---|---|---|---|
| 389 | | 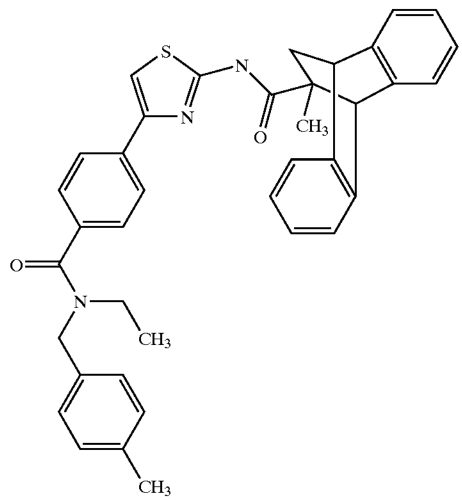 | 597.8 |
| 390 | | 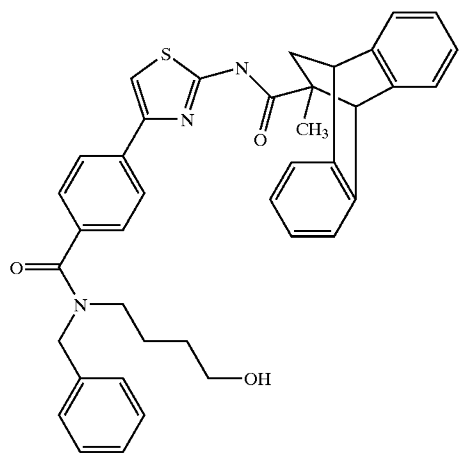 | 627.8 |
| 391 | | 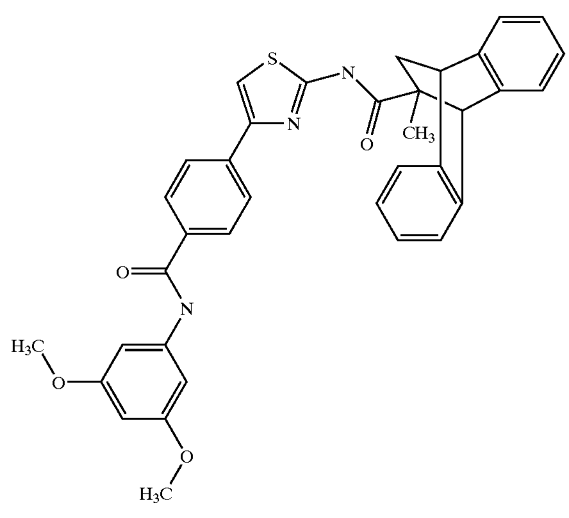 | 601.7 |

-continued
| Example | Chiral Compounds | Structure | MS: (M + H = MW +1) |
|---|---|---|---|
| 392 | | 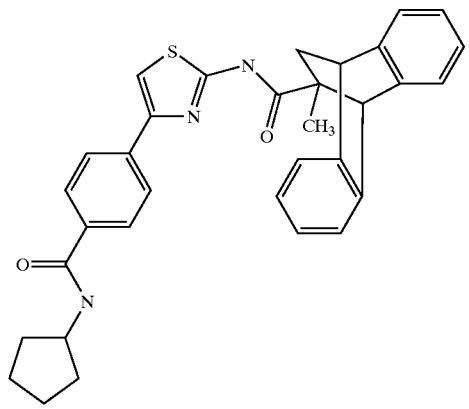 | 533.7 |
| 393 | | 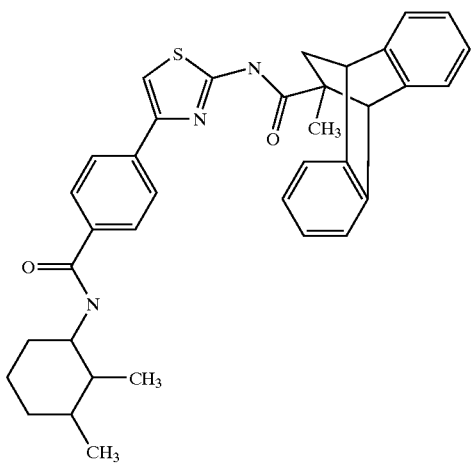 | 575.8 |
| 394 | | 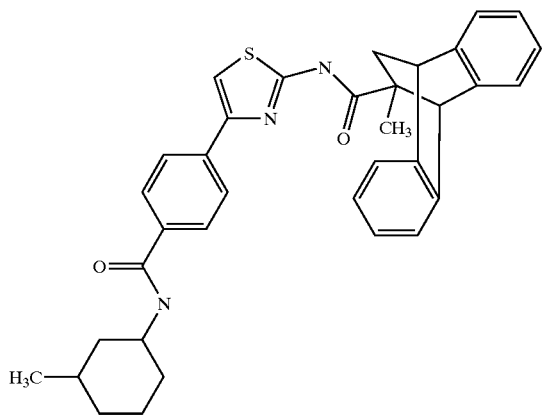 | 561.8 |

-continued
| Example | Chiral Compounds | Structure | MS: (M + H = MW +1) |
|---|---|---|---|
| 395 | | 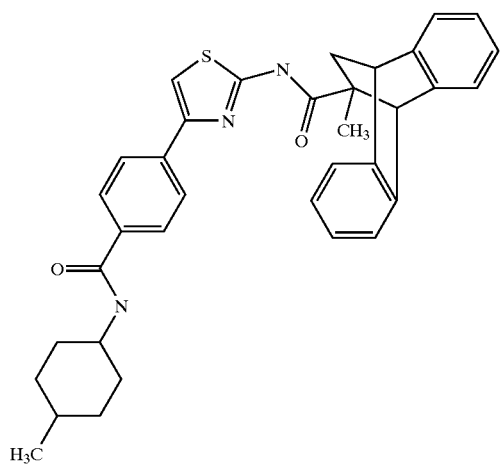 | 561.8 |
| 396 | | 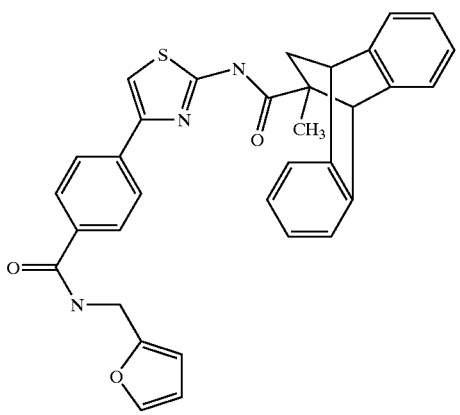 | 545.7 |
| 397 | | 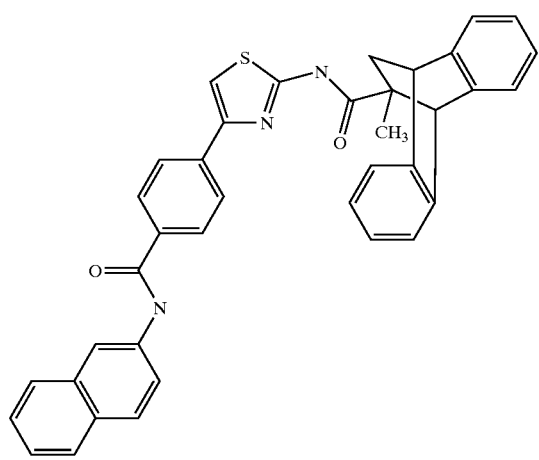 | 591.7 |

-continued
| Example | Chiral Compounds | Structure | MS: (M + H = MW +1) |
|---|---|---|---|
| 398 | | 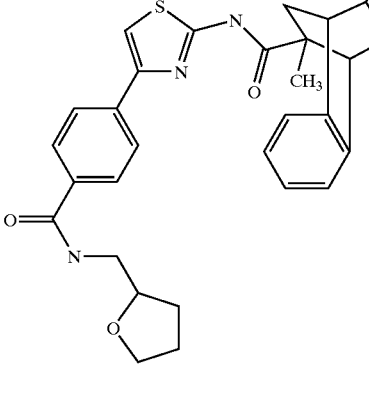 | 549.7 |
| 399 | | 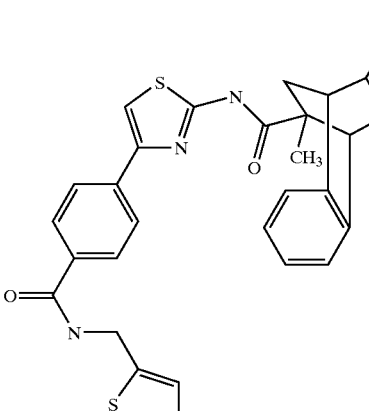 | 561.7 |
| 400 | | 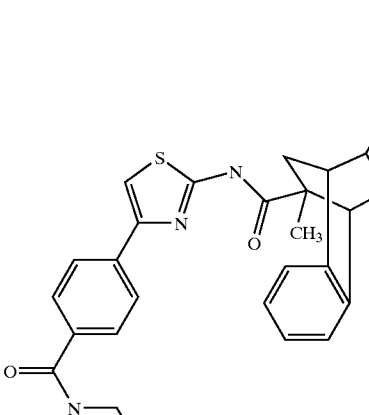 | 570.7 |

-continued
| Example | Chiral Compounds | Structure | MS: (M + H = MW +1) |
|---------|------------------|-----------|---------------------|
| 401 | | 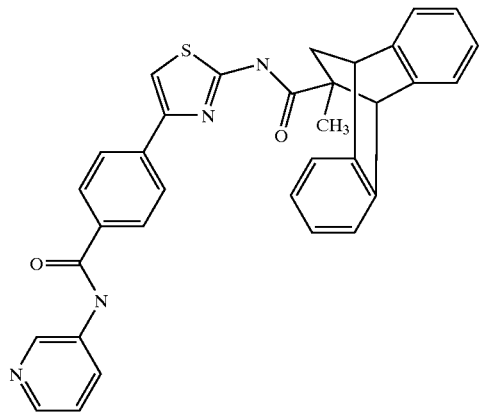 | 542.7 |
| 402 | | 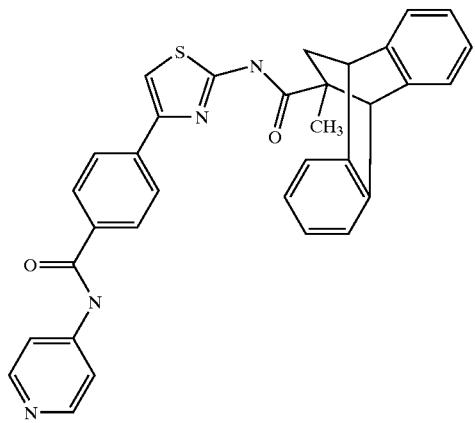 | 542.7 |
| 403 | | 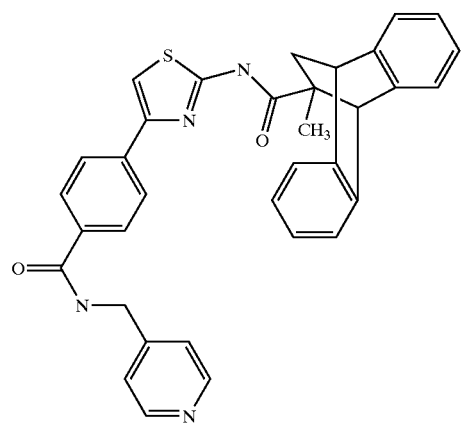 | 556.7 |

-continued

| Example | Chiral Compounds | Structure | MS: (M + H = MW +1) |
|---------|------------------|-----------|---------------------|
| 404 | | 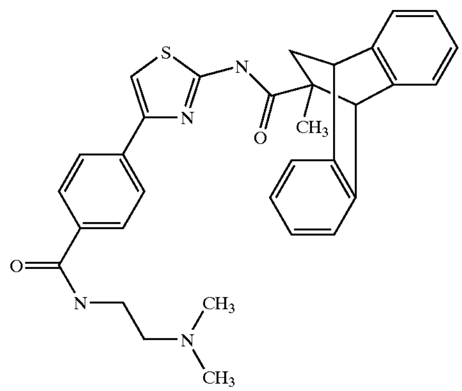 | 536.7 |
| 405 | | 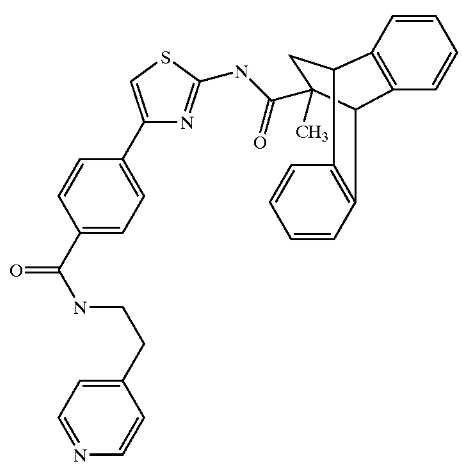 | 570.7 |
| 406 | | 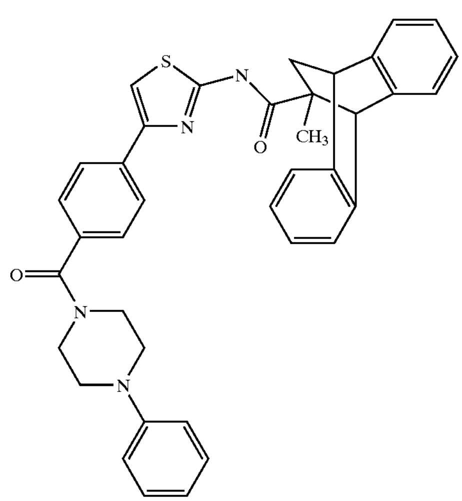 | 610.8 |

-continued

| Example | Chiral Compounds | Structure | MS: (M + H = MW +1) |
|---|---|---|---|
| 407 | | 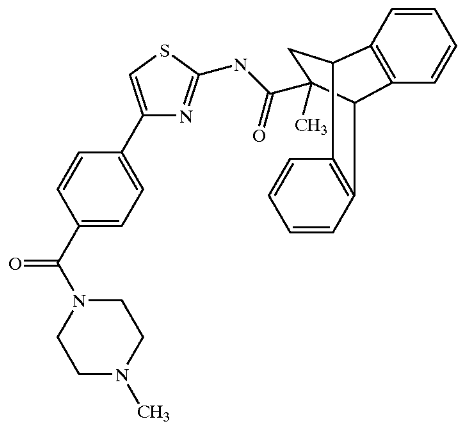 | 548.7 |
| 408 | | 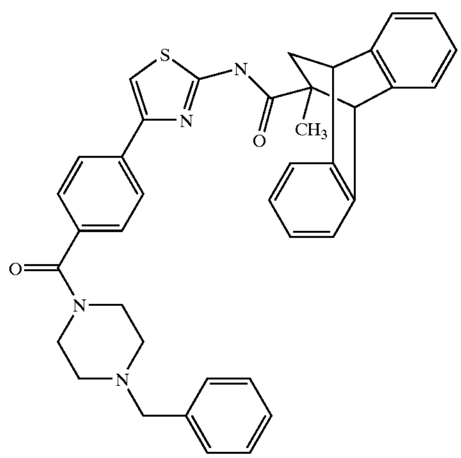 | 624.8 |
| 409 | | 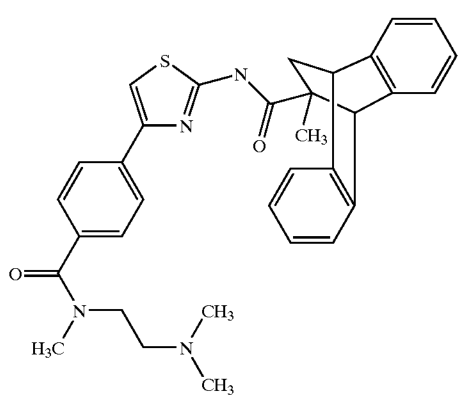 | 550.7 |

-continued
| Example | Chiral Compounds | Structure | MS: (M + H = MW +1) |
|---|---|---|---|
| 410 | | 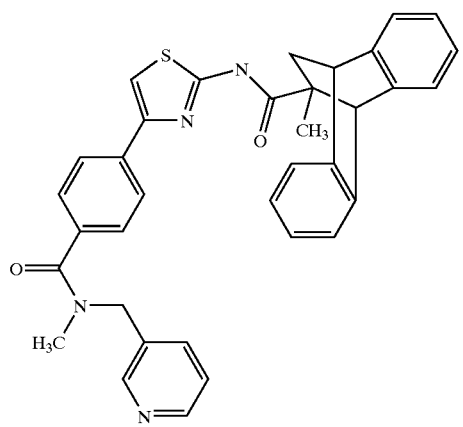 | 570.7 |
| 411 | | 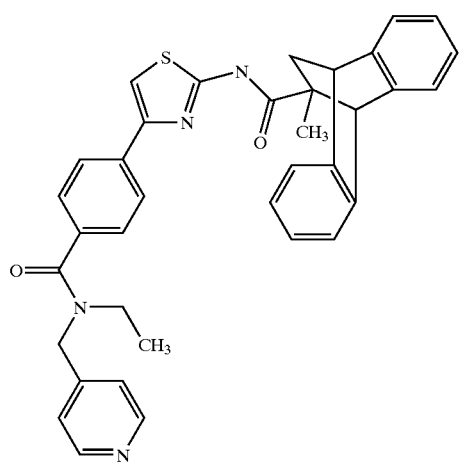 | 584.7 |
| 412 | | 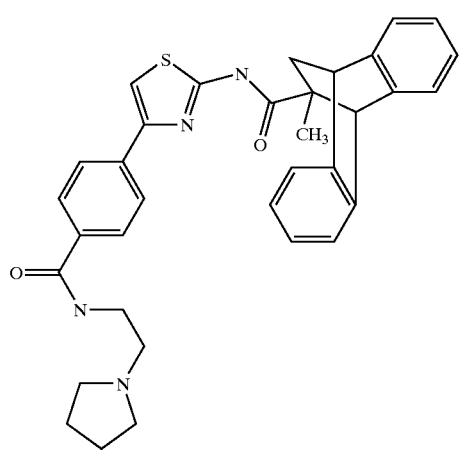 | 562.7 |

-continued

| Example | Chiral Compounds | Structure | MS: (M + H = MW +1) |
|---------|------------------|-----------|---------------------|
| 413 | | 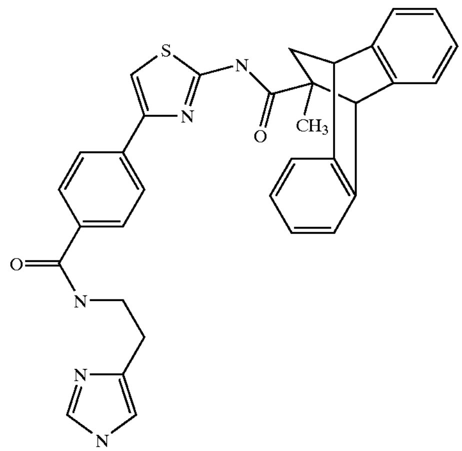 | 559.7 |
| 414 | | 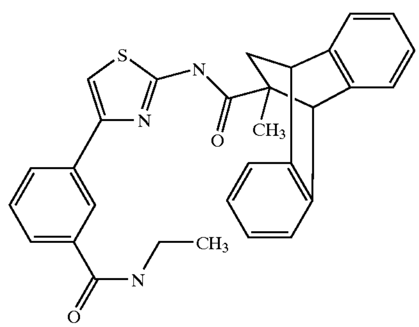 | 493.6 |
| 415 | | 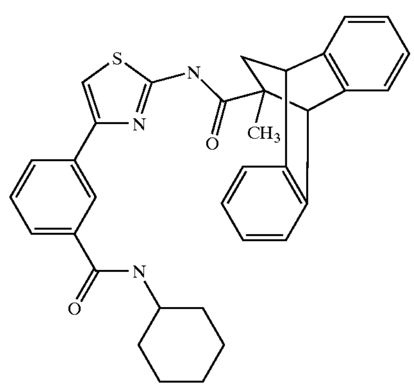 | 547.7 |
| 416 | | 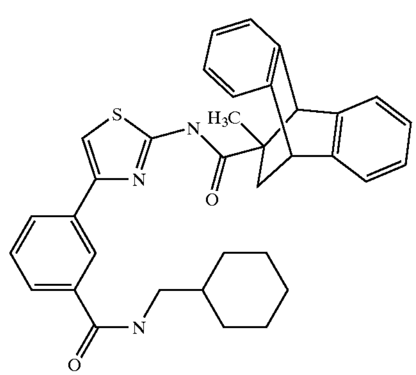 | 561.8 |

-continued

| Example | Chiral Compounds | Structure | MS: (M + H = MW +1) |
|---|---|---|---|
| 417 | | 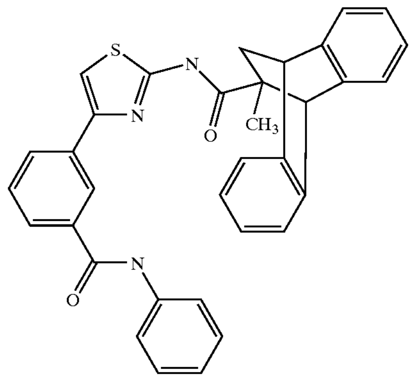 | 541.7 |
| 418 | | 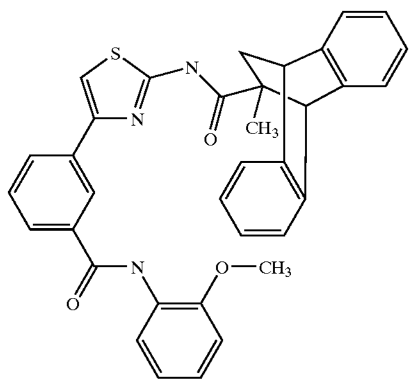 | 571.7 |
| 419 | | 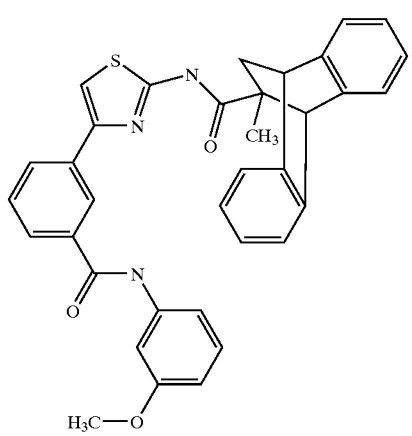 | 571.7 |

-continued
| Example | Chiral Compounds | Structure | MS: (M + H = MW +1) |
|---|---|---|---|
| 420 | | 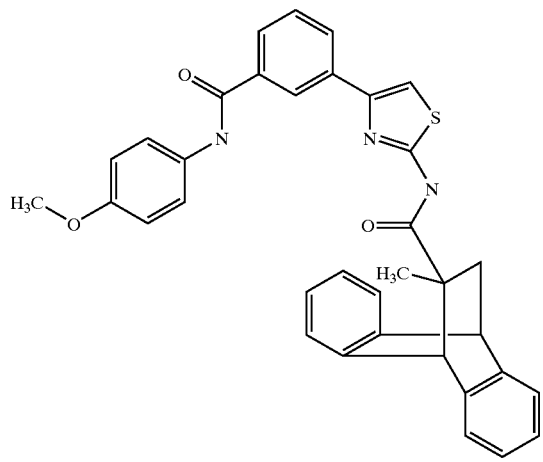 | 571.7 |
| 421 | | 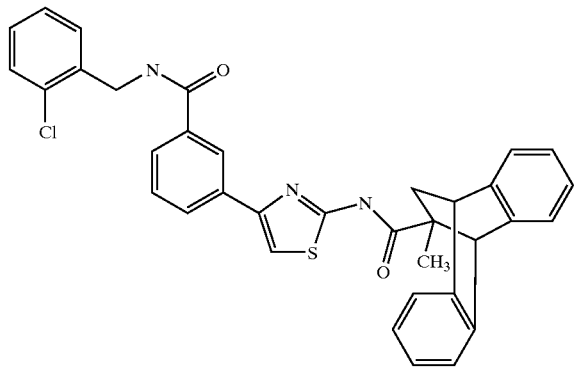 | 590.2 |
| 422 | | 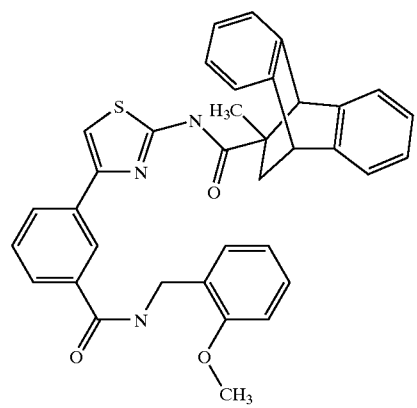 | 585.7 |

-continued

| Example | Chiral Compounds | Structure | MS: (M + H = MW +1) |
|---|---|---|---|
| 423 | | 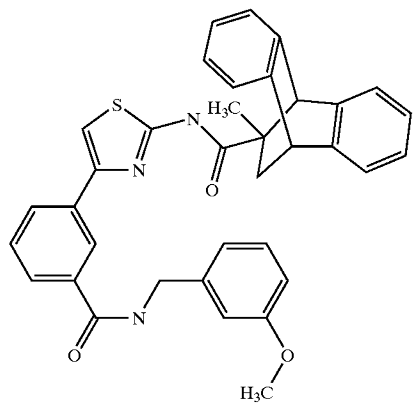 | 585.7 |
| 424 | | 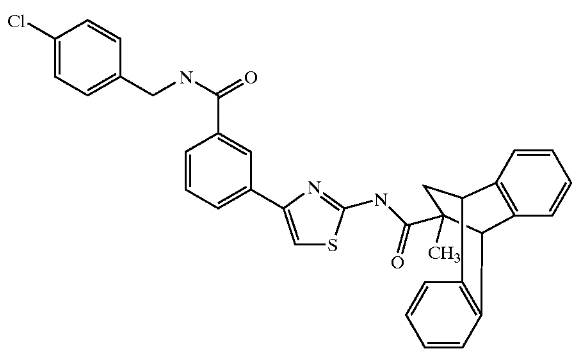 | 590.2 |
| 425 | | 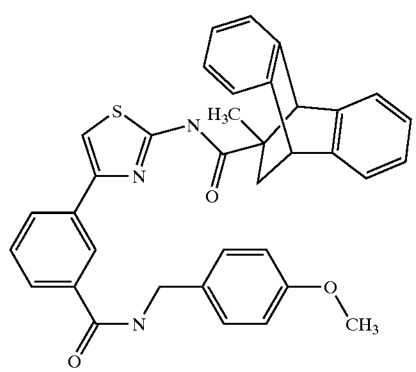 | 585.7 |
| 426 | | 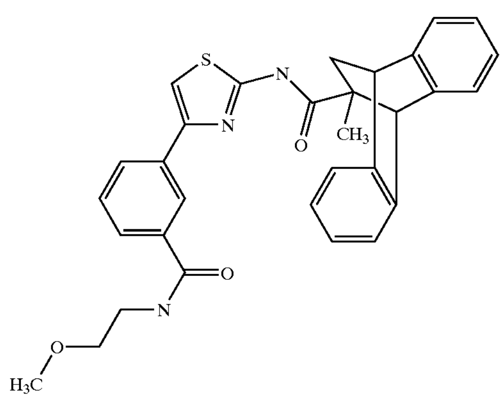 | 523.7 |

-continued

| Example | Chiral Compounds | Structure | MS: (M + H = MW +1) |
|---|---|---|---|
| 427 | | 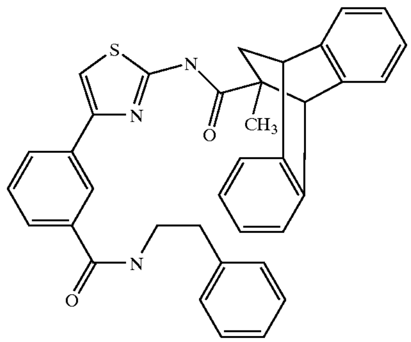 | 569.7 |
| 428 | | 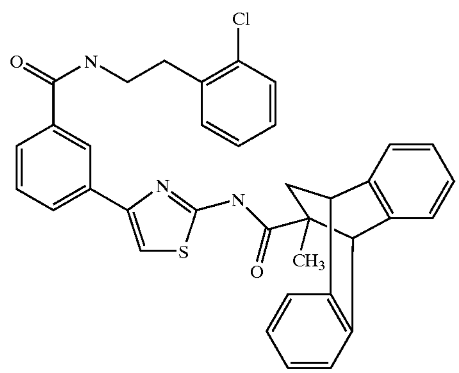 | 604.2 |
| 429 | | 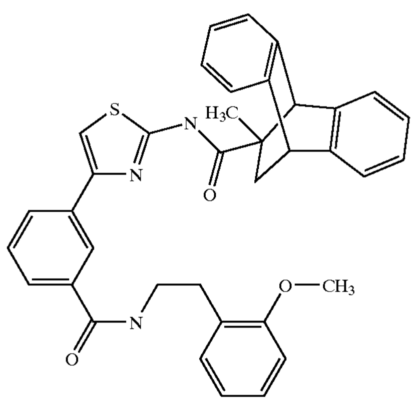 | 599.8 |
| 430 | | 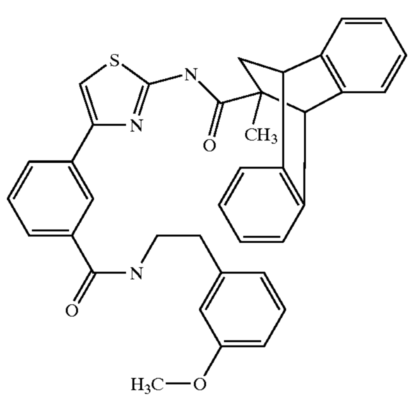 | 599.8 |

-continued

| Example | Chiral Compounds | Structure | MS: (M + H = MW +1) |
|---|---|---|---|
| 431 | | 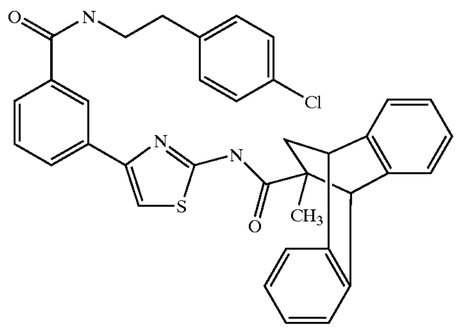 | 604.2 |
| 432 | | 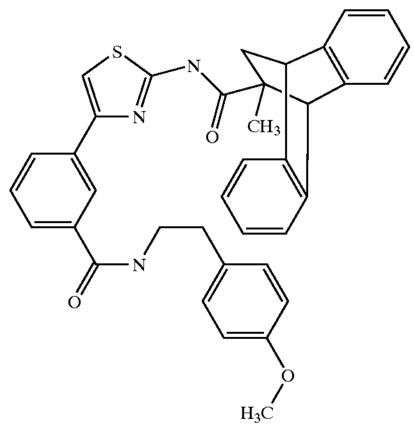 | 599.8 |
| 433 | | 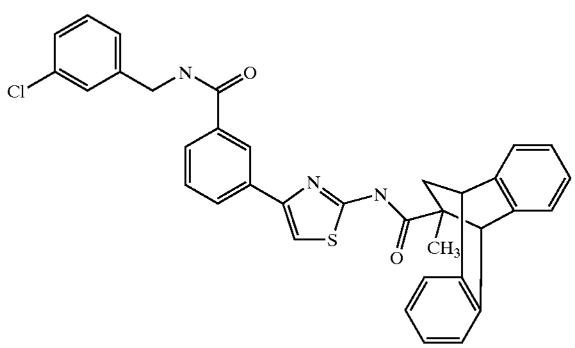 | 590.2 |
| 434 | | 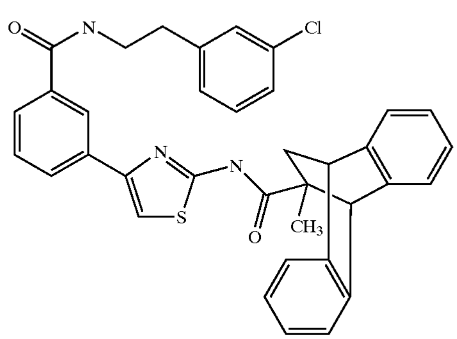 | 604.2 |

-continued
| Example | Chiral Compounds | Structure | MS: (M + H = MW +1) |
|---|---|---|---|
| 435 | | 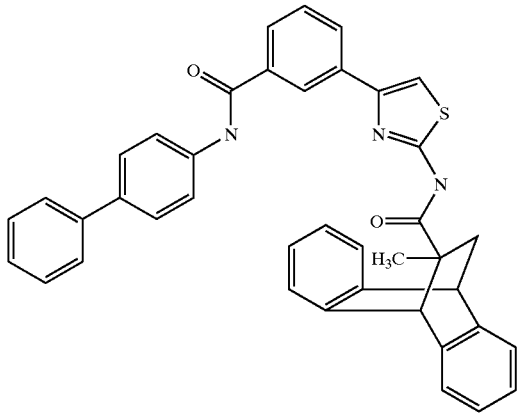 | 617.8 |
| 436 | | 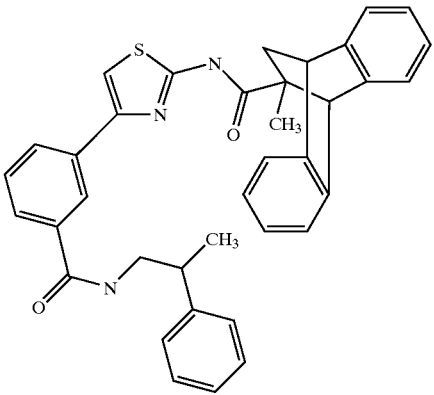 | 583.8 |
| 437 | | 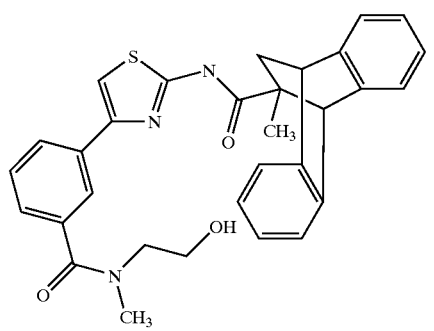 | 523.7 |
| 438 | | 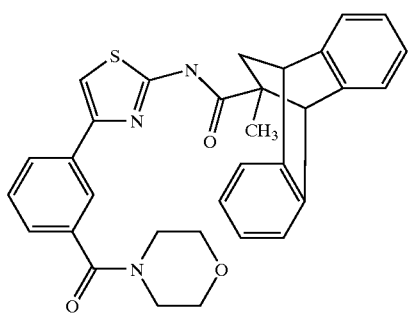 | 535.7 |

-continued

| Example | Chiral Compounds | Structure | MS: (M + H = MW +1) |
|---|---|---|---|
| 439 | | 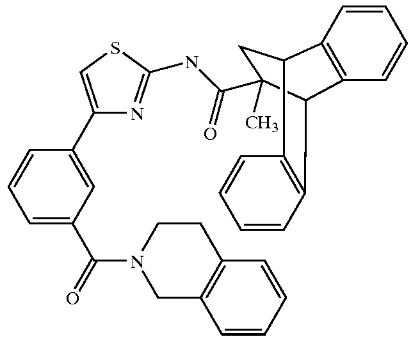 | 581.7 |
| 440 | | 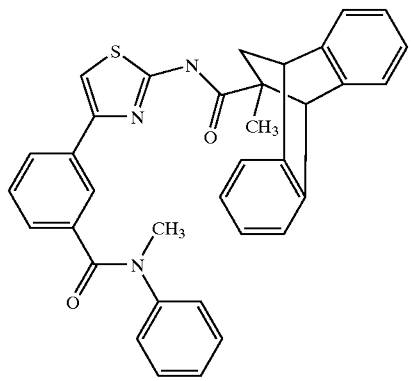 | 555.7 |
| 441 | | 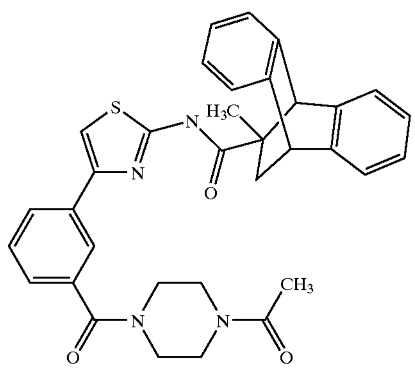 | 576.7 |
| 442 | | 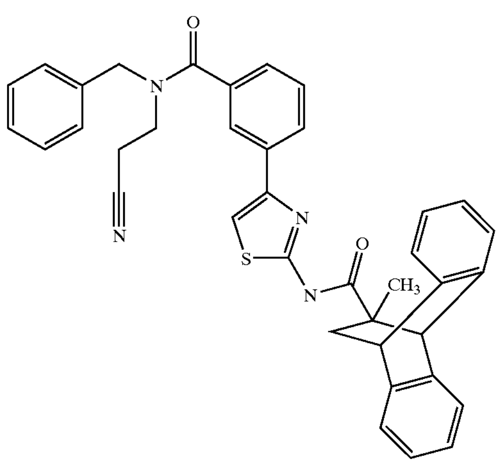 | 608.8 |

-continued

| Example | Chiral Compounds | Structure | MS: (M + H = MW +1) |
|---|---|---|---|
| 443 | | 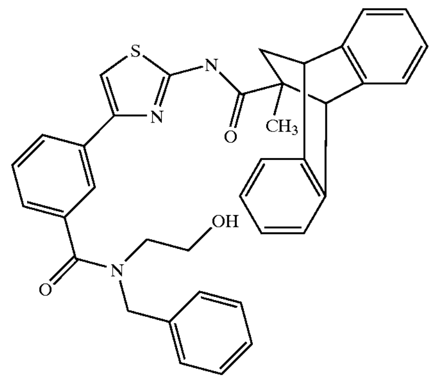 | 599.8 |
| 444 | | 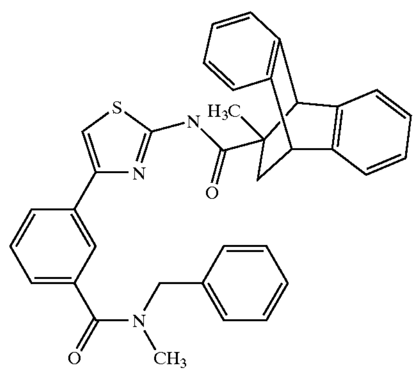 | 569.7 |
| 445 | | 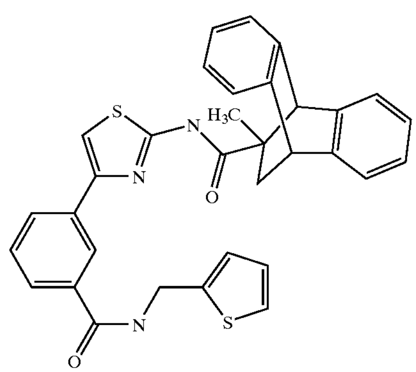 | 561.7 |
| 446 | | 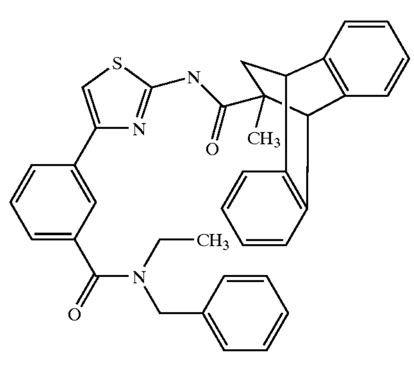 | 583.8 |

-continued
| Example | Chiral Compounds | Structure | MS: (M + H = MW +1) |
|---|---|---|---|
| 447 | | 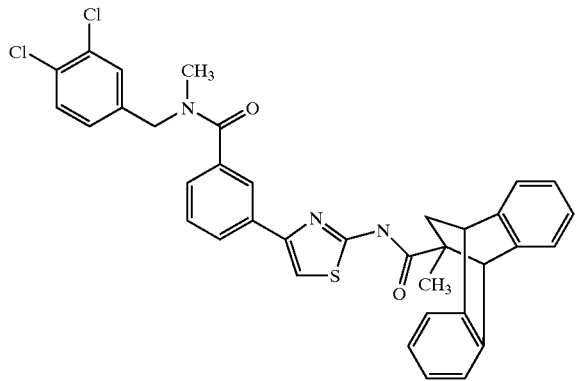 | 638.6 |
| 448 | | 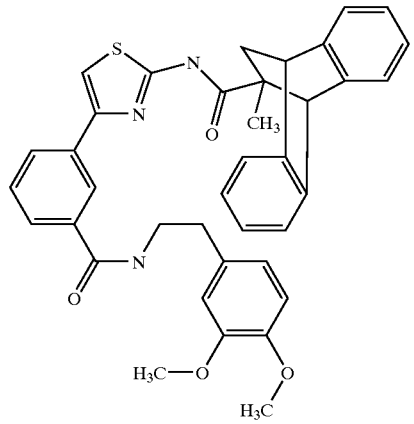 | 629.8 |
| 449 | | 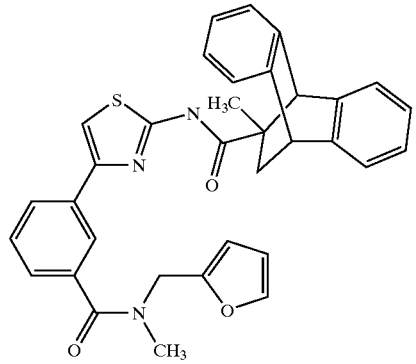 | 559.7 |

-continued

| Example | Chiral Compounds | Structure | MS: (M + H = MW +1) |
|---------|------------------|-----------|---------------------|
| 450 | | 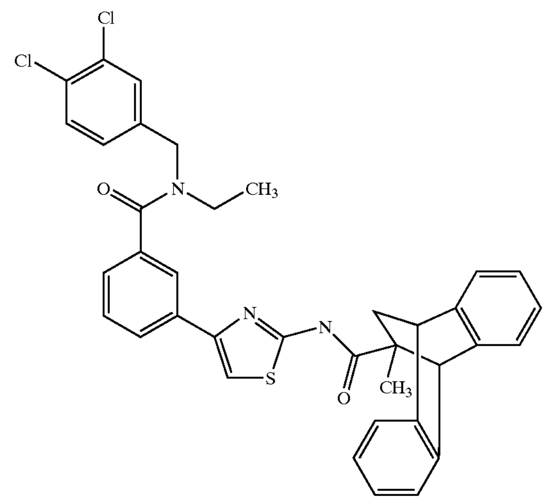 | 652.6 |
| 451 | | 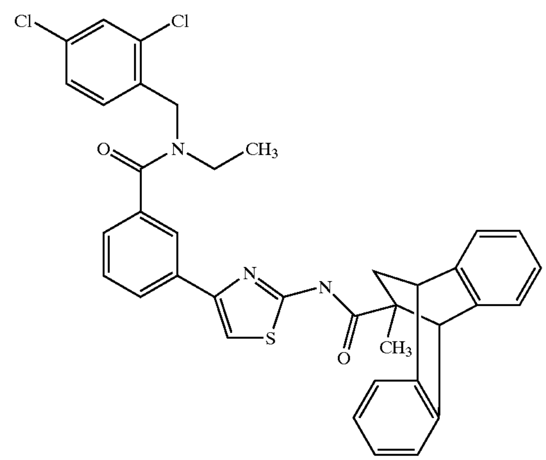 | 652.6 |
| 452 | | 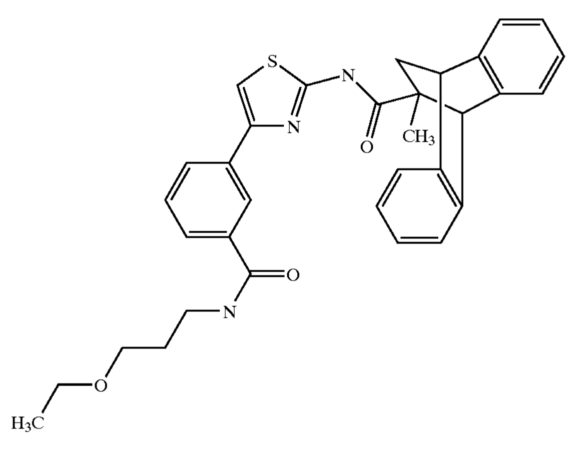 | 551.7 |

-continued
| Example | Chiral Compounds | Structure | MS: (M + H = MW +1) |
|---|---|---|---|
| 453 | | 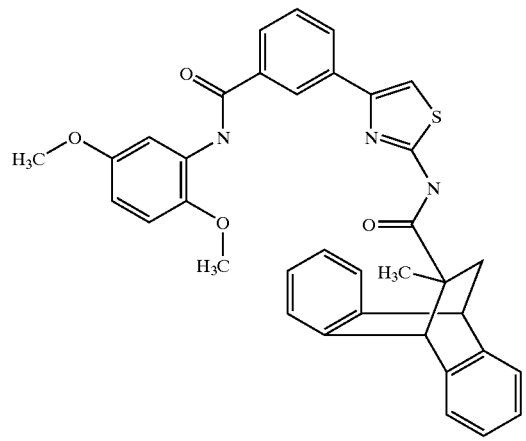 | 601.7 |
| 454 | | 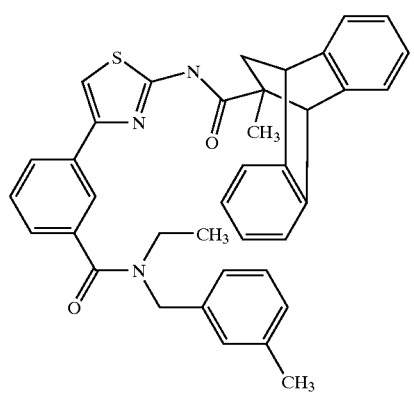 | 597.8 |
| 455 | | 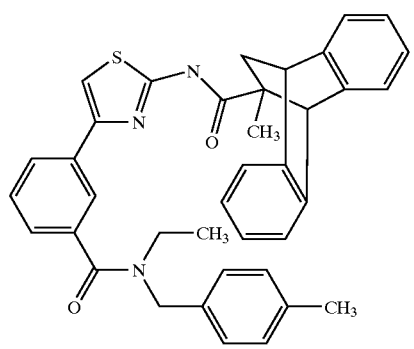 | 597.8 |

-continued
| Example | Chiral Compounds | Structure | MS: (M + H = MW +1) |
|---|---|---|---|
| 456 | | 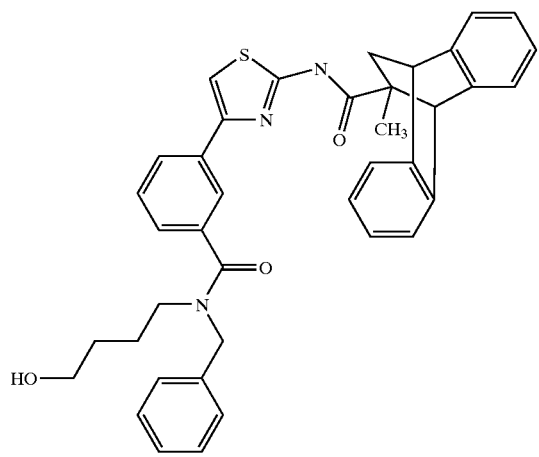 | 627.8 |
| 457 | | 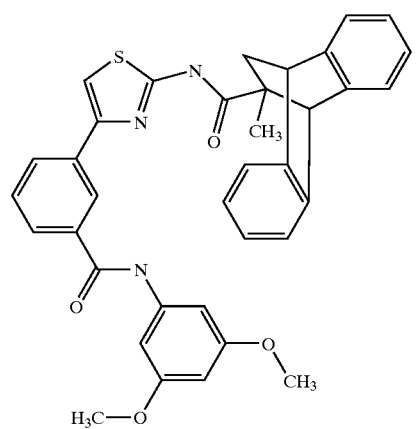 | 601.7 |
| 458 | | 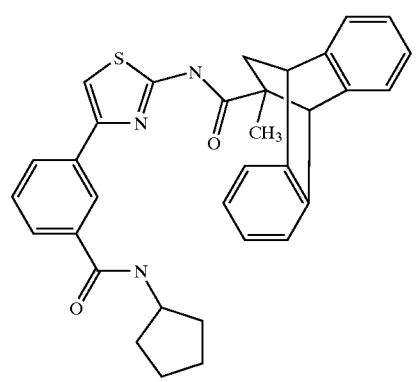 | 533.7 |

-continued

| Example | Chiral Compounds | Structure | MS: (M + H = MW +1) |
|---|---|---|---|
| 459 | | 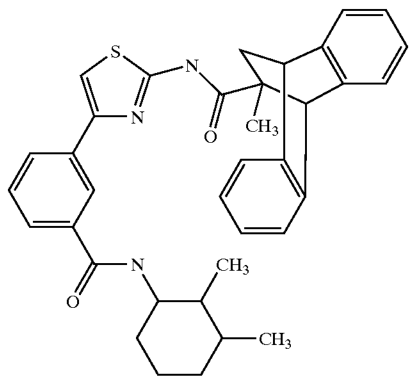 | 575.8 |
| 460 | | 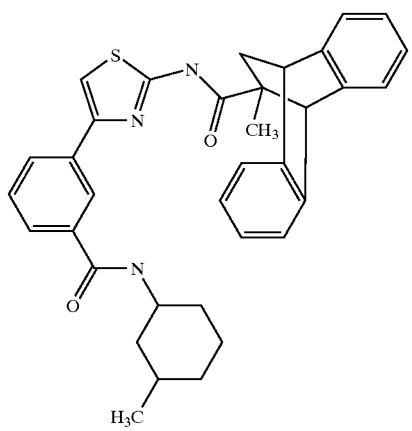 | 561.8 |
| 461 | | 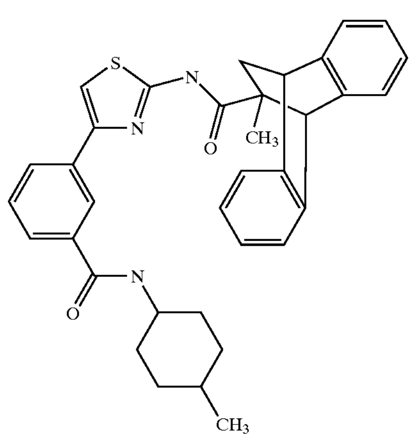 | 561.8 |

-continued

| Example | Chiral Compounds | Structure | MS: (M + H = MW +1) |
|---|---|---|---|
| 462 | | 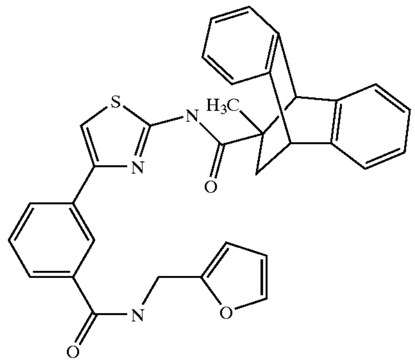 | 545.7 |
| 463 | | 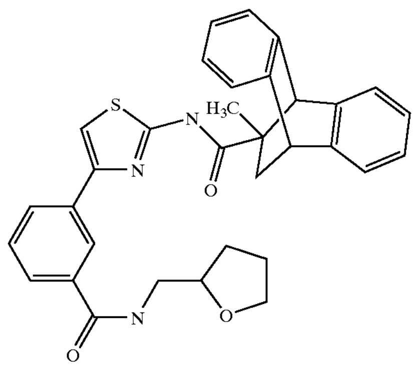 | 549.7 |
| 464 | | 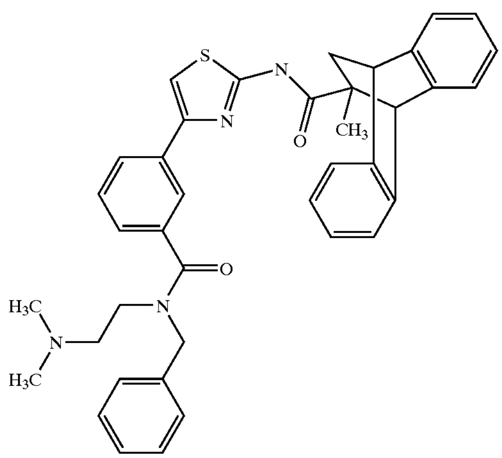 | 626.8 |
| 465 | | 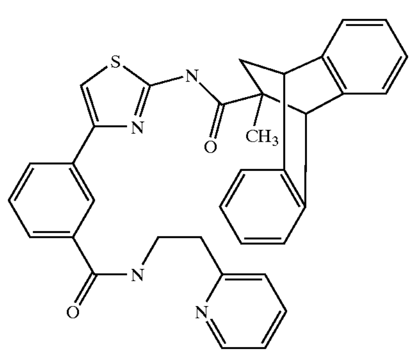 | 570.7 |

| Example | Chiral Compounds | Structure | MS: (M + H = MW +1) |
|---|---|---|---|
| 466 | | 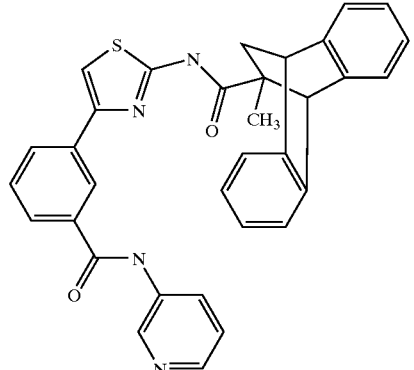 | 542.7 |
| 467 | | 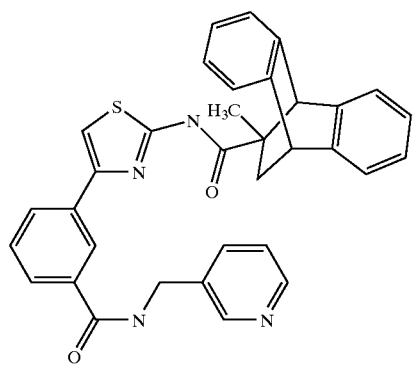 | 556.7 |
| 468 | | 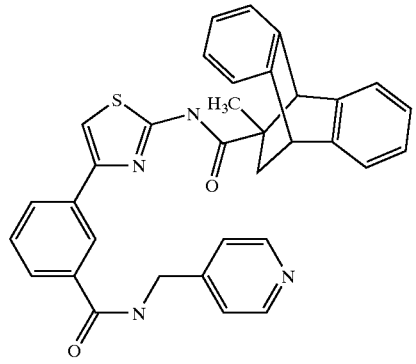 | 556.7 |
| 469 | | 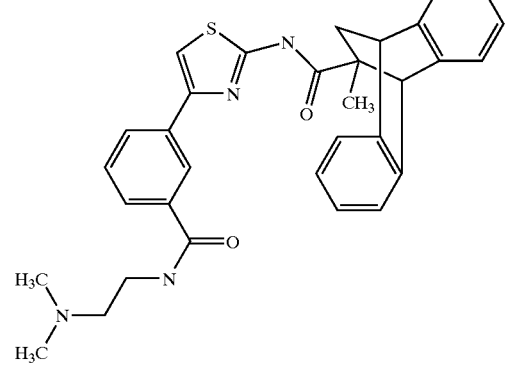 | 536.7 |

-continued

| Example | Chiral Compounds | Structure | MS: (M + H = MW +1) |
|---|---|---|---|
| 470 | | 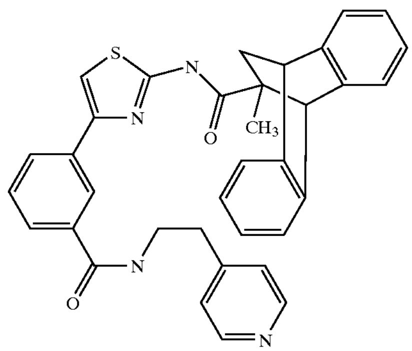 | 570.7 |
| 471 | | 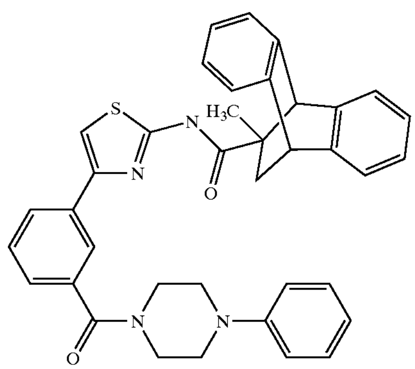 | 610.8 |
| 472 | | 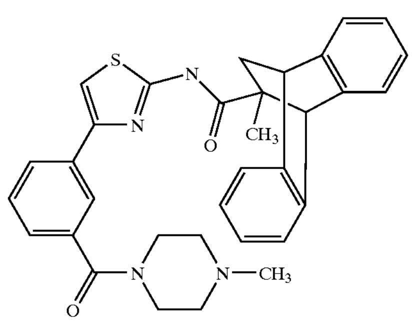 | 548.7 |
| 473 | | 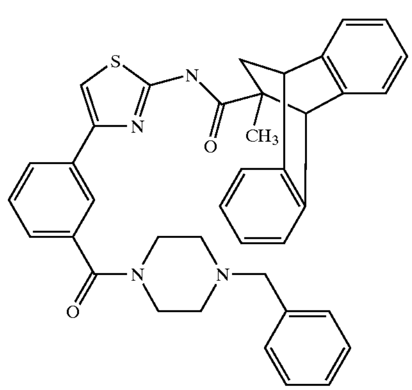 | 624.8 |

-continued
| Example | Chiral Compounds | Structure | MS: (M + H = MW +1) |
|---|---|---|---|
| 474 | | 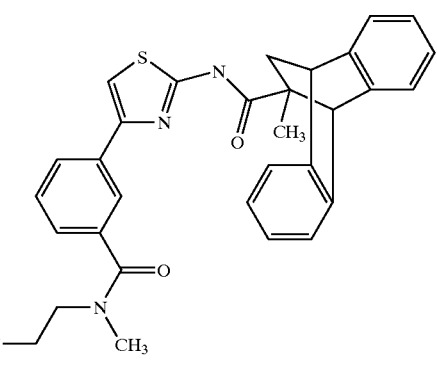 | 550.7 |
| 475 | | 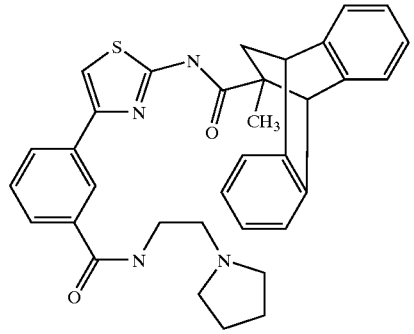 | 562.7 |
| 476 | | 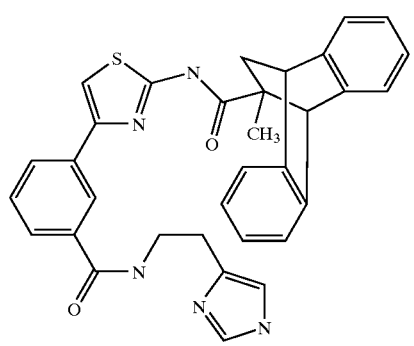 | 559.7 |
| 477 | | 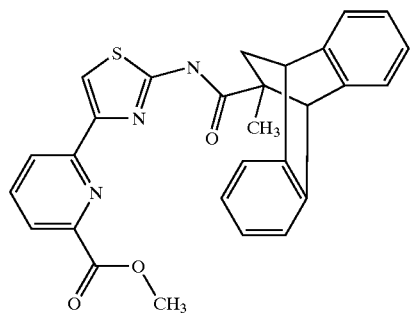 | 481.58 |

-continued

| Example | Chiral Compounds | Structure | MS: (M + H = MW +1) |
|---------|------------------|-----------|---------------------|
| 478 | | 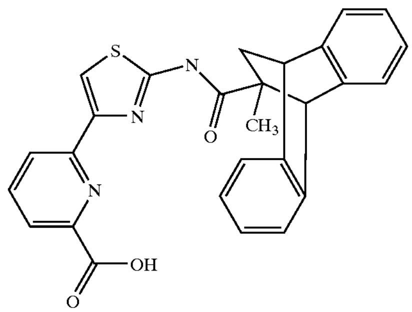 | 467.55 |
| 479 | | 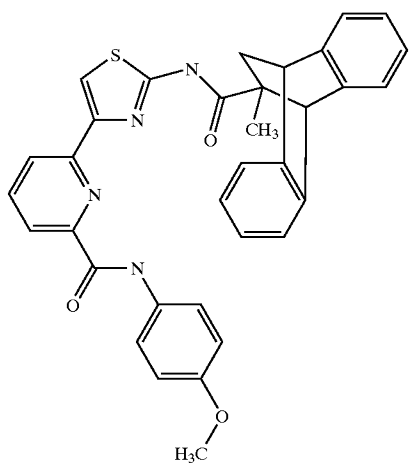 | 572.69 |
| 480 | | 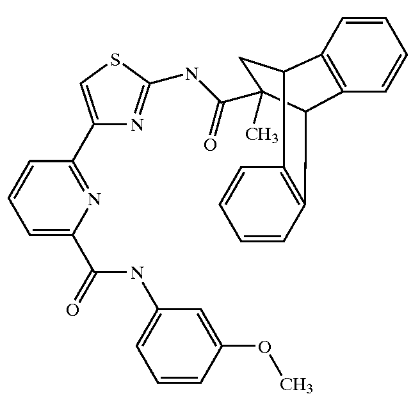 | 572.69 |

-continued

| Example | Chiral Compounds | Structure | MS: (M + H = MW +1) |
|---------|------------------|-----------|---------------------|
| 481 | | 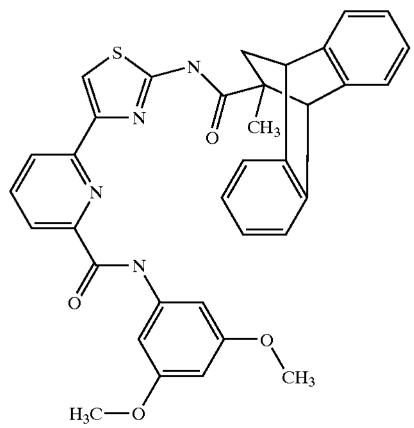 | 602.72 |
| 482 | | 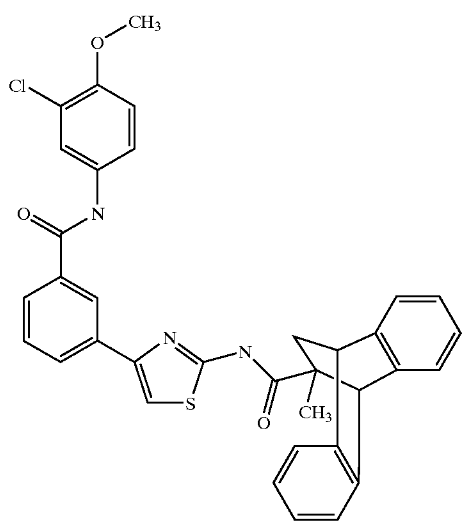 | 606.1 |
| 483 | | 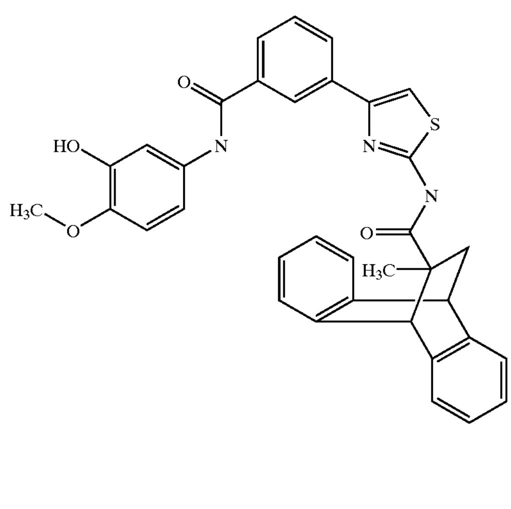 | 587.7 |

-continued
| Example | Chiral Compounds | Structure | MS: (M + H = MW +1) |
|---|---|---|---|
| 484 | | 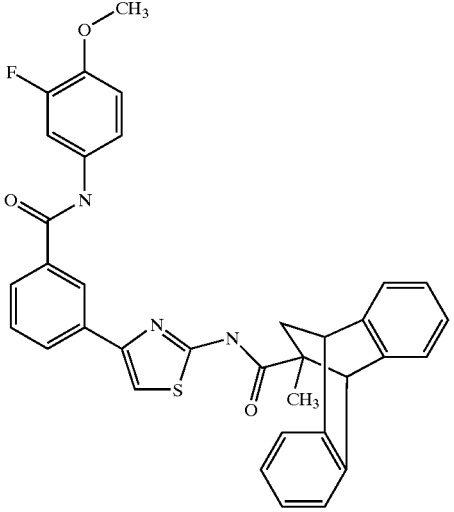 | 589.7 |
| 485 | | 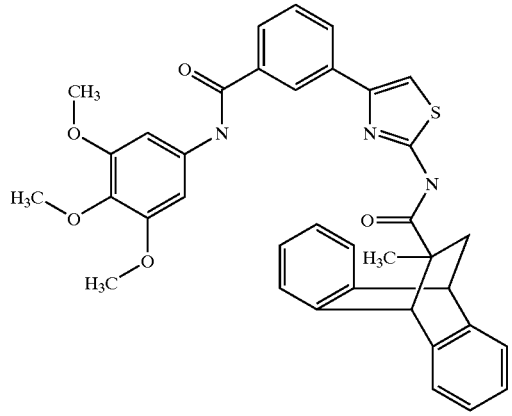 | 631.8 |
| 486 | | 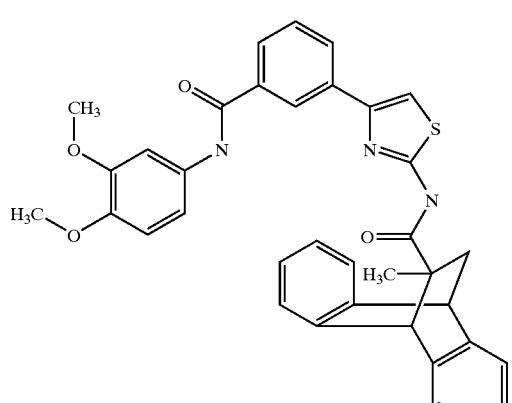 | 601.7 |

-continued

| Example | Chiral Compounds | Structure | MS: (M + H = MW +1) |
|---|---|---|---|
| 487 | | 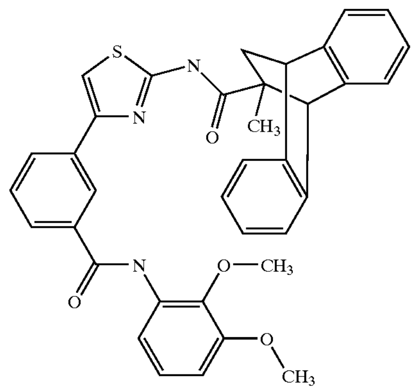 | 601.7 |
| 488 | | 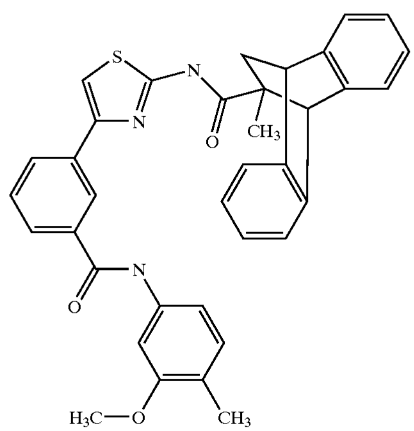 | 585.7 |
| 489 | | 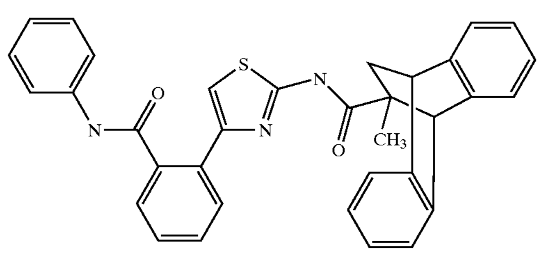 | 541.68 |
| 490 | | 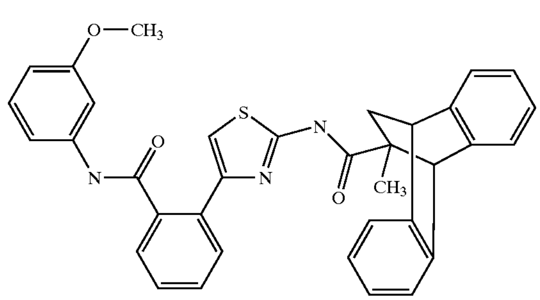 | 571.7 |

-continued

| Example | Chiral Compounds | Structure | MS: (M + H = MW +1) |
|---|---|---|---|
| 491 | | 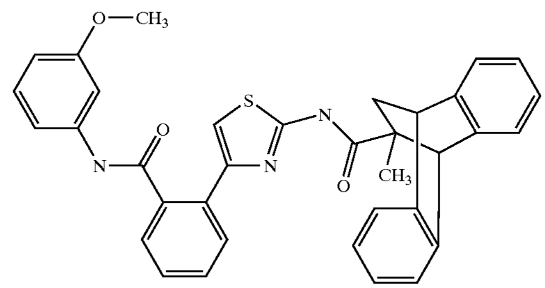 | 571.7 |
| 492 | | 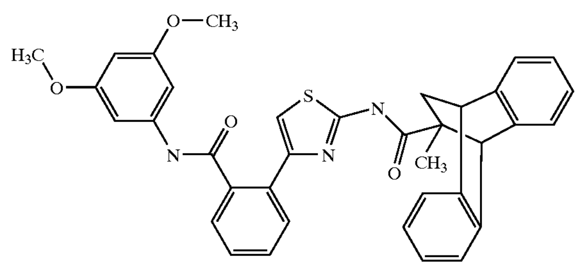 | 601.73 |
| 493 | Chiral (S) | 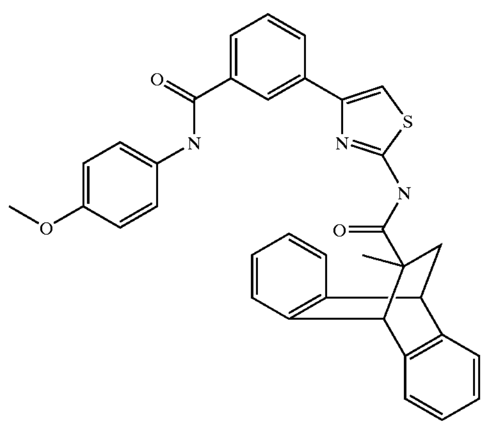 | 571.7 |
| 494 | Chiral (S) | 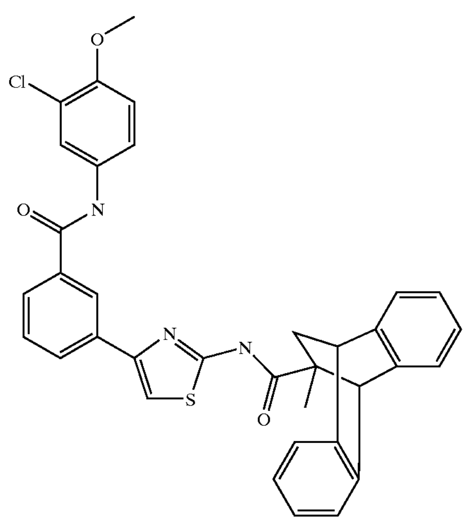 | 606.1 |

-continued

| Example | Chiral Compounds | Structure | MS: (M + H = MW +1) |
|---|---|---|---|
| 495 | Chiral (S) | 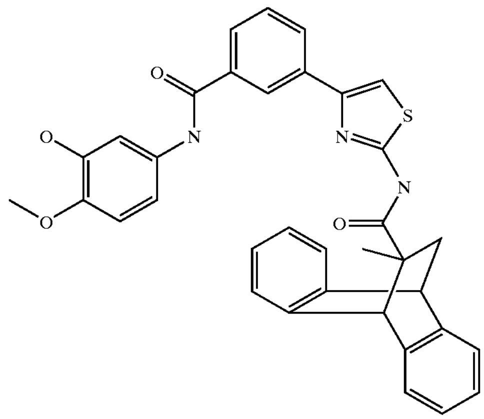 | 587.7 |
| 496 | Chiral (S) | 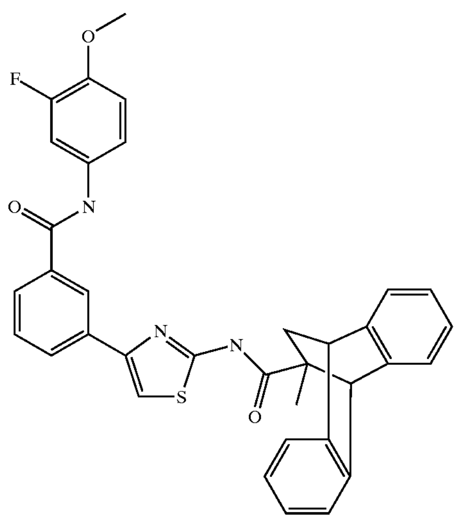 | 589.7 |
| 497 | Chiral (S) | 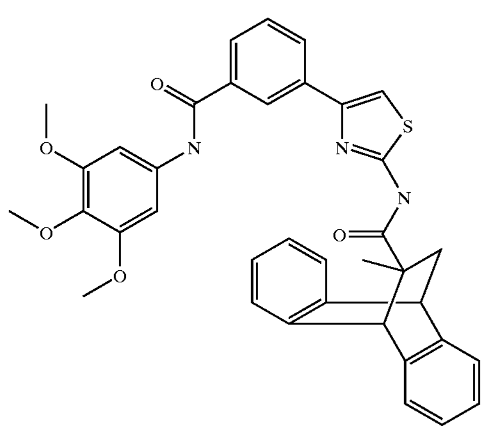 | 631.8 |

-continued

| Example | Chiral Compounds | Structure | MS: (M + H = MW +1) |
|---|---|---|---|
| 498 | Chiral (S) | 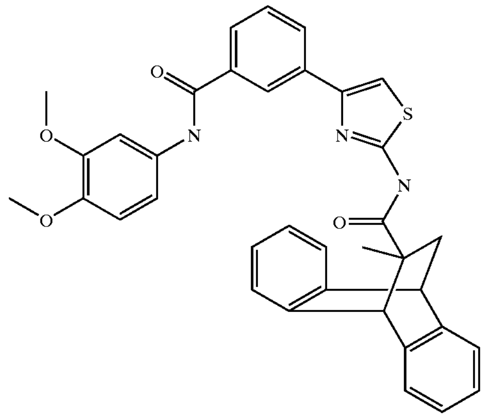 | 601.7 |
| 499 | Chiral (S) | 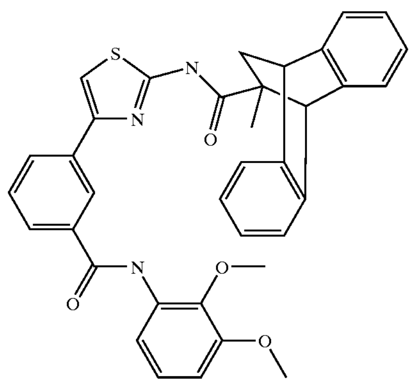 | 601.7 |
| 500 | Chiral (S) | 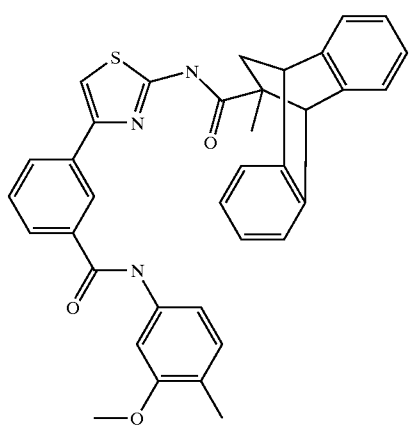 | 585.7 |

-continued

| Example | Chiral Compounds | Structure | MS: (M + H = MW +1) |
|---|---|---|---|
| 501 | | 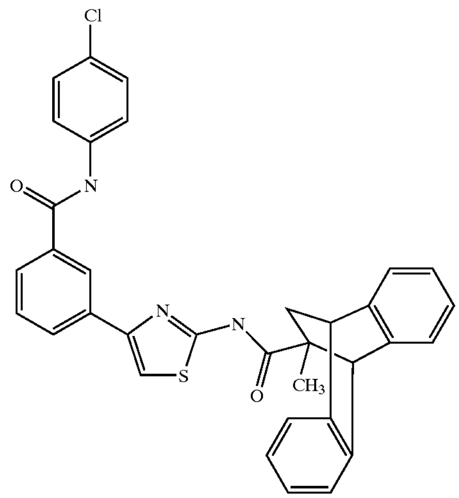 | 576.1 |
| 502 | | 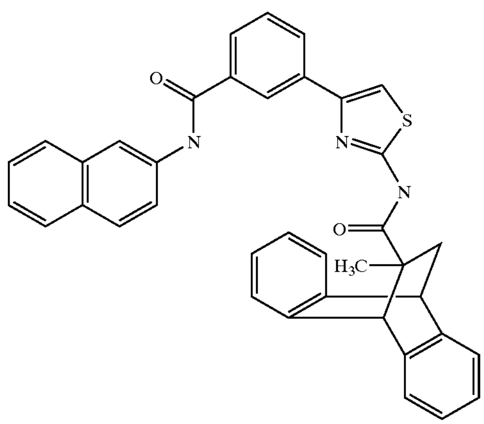 | 591.7 |
| 503 | | 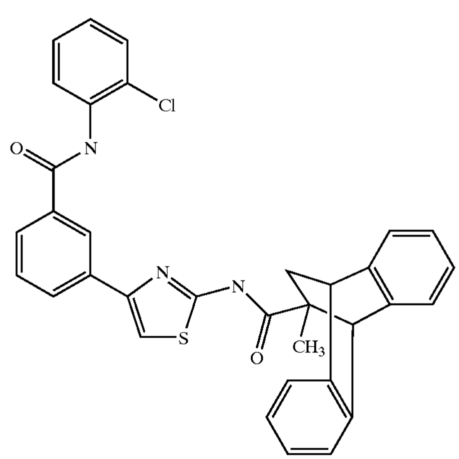 | 576.1 |

-continued

| Example | Chiral Compounds | Structure | MS: (M + H = MW +1) |
|---|---|---|---|
| 504 | | 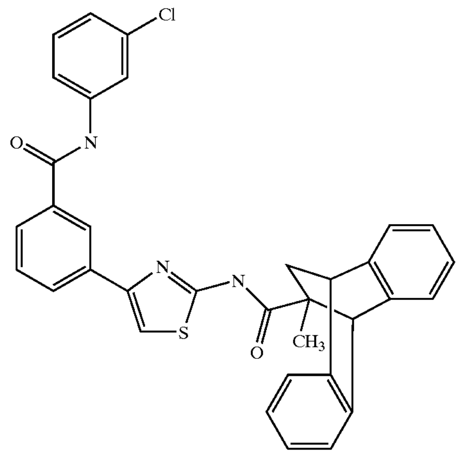 | 576.1 |
| 505 | | 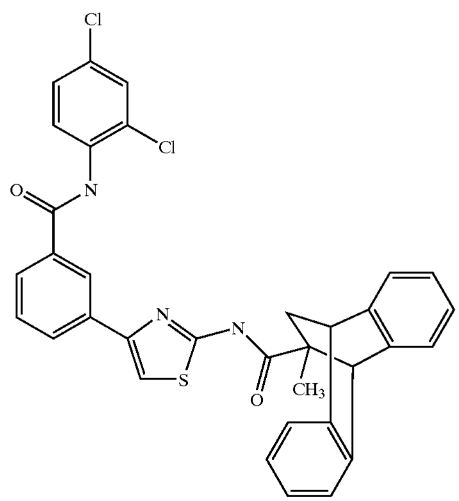 | 610.6 |
| 506 | | 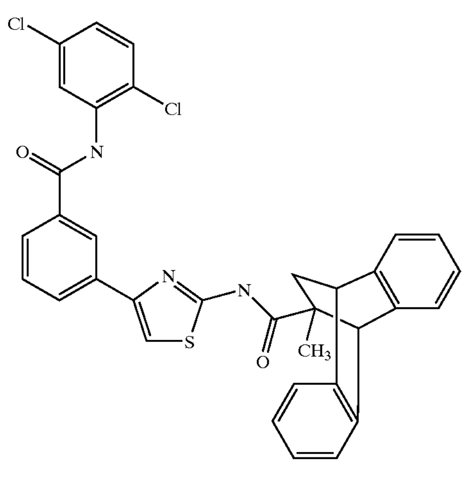 | 610.6 |

-continued
| Example | Chiral Compounds | Structure | MS: (M + H = MW +1) |
|---|---|---|---|
| 507 | | 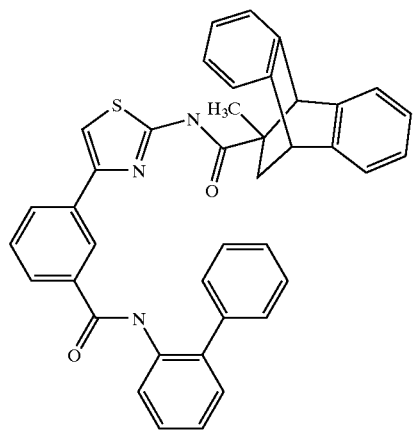 | 617.8 |
| 508 | | 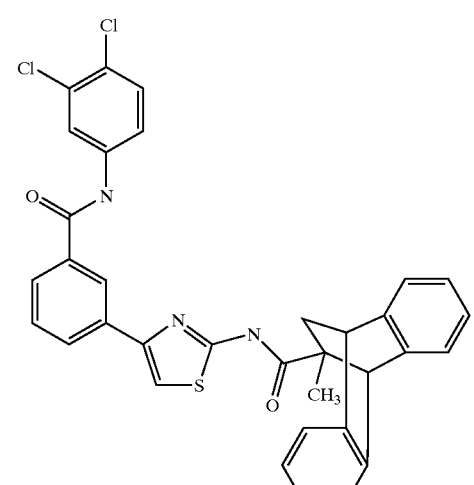 | 610.6 |
| 509 | | 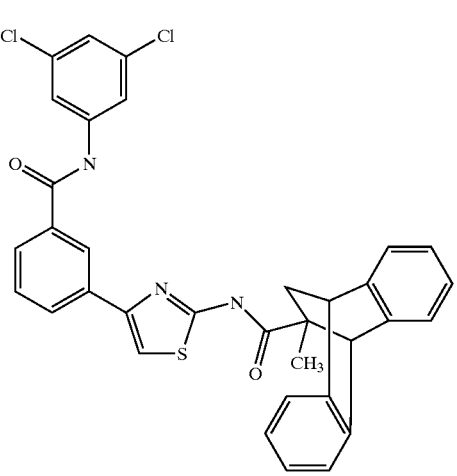 | 610.6 |

-continued

| Example | Chiral Compounds | Structure | MS: (M + H = MW +1) |
|---|---|---|---|
| 510 | | 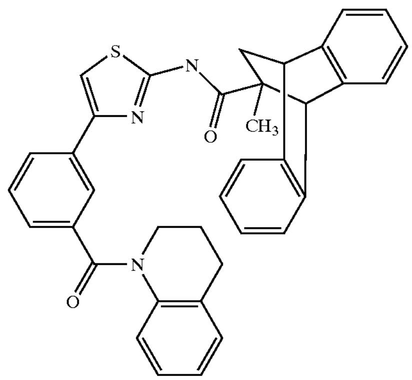 | 581.7 |
| 511 | | 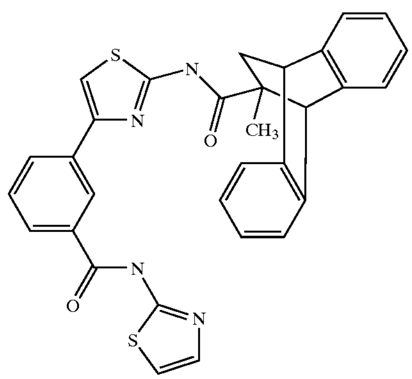 | 548.7 |
| 512 | | 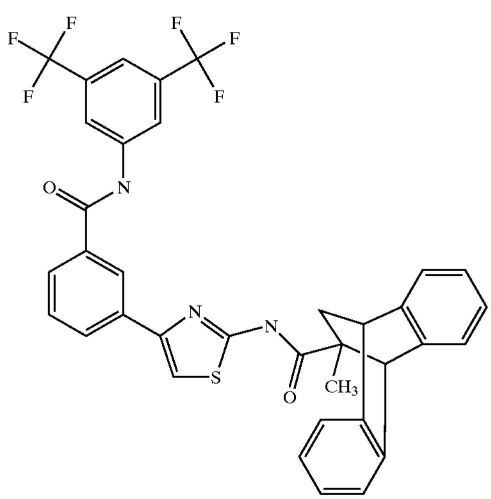 | 677.7 |

-continued

| Example | Chiral Compounds | Structure | MS: (M + H = MW +1) |
|---------|------------------|-----------|---------------------|
| 513 | | 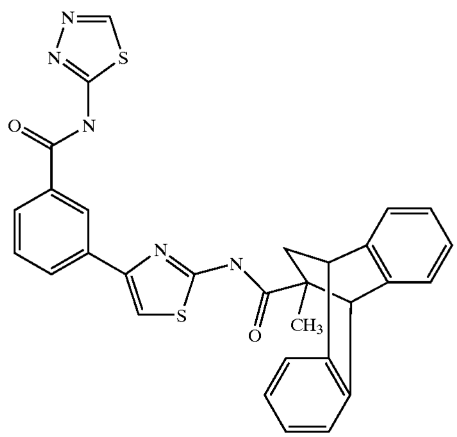 | 549.7 |
| 514 | | 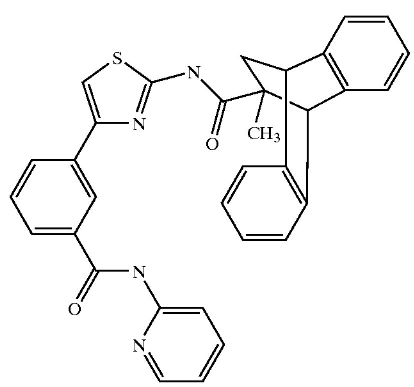 | 542.7 |
| 515 | | 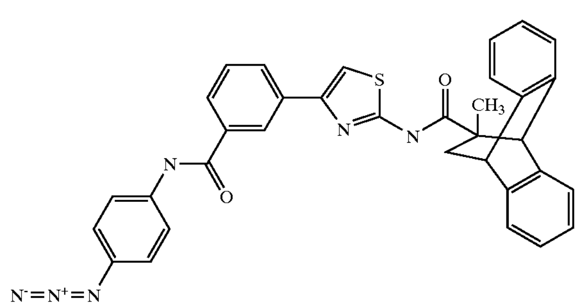 | 582.7 |

-continued

| Example | Chiral Compounds | Structure | MS: (M + H = MW +1) |
|---|---|---|---|
| 516 | | 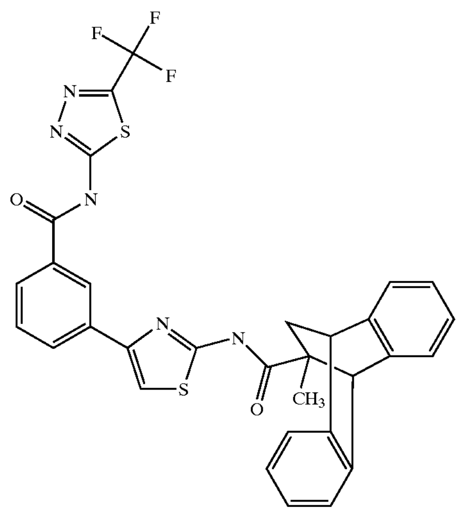 | 617.7 |
| 517 | | 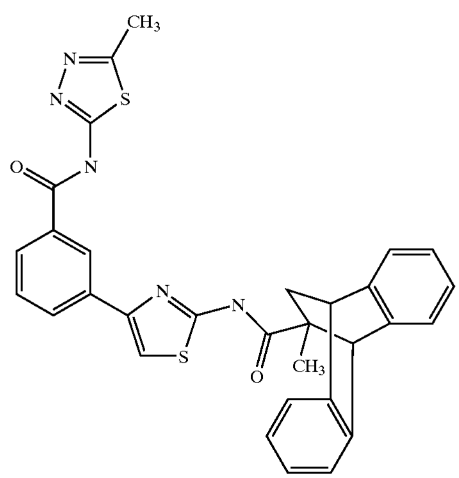 | 563.7 |
| 518 | | 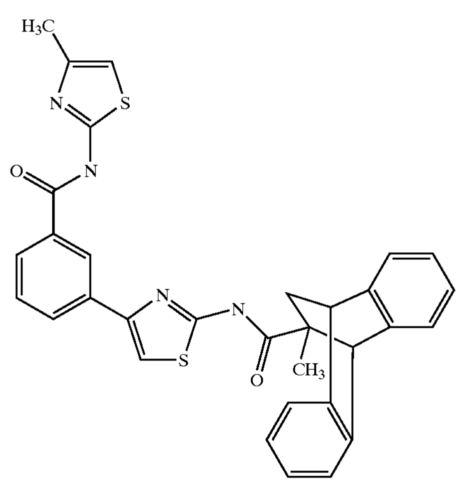 | 562.7 |

-continued

| Example | Chiral Compounds | Structure | MS: (M + H = MW +1) |
|---|---|---|---|
| 519 | | 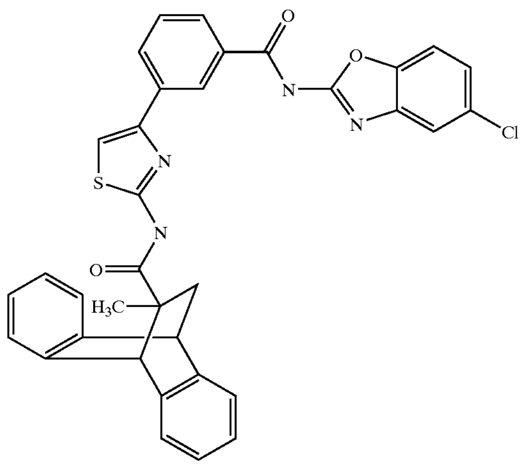 | 617.1 |
| 520 | | 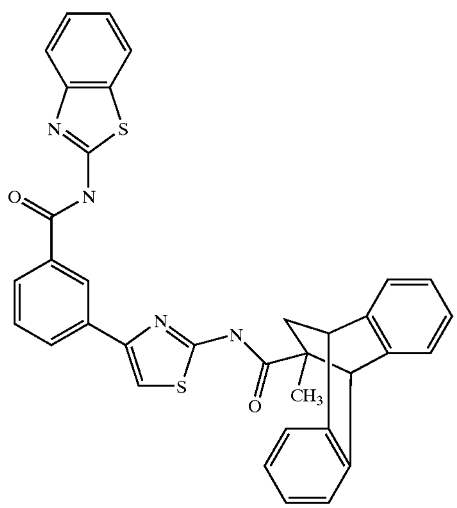 | 598.8 |
| 521 | | 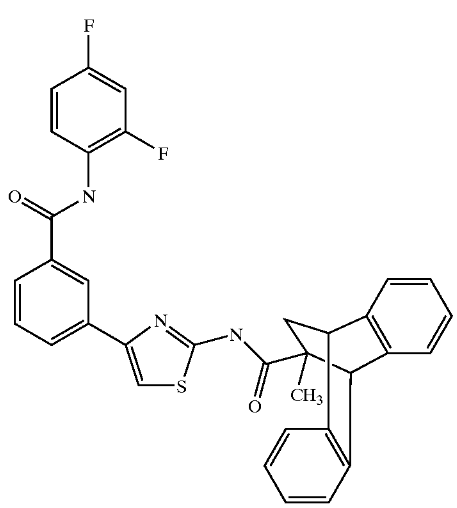 | 577.7 |

-continued

| Example | Chiral Compounds | Structure | MS: (M + H = MW +1) |
|---|---|---|---|
| 522 | | 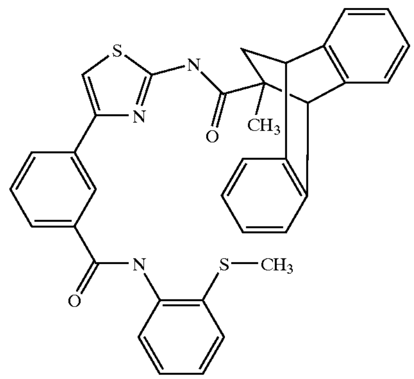 | 587.8 |
| 523 | | 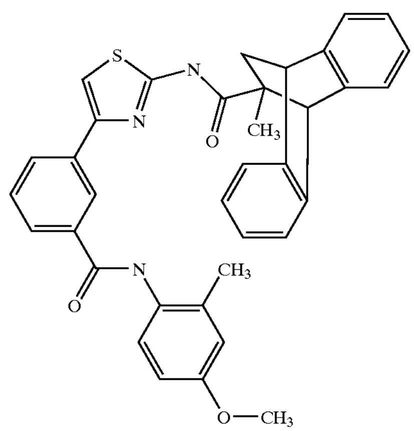 | 585.7 |
| 524 | | 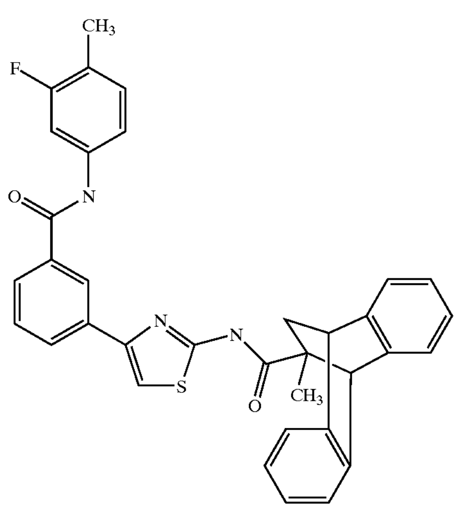 | 573.7 |

-continued

| Example | Chiral Compounds | Structure | MS: (M + H = MW +1) |
|---|---|---|---|
| 525 | | 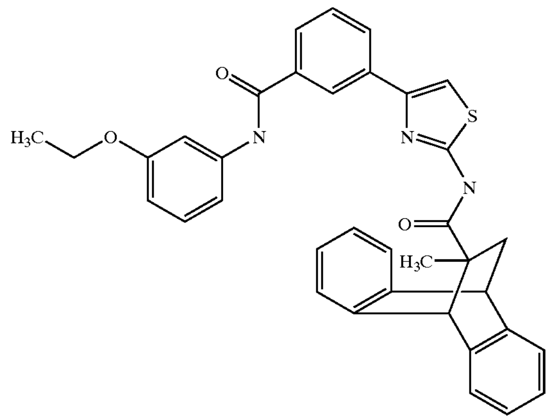 | 585.7 |
| 526 | | 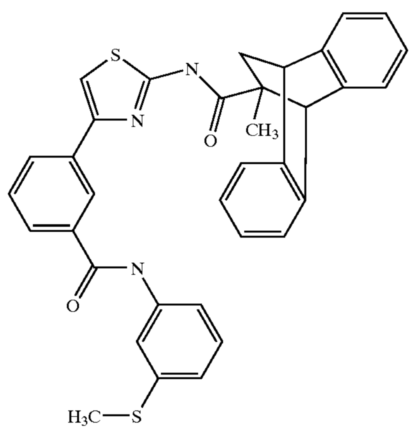 | 587.8 |
| 527 | | 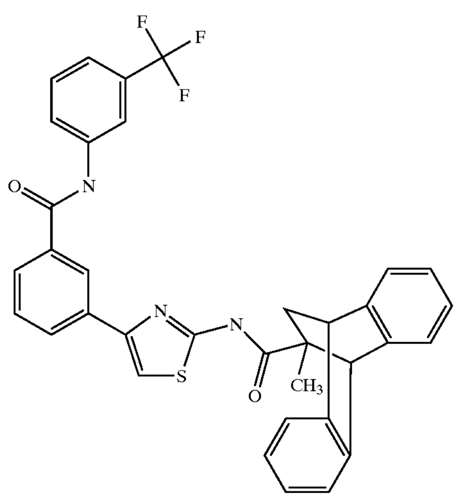 | 609.7 |

-continued
| Example | Chiral Compounds | Structure | MS: (M + H = MW +1) |
|---|---|---|---|
| 528 | | 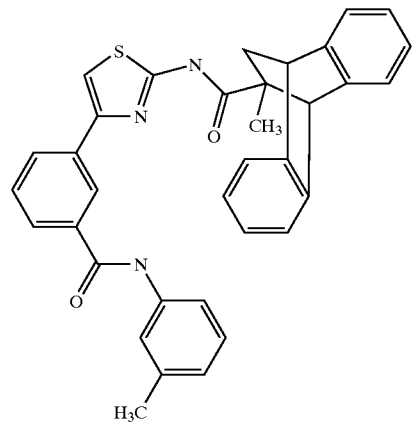 | 555.7 |
| 529 | | 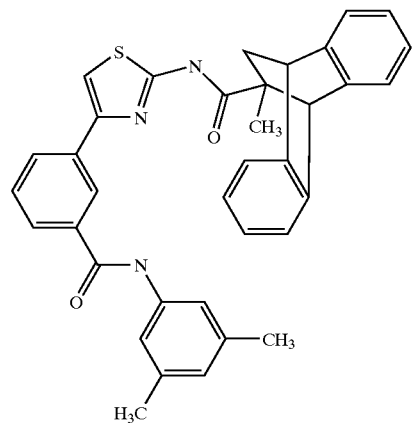 | 569.7 |
| 530 | | 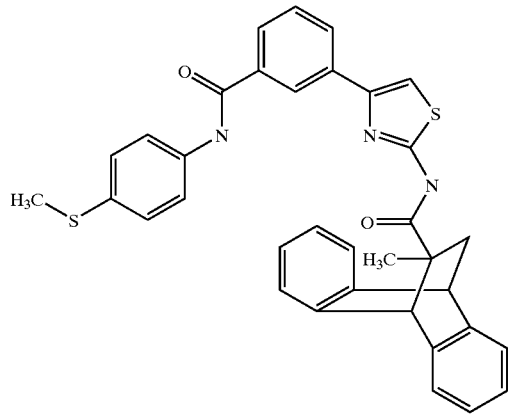 | 587.8 |

-continued

| Example | Chiral Compounds | Structure | MS: (M + H = MW +1) |
|---|---|---|---|
| 531 | | 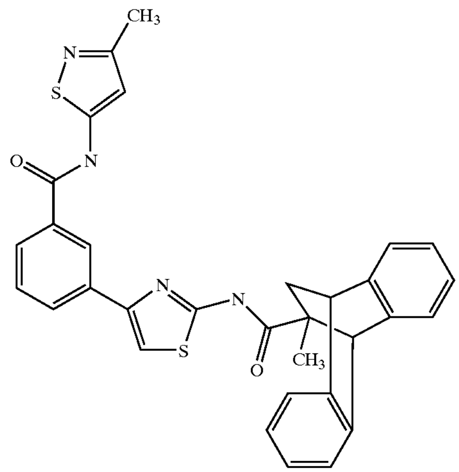 | 562.7 |
| 532 | | 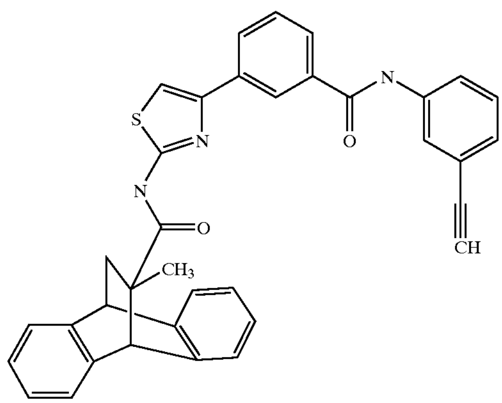 | 565.7 |
| 533 | | 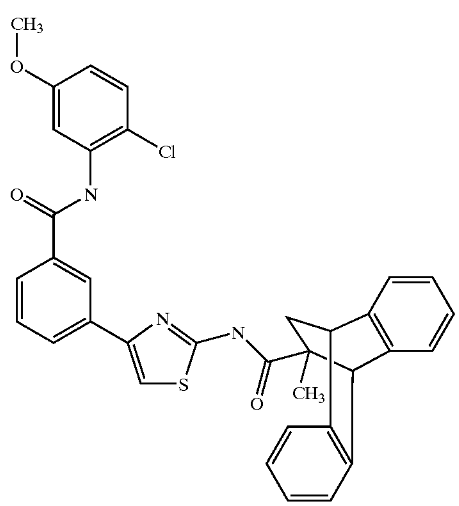 | 606.1 |

-continued
| Example | Chiral Compounds | Structure | MS: (M + H = MW +1) |
|---|---|---|---|
| 534 | | 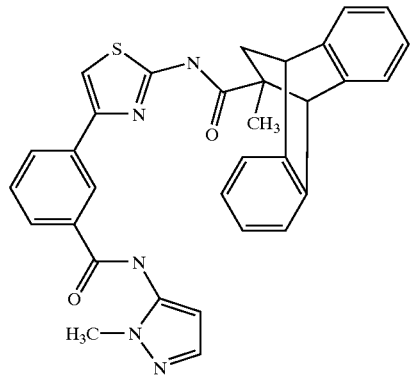 | 545.7 |
| 535 | | 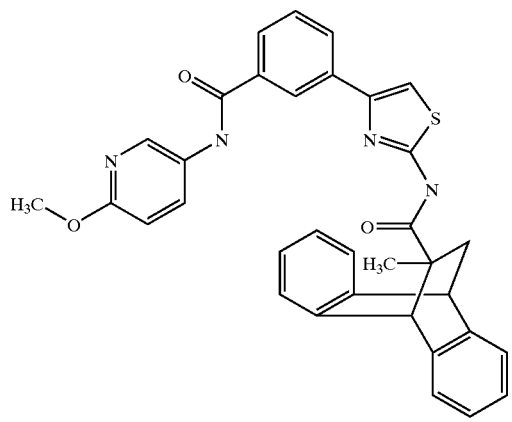 | 572.7 |
| 536 | Chiral (S) | 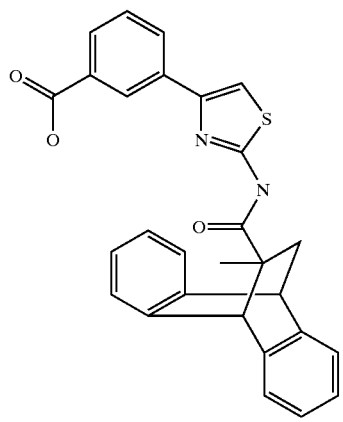 | 466.56 |

-continued
| Example | Chiral Compounds | Structure | MS: (M + H = MW +1) |
|---|---|---|---|
| 537 | Chiral (S) | 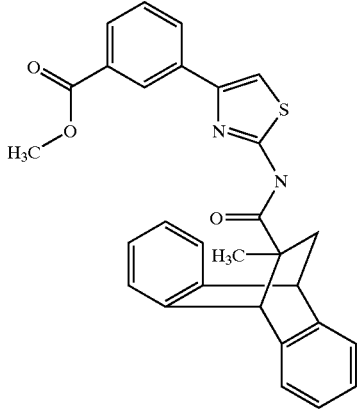 | 480.59 |
| 538 | Chiral (S) | 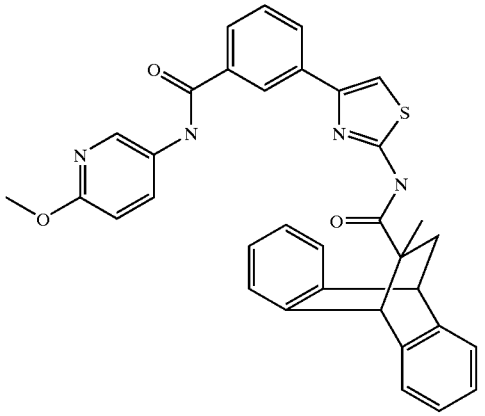 | 572.7 |
| 539 | Chiral (S) | 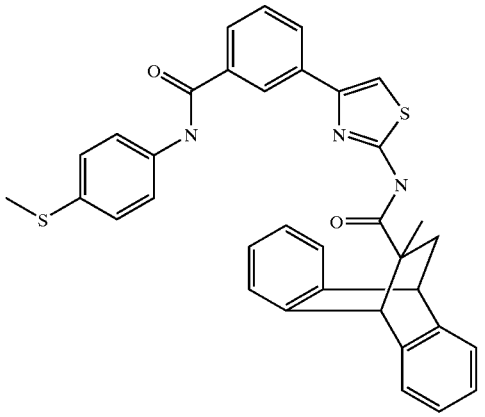 | 587.8 |

-continued
| Example | Chiral Compounds | Structure | MS: (M + H = MW +1) |
|---|---|---|---|
| 540 | Chiral (S) | 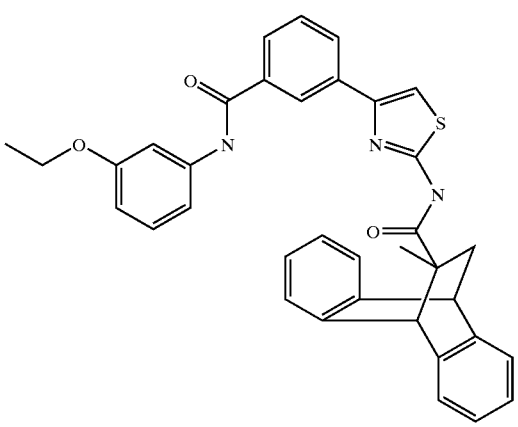 | 585.7 |
| 541 | Chiral (S) | 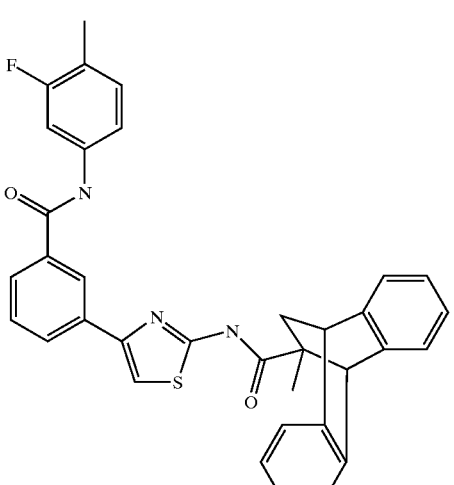 | 573.7 |
| 542 | Chiral (S) | 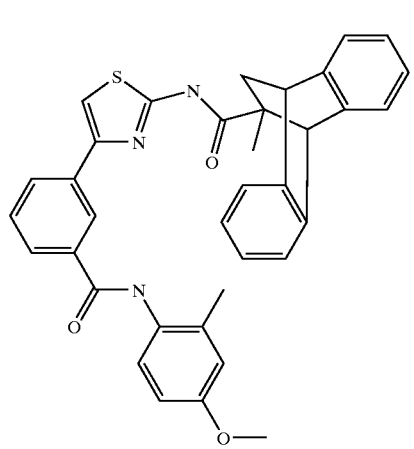 | 585.7 |

-continued
| Example | Chiral Compounds | Structure | MS: (M + H = MW +1) |
|---|---|---|---|
| 543 | Chiral (S) | 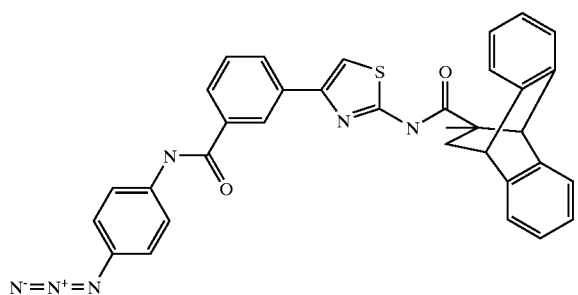 | 582.7 |
| 544 | Chiral (S) | 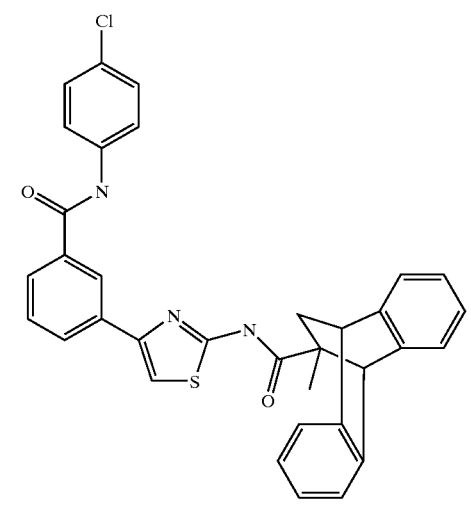 | 576.1 |
| 545 | Chiral (S) | 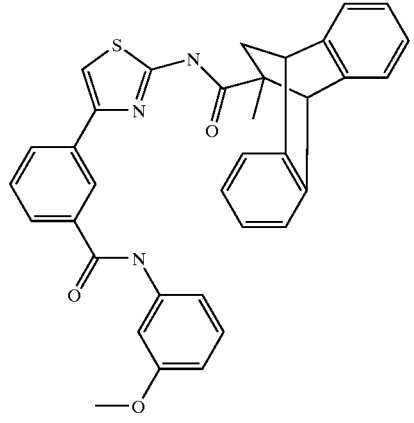 | 571.7 |
| 546 | Chiral (S) | 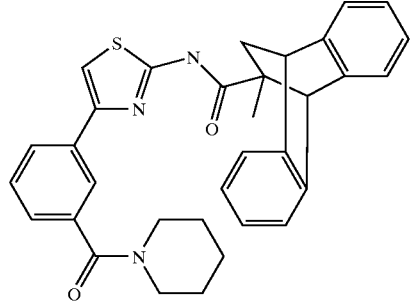 | 533.7 |

-continued
| Example | Chiral Compounds | Structure | MS: (M + H = MW +1) |
|---|---|---|---|
| 547 | Chiral (S) | 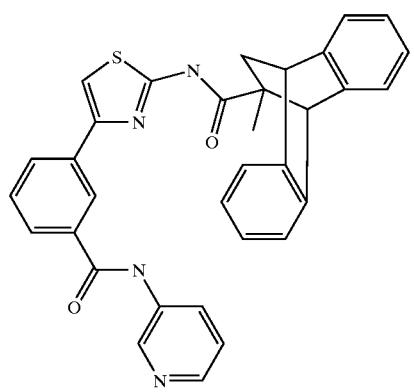 | 542.7 |
| 548 | Chiral (S) | 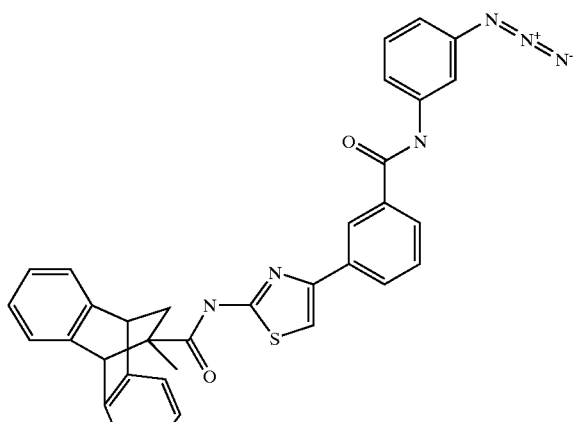 | 582.7 |
| 549 | Chiral (S) | 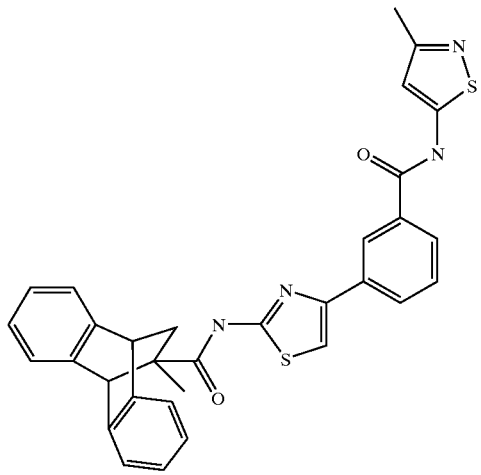 | 562.72 |

-continued
| Example | Chiral Compounds | Structure | MS: (M + H = MW +1) |
|---|---|---|---|
| 550 | Chiral (R) | 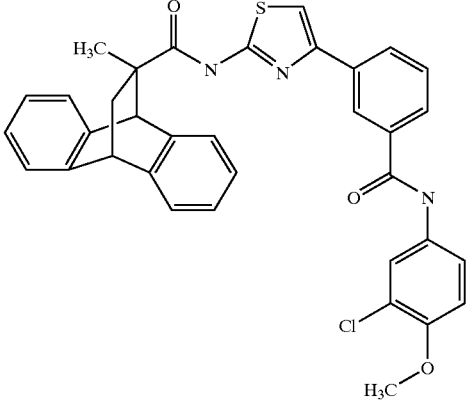 | 606.15 |
| 551 | Chiral (R) | 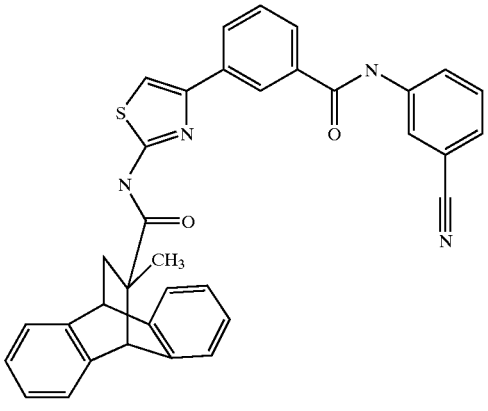 | 566.7 |
| 552 | Chiral (R) | 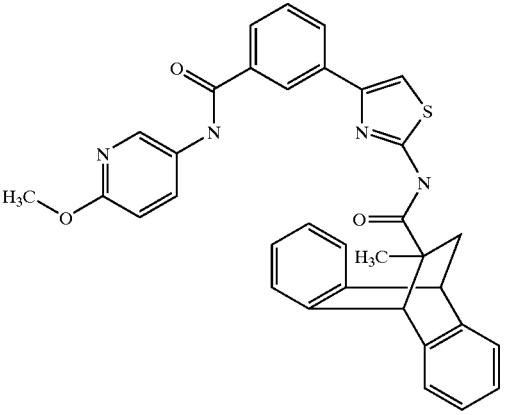 | 572.7 |

-continued

| Example | Chiral Compounds | Structure | MS: (M + H = MW +1) |
|---|---|---|---|
| 553 | Chiral (R) | 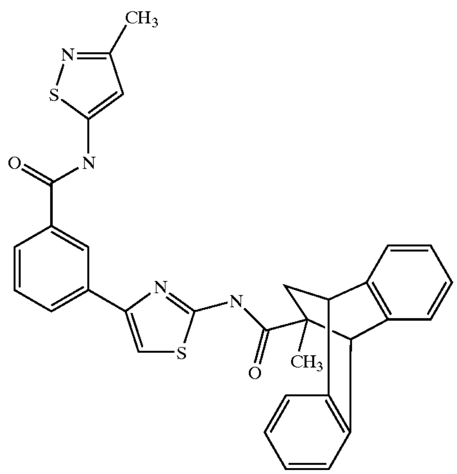 | 562.7 |
| 554 | Chiral (R) | 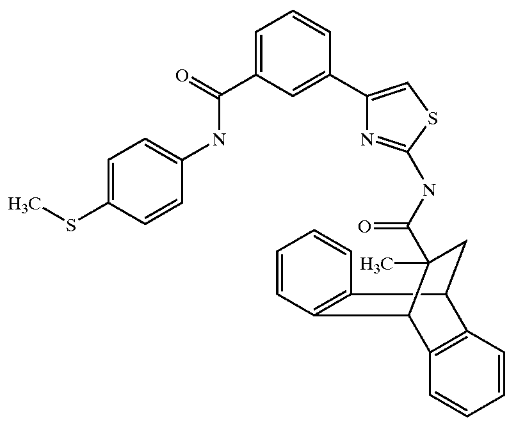 | 587.8 |
| 555 | Chiral (R) | 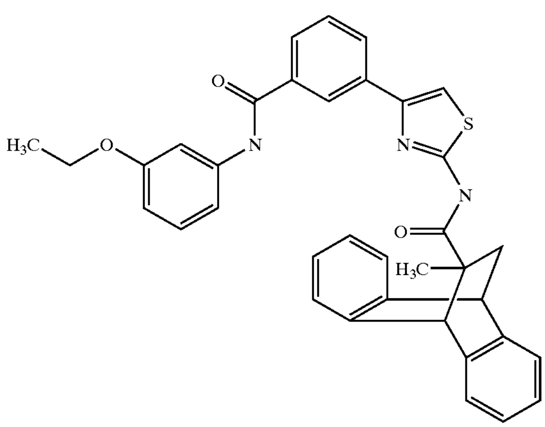 | 585.7 |

-continued

| Example | Chiral Compounds | Structure | MS: (M + H = MW +1) |
|---|---|---|---|
| 556 | Chiral (R) | 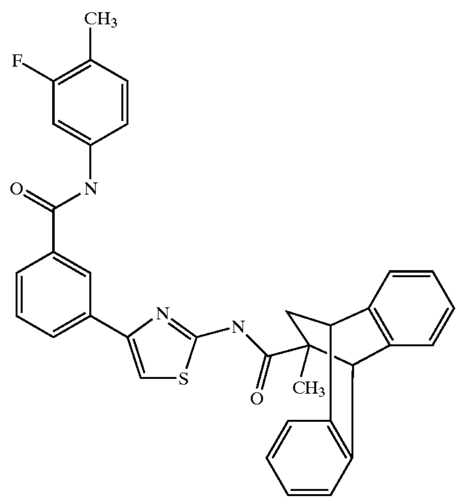 | 573.7 |
| 557 | Chiral (R) | 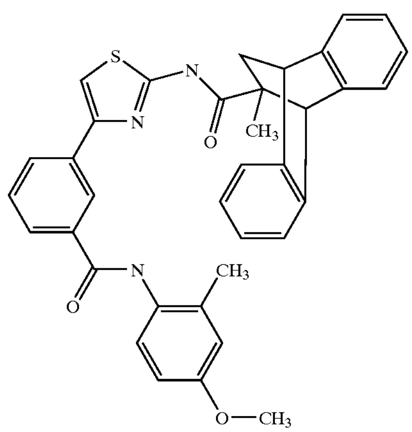 | 585.7 |
| 558 | Chiral (R) | 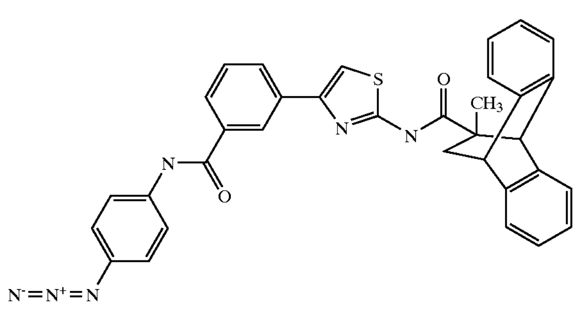 | 582.7 |

-continued
| Example | Chiral Compounds | Structure | MS: (M + H = MW +1) |
|---|---|---|---|
| 559 | Chiral (R) | 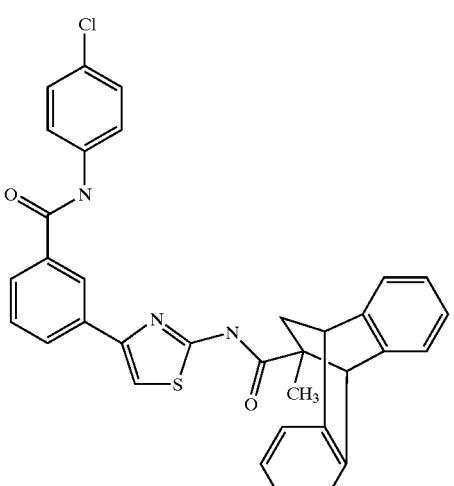 | 576.1 |
| 560 | Chiral (R) | 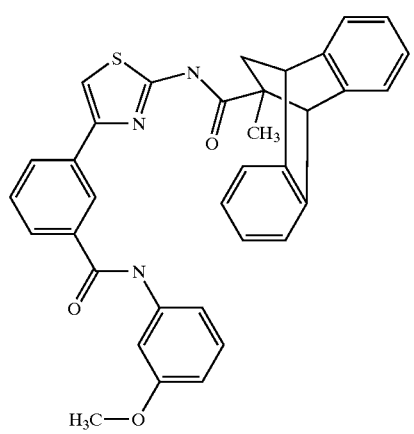 | 571.7 |

-continued

| Example | Chiral Compounds | Structure | MS: (M + H = MW +1) |
|---------|------------------|-----------|---------------------|
| 561 | Chiral (R) | 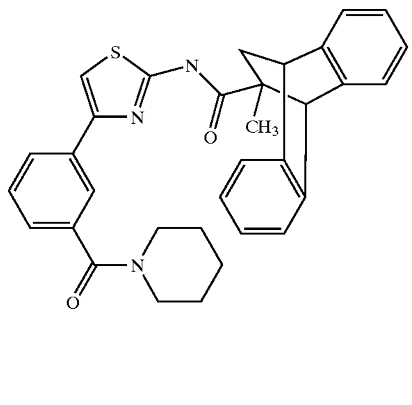 | 533.7 |
| 562 | Chiral (R) | 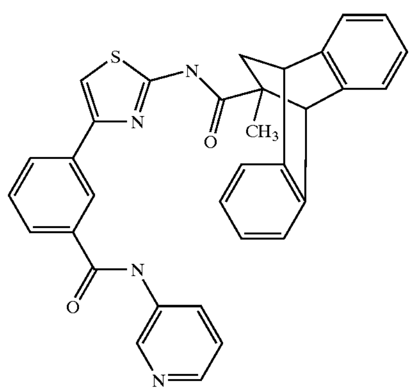 | 542.7 |
| 563 | Chiral (R) | 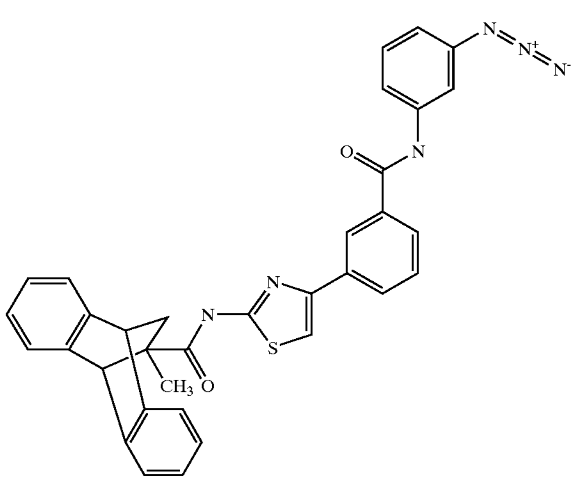 | 582.7 |

Example 564

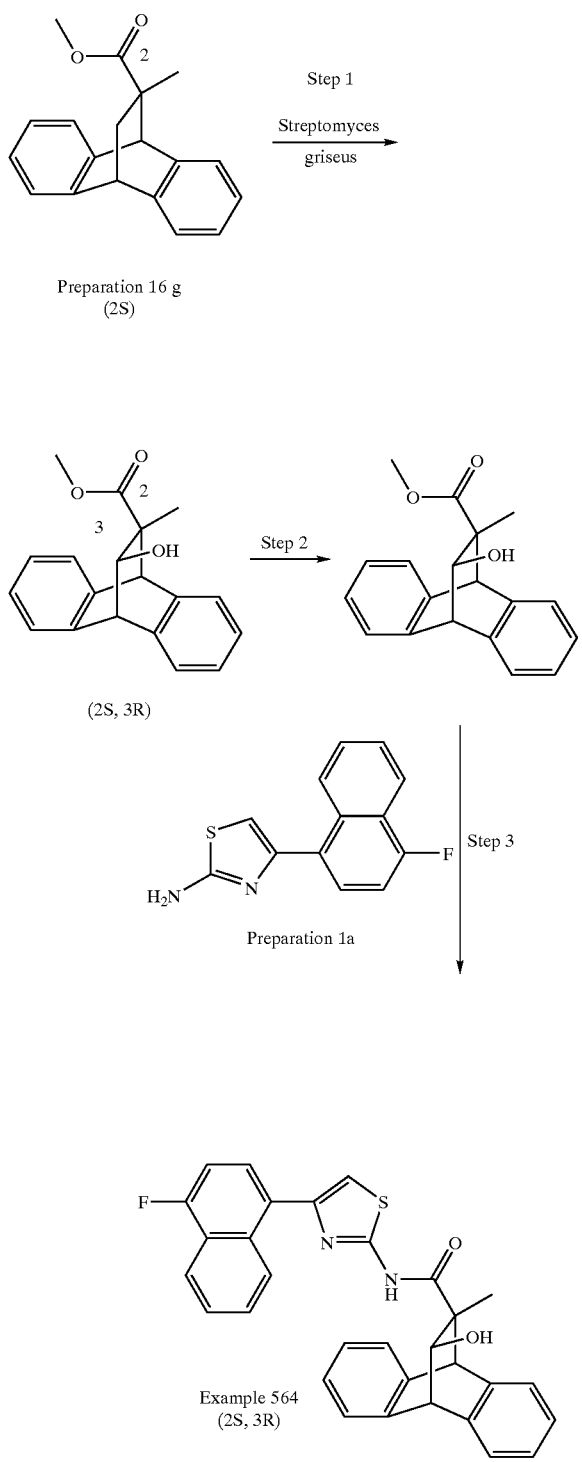

Step 1 From the frozen vegetative stock culture of *Streptomyces griseus* ATCC 10137, 2 ml was used to inoculate 100 ml of F7 medium contained the following per liter of deionized water: dextrose, 10 g; yeast extract, 10 g; malt extract, 10 g; peptone, 1 g, in a 500 ml flask (pH was adjusted to 7 before sterilization at 120° C. for 30 minutes). The culture was incubated for 3 days at 28° C. on a rotary shaker operating at 250 rpm. Two ml of this culture was used to inoculate each of twelve 500-ml flasks containing 100 ml of F7 medium. The flasks were incubated at 28° C. on a rotary shaker operating at 250 rpm for 17 hours. Eight mg of Preparation 16g S-isomer (97.9% ee) in 0.32 ml DMF was added to each flask. The flasks were then returned to the shaker and incubated for additional 9.5 hours at 28° C. and 250 rpm. The culture was pooled and subjected to sonication for total of 5 min. with a High Intensity Ultrasonic Processor (Model: VCX600, Sonics & Material Inc.) equipped with a microtip, at 40% out put. The resulting mixture was extracted with 600 ml ethyl acetate and the ethyl acetate extract was evaporated to dryness. The residue was dissolved in 2 ml of acetoniltrile and subjected to preparative HPLC with a YMC ODS-A column (30 mm ID×100 mm length, 5μ particle size). Elution flow rate was 30 ml/min. In each run, sample (0.5 to 1 ml) was loaded onto the column at water (solvent A)-acetonitrile (solvent B) 90/10 v/v and separated using the following gradient program: 10% B, 3 min; 10% to 35% B linear gradient, 1 min; 35% B. 9 min; 35% to 60% B linear gradient, 1 min; 60% B, 4 min; 60% to 90% B linear gradient, 1 min; 90% B, 4 min. Detection (UV) was at 210 nm. The fractions containing BMS-585157 was eluted between 18 to 19 minutes. The BMS-585157 fractions were pooled and evaporated in vacuo to a small volume, then was lyophilized. A total of 60 mg of BMS-585751 was obtained as light yellow solid (yield, 62.5%). The reaction and purification were monitored by analytical HPLC with a Hewlett Packard 1100 Series Liquid Chromatograph using an YMC Packed ODS-AQ column, 4.6 mm i.d.×15 cm 1. A gradient system of 1 mM HCl in water (solvent A) and acetonitrile (solvent B) was used: 70% to 90% B linear gradient, 5 min; 90% B, 1.5 min; 90% to 70% linear gradient, 0.5 min. The flow rate was 1.2 ml/min and UV detection was at 210 nm. Retention time for starting compound and product was 5.16 and 2.76 min, respectively. $^1$H-NMR Observed Chemical Shifts (relative to $CD_3CN$ signal δ1.94): δ 7.33 (3H, m), 7.21 (1H, m), 7.15 (2H, m), 7.09 (2H, m), 4.61 (1H, dd, $J_1$=5.8 Hz, $J_2$=3.2 Hz, CH-3), 4.40 (1H, s, CH-11), 4.32 (1H, d, J=3.5 Hz, CH-4), 3.51 (3H, s, $CH_3$-19), 2.90 (1H, d, J=6.0 Hz, OH), 0.93 (1H, s, $CH_3$-18). $^1$H-$^1$H NOE Observed NOE: CH-4 and OH (when CH-3 was irradiated); CH-11 and OH (when $CH_3$-18 was irradiated). MS:+c APCI (m/z): 312 ($[M+H_2O]^+$), 294, 277.

Step 2

To a solution of the product of step 1 (0.079 mmol, 23 mg) in MeOH (2 mL) was added sodium hydroxide (400 μL of 1 N NaOH, 0.4 mmol). After 4 hours at 75° C. and 16 hours at RT the reaction mixture was quenched with 1N HCl (3 mL) and extracted with dichloromethane (3×30 mL). The organic phases were dried over $Na_2SO_4$ and concentrated in vacuo to give 19.6 g (Y: 89%) of the product of step 2.

Step 3

To a solution of the product of step 2 (0.070 mmol, 19.6 mg) in acetonitrile (1.0 mL) was added 1-[3-

(dimethylamino)propyl-3-ethylcarbodiimide hydrochloride (EDCI), (0.084 mmol, 16 mg), 1-hydroxy-7-azabenzotriazole (HOAt), (0.084 mmol, 11.5 mg), triethylamine (0.175 mmol, 17.7 mg) and Preparation 1a (0.086 mmol, 21 mg). The resulting mixture was heated to 80° C. for 20 h, cooled and diluted with MeOH (1.0 mL). The diluted reaction mixture was then purified by preparative HPLC to afford the TFA salt of the title compound. The product was then neutralized using a solid phase extraction cartridge (500 mg high load, SCX strong cation exchangerfrom United Chemical Technologies, Inc). After conditioning the cartridge with MeOH (2×1.5 mL) the product was loaded on to the cartridge. The cartridge was then washed with MeOH (2×1.5 mL), followed by a 2N $NH_3$ in MeOH solution to afford 18.8 mg (55%) of Example 564. MS (E+) m/z: 507 (MH$^+$).

Example 565

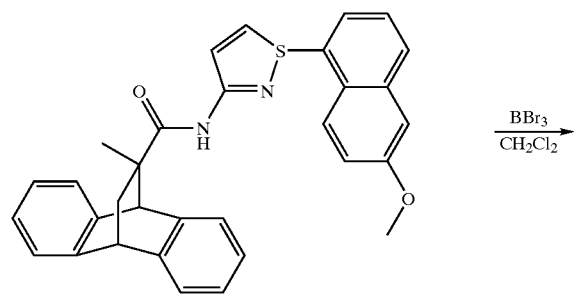

Example 178

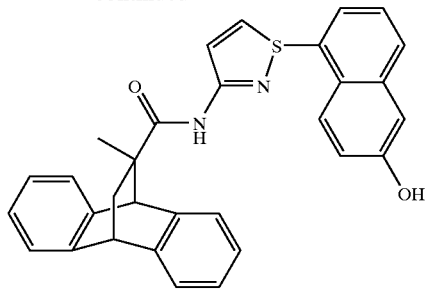

Example 565

To a solution of Example 178 (20.0 mg, 0.04 mmol, 1.0 equi.) in dichloromethane (5 mL) at 0° C., was added a solution of boron tribromide in dichloromethane (1M, 0.20 mL, 0.20 mmol, 5 equi.). The reaction solution was stirred at 0° C. for 3 hours, and let warmed up to room temperature and let stirred at room temperature overnight. The next day, the reaction solution was quenched with methanol in an ice bath. The crude product mixture was purified by reversed phased PREP HPLC, followed by neutralization with cation exchange SPE, to yield 5.4 mg (28% yield) of Example 565: LC/MS (m/z 489, (M+H)$^+$).

Examples 566 to 567

Examples 566 to 567 in the table below were prepared in a similar manner from the corresponding methyl ethers.

| Example 1 | Structure | MS: (M + H = MW + 1) |
|---|---|---|
| 566 | 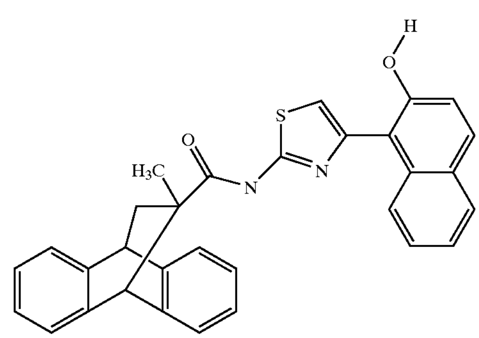 | 488.61 |
| 567 | 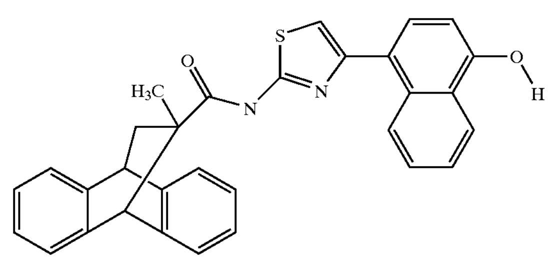 | 488.61 |

Examples 568 to 569

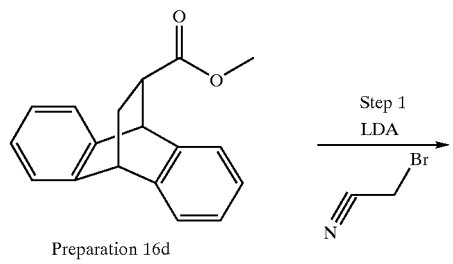

Preparation 16d

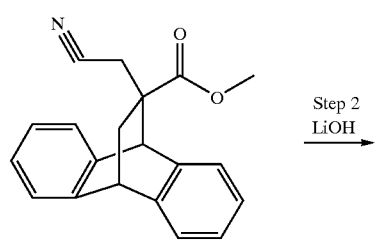

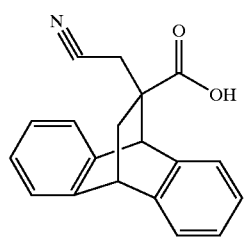

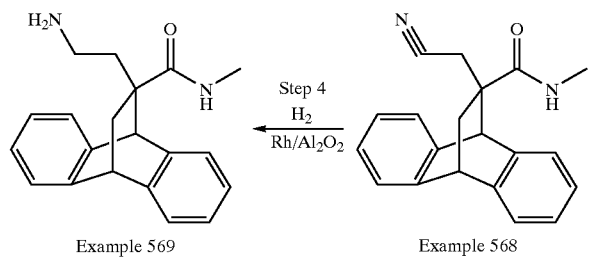

Example 569                Example 568

Step 1

To a solution of the product of preparation 16(d (2.45 mmol, 650 mg) in THF (10.0 mL) at −78° C. was added lithium diisopropylamide (2.94 mmol, 1.47 ml of a 2 M solution in heptane/THF/ethyl benzene) dropwise. After 1 hour, bromoacetonitrile (3.68 mmol, 440 mg) in THF (0.70 mL) was added dropwise. The mixture was allowed to warm to RT. After 16 hours the reaction mixture was quenched with 1N HCl (30 mL) and extracted with dichloromethane (3×30 mL). The organic phases were concentrated in vacuo and the residue chromatographed on silica gel (eluted with 20% ethyl acetate in hexane) to give 510 mg (Y: 69%) of the product of step 1.

Step 2

To a solution of the product of step 1 (1.68 mmol, 510 mg) in THF (3.4 mL) was added lithium hydroxide (1.7 mL of 5N LiOH). After 20 hours at 70° C. the reaction mixture was quenched with 1N HCl (30 ml) and extracted with dichloromethane (3×30 mL). The organic phases were dried over $Na_2SO_4$ and concentrated in vacuo to give 410 mg (Y: 84%) the product of step 2

Step 3

To a solution of the product of step 2 (0.45 mmol, 130 mg) in dichloromethane (2.0 mL) was added oxalyl chloride (0.54 mmol, 0.28 mL of a 2 N solution in dichloromethane) and DMF (2 drops). After 1 hour at RT the reaction mixture is concentrated in vacuo and then redissolved in dichloromethane (1.0 mL). To the resulting mixture is then added triethylamine (0.54 mmol, 0.075 mL) and methylamine (0.90 mmol, 0.45 mL of a 2 M solution in THF). After 2 hours the reaction mixture was quenched with saturated sodium bicarbonate solution, extracted by dichloromethane (3×30 mL), dried over $Na_2SO_4$ and concentrated under vacuo to give 53 mg (Y: 39%) of Example 568.

Step 4

To a solution of the product of step 3 (0.132 mmol, 40 mg) in methanolic ammonia (7.0 mL) was added 5% rhodium on alumina (100 mg). The reaction mixture was then allowed to hydrogenate at 55 psi of $H_2$ in a Parr apparatus. After 20 hours the reaction mixture was filtered through celite and concentrated in vacuo to give 40 mg (Y: 99%) of Example 569.

Examples 570 to 572

In a similar manner the Examples 570 to 572 were prepared.

| Example | Structure | MS: (M + H = MW + 1) |
|---|---|---|
| 570 | 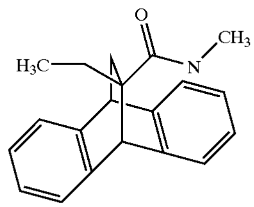 | 291.4 |
| 571 | 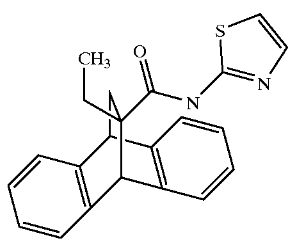 | 360.48 |
| 572 | 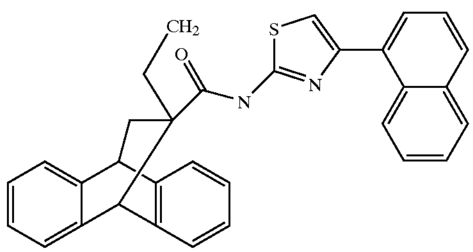 | 486.64 |

Example 573

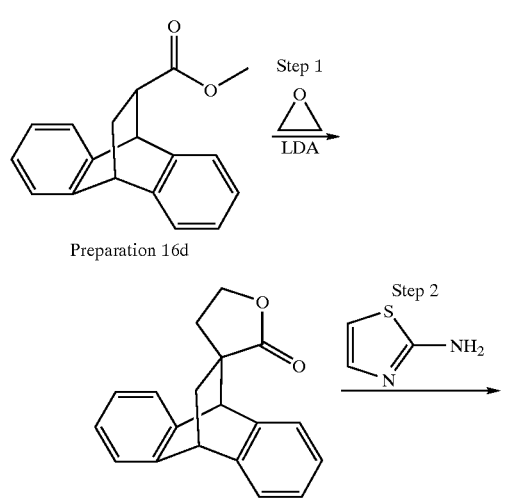

Preparation 16d

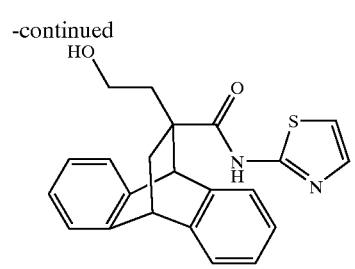

-continued

Example 573

Step 1

To a solution of the product of preparation 16d (3.90 mmol, 1.03 g) in THF (8.0 mL) and TMEDA (1.0 mL) at −78° C. was added lithium diisopropylamide (4.69 mmol, 2.35 ml of a 2 M solution in heptane/THF/ethyl benzene) dropwise. After 1 hour the reaction mixture was saturated with ethylene oxide gas. The reaction mixture was then warmed to RT over 3 hours, quenched with 1N HCl (30 mL) and extracted with dichloromethane (3×30 mL). The organic phases were concentrated in vacuo and the residue chromatographed on silica gel (eluted with 10% ethyl acetate in hexane) to give 220 mg (Y: 22%) of the product of step 1.

Step 2

To a solution of the product of step 1 (0.471 mmol, 130 mg) in dichloromethane (8.0 mL) under nitrogen at 0° C. was added trimethylaluminum (3.77 mmol, 1.88 ml of a 2 M solution in toluene). The reaction mixture was allowed to stir at 0° C. for 20 min and then at RT for 1 h. 2-Aminothiazole (3.77 mmol, 377 mg) in dichloromethane (5.0 µL) was then added. After 16 hours at reflux the reaction mixture is quenched with 1N HCl (30 mL) and extracted with dichloromethane (3×30 mL). The organic phases were concentrated in vacuo and the residue chromatographed on silica gel (eluted with 5% methanol in dichloromethane) to give 91 mg (Y: 51%) of Example 573. (E+) m/z: 376 (MH$^+$).

Examples 574 to 575

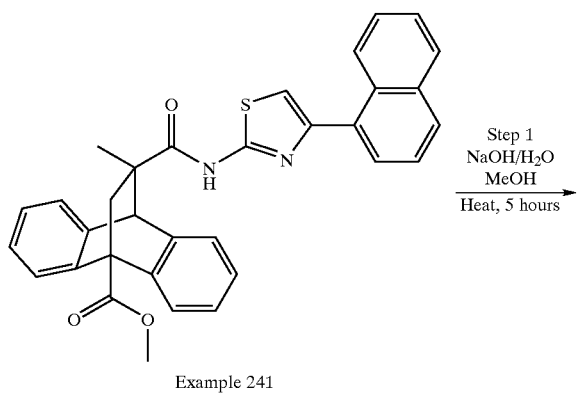

Example 241

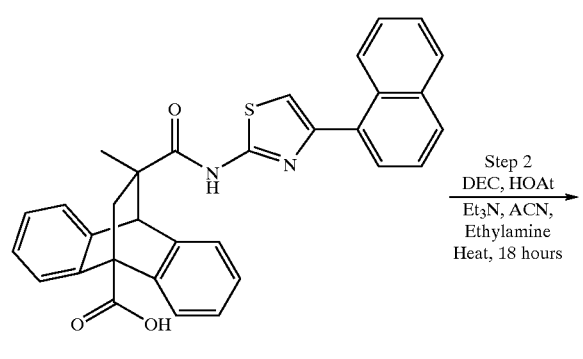

Example 574

-continued

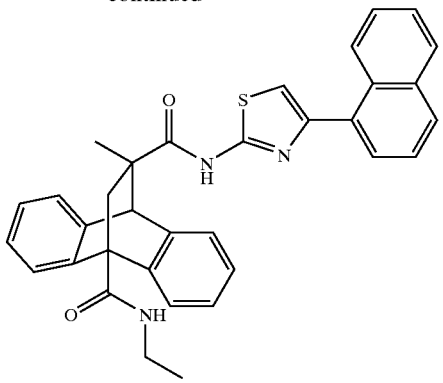

Example 575

Step 1

To a solution of Example 241 (80 mg, 0.15 mmol) in methanol (5 mL) was added a sodium hydroxide solution (1.0 mL) (solution is 1:1 of 50% NaOH and water). The reaction solution was heated to 60° C. for 5 hours. The solution was cooled and quenched with HCl (6N). The product was extracted with ethyl acetate (3×). The combined organic extracts were dried with anhydrous magnesium sulfate and concentrated in vacuo to give 68 mg (87% yield) of Example 574. LC/MS (m/z 517, (M+H)$^+$).

Step 2

To a solution of the product of step 1 (20 mg, 0.038 mmol, 1.0 equi.) in acetonitrile (2 mL) was added 1-[3-(dimethylamino) propyl]-3-ethylcarbodiimide hydrochloride (DEC) (8.9 mg, 0.046 mmol, 1.2 equi.), 1-hydroxy-7-azabenzotriazole (HOAt) (6.3 mg. 0.046 mmol, 1.2 equi.), triethylamine (0.013 mL, 0.097 mmol, 2.5 equi.), and ethylamine (2.1 mg, 0.046 mmol, 1.2 equi.). The reaction solution was heated to 80° C. for 18 hours and followed by concentrated in vacuo. The product mixture was purified by reversed phased PREP HPLC, followed by neutralization with cation exchange SPE, to yield 3.1 mg (14%) of Example 575: LC/MS (m/z 544, (M+H)$^+$); $^1$H NMR (CDCl$_3$) δ 8.22 (m, 1H), 7.89 (m, 2H), 7.60 (d, 1H), 7.14–7.53 (m, 11 H), 7.03 (s, 1H), 4.46 (s, 1H), 3.69 (q, 2H), 2.85 (d, 1H), 1.83 (d, 1H), 1.36 (t, 3H), 1.12 (s, 3H).

Examples 576 to 578
In a similar manner the Examples 576 to 578 were prepared.
| Example | Structure | MS: (M + H = MW + 1) |
|---|---|---|
| 576 | 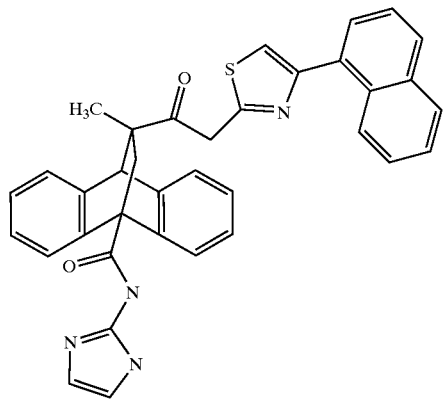 | 581.7 |
| 577 | 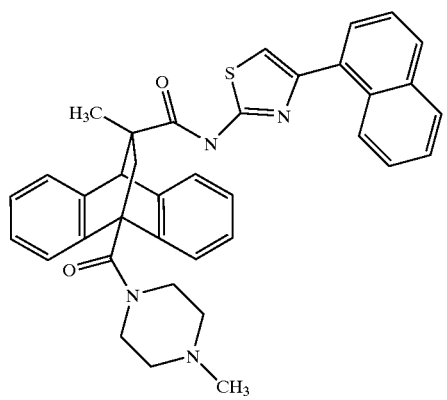 | 598.77 |
| 578 | 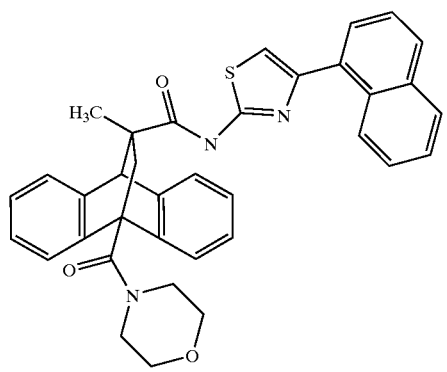 | 585.73 |

Example 579

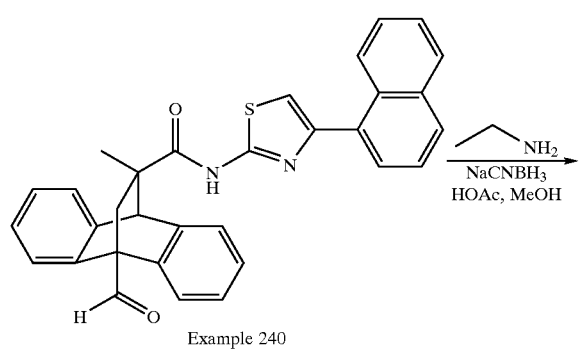

To a mixture of Example 240 (28 mg, 0.056 mmol, 1.0 equi.) and ethylamine (3.0 mg, 0.067 mmol, 1.2 equi.) in methanol (2 mL, 1.0% acetic acid) was added sodium cyanoborohydride (3.5 mg, 0.056 mmol, 1.2 equi.). The solution was stirred at room temperature for 18 hours. The crude product mixture was purified by reversed phase PREP HPLC, followed by neutralization with cation exchange SPE, to yield 3.8 mg (13%) of Example 579: LC/MS (m/z 530, (M+H)+); $^1$H NMR (CDCl$_3$) δ 8.25 (m, 1H), 7.87 (m, 2H), 7.62 (d, 1H), 7.51 (m, 3H), 7.06–7.52 (m, 7H), 7.06 (s, 1H), 4.40 (s, 1H), 3.7 (s, 2H), 2.99 (q, 2H), 2.60 (d, 1H), 1.58 (d, 1H), 1.28 (t, 3H), 1.19 (s, 3H).

Example 580

In a similar manner the Example 580 was prepared.

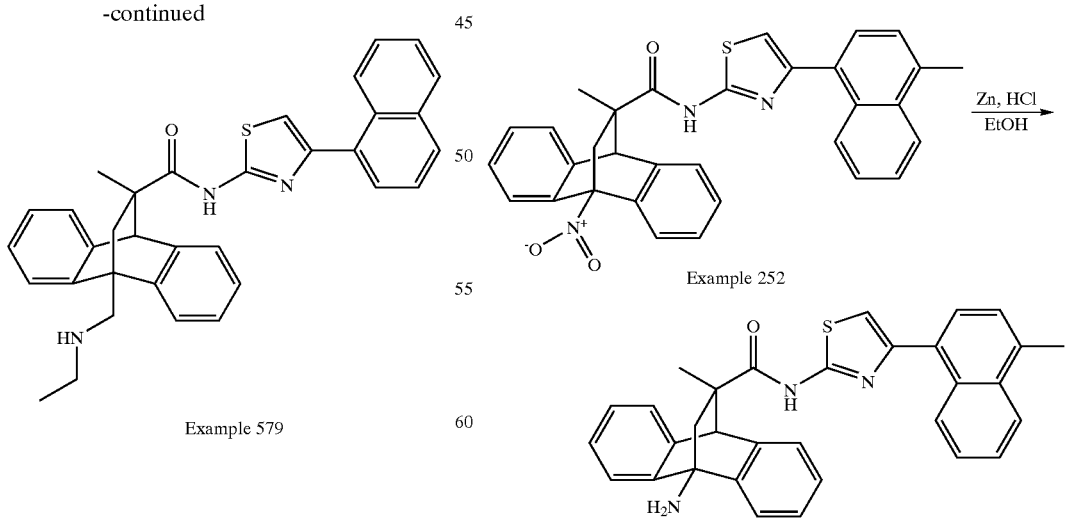

Example 252 (25 mg, 0.05 mmol) was dissolved in a solution of ethanol (5 mL) and hydrochloric acid (concentrated, 0.25 mL) at room temperature. Zinc dust (20 mg) was added in and the reaction solution was stirred at room temperature for 24 hours. The reaction was quenched with sodium bicarbonate solution (10%) and ethyl acetate. The organic phase was washed with 1N sodium hydroxide solution, dried and concentrated in vacuo to give the crude product mixture. The product was purified by PREP HPLC, followed by cation exchange SPE to give 4.1 mg (16% yield) of Example 581: MS (m/z 502 (M+H)$^+$).

Example 582

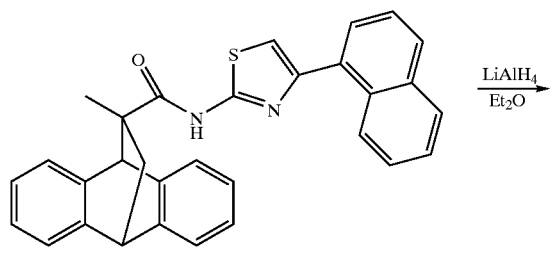

Example 112

Example 582

To a solution of Example 112 (33 mg, 0.070 mmol) in 1.50 mL anhydrous diethyl ether at room temperature was added 0.18 mL of a 1.0M solution of lithium aluminum hydride in THF (0.180 mmol, 2.6 eq). After stirring at room temperature for 3 h an additional 0.18 mL lithium aluminum hydride solution (0.180 mmol, 2.6 eq) was added to push the reaction further. The mixture was allowed to stir for 48 h at rt, and quenched by adding 0.15 mL methanol dropwise, then 0.15 mL water, then 20 mL saturated aqueous KOH. Extracted 2×30 mL ethyl acetate. Dried over sodium sulfate. Concentrated under vacuum. Purified the crude material using prep HPLC. Free-based the product by passing through a basic SCX cartridge using methanol as the eluent. Removal of the solvent afforded 2.5 mg of Example 582 as a solid white film (8%) LC/MS (m/z 459, (M+H)$^+$).

Example 583

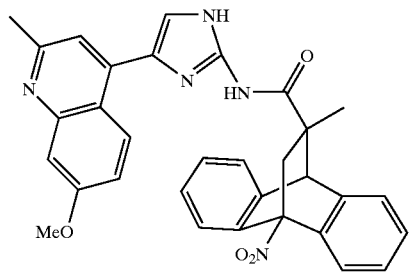

Step 1: 7-methoxy-2-methyl-quinolinyl-4-boronic acid

To a solution of 4-bromo-7-methoxy-2-methylquinoline (700 mg, 2.8 mmol), prepared according to a known procedure (Reference: Abe, Y. et. al. *J. Med. Chem.* 1998, 41, 40624097), in THF (15 mL) at −78° C. were added triisopropyl borate (1.3 mL, 5.6 mmol) and t-butyllithium (1.7 M, 5.0 mL). The solution was then slowly warmed to room temperature and kept stirring overnight. Next morning, the solution was quenched with 1N HCl (1.5 mL) and the solid was thus obtained after decanting THF. The solid was dissolved in MeOH and diluted with CH$_2$Cl$_2$. The solution was filtered and the filtrate was concentrated to provide 7-methoxy-2-methyl-quinolinyl-4-boronic acid (560 mg, 90%). MS (ESI) (M+1)=218.26.

Step 2: 4-(5-bromo-2-nitro-1H-imidazol-4-yl)-7-methoxy-2-methyl-quinoline

To a solution of the boronic acid from Step 1 (560 mg, 2.6 mmol) and 4,5-dibromo-2-nitro-1H-imidazole (380 mg, 1.4 mmol), prepared according to a known procedure (Reference: Palmer, B. D. et. al. J. Chem. Soc. Perkin Trans 1, 1989, 95–99), in 50 mL of THF was added 20 mL of sat. K$_2$CO$_3$. To this solution was bubbled a flow of N$_2$ for 30 minutes and then 200 mg of tetrakis(triphenylphosphine) palladium(0) (0.17 mmol) was added. The solution was heated at 80° C. overnight. After cooling down, the solution was diluted with EtOAc and the organic layer was separated and washed with brine. The organic layer was dried over MgSO$_4$. After filtration and concentration, the residue was purified by flash column chromatography to provide the desired 4-(5-bromo-2-nitro-1H-imidazole-4-yl)-7-methoxy-2-methyl-quinoline (114 mg, 15%). MS (ESI) (M+1)= 363.29,365.29.

Step 3: 4-(7-methoxy-2-methyl-quinolin-4-yl]-1H-imidazole-2-ylamine

To a solution of the product of Step 2 (114 mg, 0.31 mmol) in 15 mL of MeOH was added 100 mg of 10% Pd/C and the solution was purged with H$_2$. The solution was then stirred under H$_2$ atmosphere overnight. After filtration and concentration, the desired 4-(7-methoxy-2-methyl-quinolin-4-yl)-1H-imidazole-2-ylamine (90 mg, 87%) was obtained as a HBr salt. MS (ESI) (M+1)=255.33.

Step 4

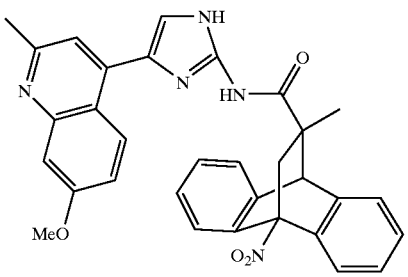

Following a similar procedure as described in Example 1, the coupling reaction of the product of Step 3 (32 mg, 0.095 mmol), and the acid of Preparation 17E (39 mg, 0.12 mmol) provided compound of Example 583 (26 mg, 50%). MS (ESI) (M+1)=546.33.

Examples 584 to 586

In a similar manner to the procedure of Example 583, Examples 584 to 586 were prepared from acid of Preparation 17E and the appropriate 4-(quinolin-4-yl)-1H-imidazole-2-ylamine or 4-isoquinolin-5-yl-]H-imidazol-2-ylamine. The amines were prepared according to the procedures described in Steps 1 to 3 of Example 583, i.e. via the Pd-catalyzed coupling reaction of 4,5-dibromo-2-nitro-1H-imidazole and the boronic acid derived from corresponding bromo-quinoline or bromo-isoquinoline, followed by the hydrogenation reaction.

| Example | Structure |
|---------|-----------|
| 584 | 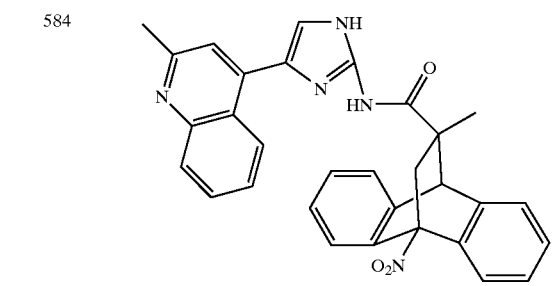 |
| 585 | 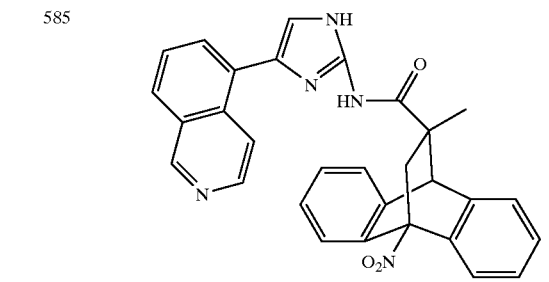 |
| 586 | (see continued) |

-continued

| Example | Structure |
|---------|-----------|
| 586 | (shown at top of next column) |

Example 587

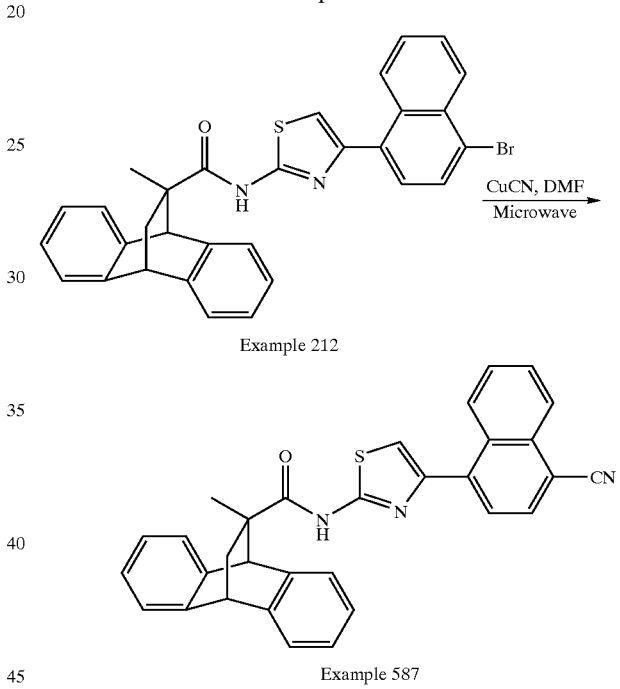

Example 587

A suspension Example 212 (50 mg, 0.091 mmol) and cuprious cyanide (10 mg, 0.11 mmol) in DMF (2 mL) was introduced into a dried heavy wall Pyrex tube, flushed with nitrogen and tightly sealed. The tube was placed in a microwave (Smith Workstation 300W from Magnetron @ 2.45 GHz) and heated to 200° C. while stirring for 2.25 h. After the tube had cool down to room temperature, the reaction mixture was diluted with dichloromethane, washed with saturated sodium bicarbonate, dried over magnesium sulfate, filtered and concentrated in vacuo to provide a brown oil. Flash chromatography (Isco silica gel, 4 g column, 10% ethyl acetate/hexane) provided Example 587 as an off-white solid (25 mg, 55% yield): $^1$H NMR (CDCl$_3$) δ 8.67 (bs, NH), 8.36 (d, 1H), 8.32 (d, 1H), 7.95 (d, 1H), 7.73 (t, 1H), 7.62–7.69 (m, 2H), 7.26–7.38 (m, 4H), 7.15–7.20 (m, 3H), 7.14 (s, 1H), 7.09 (t, 1H), 4.37–4.46 (m, 2H), 2.65 (dd, 1H), 1.65 (dd, 1H), 1.18 (s, 3H); HPLC $t_R$=4.2 min.; LC/MS m/z 498 (M+H)$^+$.

Examples 588 to 645

In a similar manner as described in Example 1, Examples 588 to 645 were prepared from the coupling of corresponding acids and amines. Preparations of amines or acids not commercially available are described in the preceding preparations section of this document. All examples in the table are racemic unless specified otherwise. Examples in the table where one enantiomer predominates or is the sole component, are designated as either R or S. Separation of the enantiomers on a chiral column employed procedures described in the preceding preparations section of this document.

| Example No. | Structure | Chiral Compounds | MS: (M + H = MW + 1) |
|---|---|---|---|
| 588 | 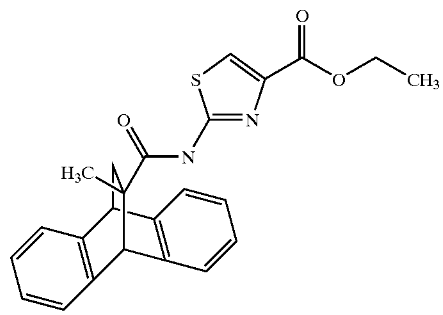 | | 419.18 |
| 589 | 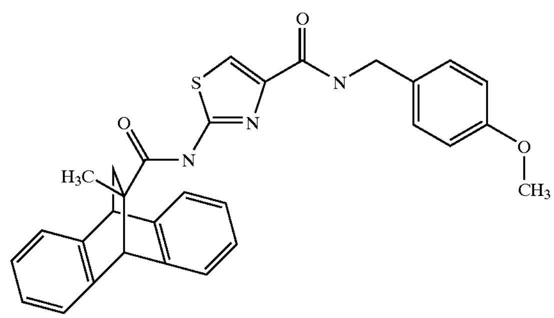 | | 510.34 |
| 590 | 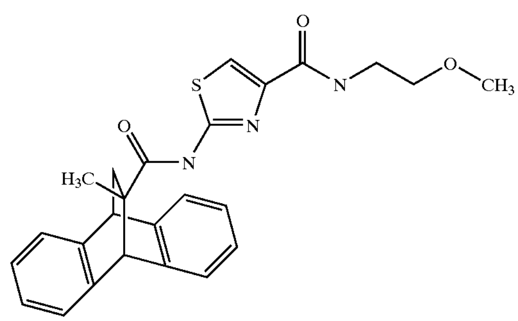 | | 448.38 |
| 591 | 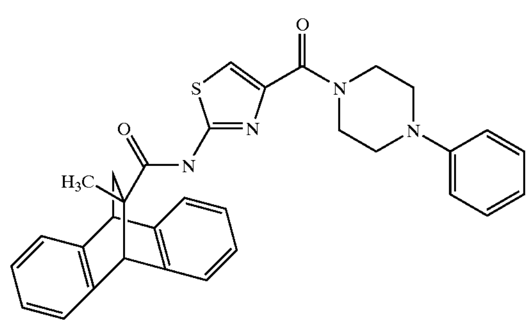 | | 535.2 |

-continued

| Example No. | Structure | Chiral Compounds | MS: (M + H = MW + 1) |
|---|---|---|---|
| 592 | 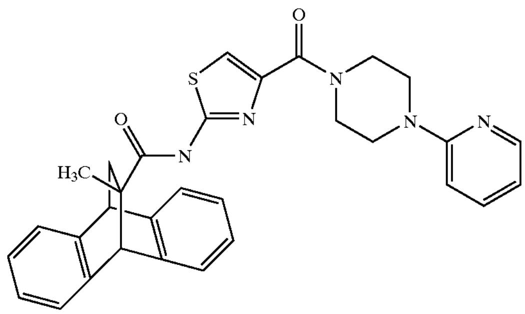 | | 536.21 |
| 593 | 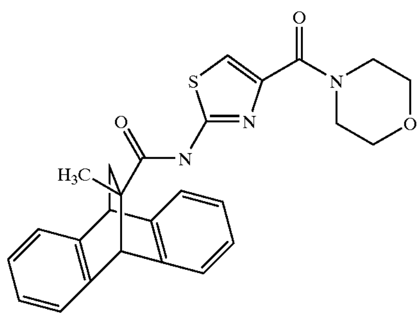 | | 460.38 |
| 594 | 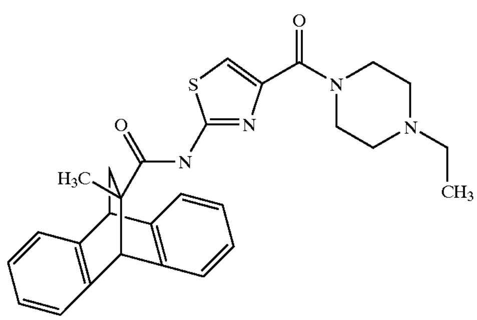 | | 487.46 |
| 595 | 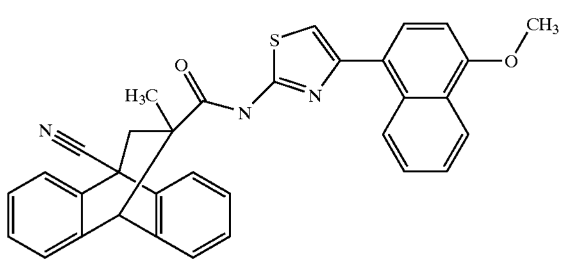 | | 528.32 |
| 596 | 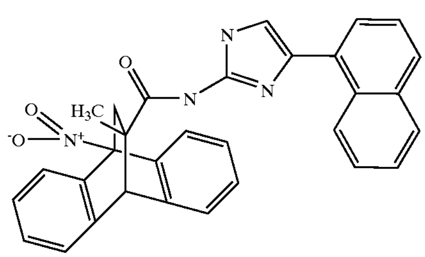 | | 501.3 |

-continued

| Example No. | Structure | Chiral Compounds | MS: (M + H = MW + 1) |
|---|---|---|---|
| 597 | 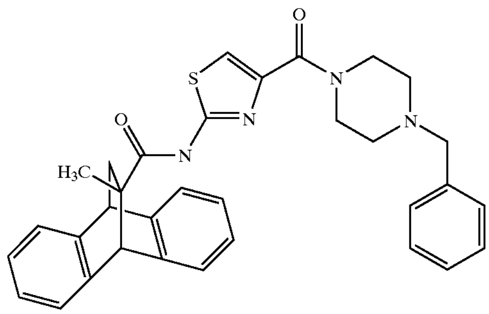 | | 549.28 |
| 598 | 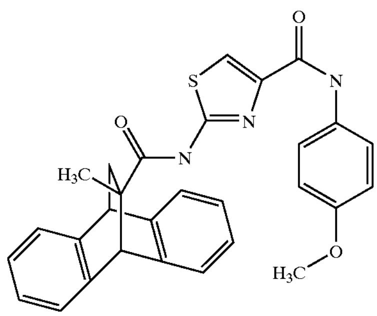 | | 496.16 |
| 599 | 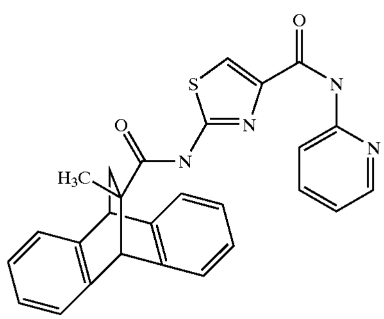 | | 467.2 |
| 600 | 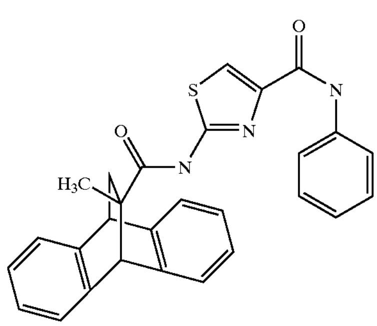 | | 466.13 |

-continued

| Example No. | Structure | Chiral Compounds | MS: (M + H = MW + 1) |
|---|---|---|---|
| 601 | 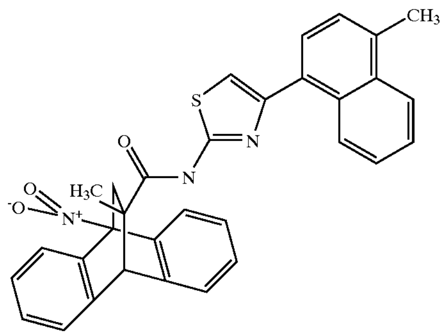 | Chiral (R) | 532.29 |
| 602 | 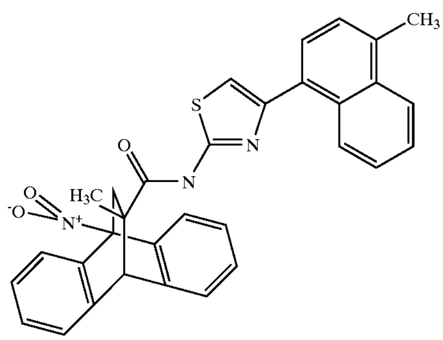 | Chiral (S) | 532.26 |
| 603 | 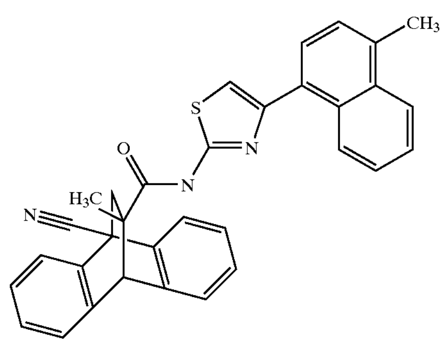 | Chiral (R) | 512.27 |
| 604 | 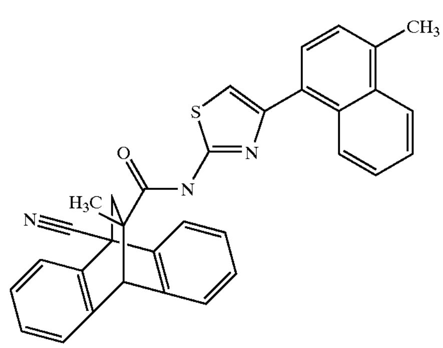 | Chiral (S) | 512.24 |

| Example No. | Structure | Chiral Compounds | MS: (M + H = MW + 1) |
|---|---|---|---|
| 605 | 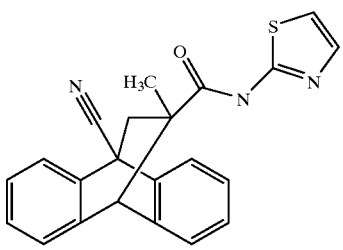 | | 372.09 |
| 606 | 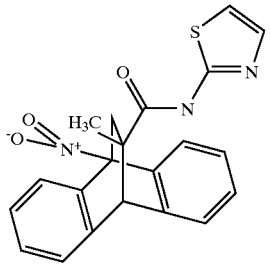 | | 392.04 |
| 607 | 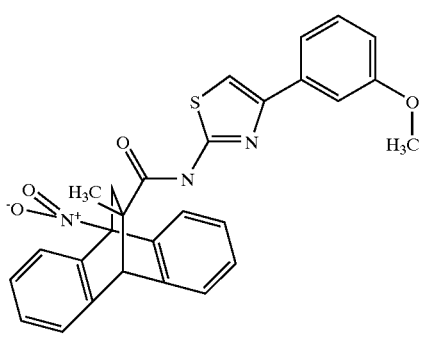 | | 498.24 |
| 608 | 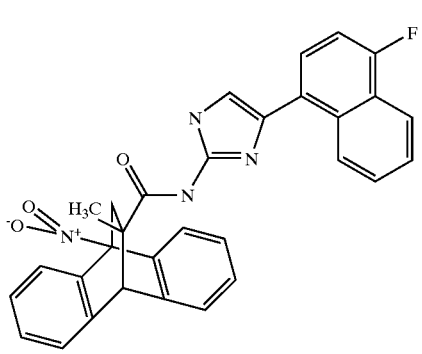 | | 519.27 |
| 609 | 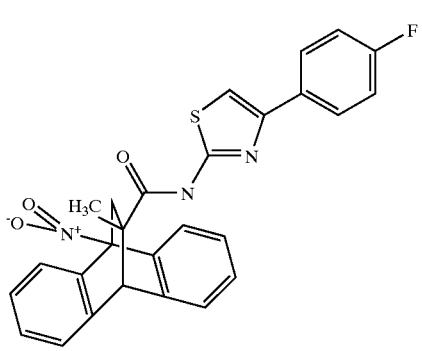 | | 486.07 |

-continued

| Example No. | Structure | Chiral Compounds | MS: (M + H = MW + 1) |
|---|---|---|---|
| 610 | 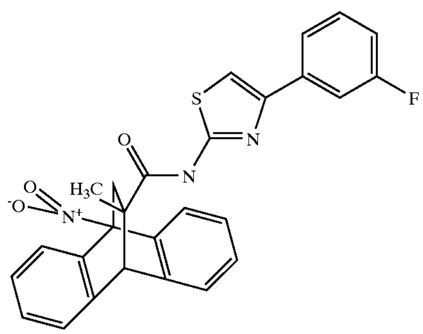 | | 486.06 |
| 611 | 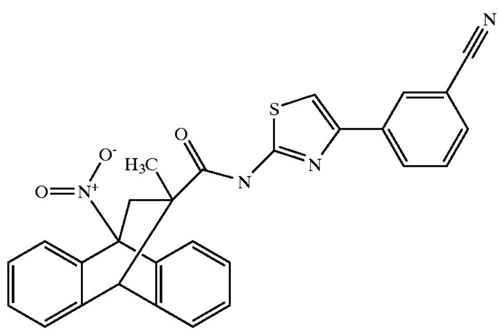 | | 493.07 |
| 612 | 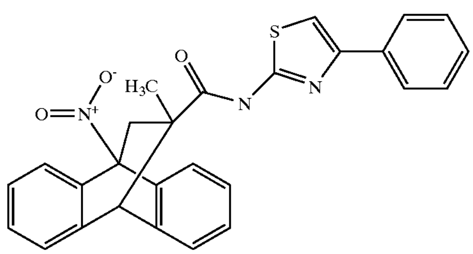 | | 468.13 |
| 613 | 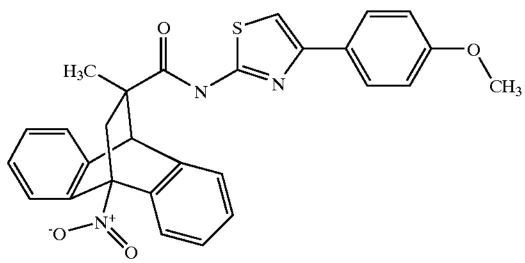 | | 496.13 |
| 614 | 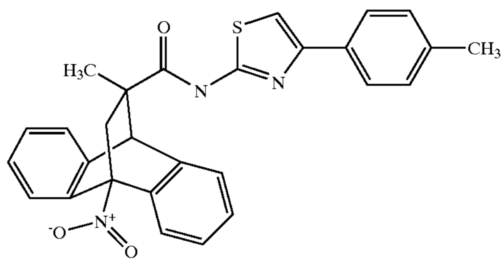 | | 482.09 |

-continued

| Example No. | Structure | Chiral Compounds | MS: (M + H = MW + 1) |
|---|---|---|---|
| 615 | 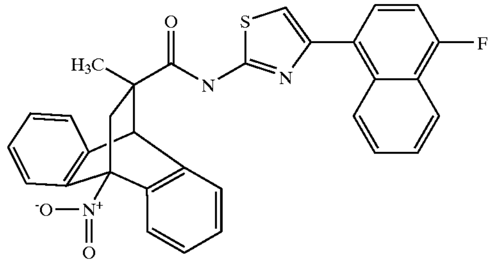 | Chiral (R) | 536.25 |
| 616 | 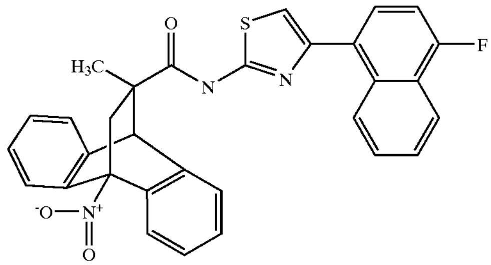 | Chiral (S) | 536.27 |
| 617 | 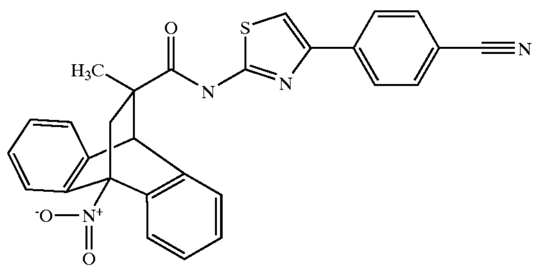 | | 493.01 |
| 618 | 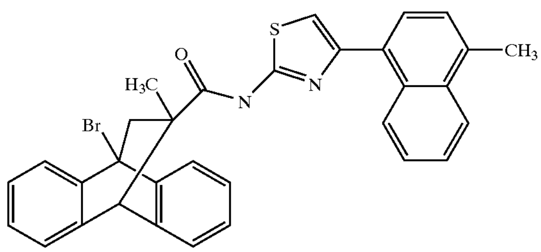 | | 565.03 |
| 619 | 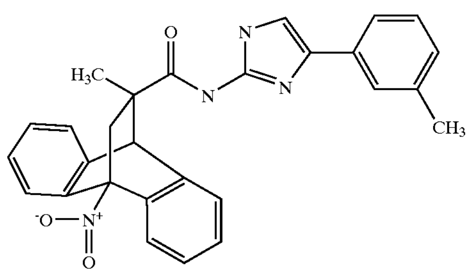 | | 465.05 |

-continued

| Example No. | Structure | Chiral Compounds | MS: (M + H = MW + 1) |
|---|---|---|---|
| 620 | 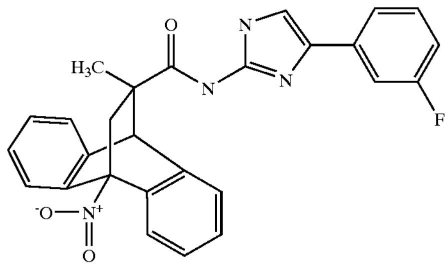 | | 469.05 |
| 621 | 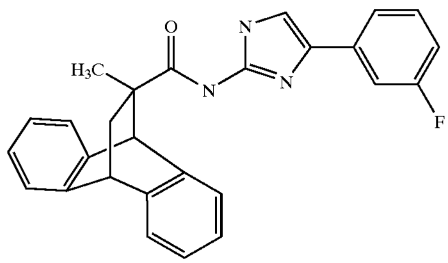 | | 424.33 |
| 622 | 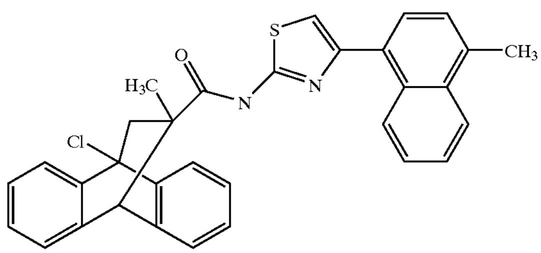 | | 521.05 |
| 623 | 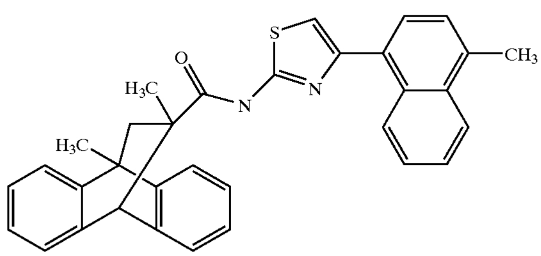 | | 501.09 |
| 624 | 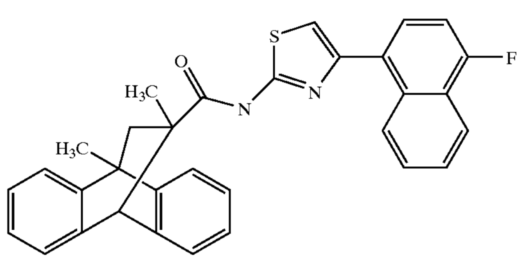 | | 504.99 |

-continued

| Example No. | Structure | Chiral Compounds | MS: (M + H = MW + 1) |
|---|---|---|---|
| 625 | 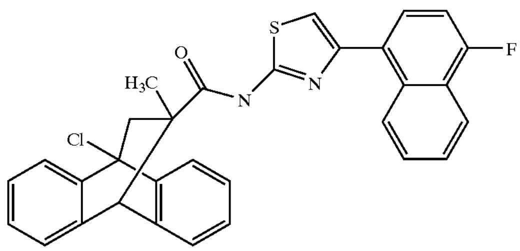 | | 524.95 |
| 626 | 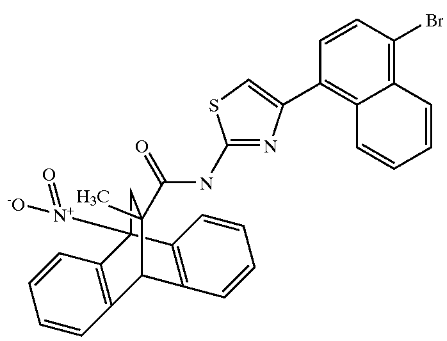 | | 596 |
| 627 | 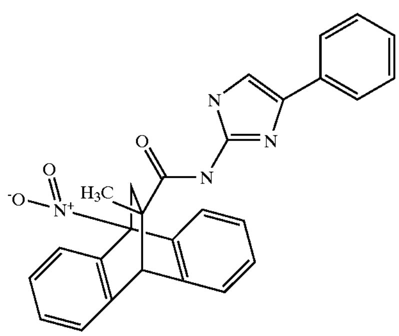 | | 451.15 |
| 628 | 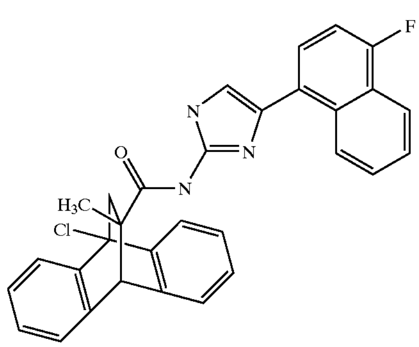 | | 508.14 |

-continued
| Example No. | Structure | Chiral Compounds | MS: (M + H = MW + 1) |
|---|---|---|---|
| 629 | 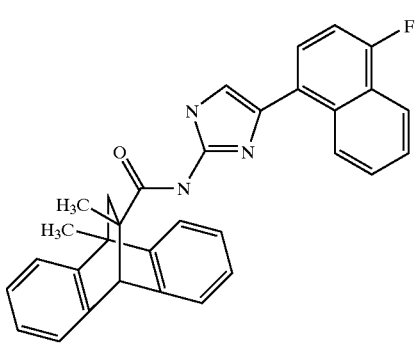 | | 488.17 |
| 630 | 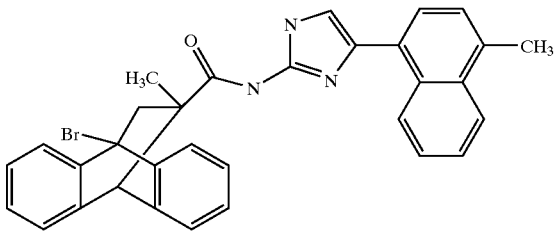 | | 548.03 |
| 631 | 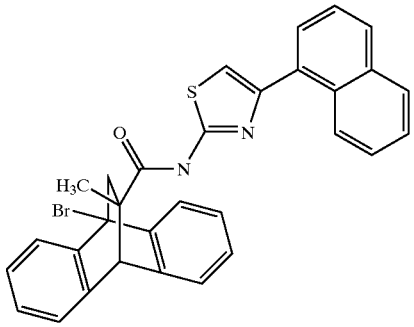 | | 551 |
| 632 | 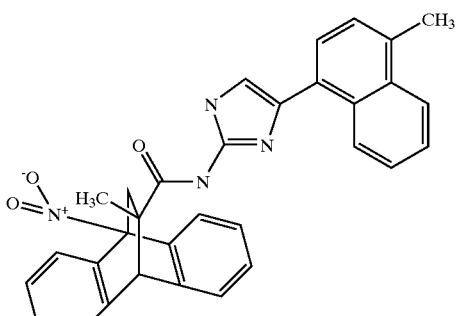 | | 515.18 |

| Example No. | Structure | Chiral Compounds | MS: (M + H = MW + 1) |
|---|---|---|---|
| 633 | 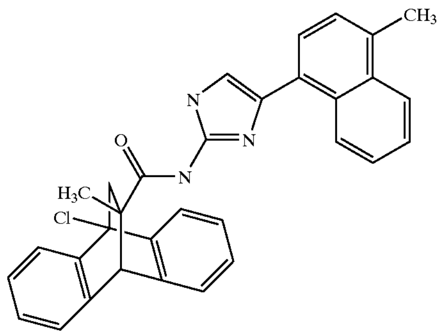 | | 504.13 |
| 634 | 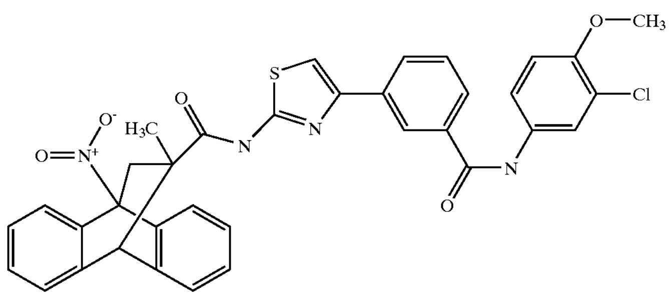 | | 651.11 |
| 635 | 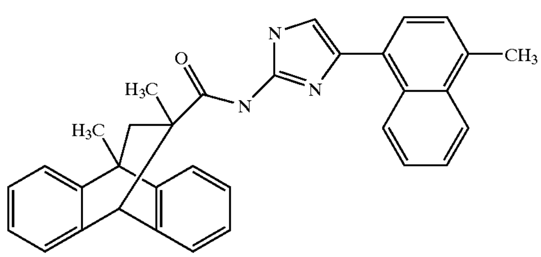 | | 484.17 |
| 636 | 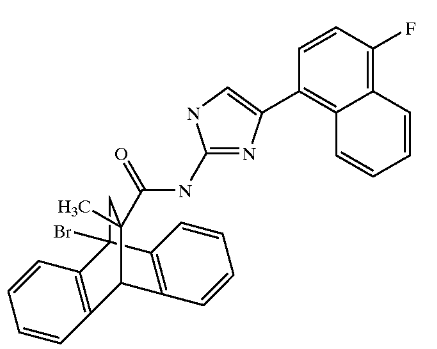 | | 552 |

-continued
| Example No. | Structure | Chiral Compounds | MS: (M + H = MW + 1) |
|---|---|---|---|
| 637 | 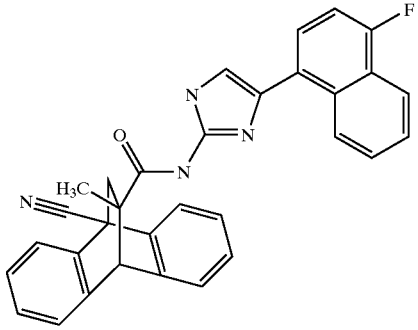 | | 499.1 |
| 638 | 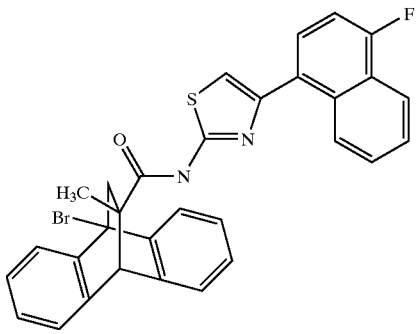 | | 569 |
| 639 | 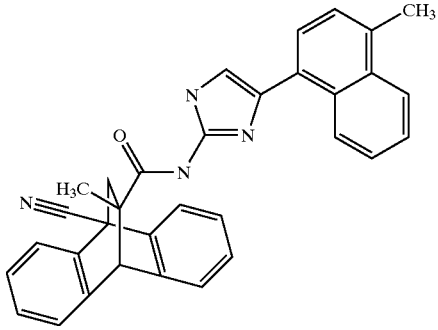 | | 495.05 |
| 640 | 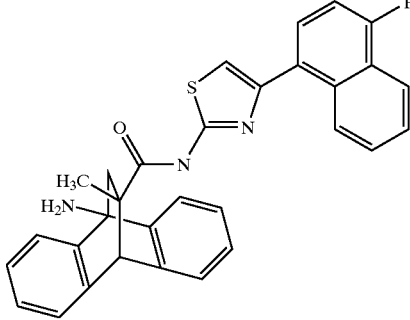 | | 506.1 |

-continued

| Example No. | Structure | Chiral Compounds | MS: (M + H = MW + 1) |
|---|---|---|---|
| 641 | 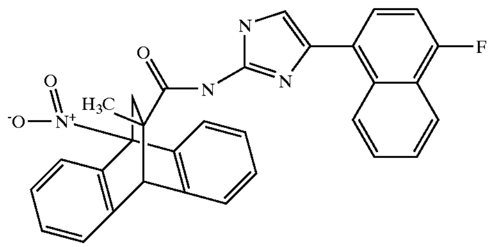 | Chiral (S) | 519.05 |
| 642 | 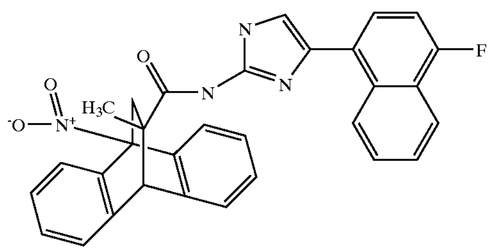 | Chiral (R) | 519.01 |
| 643 | 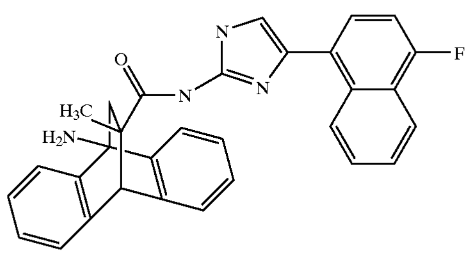 | | 489.07 |
| 644 | 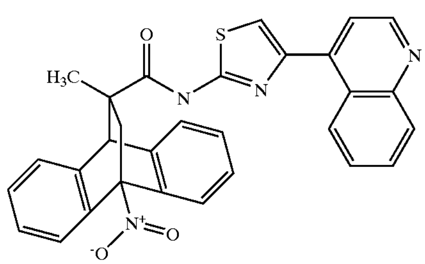 | | 519.19 |

-continued

| Example No. | Structure | Chiral Compounds | MS: (M + H = MW + 1) |
|---|---|---|---|
| 645 | 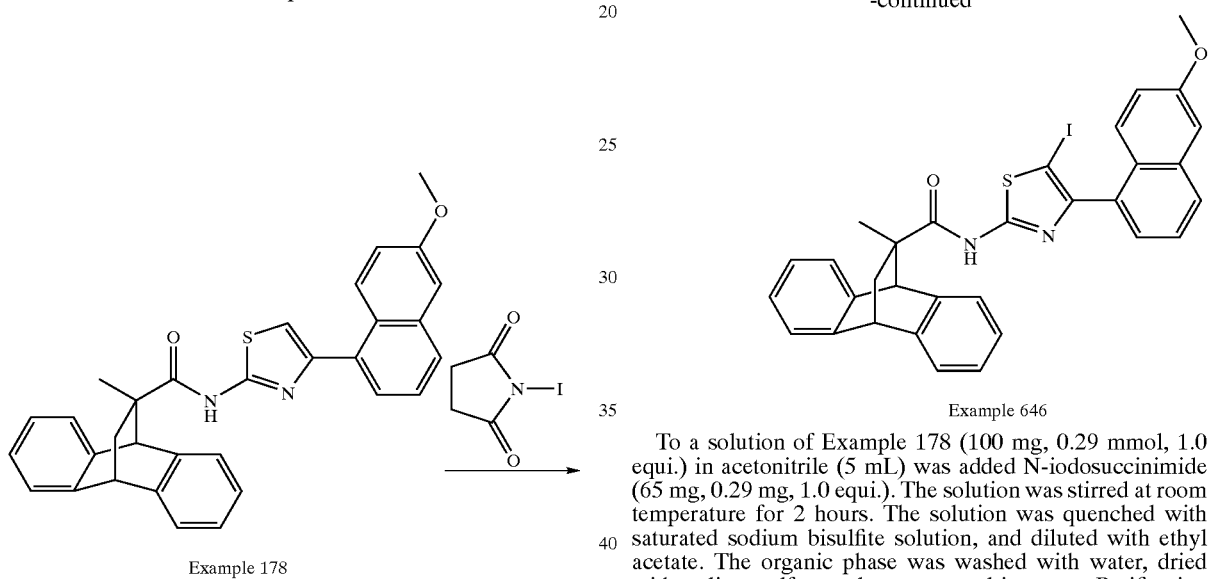 | | 481.34 |

Example 646

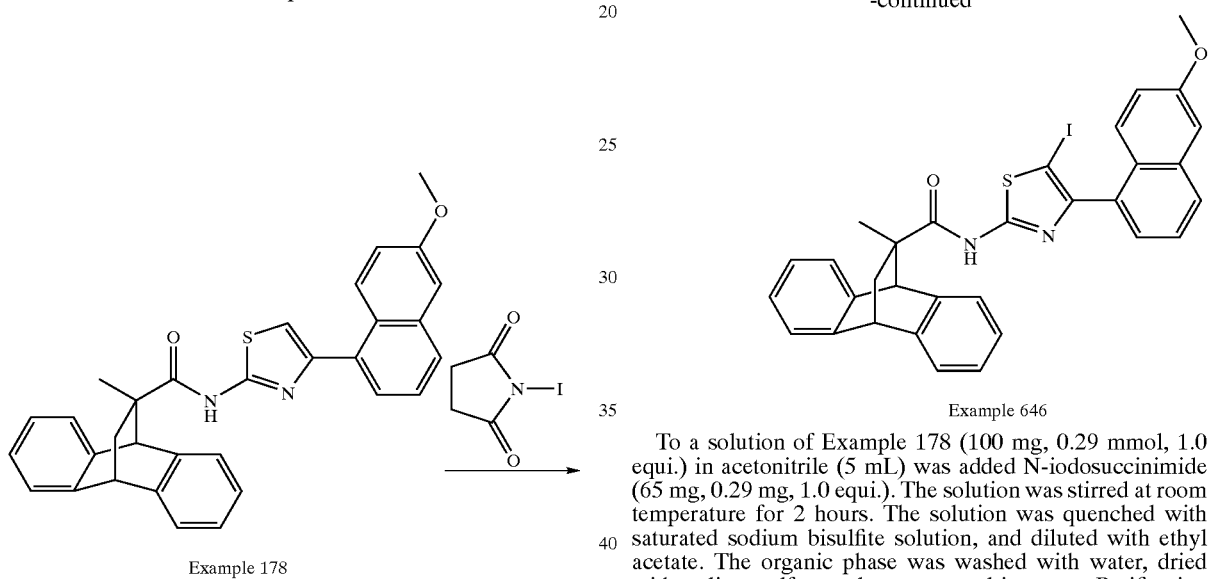

Example 646

To a solution of Example 178 (100 mg, 0.29 mmol, 1.0 equi.) in acetonitrile (5 mL) was added N-iodosuccinimide (65 mg, 0.29 mg, 1.0 equi.). The solution was stirred at room temperature for 2 hours. The solution was quenched with saturated sodium bisulfite solution, and diluted with ethyl acetate. The organic phase was washed with water, dried with sodium sulfate and concentrated in vacuo. Purification of the crude product mixture by flash chromatography (20% ethyl acetate in hexane) yielded 22.7 my (16%) of Example 647: LC/MS (m/z 629, (M+H)$^+$).

Examples 647 to 648

In a manner similar to Example 646, Examples 647 to 649 were prepared.

| Example | Chiral Compounds | Structure | MS: (M + H = MW + 1) |
|---|---|---|---|
| 647 | | 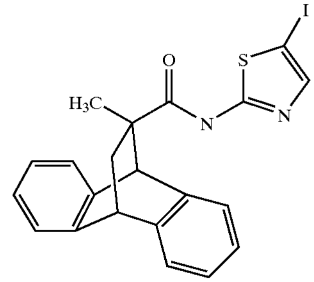 | 472.35 |

| Example | Chiral Compounds | Structure | MS: (M + H = MW + 1) |
|---|---|---|---|
| 648 | Chiral (S) | 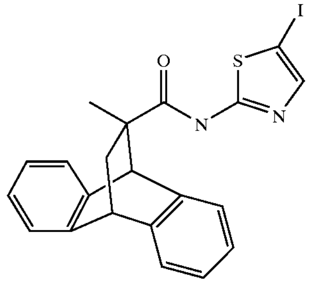 | 472.35 |
| 649 | Chiral (R) | 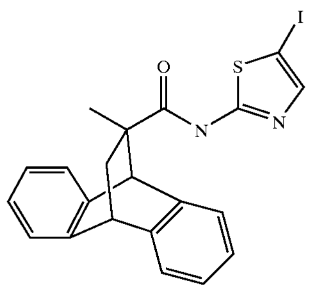 | 472.35 |

What is claimed is:

1. A compound having below structure:

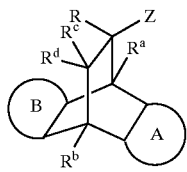

including all stereoisomers thereof, or a pharmaceutically acceptable salt thereof, wherein R is hydrogen, alkyl, alkenyl, alkynyl, alkoxy, aryl, arylalkyl, aryloxy, heteroaryl, cycloheteroalkyl, heteroarylalkyl, cycloheteroalkylalkyl, cycloalkyl, cycloalkylalkyl, cyanoalkyl, aminoalkyl, hydroxyalkyl, aryloxyalkyl, or hydroxyaryl;

$R^a$ is hydrogen, alkyl, alkenyl, alkynyl, alkoxy, aryl, aryloxy, heteroaryl, cycloheteroalkyl, heteroarylalkyl, cycloheteroalkylalkyl, cyano, halogen, heteroarylaminocarboyl, cycloheteroalkylcarbonyl, cyanoalkyl, alkylaminoalkyl, hydroxyalkyl, hydroxyaryl, aryloxyalkyl, nitro, amino, CHO, $CO_2$ alkyl, $CONR^eR^f$, $CH_2NR^gR^h$, $CO_2H$, $CH_2OH$, $CH_2NHR^g$, $NHCH_2R^g$, $NHCHR^gR^h$, $NHCOR^e$, $NHCONR^eR^f$ or $NHSO_2R^e$;

$R^b$ is hydrogen, alkyl, alkenyl, alkynyl, alkoxy, aryl, aryloxy, heteroaryl, cycloheteroalkyl, heteroarylalkyl, cycloheteroalkylalkyl, cyano, halogen, heteroarylaminocarbonyl, cycloheteroalkylcarbonyl, cyanoalkyl, alkylaminoalkyl, hydroxyalkyl, nitro, amino, CHO, $CO_2$ alkyl, hydroxyaryl, aryloxyalkyl, $CONR^iR^j$, $CH_2NR^kR^l$, $CO_2H$, $CH_2OH$, $CH_2NHR^k$, $NHCH_2R^k$, $NHCHR^kR^l$, $NHCOR^i$, $NHCONR^iR^j$ or $NHSO_2R^i$;

where $R^e$ and $R^f$ are the same or different and are independently selected from hydrogen, aryl, alkyl, alkenyl, alkynyl, alkoxy, amino, alkoxyalkyl, alkylaminoalkyl, dialkylaminoalkyl, heteroaryl, cycloheteroalkyl, heteroarylalkyl, cycloheteroalkylalkyl, cycloalkyl, and cycloalkylalkyl, and Re and $R^f$ can be taken together with the nitrogen to which they are attached to form a 5-, 6- or 7-membered heteroaryl or cycloheteroalkyl ring which contains 1, 2 or 3 hetero atoms which can be N, O or S;

$R^g$ and $R^h$ are the same or different and are independently selected from hydrogen, aryl, alkyl, alkenyl, alkynyl, alkoxy, amino, alkoxyalkyl, alkylaminoalkyl, dialkylaminoalkyl, heteroaryl, cycloheteroalkyl, heteroarylalkyl, cycloheteroalkylalkyl, cycloalkyl, and cycloalkylalkyl, and $R^g$ and Rh can be taken together with the nitrogen to which they are attached to form a 5-, 6- or 7-membered heteroaryl ring or cycloheteroalkyl ring which contains 1, 2 or 3 hetero atoms which can be N, O or S;

$R^i$ and $R^j$ are the same or different and are independently selected from hydrogen, aryl, alkyl, alkenyl, alkynyl, alkoxy, amino, alkoxyalkyl, alkylaminoalkyl, dialkylaminoalkyl, heteroaryl, cycloheteroalkyl, heteroarylalkyl, cycloheteroalkylalkyl, cycloalkyl, and cycloalkylalkyl, and $R^i$ and $R^j$ can be taken together with the nitrogen to which they are attached to form a 5-, 6-or 7-membered heteroaryl ring or cycloheteroalkyl ring which contains 1, 2 or 3 hetero atoms which can be N, O or S;

$R^k$ and $R^l$ are the same or different and are independently selected from hydrogen, aryl, alkyl, alkenyl, alkynyl, alkoxy, amino, alkoxyalkyl, alkylaminoalkyl, dialkylaminoalkyl, heteroaryl, cycloheteroalkyl, heteroarylalkyl, cycloheteroalkylalkyl, cycloalkyl, and cycloalkylalkyl, and $R^k$ and $R^l$ can be taken together with the nitrogen to which they are attached to form a 5-, 6- or 7-membered heteroaryl ring or cycloheteroalkyl ring which contains 1, 2 or 3 hetero atoms which can be N, O or S;

$R^c$ and $R^d$ are the same or different and are independently selected from hydrogen, alkyl, alkenyl, alkynyl, alkoxy, aryl, hydroxy, aryloxy, heteroaryl, cycloheteroalkyl, heteroarylalkyl, cycloheteroalkylalkyl, hydroxyaryl, and aryloxyalkyl;

$R^c$ and $R^d$ may optionally be taken together with the carbon to which they are attached to form a 3- to 7-membered ring which may optionally include an O atom or an N atom;

Z is $CONR^1R^2$ or $CH_2NR^1R^2$ wherein at least one of $R^1$ and $R^2$ is heteroaryl and the other of $R^1$ and $R^2$ is selected from hydrogen, alkyl, alkenyl, alkynyl, alkoxy, cycloalkyl, cycloalkylalkyl, aryl, heteroaryl, heteroarylalkyl, cycloheteroalkyl, cycloalkenyl, monoalkylaminoalkyl, dialkylaminoalkyl, cycloheteroalkylalkyl, hydroxyaryl, aryloxyalkyl, alkoxyalkyl and hydroxyalkyl;

the A ring represents an unsaturated 6-membered carbocyclic ring; and the B ring represents an unsaturated 6-membered carbocyclic ring;

with the following provisos:

I. provided that where Z is $CONR^1R^2$ and (a) R is $CH_3$ or H and $R^a$, $R^b$, $R^c$ and $R^d$ are each hydrogen, or (b) $R^a$ and $R^b$ are each hydrogen and one of $R^c$ and $R^d$ is alkyl, then (1) at least one of $R^1$ and $R^2$ is heteroaryl, but where the heteroaryl is unsubstituted

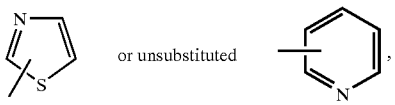

or unsubstituted then the other of $R^1$ and $R^2$ is other than hydrogen; or (2) where one of $R^1$ and $R^2$ is phenyl which is substituted with alkyl, hydroxy, halo, $C_1$, $-C_2$-alkoxycarbonyl or nitro, then (a) the phenyl must be substituted with at least one other group other than hydrogen, alkyl, hydroxy, halo, $C_1$,-$C_2$-alkoxycarbonyl or nitro, except that the phenyl may be substituted with two or more halo atoms, and/or two or more hydroxy groups and/or (b) the other of $R^1$ and $R^2$ is heteroaryl; or (3) where at least one of $R^1$ and $R^2$ is hydrogen, unsubstituted alkyl, alkenyl, cycloalkyl, alkylcycloalkyl, cycloalkenyl, alkylcycloalkenyl, alkylphenyl, monoalkylaminoalkyl, dialkylaminoalkyl, arylalkyl, aryl, alkoxyalkyl or hydroxyalkyl then (a) the other of $R^1$ and $R^2$ is heteroaryl and/or (b) at least one of $R^a$, $R^b$, $R^c$ and/or $R^d$ is other than hydrogen and/or (c) R is other than hydrogen or $C_1$–$C_2$ alkyl; and II. provided that where Z is CH2NR1R2 and where at least one of R1 and R2 is a heteroaryl selected from pyridinyl, pyrimidinyl, pyridazinyl, pyrazinyl or imidazolinyl, then (a) the other of R1 and R2 is other than hydrogen, alkyl, alkenyl, cycloalkyl, alkylcycloalkyl, phenyl, alkylphenyl, phenylalkyl, monoalkylaminoalkyl, dialkylaminoalkyl, arylalkyl, aryl, alkoxyalkyl, or hydroxyalkyl, and/or (b) at least one of Ra, Rb, Rc and/or Rd is other than hydrogen or C1–2 alkyl, and/or (c) R is other than hydrogen or C1–C2 alkyl and/or (d) one of Rc and Rd is other than hydroxyalkyl.

2. The compound as defined in claim 1 wherein the A ring has the structure

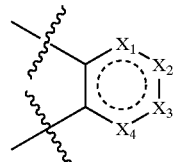

and the B ring has the structure

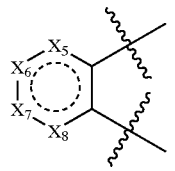

wherein $X_1$, $X_2$, $X_3$ and $X_4$, are the same or different and are independently selected from CH or $CR^{16}$, and $X_5$, $X_6$, $X_7$ and $X_8$ are the same or different and are independently selected from CH or $CR^{20}$, wherein $R^{16}$, and $R^{20}$ are the same or different and are independently selected from hydrogen, alkyl, aryl, cycloalkyl, heteroaryl, and cycloheteroalkyl.

3. The compound as defined in claim 1 having the structure

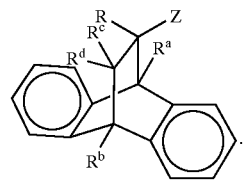

4. The compound as defined in claim 1 having the structure

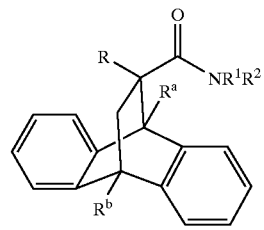

where R is H or alkyl;

$R^a$ is selected from H, CN, $NO_2$, $NH_2$, CHO, $CO_2$ alkyl, $CONR^eR^f$ or $CH_2NR^gR^h$ and $R^b$ is selected from H, CN, $NO_2$, $NH_2$, CHO, $CO_2$ alkyl, $CONR^iR^j$ or $CH_2NR^kR^l$.

5. The compound as defined in claim 1 having the structure

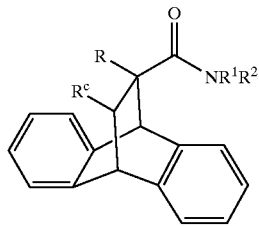

where R is H, CH$_3$ or C$_2$H$_5$ and R$^c$ is H or OH, and one of R$^1$ and R$^2$ is heteroaryl.

6. The compound as defined in claim 5 wherein one of R$^1$ and R$^2$ is

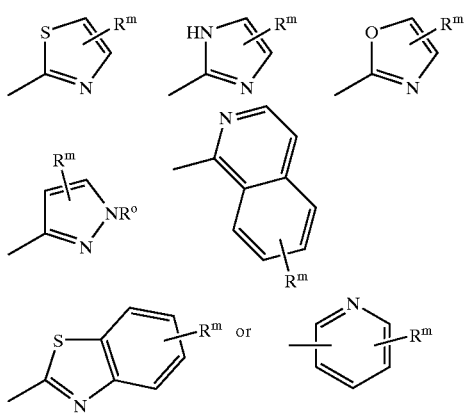

where R$^m$ is selected from H, alkyl, aryl, heteroaryl, halo, and alkoxy and R$^o$ is H or alkyl.

7. A compound having the structure

A.

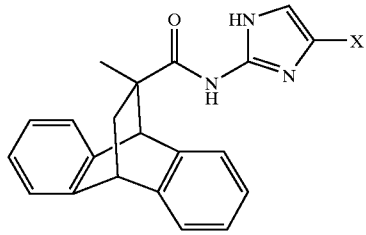

where X is aryl or alkyl;

B.

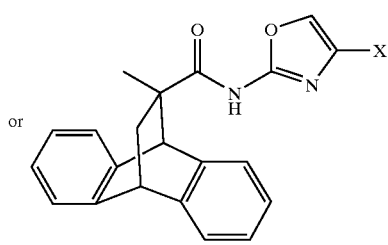

where X is aryl;

C.

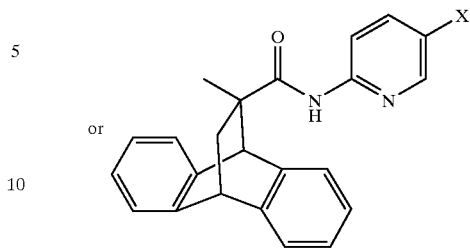

where X is aryl;

D.

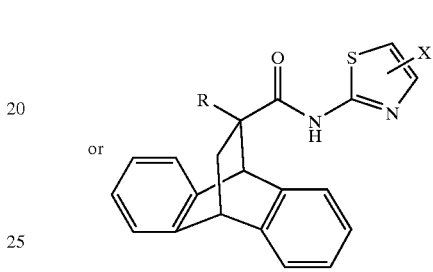

where X is aryl, alkyl, heteroaryl or halo and R is alkyl;

E.

or

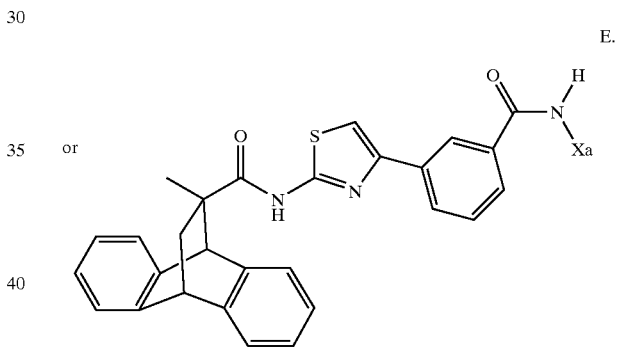

where X$_a$ is aryl, heteroaryl or heteroarylalkyl;

F.

or

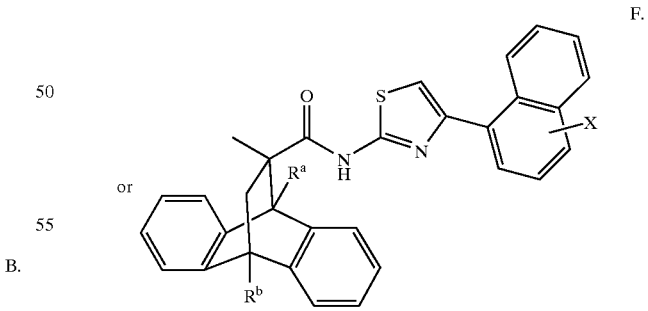

where R$^a$ is alkoxycarbonyl (CO$_2$ alkyl), nitro, cyano, or hydrogen;

R$^b$ is hydrogen, CO$_2$ alkyl, nitro, cyano, formyl, cycloheteroalkylcarbonyl, alkylaminoalkyl or amino; and X is hydrogen, alkyl or halo.

8. The compound as defined in claim 7 having the structure

A.

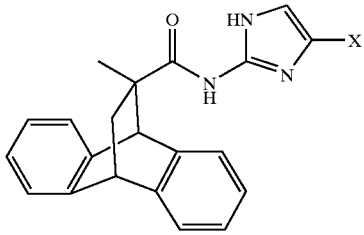

where X is 1-naphthyl, 1-(4-methyl)naphthyl, 1-(4-fluoro)naphthyl, 1-(6-methoxy)naphthyl, phenyl, or, t-butyl,

B.

or 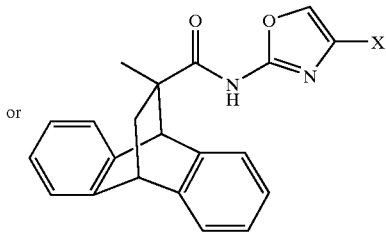

where X is 1-naphthyl,

C.

or 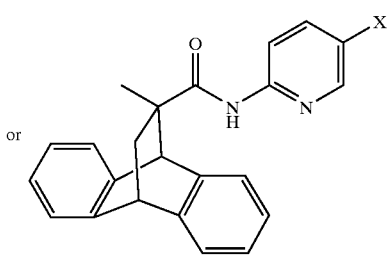

where X=1-naphthyl,

D.

or 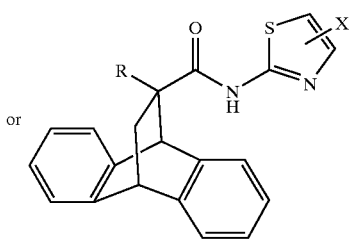

where R is CH₃ or C₂H₅ and X is phenyl, t-butyl, 1-naphthyl, 1-(4-fluoro)naphthyl, benzthiophen-3-yl, 1-(4-methyl)naphthyl, 1-(2-methoxy)naphthyl, 1-(6-methoxy)naphthyl, 3-fluorophenyl, 4-fluorophenyl, 3-methylphenyl, 2-chlorophenyl, 1-(4-methoxy)naphthyl, 1-(4-bromo)naphthyl, 1-(4-iodo)naphthyl, 5-anthracenyl, 1-anthracenyl, 4-quinolin-1-yl, 2-quinolin-1-yl, 1-(4-cyano)naphthyl, 5-iodo, 4-benzthiophenyl, 1-(2-hydroxy)naphthyl, 1-(6-hydroxy)naphthyl, or 1-(4-hydroxy)naphthyl,

E.

or 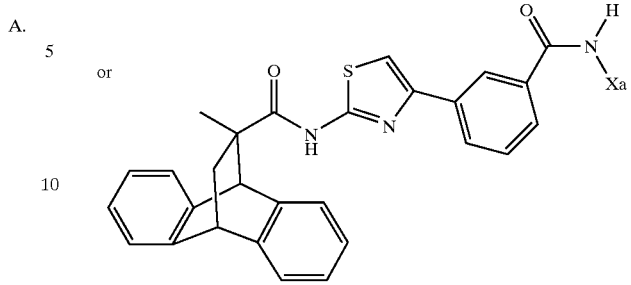

where $X_a$ is phenyl, 3-methoxyphenyl, 4-methoxyphenyl, 2,5-dimethoxyphenyl, 3,5-dimethoxyphenyl, 3-pyridyl, 2-(4-pridyl)ethyl, 2-(4-imidazolyl)ethyl, 3-chloro-4-methoxyphenyl, 3-hydroxy-4-methoxyphenyl, 3-fluoro-4-methoxyphenyl, 3,4,5-trimethoxyphenyl, 3,4-dimethoxyphenyl, 4-methyl-3-methoxyphenyl, 3-methoxyphenyl, 3,5-dimethoxyphenyl, 2,3-dimethoxyphenyl, 4-chlorophenyl, 2-naphthyl, 3-chlorophenyl, 3,4-dichlorophenyl, 4-azidophenyl, 2,4-dimethoxyphenyl, 3-ethoxyphenyl, 3-(methylthio)phenyl, 4-(methylthio)phenyl, 3-(acetylenyl)phenyl, 4-methoxy-3-pyridyl, 3-cyanophenyl, 2-methyl-4-methoxyphenyl, 3-azidophenyl, 3-methyl-isothiazolyl, 1-methyl-pyrazol-5-yl, or 5-trifluoromethyl-1,3,4-thiadiazol-2-yl, or F.

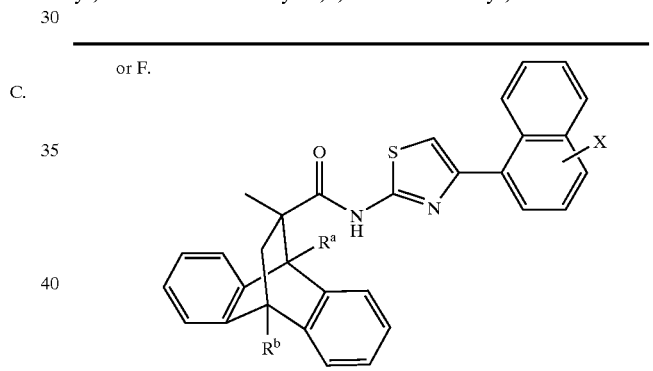

| $R^a$ | $R^b$ | X |
|---|---|---|
| CH₃OOC— | H | H |
| Nitro | H | H |
| Cyano | H | H |
| CH₃OOC— | H | Methyl |
| Nitro | H | Methyl |
| Cyano | H | Methyl |
| H | CH₃OOC— | H |
| H | Nitro | H |
| H | Cyano | H |
| H | formyl | H |
| H | CO—(N-morpholine) | H |
| H | —CH2—NH-Ethyl | H |
| H | —CH2—(N-morpholine) | H |
| H | Nitro | Methyl |
| H | Cyano | Methyl |
| H | NH2 | Methyl |
| H | Nitro | F |
| H | Cyano | F |
| H | Cl | H |
| H | Cl | F |
| H | Cl | Methyl |
| H | Br | F |
| H | Br | Methyl |
| H | CH3 | H |
| H | CH3 | F |
| H | CH3 | Methyl |

397
-continued
or F.
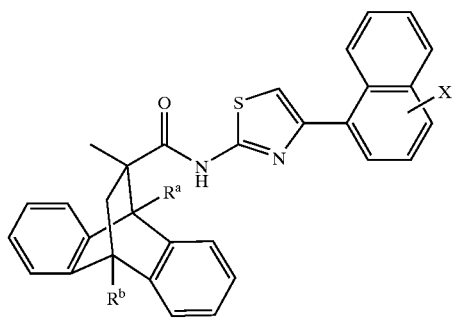
| Rª | Rᵇ | X |
|---|---|---|
or G.
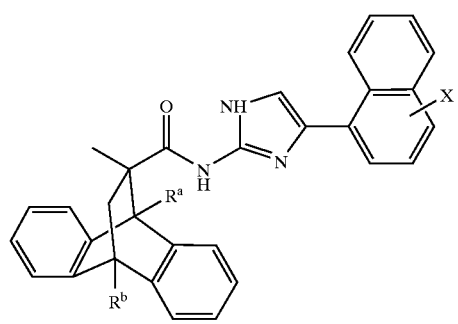
| CH₃OOC— | H | H |
|---|---|---|
| Nitro | H | H |
| Cyano | H | H |
| CH₃OOC— | H | Methyl |
| Nitro | H | Methyl |
| Cyano | H | Methyl |
| H | CH₃OOC— | H |
| H | Nitro | H |
| H | Cyano | H |
| H | formyl | H |
| H | CO—(N-morpholine) | H |
| H | —CH2—NH-Ethyl | H |
| H | —CH2—(N-morpholine) | H |
| H | Nitro | Methyl |
| H | Cyano | Methyl |
| H | NH2 | Methyl |
| H | Nitro | F |
| H | Cyano | F |
| H | Cl | H |
| H | Cl | F |
| H | Cl | Methyl |
| H | Br | F |
| H | Br | Methyl |
| H | CH3 | H |
| H | CH3 | F |
| H | CH3 | Methyl |
or H.
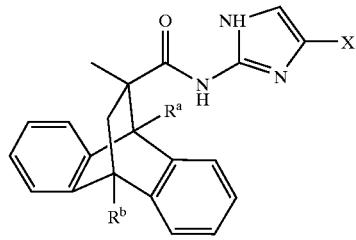
| H | H | 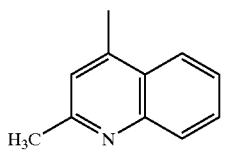 |
|---|---|---|
398
-continued
or F.
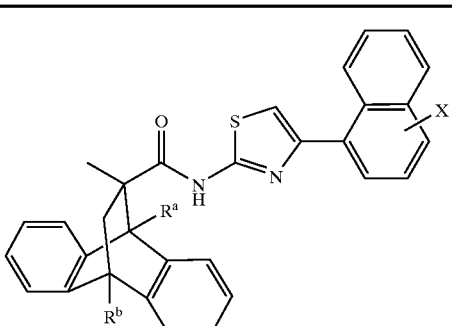
| Rª | Rᵇ | X |
|---|---|---|
| H | nitro | 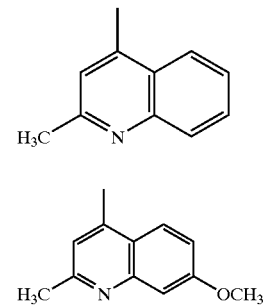 |
| H | H | 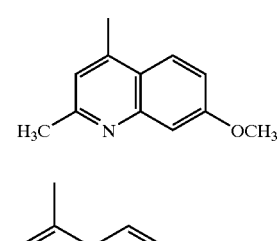 |
| H | nitro | 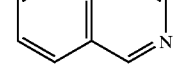 |
| H | H | 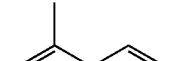 |
| H | nitro | 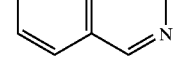 |
| H | H | 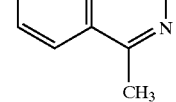 |
| H | nitro | 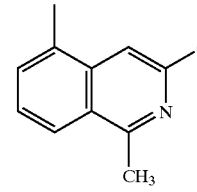 |

9. A compound having the structure

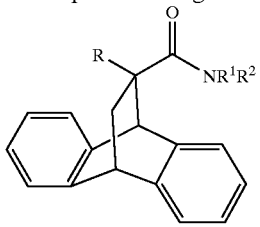

where R is $CH_3$, $C_2H_5$ or 2-hydroxyethyl, and one of $R^1$ and $R^2$ is H and the other of $R^1$ and $R^2$ is benzothiazol-2-yl, alkylbenzothiazol-2-yl, alkoxybenzothiazol-2-yl, halobenzothiazol-2-yl, thiazol-2-yl, 4-(1-naphthyl)thiazol-2-yl, 2-quinolin-1-yl, or a thiazole which is optionally substituted with heteroarylthio, heteroaryl, dialkyl, alkyl, or aryl, where the aryl may be optionally substituted with halo, alkyl, nitro, hydroxy, alkoxy, dialkoxy, carboxy, alkylaminocarbonyl, arylaminocarbonyl, hydroxyalkylaminocarbonyl, cycloheteroalkylcarbonyl, alkoxyalkylaminocarbonyl or heteroarylaminocarbonyl; with the proviso that where one of $R^1$ and $R^2$ is thiazol-2-yl, then R is $C_2H_5$ or 2-hydroxyethyl.

10. The compound as defined in claim 9 having the structure

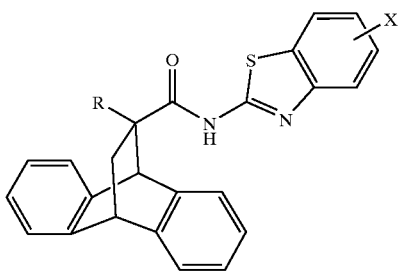

where X is H, 6-$CH_3$, 4-$CH_3O$, 6-Cl or 6-F;

or

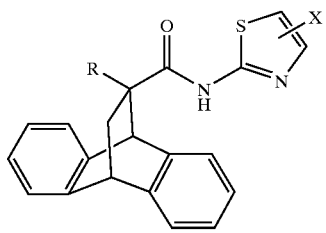

where X is 4,5-dimethyl, 5-chloro, 4-methyl, 5-methyl, 4-phenyl, 4-(1-naphthyl), 4-(2-naphthyl), 4-(4-fluoronaphth-1-yl), 4-(4-methylnaphth-1-yl), 4-(3-nitrophenyl), 4-(6-hydroxynaphth-1-yl), 4-[(1,2,4-triazol-5-yl)thio]methyl, 4-benzoic acid, 4-(4-bromonaphth-1-yl), 4-(N-ethyl)benzamide, 4-(N-2-methoxyphenyl)benzamide, 4-(N-methyl-N-2-hydroxyethyl)benzamide, 4-(N-(pyrrolidinyl)benzamide, 4-(N-mopholinyl)benzamide, 4-(N-phenyl-N-methyl)benzamide, 3-(N-ethyl)benzamide, 3-(N-2-methoxyphenyl)benzamide, 3-(N-2-methoxyethyl)benzamide, 3-(N-methyl-N-2-hydroxyethyl)benzamide, 3-(N-methyl-N-phenyl)benzamide, 3-(N-4-acetylpiperaziny-1-yl)benzamide, 3-(N-3-methoxypropyl)benzamide, 2-(6-carboxy)pyridine, 3-(N-3-hydroxy-4-methoxyphenyl)benzamide, 3-(N-3-fluoro-4-methoxyphenyl)benzamide, 3-(N-2,3-dimethoxyphenyl)benzamide, 3-(N-3-dimethoxyphenyl)benzamide, 3-(N-5-trifluormethyl-1,3,4-thiadiazol-2-yl)benzamide, 3-(N-5-methyl-1,3,4-thiadiazol-2-yl)benzamide, 3-(N-5-chlorobenzoxazol-2-yl)benzamide, 3-(N-3-benzonitrile)benzamide, 3-(N-4-methoxypyrid-3-yl)benzamide, 5-(1,4-benzodioxane), or 4-(1,3-benzodioxole).

11. The compound as defined in claim 1 having the structure:

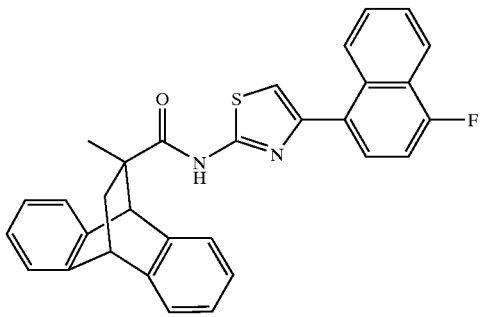

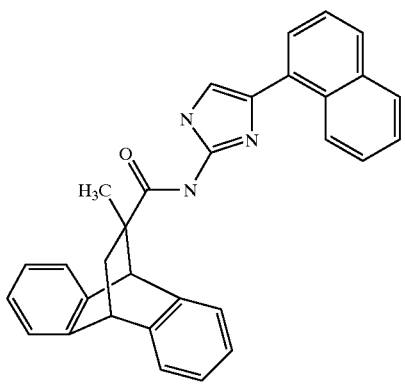

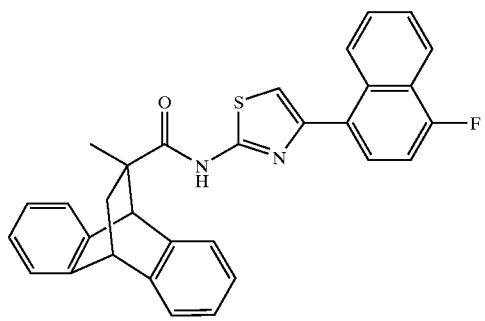
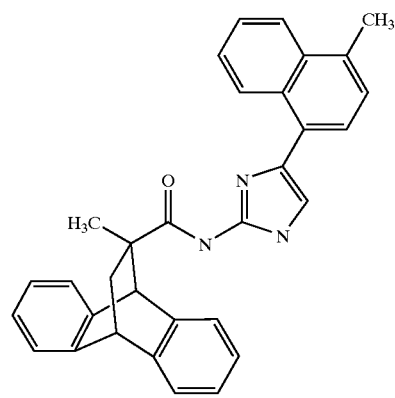
Chiral (S)
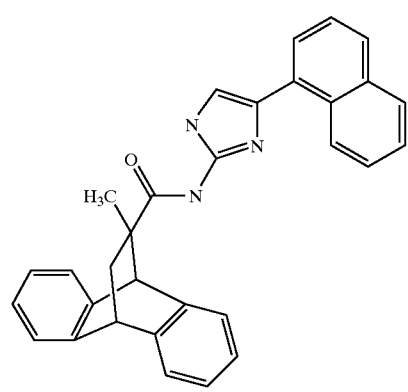
Chiral (S)
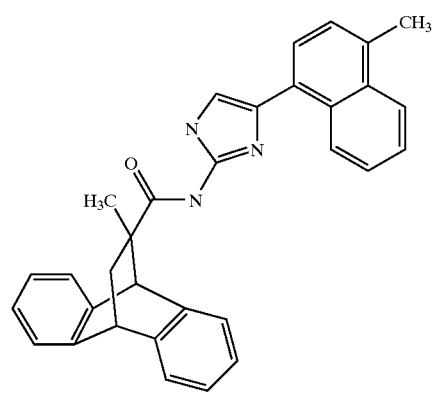

-continued
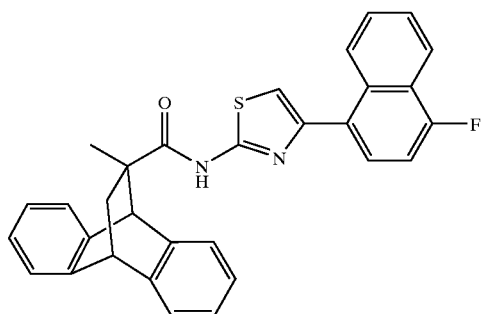
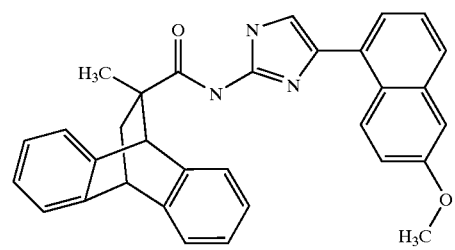
Chiral (S)
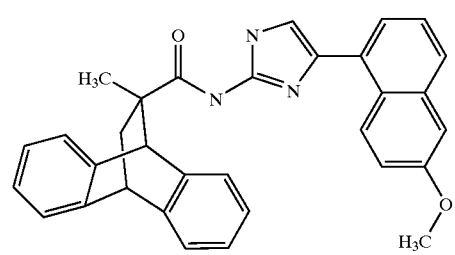
Chiral (S)
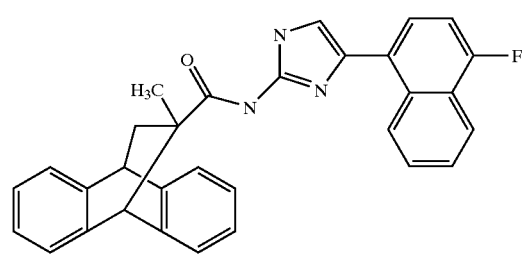
Chiral (S)
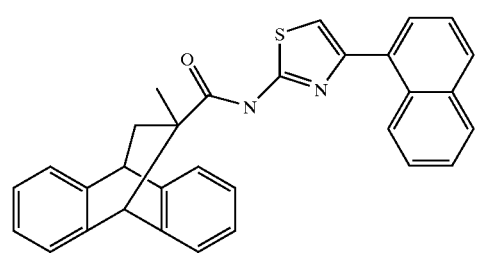
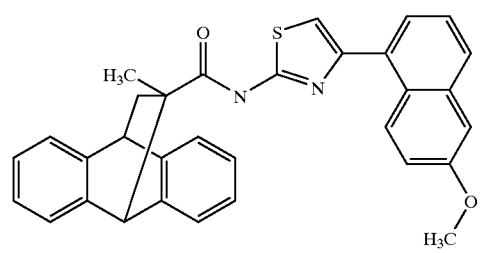

-continued
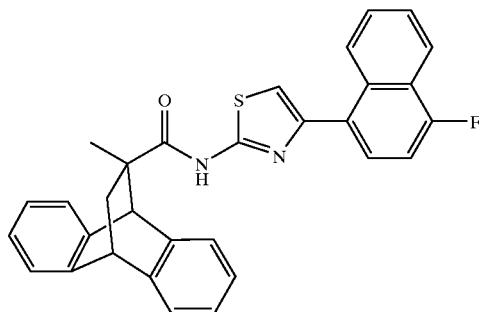
Chiral (S)
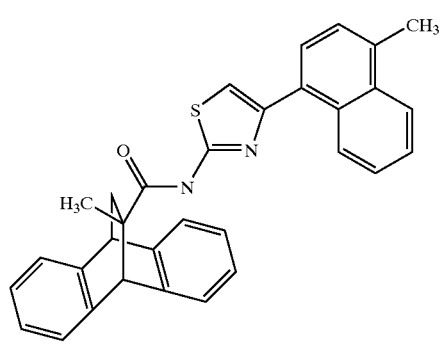
Chiral (S)
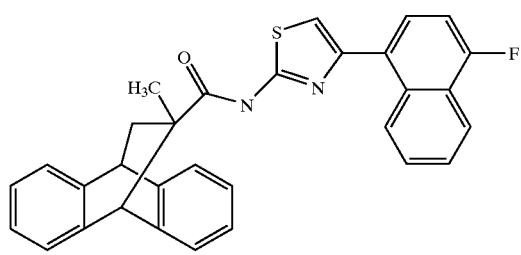
Chiral (S)
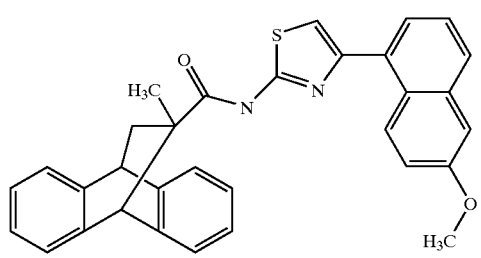
Chiral (S)
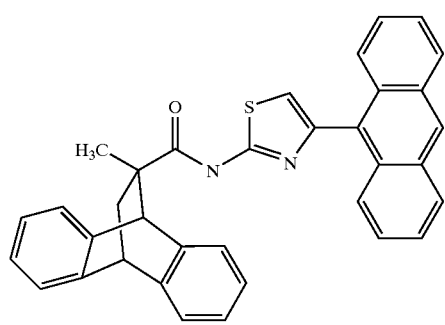

-continued
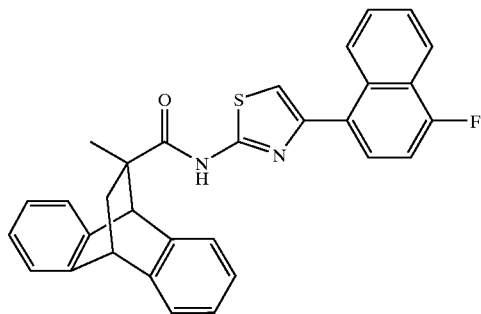
Chiral (S)
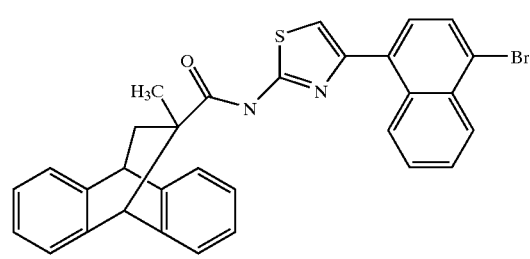
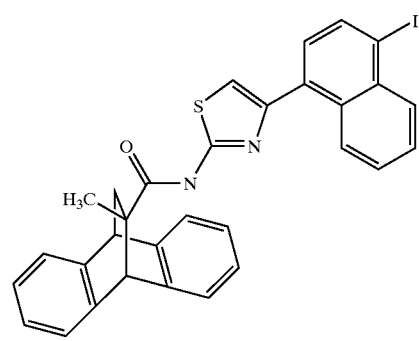
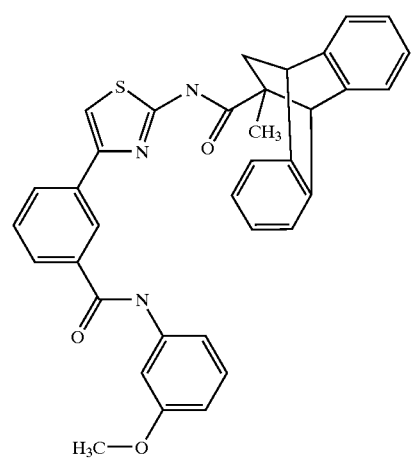

-continued
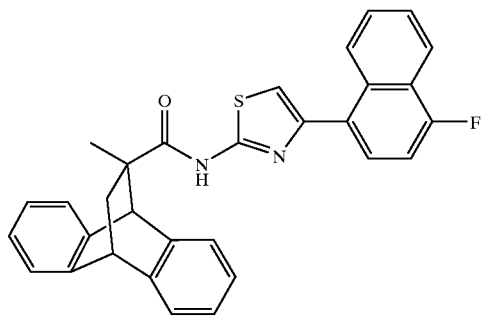
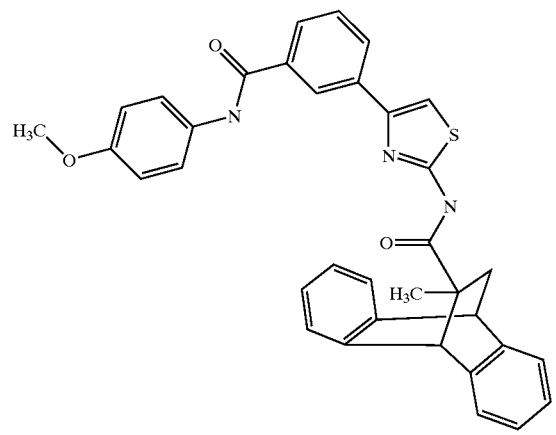
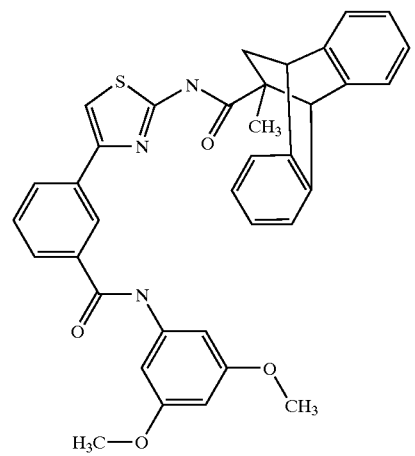
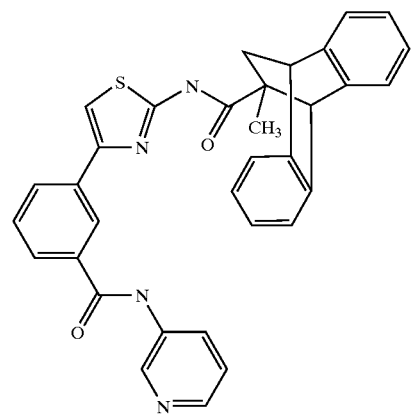

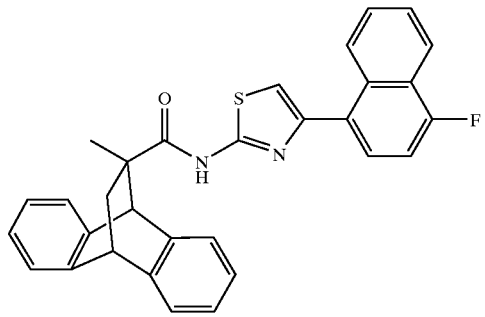
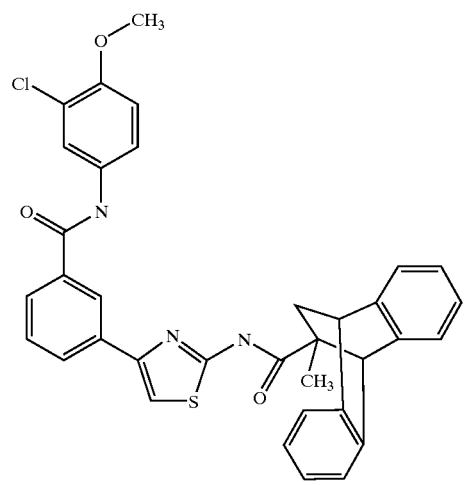
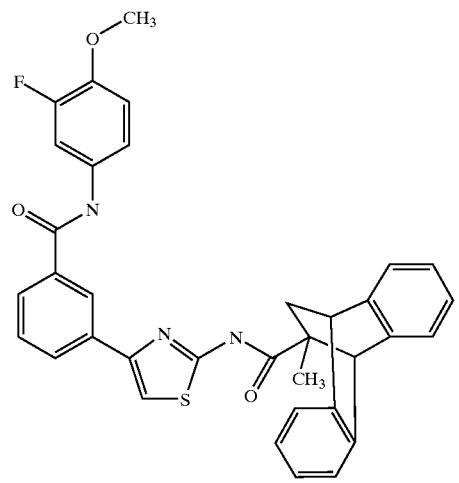

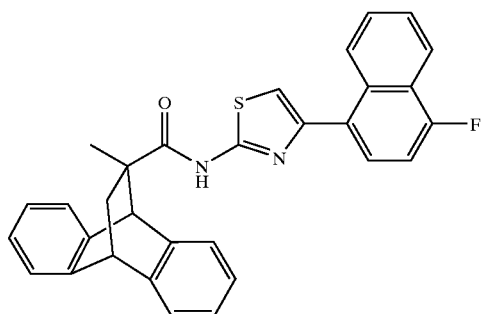
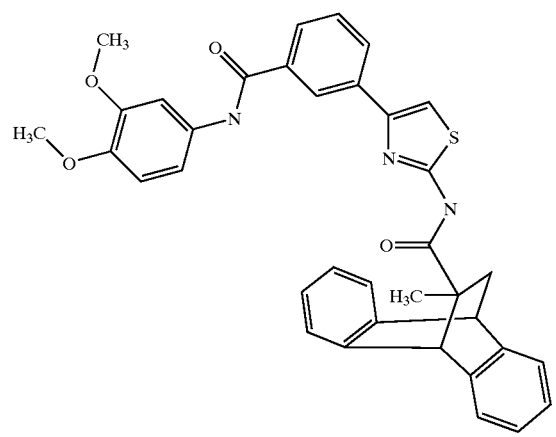
Chiral (S)
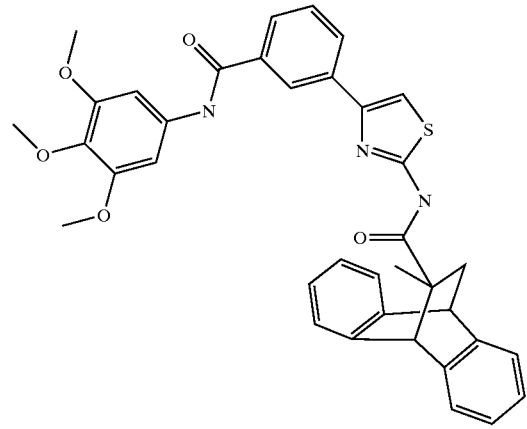
Chiral (S)
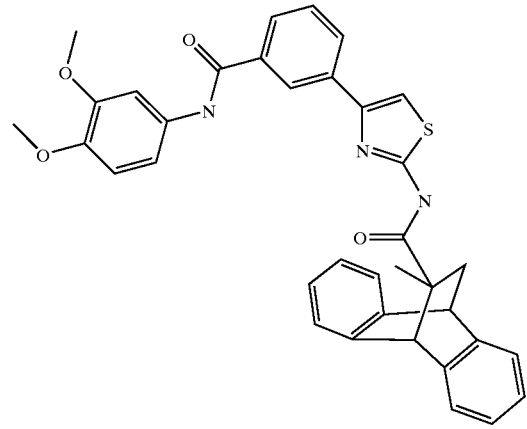

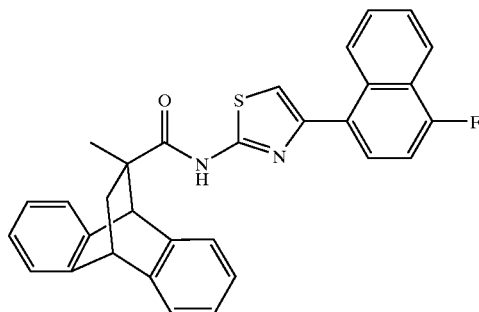
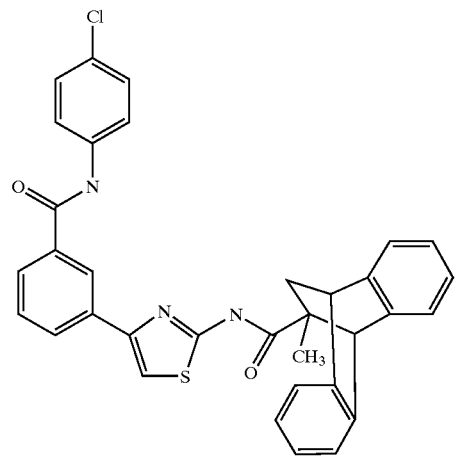
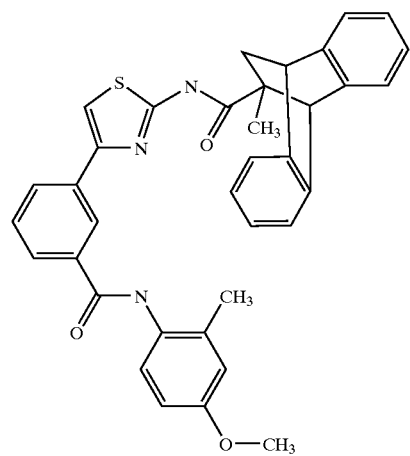

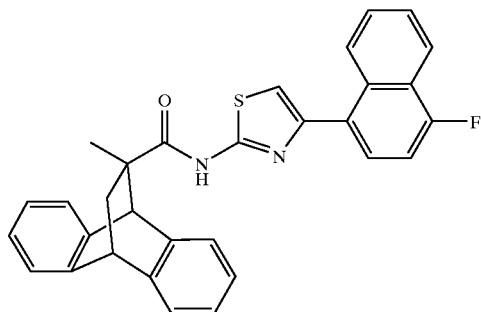
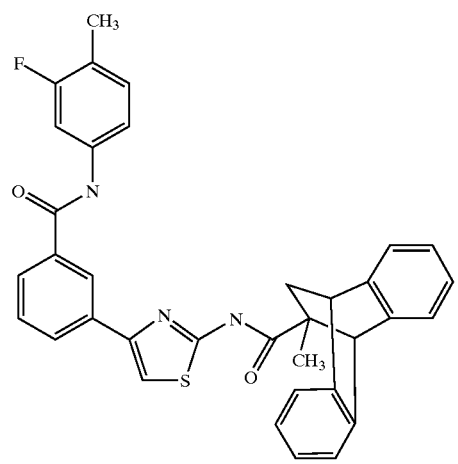
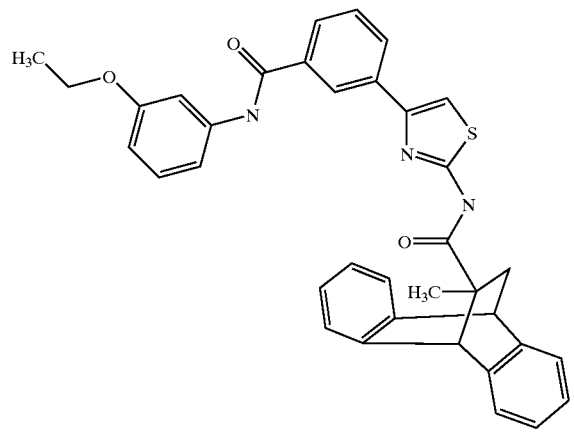

-continued
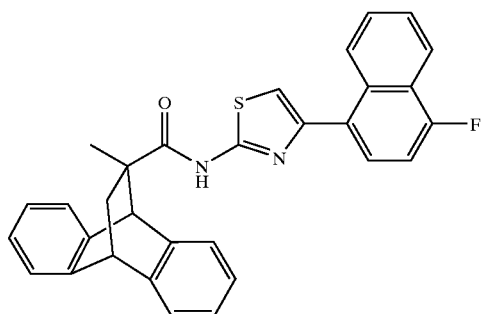
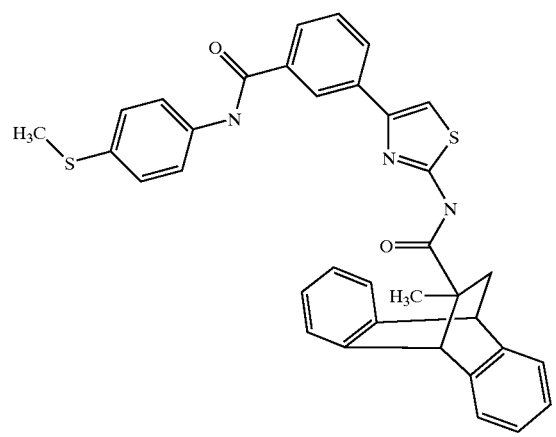
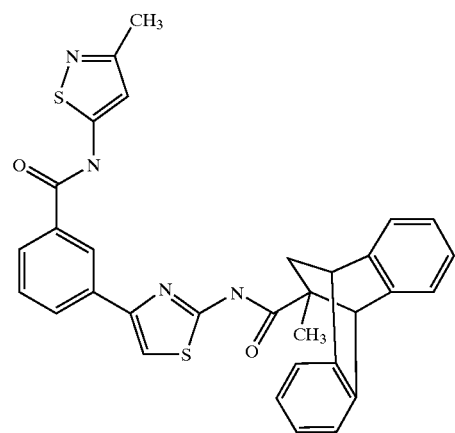
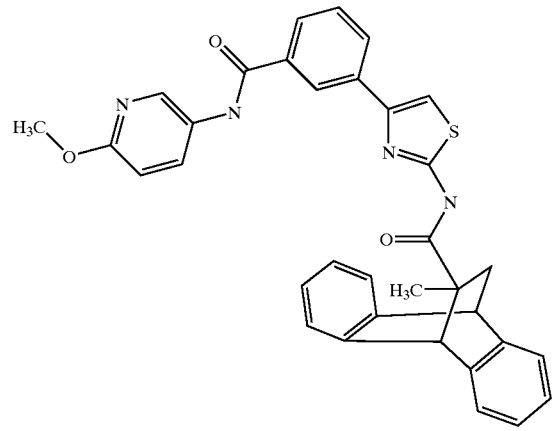

-continued
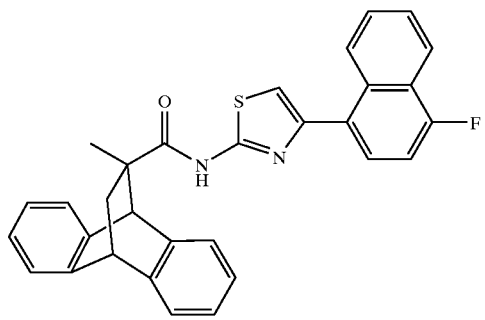
Chiral (R)
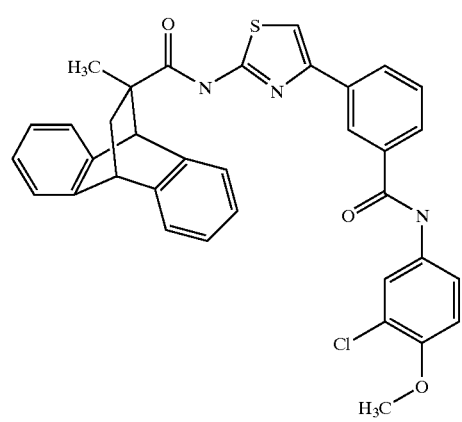
Chiral (R)
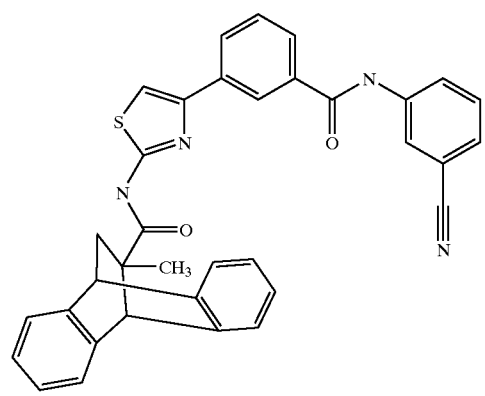
Chiral (R)
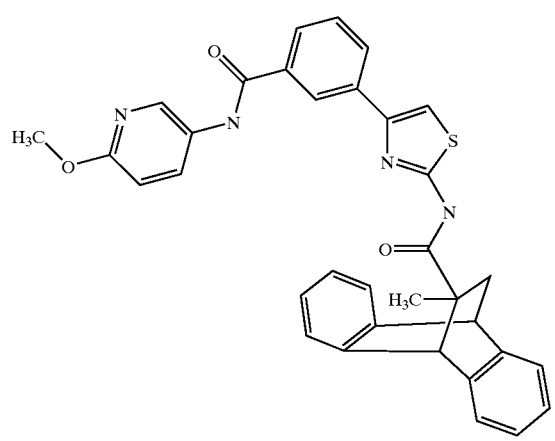

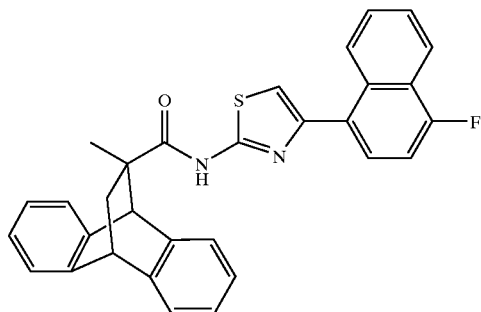
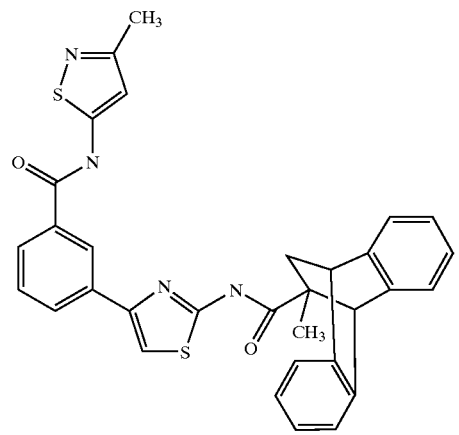
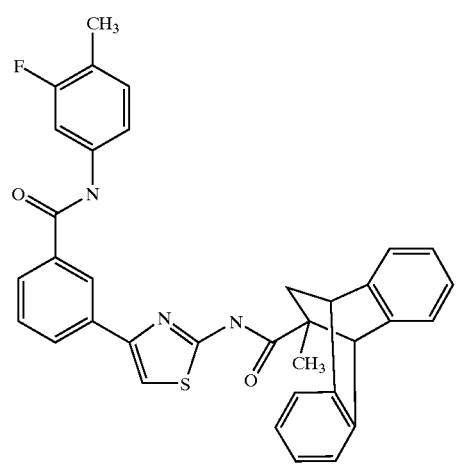

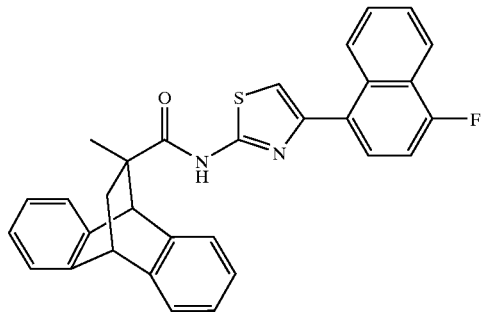
Chiral (R)
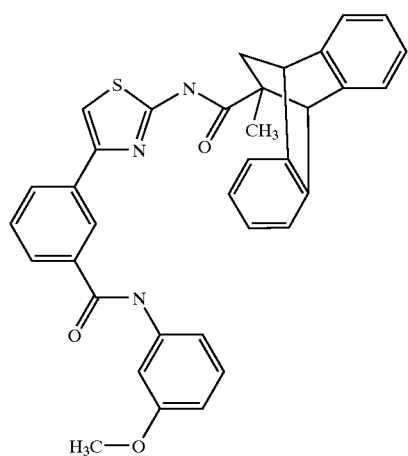
Chiral (R)
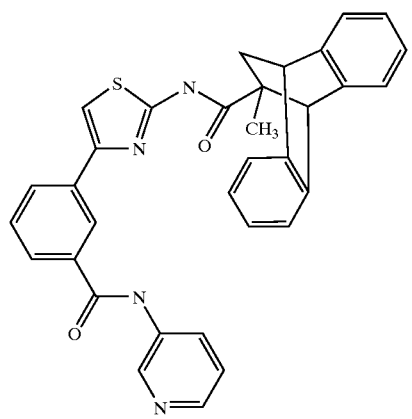
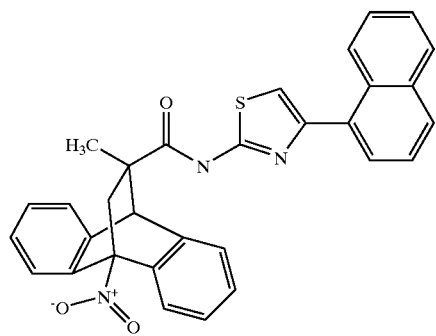

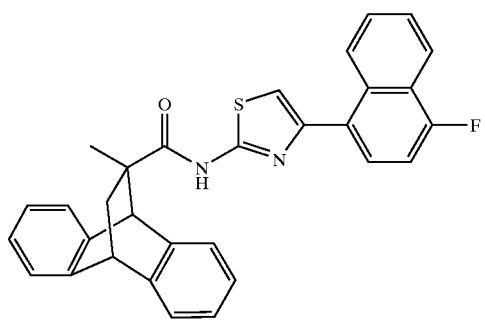
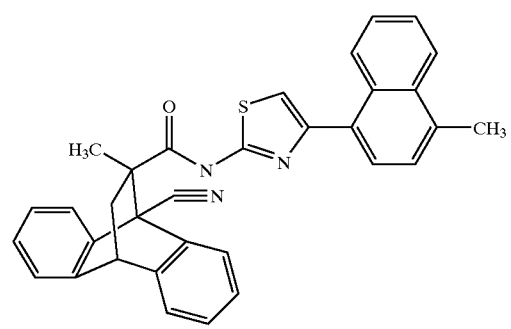
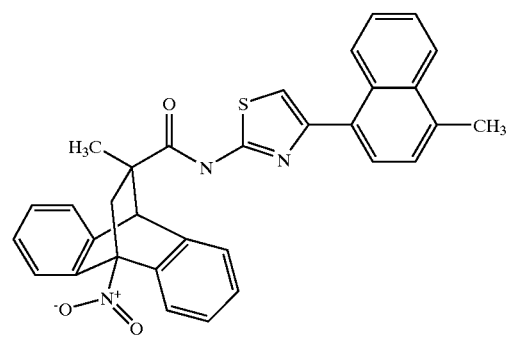
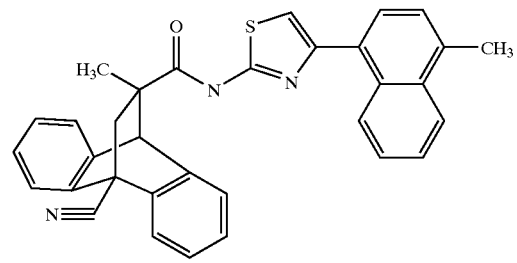
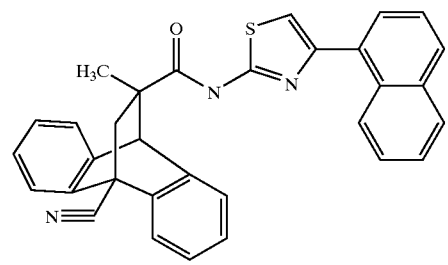

-continued
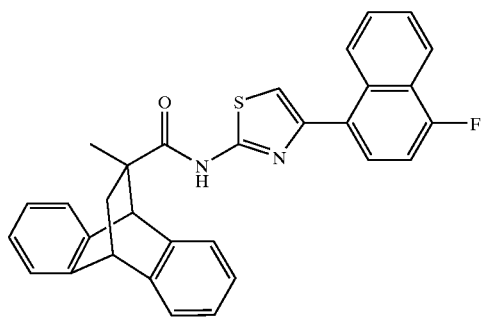
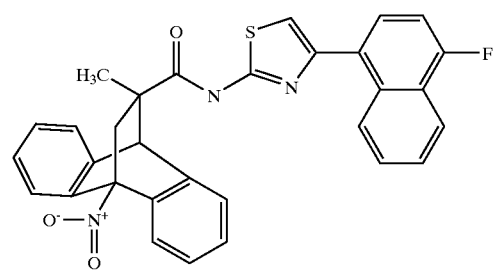
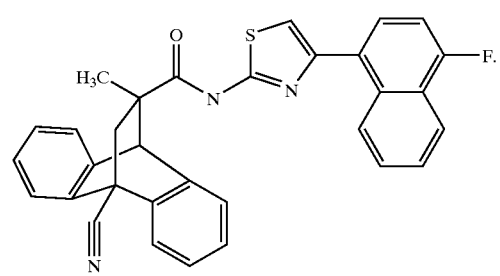
12. The compound as defined in claim 1 having the structure:
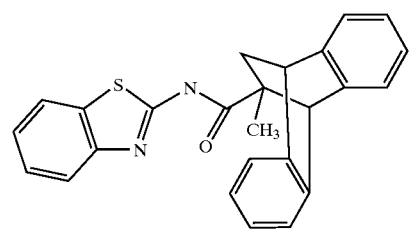
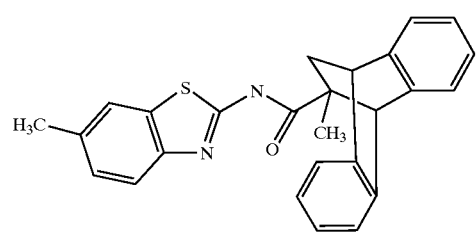

-continued
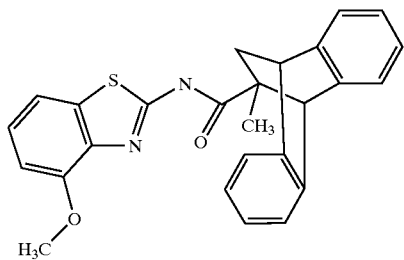
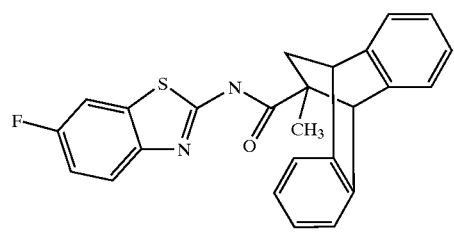
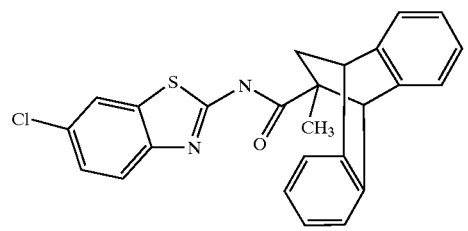
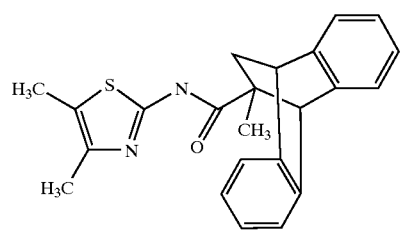
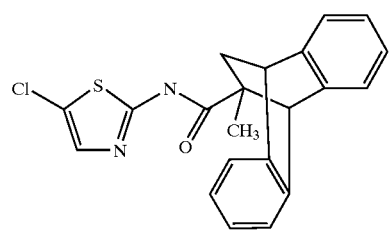
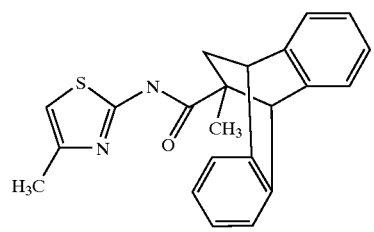

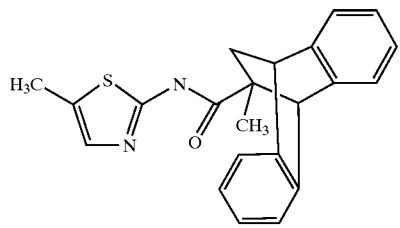
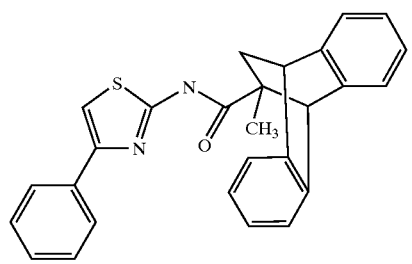
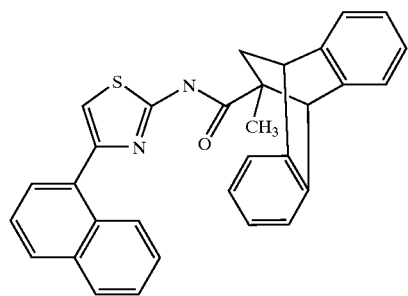
Chiral (R)
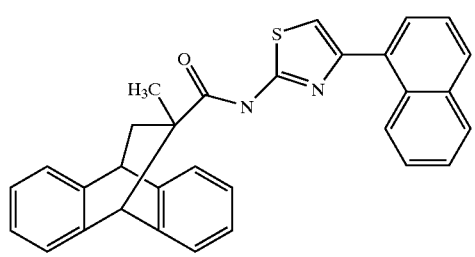
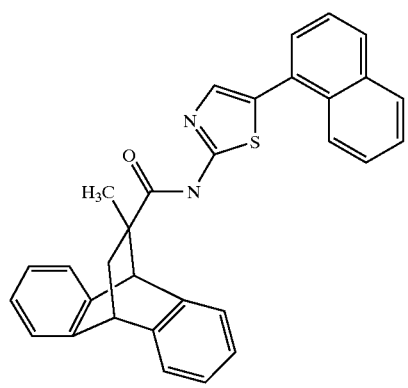

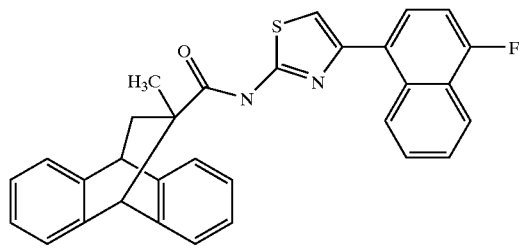
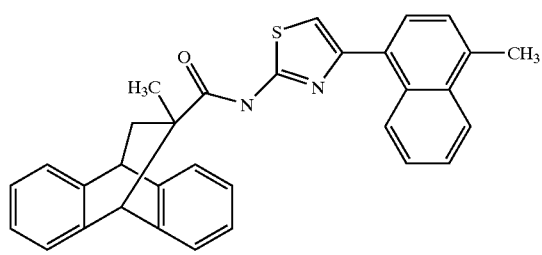
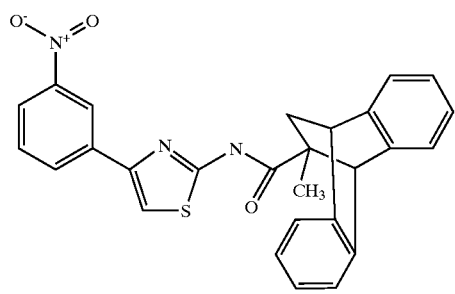
Chiral (R)
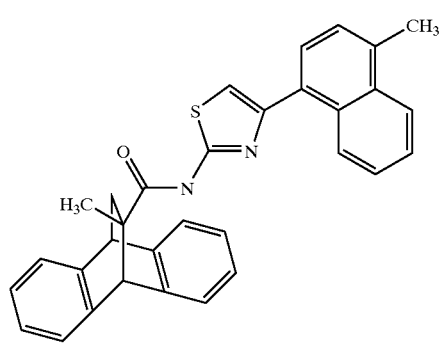
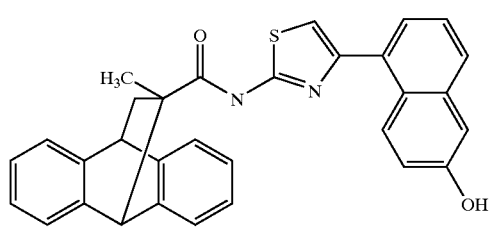

-continued
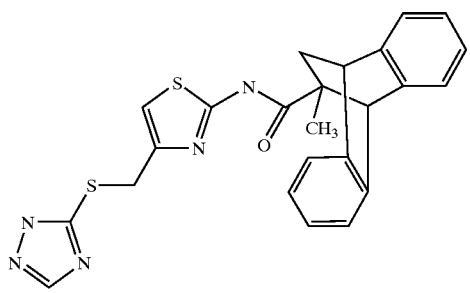
Chiral (R)
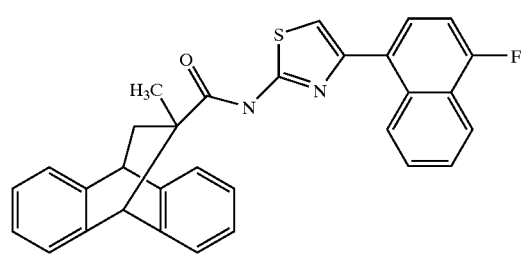
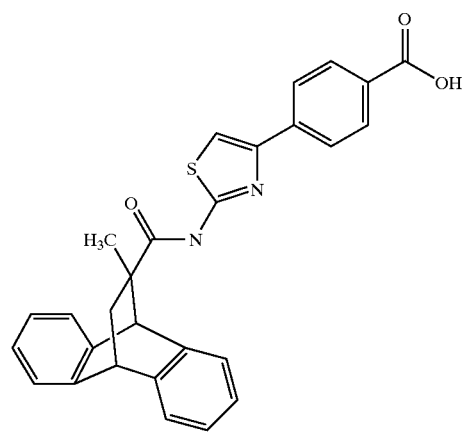
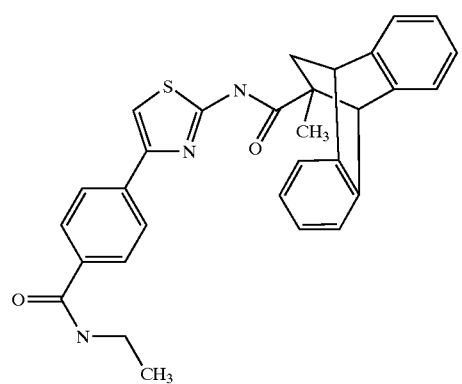

-continued
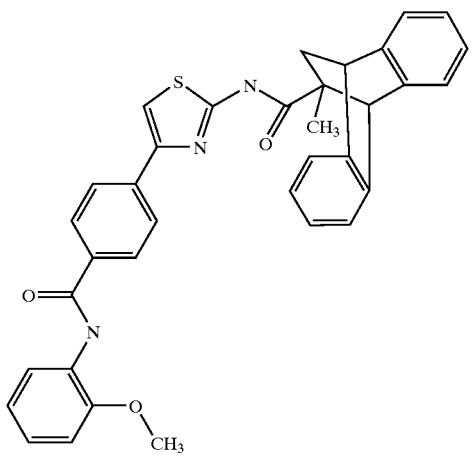
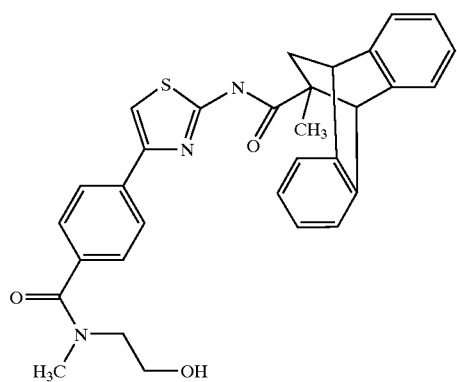
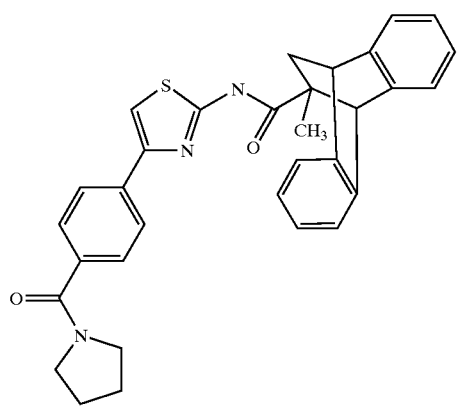

-continued
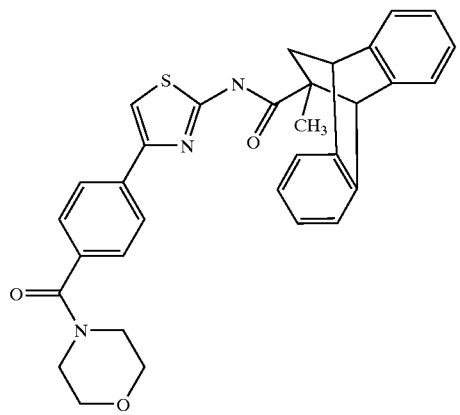
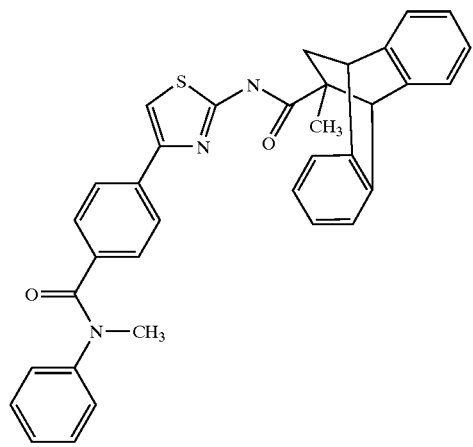
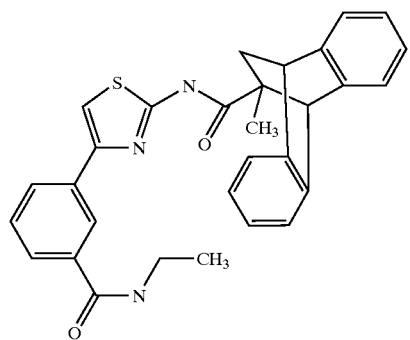
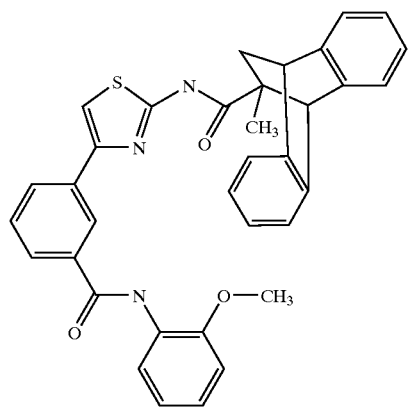

-continued
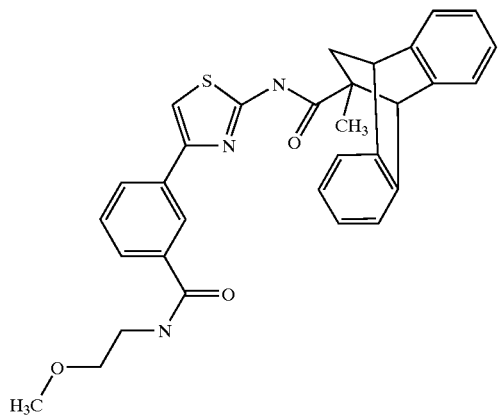
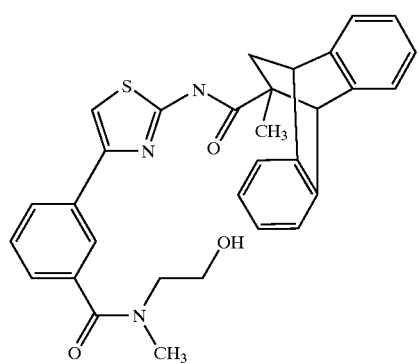
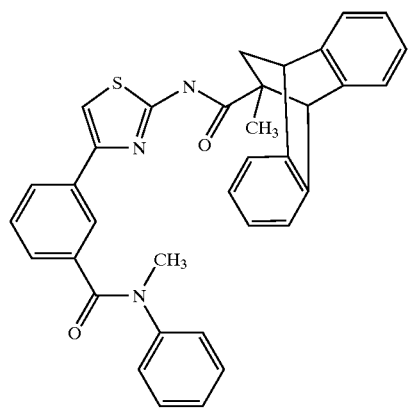
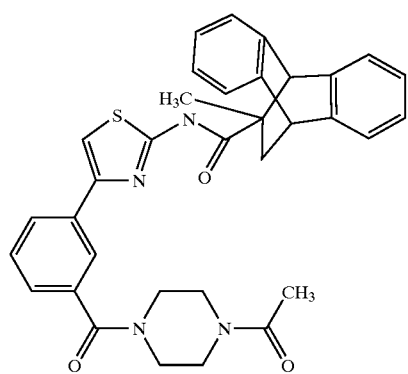

-continued
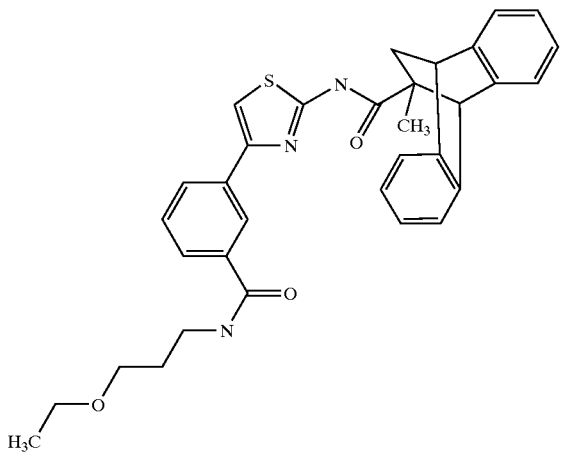
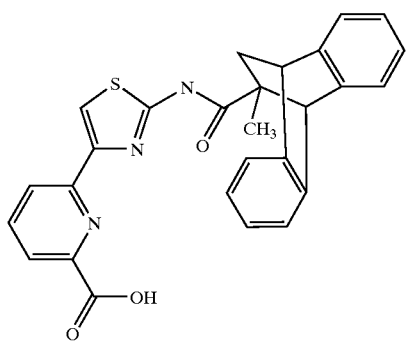
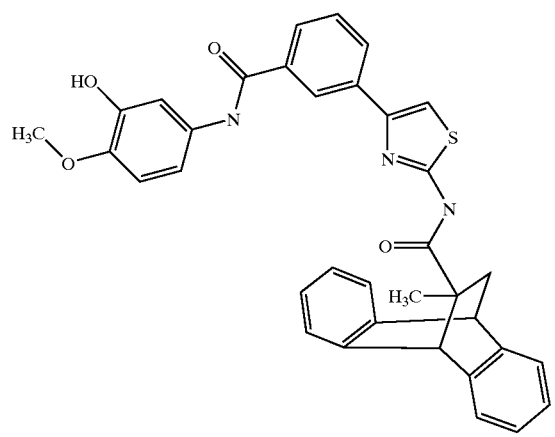

-continued
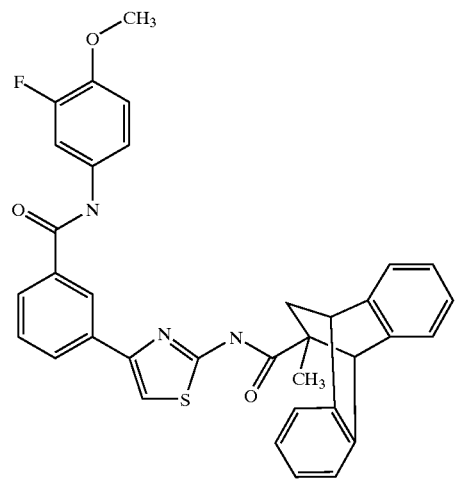
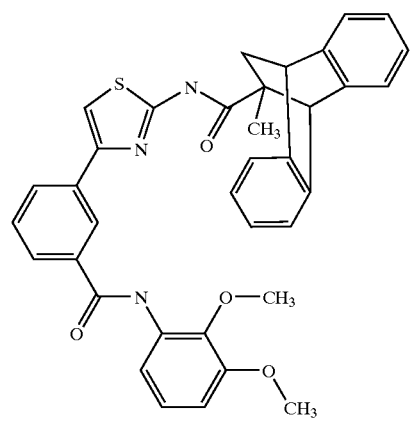
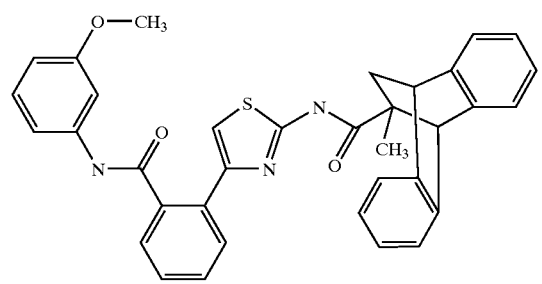

-continued
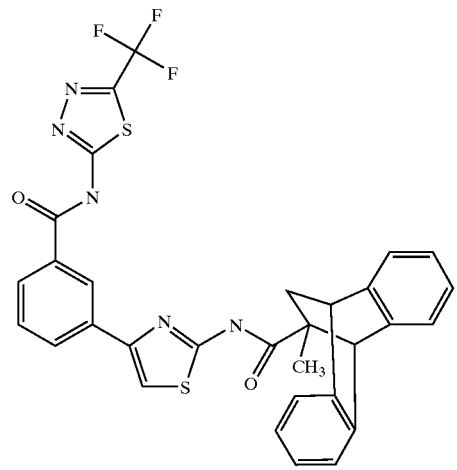
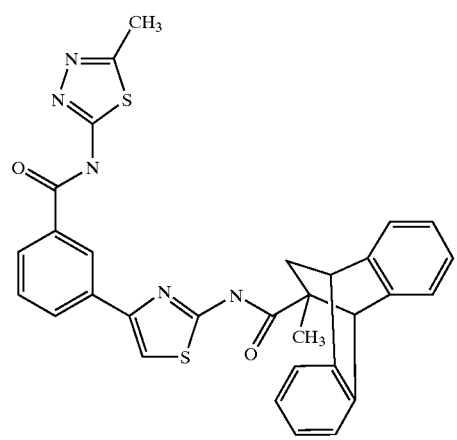
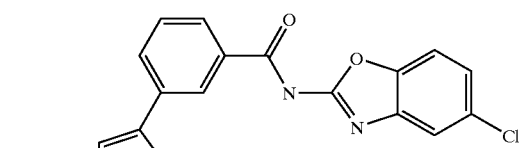
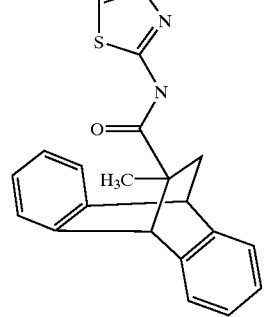
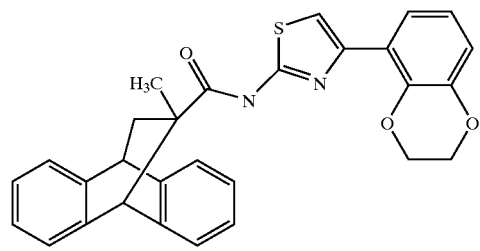

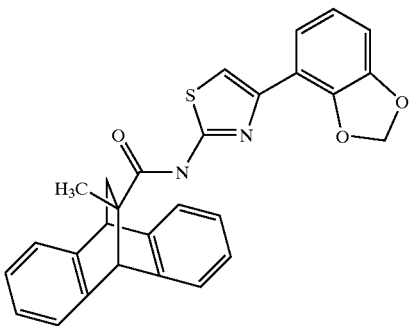
Chiral (R)
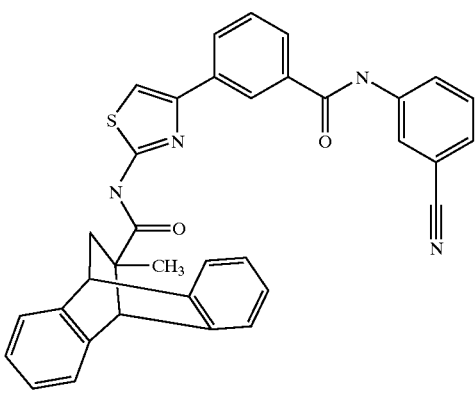
Chiral (R)
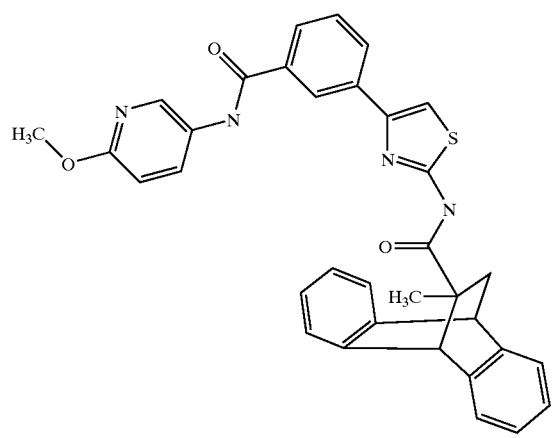
Chiral (R)
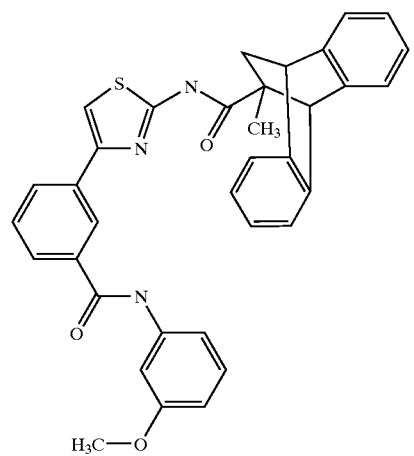

-continued

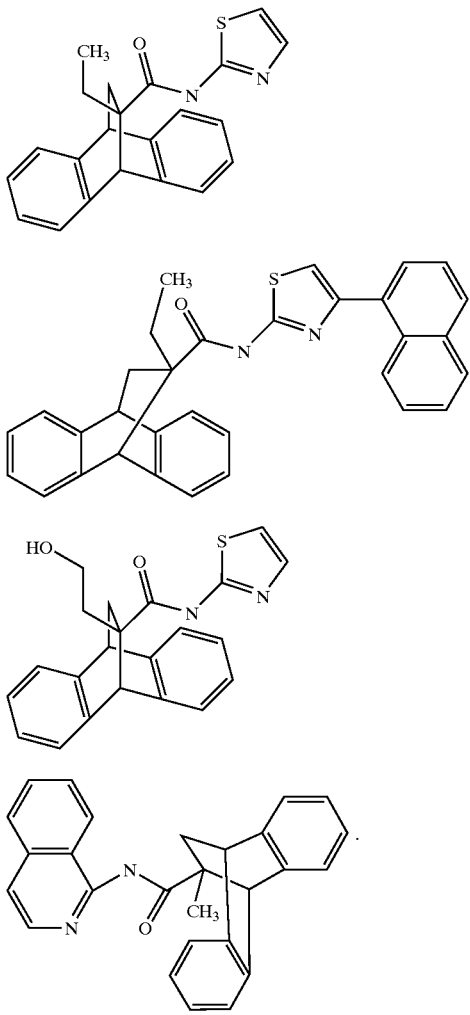

13. The compound as defined in claim 1 having the structure:

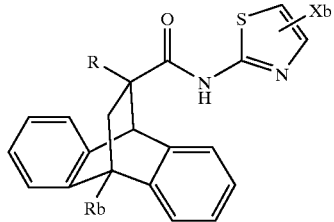

where R is CH₃, C₂H₅ or 2-hydroxyethyl, and Rb is H, CN, NO₂, halogen, alkyl or amino;

Xb is H, arylalkoxycarbonyl, arylalkylaminocarbonyl, alkoxyalkylaminocarbonyl, heteroarylcarbonyl, aryl, alkoxyalkylamidocarbonyl, arylaminocarbonyl, heteroarylaminocarbonyl, arylaminocarbonylaryl or heteroaryl;

provided that where Xb is H, then R is C₂H₅ or 2-hydroxymethyl or Rb is CN or NO₂.

14. The compound as defined in claim 13 having the structure

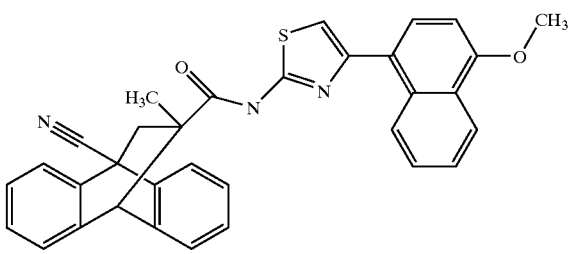

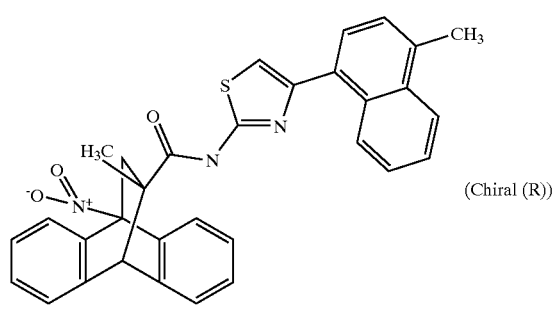

(Chiral (R))

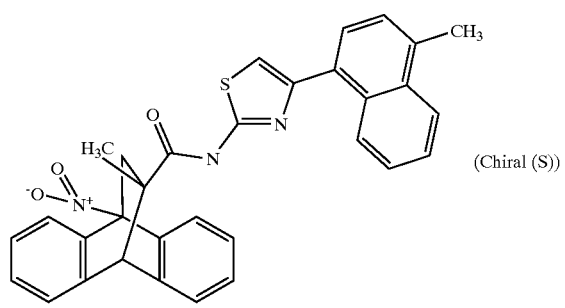
(Chiral (S))
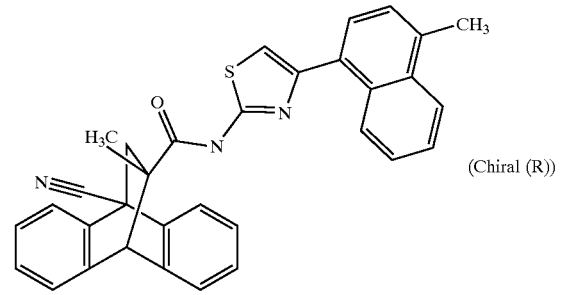
(Chiral (R))
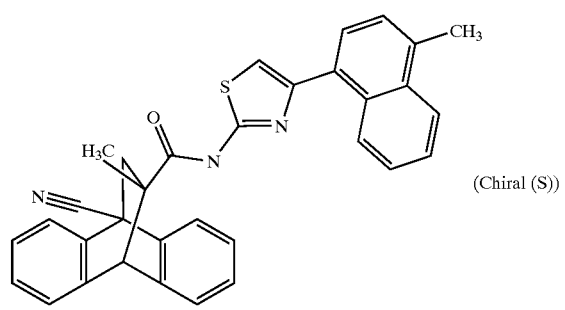
(Chiral (S))
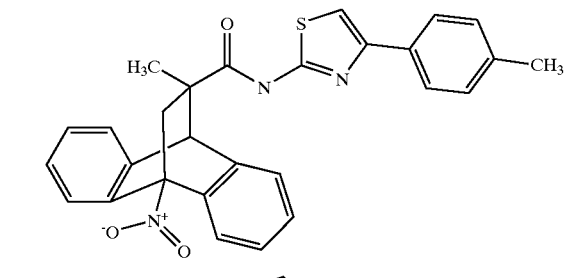
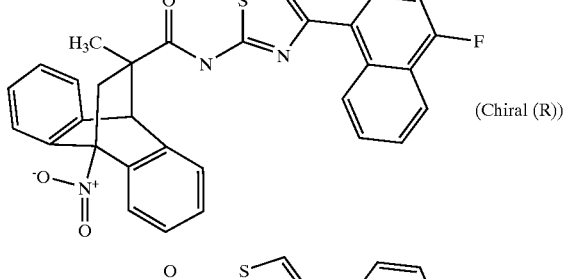
(Chiral (R))
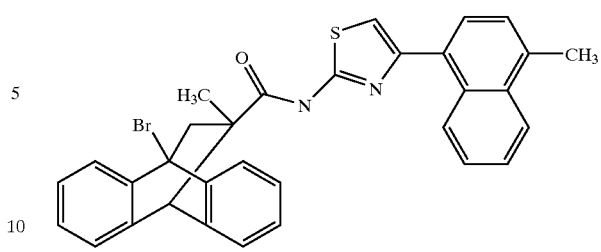
(Chiral (S))
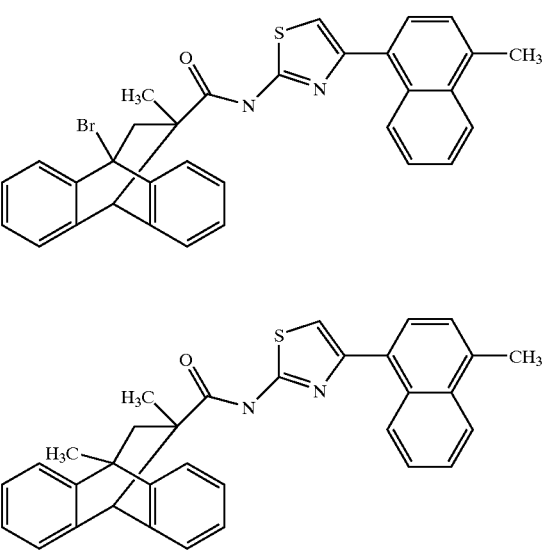
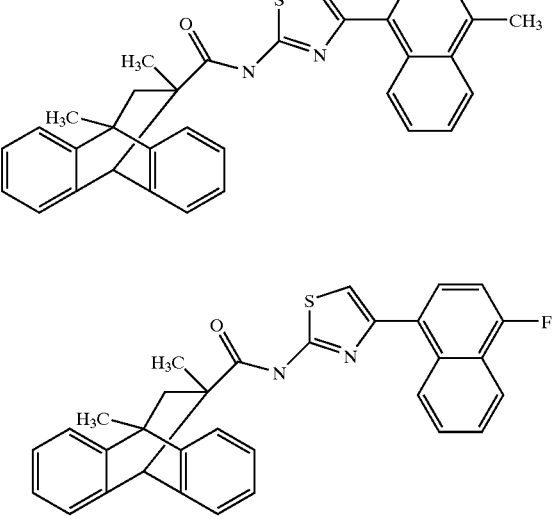
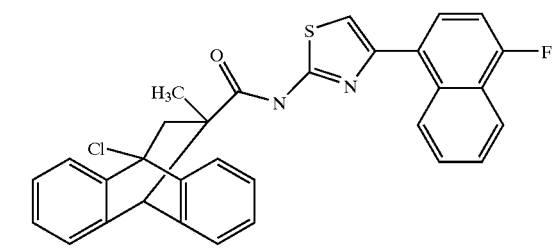
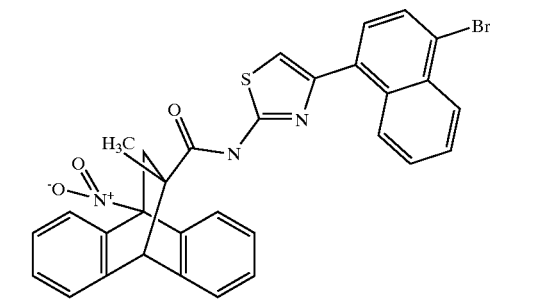
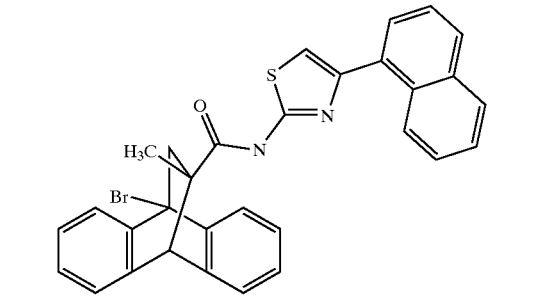

457
-continued
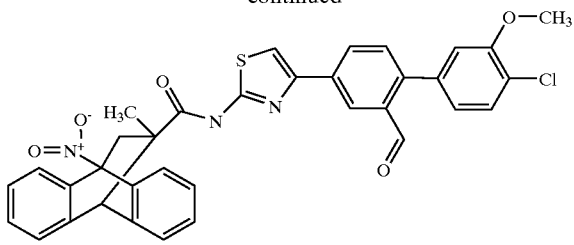
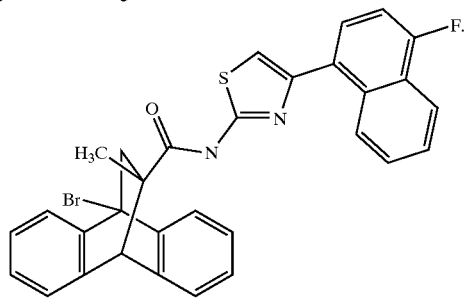
15. The compound as defined in claim 1 having the structure
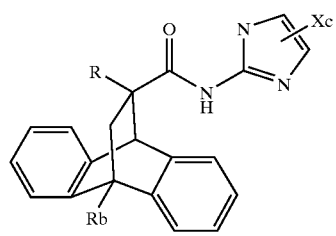
where R is CH₃, C₂H₅ or 2-hydroxyethyl, Rb is H, CN, NO₂, halogen, alkyl or amino; and Xc is aryl, quinolinyl or isoquinolinyl.
16. The compound as defined in claim 15 having the structure
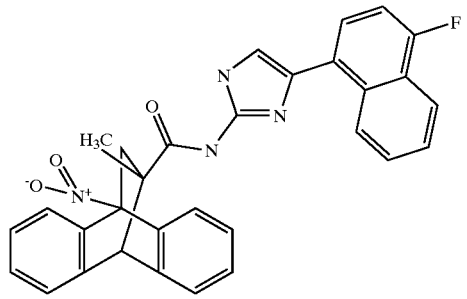
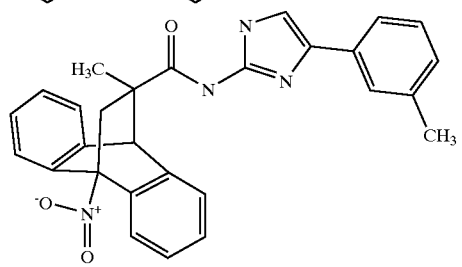
458
-continued
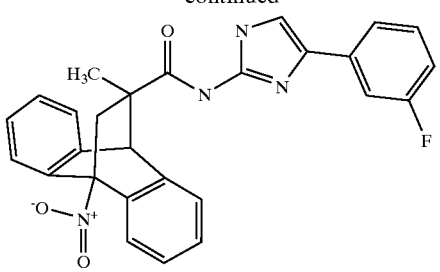
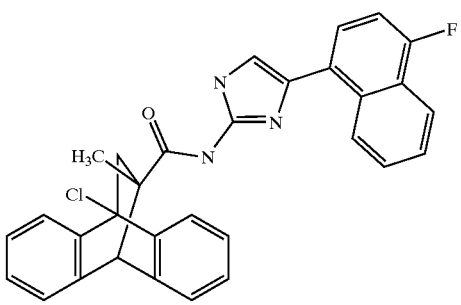
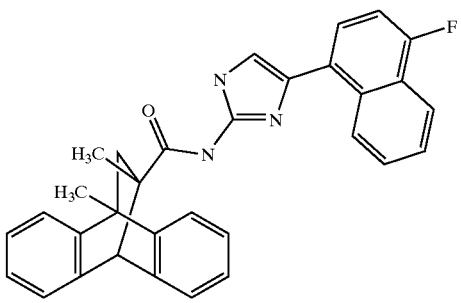
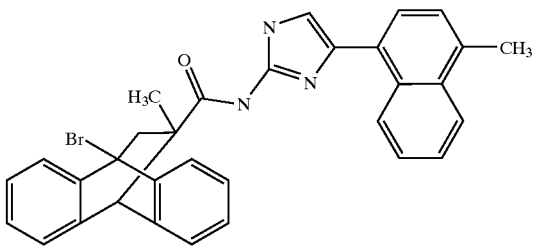
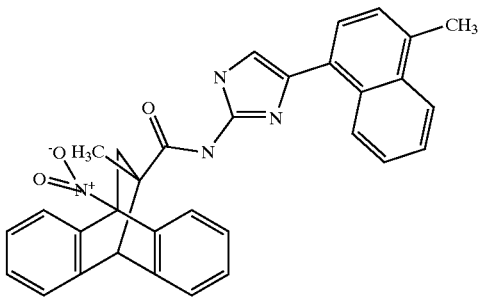
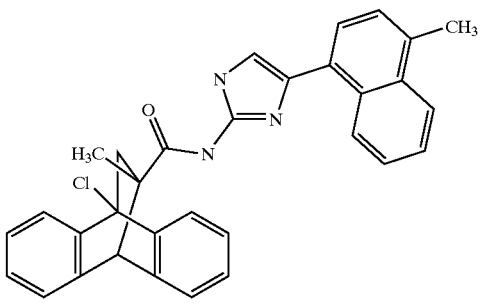

-continued
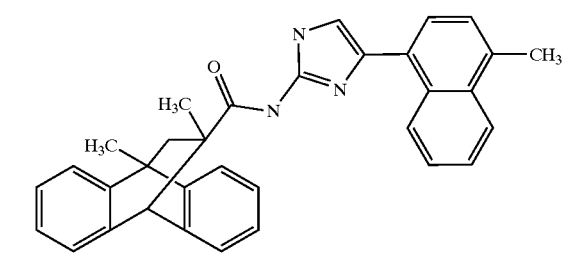
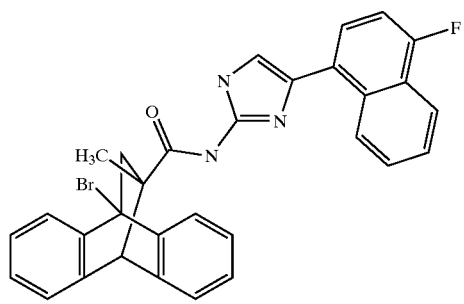
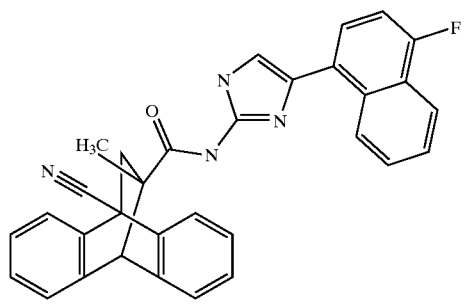
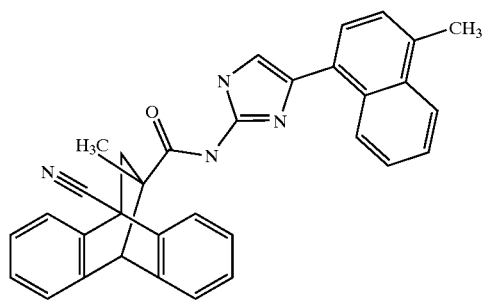
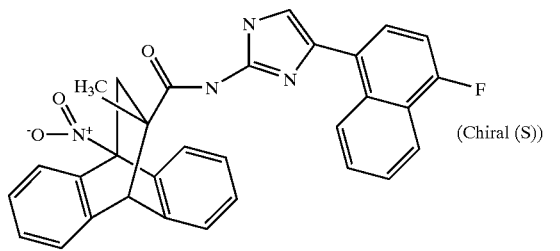
(Chiral (S))
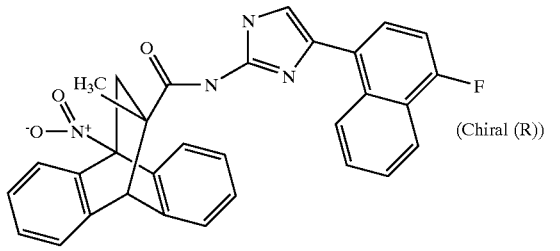
(Chiral (R))
-continued
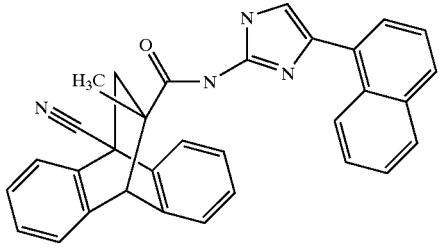
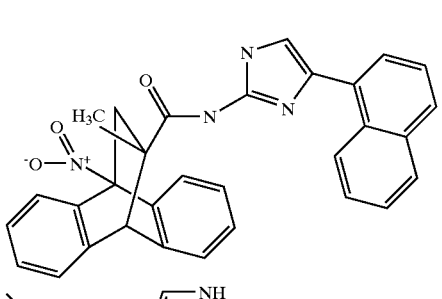
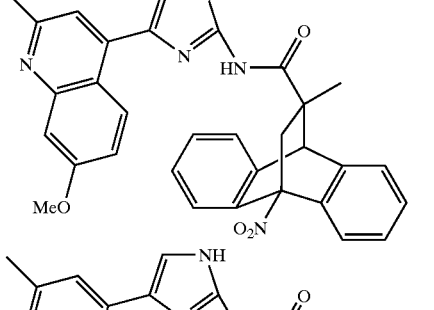
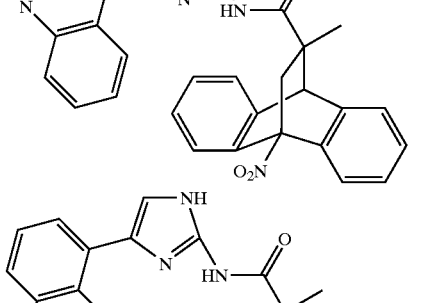
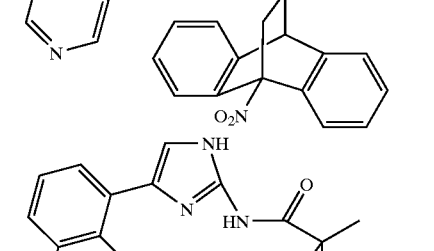
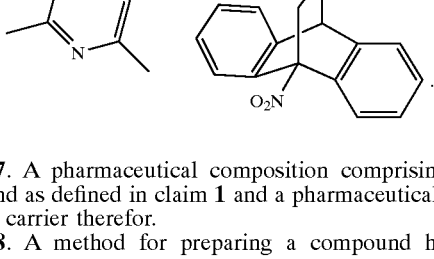
17. A pharmaceutical composition comprising a compound as defined in claim 1 and a pharmaceutically acceptable carrier therefor.
18. A method for preparing a compound having the structure:

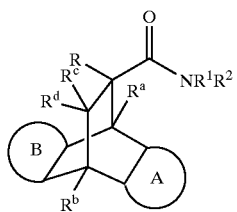

including all stereoisomers thereof or a pharmaceutically acceptable salt thereof, wherein R is hydrogen, alkyl, alkenyl, alkynyl, alkoxy, aryl, arylalkyl, aryloxy, heteroaryl, cycloheteroalkyl, heteroarylalkyl, cycloheteroalkylalkyl, cycloalkyl, cycloalkylalkyl, cyanoalkyl, aminoalkyl, hydroxyalkyl, aryloxyalkyl, or hydroxyaryl;

$R^a$ is hydrogen, alkyl, alkenyl, alkynyl, alkoxy, aryl, aryloxy, heteroaryl, cycloheteroalkyl, heteroarylalkyl, cycloheteroalkylalkyl, cyano, halogen, heteroarylaminocarboyl, cycloheteroalkylcarbonyl, cyanoalkyl, alkylaminoalkyl, hydroxyalkyl, hydroxyaryl, aryloxyalkyl, nitro, amino, CHO, $CO_2$ alkyl, $CONR^eR^f$, $CH_2NR^gR^h$, $CO_2H$, $CH_2OH$, $CH_2NRH^g$, $NHCH_2R^g$, $NHCHR^gR^h$, $NHCOR^e$, $NHCONR^eR^f$ or $NHSO_2R^e$;

$R^b$ is hydrogen, alkyl, alkenyl, alkynyl, alkoxy, aryl, aryloxy, heteroaryl, cycloheteroalkyl, heteroarylalkyl, cycloheteroalkylalkyl, cyano, halogen, heteroarylaminocarbonyl, cycloheteroalkylcarbonyl, cyanoalkyl, alkylaminoalkyl, hydroxyalkyl, nitro, amino, CHO, $CO_2$ alkyl, hydroxyaryl, aryloxyalkyl, $CONR^iR^j$, $CH_2NR^kR^l$, $CO_2H$, $CH_2OH$, $CH_2NHR^k$, $NHCH_2R^k$, $NHCHR^kR^l$, $NHCOR^i$, $NHCONR^iR^j$ or $NHSO_2R^i$;

where $R^e$ and $R^f$ are the same or different and are independently selected from hydrogen, aryl, alkyl, alkenyl, alkynyl, alkoxy, amino, alkoxyalkyl, alkylaminoalkyl, dialkylaminoalkyl, heteroaryl, cycloheteroalkyl, heteroarylalkyl, cycloheteroalkylalkyl, cycloalkyl, and cycloalkylalkyl, and $R^e$ and $R^f$ can be taken together with the nitrogen to which they are attached to form a 5-, 6- or 7-membered heteroaryl or cycloheteroalkyl ring which contains 1, 2 or 3 hetero atoms which can be N, O or S;

$R^g$ and $R^h$ are the same or different and are independently selected from hydrogen, aryl, alkyl, alkenyl, alkynyl, alkoxy, amino, alkoxyalkyl, alkylaminoalkyl, dialkylaminoalkyl, heteroaryl, cycloheteroalkyl, heteroarylalkyl, cycloheteroalkylalkyl, cycloalkyl, and cycloalkylalkyl, and $R^g$ and $R^h$ can be taken together with the nitrogen to which they are attached to form a 5-, 6- or 7-membered heteroaryl ring or cycloheteroalkyl ring which contains 1, 2 or 3 hetero atoms which can be N, O or S;

$R^i$ and $R^j$ are the same or different and are independently selected from hydrogen, aryl, alkyl, alkenyl, alkynyl, alkoxy, amino, alkoxyalkyl, alkylaminoalkyl, dialkylaminoalkyl, heteroaryl, cycloheteroalkyl, heteroarylalkyl, cycloheteroalkylalkyl, cycloalkyl, and cycloalkylalkyl, and $R^i$ and $R^j$ can be taken together with the nitrogen to which they are attached to form a 5-, 6-or 7-membered heteroaryl ring or cycloheteroalkyl ring which contains 1, 2 or 3 hetero atoms which can be N, O or S;

$R^k$ and $R^l$ are the same or different and are independently selected from hydrogen, aryl, alkyl, alkenyl, alkynyl, alkoxy, amino, alkoxyalkyl, alkylaminoalkyl, dialkylaminoalkyl, heteroaryl, cycloheteroalkyl, heteroarylalkyl, cycloheteroalkylalkyl, cycloalkyl, or cycloalkylalkyl, and $R^k$ and $R^l$ can be taken together with the nitrogen to which they are attached to form a 5-, 6- or 7-membered heteroaryl ring or cycloheteroalkyl ring which contains 1, 2 or 3 hetero atoms which can be N, O or S;

$R^c$ and $R^d$ are the same or different and are independently selected from hydrogen, alkyl, alkenyl, alkynyl, alkoxy, aryl, hydroxy, aryloxy, heteroaryl, cycloheteroalkyl, heteroarylalkyl, cycloheteroalkylalkyl, hydroxyaryl, and aryloxyalkyl;

$R^c$ and $R^d$ can be optionally taken together with the carbon to which they are attached to form a 3- to 7-membered ring which may optionally include an O atom or an N atom;

at least one of $R^1$ and $R^2$ is heteroaryl and the other of $R^1$ and $R^2$ is selected from hydrogen, alkyl, alkenyl, alkynyl, alkoxy, cycloalkyl, cycloalkylalkyl, aryl, heteroaryl, heteroarylalkyl, cycloheteroalkyl, cycloalkenyl, monoalkylaminoalkyl, dialkylaminoalkyl, cycloheteroalkylalkyl, hydroxyaryl, aryloxyalkyl, alkoxyalkyl and hydroxyalkyl;

the A ring represents an unsaturated 6-membered carbocyclic ring which is a fused phenyl or; and the B ring represents an unsaturated 6-membered carbocyclic ring which is fused phenyl;

with the following provisos:

provided that where (a) R is $CH_3$ or H and $R^a$, $R^b$, $R^c$ and Rd are each hydrogen, or (b) $R^a$ and $R^b$ are each hydrogen and one of $R^c$ and $R^d$ is alkyl, then (1) at least one of $R^1$ and $R^2$ is heteroaryl, but where the heteroaryl is unsubstituted

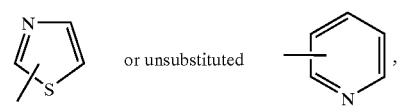

then the other of $R^1$ and $R^2$ is other than hydrogen; or (2) where one of $R^1$ and $R^2$ is phenyl which is substituted with alkyl, hydroxy, halo, $C_1$–$C_2$-alkoxycarbonyl or nitro, then (a) the phenyl must be substituted with at least one other group other than hydrogen, alkyl, hydroxy, halo, $C_1$-$C_2$-alkoxycarbonyl or nitro, except that the phenyl may be substituted with two or more halo atoms, and/or two or more hydroxy groups and/or (b) the other of $R^1$ and $R^2$ is heteroaryl; or (3) where at least one of $R^1$ and $R^2$ is hydrogen, unsubstituted alkyl, alkenyl, cycloalkyl, alkylcycloalkyl, cycloalkenyl, alkylcycloalkenyl, alkylphenyl, monoalkylaminoalkyl, dialkylaminoalkyl, arylalkyl, aryl, alkoxyalkyl or hydroxyalkyl then (a) the other of $R^1$ and $R^2$ is heteroaryl and/or (b) at least one of $R^a$, $R^b$, $R^c$ and/or $R^d$ is other than hydrogen and/or (c) R is other than hydrogen or $C_1$–$C_2$ alkyl;

the method comprises treating a compound of the structure

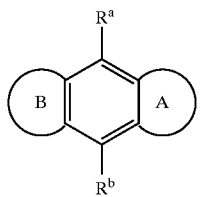

with an unsaturated compound of the structure

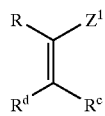

to form the intermediate

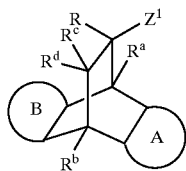

where $Z^1$ is $CO_2H$ or $CO_2$ alkyl,
reacting the above intermediate with an amine of the structure
to form a compound of the structure

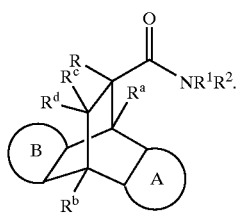

19. A method for preparing an amide having the structure:

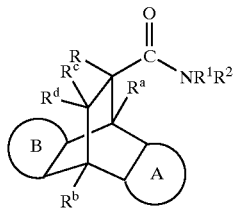

including all stereoisomers thereof or a pharmaceutically acceptable salt thereof, wherein R is alkyl, alkenyl, alkynyl, alkoxy, aryl, arylalkyl, aryloxy, heteroaryl, cycloheteroalkyl, heteroarylalkyl, cycloheteroalkylalkyl, cycloalkyl, cycloalkylalkyl, cyanoalkyl, aminoalkyl, hydroxyalkyl, aryloxyalkyl, or hydroxyaryl;

$R^a$ is hydrogen, alkyl, alkenyl, alkynyl, alkoxy, aryl, aryloxy, heteroaryl, cycloheteroalkyl, heteroarylalkyl, cycloheteroalkylalkyl, cyano, halogen, heteroarylaminocarboyl, cycloheteroalkylcarbonyl, cyanoalkyl, alkylaminoalkyl, hydroxyalkyl, hydroxyaryl, aryloxyalkyl, nitro, amino, CHO, $CO_2$ alkyl, $CONR^eR^f$, $CH_2NR^gR^h$, $CO_2H$, $CH_2OH$, $CH_2NRH^g$, $NHCH_2R^g$, $NHCHR^gR^h$, $NHCOR^e$, $NHCONR^eR^f$ or $NHSO_2R^e$;

$R^b$ is hydrogen, alkyl, alkenyl, alkynyl, alkoxy, aryl, aryloxy, heteroaryl, cycloheteroalkyl, heteroarylalkyl, cycloheteroalkylalkyl, cyano, halogen, heteroarylaminocarbonyl, cycloheteroalkylcarbonyl, cyanoalkyl, alkylaminoalkyl, hydroxyalkyl, nitro, amino, CHO, $CO_2$ alkyl, hydroxyaryl, aryloxyalkyl, $CONR^iR^j$, $CH_2NR^kR^l$, $CO_2H$, $CH_2OH$, $CH_2NHR^k$, $NHCH_2R^k$, $NHCHR^kR^l$, $NHCOR^i$, $NHCONR^iR^j$ or $NHSO_2R^i$;

where $R^e$ and $R^f$ are the same or different and are independently selected from hydrogen, aryl, alkyl, alkenyl, alkynyl, alkoxy, amino, alkoxyalkyl, alkylaminoalkyl, dialkylaminoalkyl, heteroaryl, cycloheteroalkyl, heteroarylalkyl, cycloheteroalkylalkyl, cycloalkyl, and cycloalkylalkyl, and $R^e$ and $R^f$ can be taken together with the nitrogen to which they are attached to form a 5-, 6- or 7-membered heteroaryl or cycloheteroalkyl ring which contains 1, 2 or 3 hetero atoms which can be N, O or S;

$R^g$ and $R^h$ are the same or different and are independently selected from hydrogen, aryl, alkyl, alkenyl, alkynyl, alkoxy, amino, alkoxyalkyl, alkylaminoalkyl, dialkylaminoalkyl, heteroaryl, cycloheteroalkyl, heteroarylalkyl, cycloheteroalkylalkyl, cycloalkyl, and cycloalkylalkyl, and $R^g$ and $R^h$ can be taken together with the nitrogen to which they are attached to form a 5-, 6- or 7-membered heteroaryl ring or cycloheteroalkyl ring which contains 1, 2 or 3 hetero atoms which can be N, O or S;

$R^i$ and $R^j$ are the same or different and are independently selected from hydrogen, aryl, alkyl, alkenyl, alkynyl, alkoxy, amino, alkoxyalkyl, alkylaminoalkyl, dialkylaminoalkyl, heteroaryl, cycloheteroalkyl, heteroarylalkyl, cycloheteroalkylalkyl, cycloalkyl, and cycloalkylalkyl, and $R^i$ and $R^j$ can be taken together with the nitrogen to which they are attached to form a 5-, 6-or 7-membered heteroaryl ring or cycloheteroalkyl ring which contains 1, 2 or 3 hetero atoms which can be N, O or S;

$R^k$ and $R^l$ are the same or different and are independently selected from hydrogen, aryl, alkyl, alkenyl, alkynyl, alkoxy, amino, alkoxyalkyl, alkylaminoalkyl, dialkylaminoalkyl, heteroaryl, cycloheteroalkyl, heteroarylalkyl, cycloheteroalkylalkyl, cycloalkyl, and cycloalkylalkyl, and $R^k$ and $R^l$ can be taken together with the nitrogen to which they are attached to form a 5-, 6- or 7-membered heteroaryl ring or cycloheteroalkyl ring which contains 1, 2 or 3 hetero atoms which can be N, O or S;

$R^c$ and $R^d$ are the same or different and are independently selected from hydrogen, alkyl, alkenyl, alkynyl, alkoxy, aryl, hydroxy, aryloxy, heteroaryl, cycloheteroalkyl, heteroarylalkyl, cycloheteroalkylalkyl, hydroxyaryl, and aryloxyalkyl;

$R^c$ and $R^d$ can be optionally taken together with the carbon to which they are attached to form a 3- to 7-membered ring which may optionally include an O atom or an N atom;

at least one of $R^1$ and $R^2$ is heteroaryl and the other of $R^1$ and $R^2$ is selected from hydrogen, alkyl, alkenyl, alkynyl, alkoxy, cycloalkyl, cycloalkylalkyl, aryl, heteroaryl, heteroarylalkyl, cycloheteroalkyl, cycloalkenyl, monoalkylaminoalkyl, dialkylaminoalkyl, cycloheteroalkylalkyl, hydroxyaryl, aryloxyalkyl, alkoxyalkyl and hydroxyalkyl;

the A ring represents an unsaturated 6-membered carbocyclic ring which is a fused phenyl; and the B ring represents an unsaturated 6-membered carbocyclic ring which is fused phenyl;

with the following provisos:

(1) at least one of $R^1$ and $R^2$ is heteroaryl, but where the heteroaryl is unsubstituted

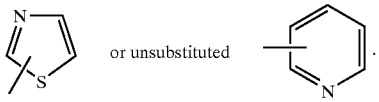

then the other of $R^1$ and $R^2$ is other than hydrogen; or (2) where one of $R^1$ and $R^2$ is phenyl which is substituted with alkyl, hydroxy, halo, $C_1$–$C_2$-alkoxycarbonyl or nitro, then (a) the phenyl must be substituted with at least one other group other than hydrogen, alkyl, hydroxy, halo, $C_1$-$C_2$-alkoxycarbonyl or nitro, except that the phenyl may be substituted with two or more halo atoms, and/or two or more hydroxy groups and/or (b) the other of $R^1$ and $R^2$ is heteroaryl; or (3) where at least one of $R^1$ and $R^2$ is hydrogen, unsubstituted alkyl, alkenyl, cycloalkyl, alkylcycloalkyl, cycloalkenyl, alkylcycloalkenyl, alkylphenyl, monoalkylaminoalkyl, dialkylaminoalkyl, arylalkyl, aryl, alkoxyalkyl or hydroxyalkyl then (a) the other of $R^1$ and $R^2$ is heteroaryl and/or (b) at least one of $R^a$, $R^b$, $R^c$ and/or $R^d$ is other than hydrogen and/or (c) R is other than hydrogen or $C_1$–$C_2$ alkyl;

the method comprises treating a compound of the structure

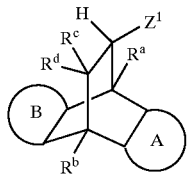

where $Z^1$ is $CO_2H$ or $CO_2$ alkyl, with a base and a compound of the structure

R-LG where LG is a leaving group, to form the compound of the structure

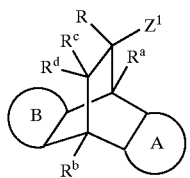

and treating the above compound with an amine of the structure $HNR^1R^2$ to form the corresponding amide.

20. A method for preparing an amide compound having the structure:

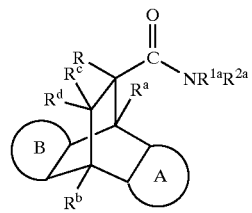

including all stereoisomers thereof or a pharmaceutically acceptable salt thereof, wherein R is hydrogen, alkyl, alkenyl, alkynyl, alkoxy, aryl, arylalkyl, aryloxy, heteroaryl, cycloheteroalkyl, heteroarylalkyl, cycloheteroalkylalkyl, cycloalkyl, cycloalkylalkyl, cyanoalkyl, aminoalkyl, hydroxyalkyl, aryloxyalkyl, or hydroxyaryl;

$R^a$ is hydrogen, alkyl, alkenyl, alkynyl, alkoxy, aryl, aryloxy, heteroaryl, cycloheteroalkyl, heteroarylalkyl, cycloheteroalkylalkyl, cyano, halogen, heteroarylaminocarboyl, cycloheteroalkylcarbonyl, cyanoalkyl, alkylaminoalkyl, hydroxyalkyl, hydroxyaryl, aryloxyalkyl, nitro, amino, CHO, $CO_2$ alkyl, $CONR^eR^f$, $CH_2NR^gR^h$, $CO_2H$, $CH_2OH$, $CH_2NRH^g$, $NHCH_2R^g$, $NHCHR^gR^h$, $NHCOR^e$, $NHCONR^eR^f$ or $NHSO_2R^e$;

$R^b$ is hydrogen, alkyl, alkenyl, alkynyl, alkoxy, aryl, aryloxy, heteroaryl, cycloheteroalkyl, heteroarylalkyl, cycloheteroalkylalkyl, cyano, halogen, heteroarylaminocarbonyl, cycloheteroalkylcarbonyl, cyanoalkyl, alkylaminoalkyl, hydroxyalkyl, nitro, amino, CHO, $CO_2$ alkyl, hydroxyaryl, aryloxyalkyl, $CONR^iR^j$, $CH_2NR^kR^l$, $CO_2H$, $CH_2OH$, $CH_2NHR^k$, $NHCH_2R^k$, $NHCHR^kR^l$, $NHCOR^i$, $NHCONR^iR^j$ or $NHSO_2R^i$;

where $R^e$ and $R^f$ are the same or different and are independently selected from hydrogen, aryl, alkyl, alkenyl, alkynyl, alkoxy, amino, alkoxyalkyl, alkylaminoalkyl, dialkylaminoalkyl, heteroaryl, cycloheteroalkyl, heteroarylalkyl, cycloheteroalkylalkyl, cycloalkyl, and cycloalkylalkyl, and $R^e$ and $R^f$ can be taken together with the nitrogen to which they are attached to form a 5-, 6- or 7-membered heteroaryl or cycloheteroalkyl ring which contains 1, 2 or 3 hetero atoms which can be N, O or S;

$R^g$ and $R^h$ are the same or different and are independently selected from hydrogen, aryl, alkyl, alkenyl, alkynyl, alkoxy, amino, alkoxyalkyl, alkylaminoalkyl, dialkylaminoalkyl, heteroaryl, cycloheteroalkyl, heteroarylalkyl, cycloheteroalkylalkyl, cycloalkyl, and cycloalkylalkyl, and $R^g$ and $R^h$ can be taken together with the nitrogen to which they are attached to form a 5-, 6- or 7-membered heteroaryl ring or cycloheteroalkyl ring which contains 1, 2 or 3 hetero atoms which can be N, O or S;

$R^i$ and $R^j$ are the same or different and are independently selected from hydrogen, aryl, alkyl, alkenyl, alkynyl, alkoxy, amino, alkoxyalkyl, alkylaminoalkyl, dialkylaminoalkyl, heteroaryl, cycloheteroalkyl, heteroarylalkyl, cycloheteroalkylalkyl, cycloalkyl, and cycloalkylalkyl, and $R^i$ and $R^j$ can be taken together with the nitrogen to which they are attached to form a 5-, 6-or 7-membered heteroaryl ring or cycloheteroalkyl ring which contains 1, 2 or 3 hetero atoms which can be N, O or S;

$R^k$ and $R^l$ are the same or different and are independently selected from hydrogen, aryl, alkyl, alkenyl, alkynyl, alkoxy, amino, alkoxyalkyl, alkylaminoalkyl, dialkylaminoalkyl, heteroaryl, cycloheteroalkyl, heteroarylalkyl, cycloheteroalkylalkyl, cycloalkyl, or cycloalkylalkyl, and $R^k$ and $R^l$ can be taken together with the nitrogen to which they are attached to form a 5-, 6- or 7-membered heteroaryl ring or cycloheteroalkyl ring which contains 1, 2 or 3 hetero atoms which can be N, O or S;

$R^c$ and $R^d$ are the same or different and are independently selected from hydrogen, alkyl, alkenyl, alkynyl, alkoxy, aryl, hydroxy, aryloxy, heteroaryl, cycloheteroalkyl, heteroarylalkyl, cycloheteroalkylalkyl, hydroxyaryl, and aryloxyalkyl;

$R^c$ and $R^d$ can be optionally taken together with the carbon to which they are attached to form a 3- to 7-membered ring which may optionally include an O atom or an N atom;

at least one of $R^{1a}$ and $R^{2a}$ is heteroaryl and the other of $R^{1a}$ and $R^{2a}$ is selected from alkyl, alkenyl, alkynyl, alkoxy, cycloalkyl, cycloalkylalkyl, aryl, heteroaryl, heteroarylalkyl, cycloheteroalkyl, cycloalkenyl, monoalkylaminoalkyl, dialkylaminoalkyl, cycloheteroalkylalkyl, hydroxyaryl, aryloxyalkyl, alkoxyalkyl and hydroxyalkyl;

the A ring represents an unsaturated 6-membered carbocyclic ring; and the B ring represents an unsaturated 6-membered carbocyclic ring; the method comprises treating a compound

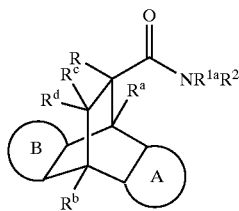

where $R^2$ is H with a base and a compound of the structure $R^{2a}$-LG where LG is a leaving group, to form the compound of the structure

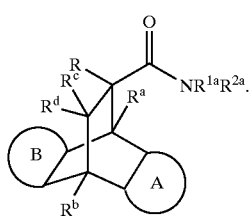

21. A method for preparing an amine compound having the structure:

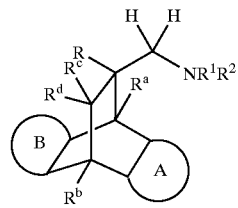

including all stereoisomers thereof or a pharmaceutically acceptable salt thereof, wherein R is hydrogen, alkyl, alkenyl, alkynyl, alkoxy, aryl, arylalkyl, aryloxy, heteroaryl, cycloheteroalkyl, heteroarylalkyl, cycloheteroalkylalkyl, cycloalkyl, cycloalkylalkyl, cyanoalkyl, aminoalkyl, hydroxyalkyl, aryloxyalkyl, or hydroxyaryl;

$R^a$ is hydrogen, alkyl, alkenyl, alkynyl, alkoxy, aryl, aryloxy, heteroaryl, cycloheteroalkyl, heteroarylalkyl, cycloheteroalkylalkyl, cyano, halogen, heteroarylaminocarboyl, cycloheteroalkylcarbonyl, cyanoalkyl, alkylaminoalkyl, hydroxyalkyl, hydroxyaryl, aryloxyalkyl, nitro, amino, CHO, $CO_2$alkyl, $CONR^eR^f$, $CH_2NR^gR^h$, $CO_2H$, $CH_2OH$, $CH2NRH^g$, $NHCH_2R^g$, $NHCHR^gR^h$, $NHCOR^e$, $NHCONR^eR^f$ or $NHSO_2R^e$;

$R^b$ is hydrogen, alkyl, alkenyl, alkynyl, alkoxy, aryl, aryloxy, heteroaryl, cycloheteroalkyl, heteroarylalkyl, cycloheteroalkylalkyl, cyano, halogen, heteroarylaminocarbonyl, cycloheteroalkylcarbonyl, cyanoalkyl, alkylaminoalkyl, hydroxyalkyl, nitro, amino, CHO, $CO_2$ alkyl, hydroxyaryl, aryloxyalkyl, $CONR^iR^j$, $CH_2NR^kR^l$, $CO_2H$, $CH_2OH$, $CH_2NHR^k$, $NHCH_2R^k$, $NHCHR^kR^l$, $NHCOR^i$, $NHCONR^iR^j$ or $NHSO_2R^i$;

where $R^e$ and $R^f$ are the same or different and are independently selected from hydrogen, aryl, alkyl, alkenyl, alkynyl, alkoxy, amino, alkoxyalkyl, alkylaminoalkyl, dialkylaminoalkyl, heteroaryl, cycloheteroalkyl, heteroarylalkyl, cycloheteroalkylalkyl, cycloalkyl, and cycloalkylalkyl, and $R^e$ and $R^f$ can be taken together with the nitrogen to which they are attached to form a 5-, 6- or 7-membered heteroaryl or cycloheteroalkyl ring which contains 1, 2 or 3 hetero atoms which can be N, O or S;

$R^g$ and $R^h$ are the same or different and are independently selected from hydrogen, aryl, alkyl, alkenyl, alkynyl, alkoxy, amino, alkoxyalkyl, alkylaminoalkyl, dialkylaminoalkyl, heteroaryl, cycloheteroalkyl, heteroarylalkyl, cycloheteroalkylalkyl, cycloalkyl, and cycloalkylalkyl, and $R^g$ and $R^h$ can be taken together with the nitrogen to which they are attached to form a 5-, 6- or 7-membered heteroaryl ring or cycloheteroalkyl ring which contains 1, 2 or 3 hetero atoms which can be N, O or S;

$R^i$ and $R^j$ are the same or different and are independently selected from hydrogen, aryl, alkyl, alkenyl, alkynyl, alkoxy, amino, alkoxyalkyl, alkylaminoalkyl, dialkylaminoalkyl, heteroaryl, cycloheteroalkyl, heteroarylalkyl, cycloheteroalkylalkyl, cycloalkyl, and cycloalkylalkyl, and $R^i$ and $R^j$ can be taken together with the nitrogen to which they are attached to form a 5-, 6-or 7-membered heteroaryl ring or cycloheteroalkyl ring which contains 1, 2 or 3 hetero atoms which can be N, O or S;

$R^k$ and $R^l$ are the same or different and are independently selected from hydrogen, aryl, alkyl, alkenyl, alkynyl, alkoxy, amino, alkoxyalkyl, alkylaminoalkyl, dialkylaminoalkyl, heteroaryl, cycloheteroalkyl, heteroarylalkyl, cycloheteroalkylalkyl, cycloalkyl, and cycloalkylalkyl, and $R^k$ and $R^l$ can be taken together with the nitrogen to which they are attached to form a 5-, 6- or 7-membered heteroaryl ring or cycloheteroalkyl ring which contains 1, 2 or 3 hetero atoms which can be N, O or S;

$R^c$ and $R^d$ are the same or different and are independently selected from hydrogen, alkyl, alkenyl, alkynyl, alkoxy, aryl, hydroxy, aryloxy, heteroaryl, cycloheteroalkyl, heteroarylalkyl, cycloheteroalkylalkyl, hydroxyaryl, or aryloxyalkyl;

$R^c$ and $R^d$ can be optionally taken together with the carbon to which they are attached to form a 3- to 7-membered ring which may optionally include an O atom or an N atom;

at least one of $R^1$ and $R^2$ is heteroaryl and the other of $R^1$ and $R^2$ is selected from hydrogen, alkyl, alkenyl, alkynyl, alkoxy, cycloalkyl, cycloalkylalkyl, aryl, heteroaryl, heteroarylalkyl, cycloheteroalkyl, cycloalkenyl, monoalkylaminoalkyl, dialkylaminoalkyl, cycloheteroalkylalkyl, hydroxyaryl, aryloxyalkyl, alkoxyalkyl and hydroxyalkyl;

the A ring represents an unsaturated 6-membered carbocyclic ring; and the B ring represents an unsaturated 6-membered carbocyclic ring;

provided that where at least one of R1 and R2 is a heteroaryl selected from pyridinyl, pyrimidinyl, pyridazinyl, pyrazinyl or imidazolinyl, then (a) the other of R1 and R2 is other than hydrogen, alkyl, alkenyl, cycloalkyl, alkylcycloalkyl, phenyl, alkylphenyl, phenylalkyl, monoalkylaminoalkyl, dialkylaminoalkyl, arylalkyl, aryl, alkoxyalkyl, or hydroxyalkly, and/or (b) at least one of Ra, Rb, Rc and/or Rd is other than hydrogen or C1–2 alkyl, and/or (c) R is other than hydrogen or C1–C2 alkyl and/or (d) one of Rc and Rd is other than hydroxyalkyl the method comprises treating an amide compound of the structure

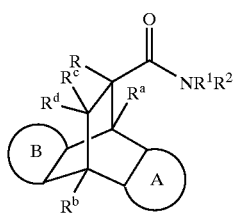

as defined in claim 1 with a reducing agent to form the corresponding amine compound.

22. The method as defined in claim 21 wherein the reducing agent is lithium aluminum hydride.

23. A method for preparing a compound as defined in claim 1 where A, B, Z, R, $R^a$, $R^b$, $R^c$ or $R^d$ contains a hydroxyaryl group, which comprises providing a compound of the structure

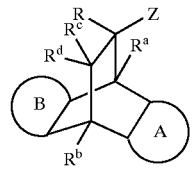

where one or more of A, B, Z, R, $R^a$, $R^b$, $R^c$ or $R^d$ contains aryl-Oalkyl, and reacting the above compound with a dealkylating agent to form a phenol of the structure

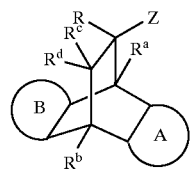

where the corresponding A, B, Z, R, $R^a$, $R^b$, $R^c$ or $R^d$ contains aryl-OH.

24. The method as defined in claim 23 wherein the dealkylating agent is boron tribromide or sodium methyl sulfide.

25. A method for preparing a compound as defined in claim 1 wherein $R^a$ or $R^b$ is $CH_2OH$, $CH_2NHR^a$, $CH_2NR^gR^h$, $CH_2NHR^k$ or $CH_2NR^kR^l$, which comprises providing an aldehyde compound as defined in claim 1 wherein $R^a$ or $R^b$ is CHO, and subjecting the aldehyde compound to reduction or reductive animation.

26. A method for preparing an amide compound as defined in claim 1 where $R^a$ or $R^b$ is $NHCH_2R^g$, $NHCHR^gR^h$, $NHCH_2R^k$ or $NHCHR^kR^l$, which comprises providing an amine compound as defined in claim 1 where $R^a$ or $R^b$ is $NH_2$, and subjecting the amine compound to reductive animation.

27. A method for preparing an amide compound as defined in claim 1 where $R^a$ or $R^b$ is $CONR^eR^f$ or $CONR^iR^j$, which comprises providing an acid compound as defined in claim 1 where $R^a$ or $R^b$ is $CO_2H$, subjecting the acid to amidation to form the corresponding amide.

28. A method for preparing an amine as defined in claim 1 where $R^a$ or $R^b$ is $NH_2$, which comprises providing a nitro compound as defined in claim 1 where $R^a$ or $R^b$ is $NO_2$ and subjecting the nitro compound to reduction to form the corresponding amine compound.

* * * * *

UNITED STATES PATENT AND TRADEMARK OFFICE
CERTIFICATE OF CORRECTION

PATENT NO. : 6,995,181 B2
APPLICATION NO. : 10/621909
DATED : February 7, 2006
INVENTOR(S) : Wayne Vaccaro et al.

It is certified that error appears in the above-identified patent and that said Letters Patent is hereby corrected as shown below:

In the Claims:

Col. 390, line 34, "Re" should read -- $R^e$ --.
Col. 391, line 56, "CH2NR1R2" should read -- $CH_2NR^1R^2$ --.
Col. 391, line 57, "R1 and R2" should read -- $R^1$ and $R^2$ --.
Col. 391, line 59, "R1 and R2" should read -- $R^1$ and $R^2$ --.
Col. 391, line 64, "Ra, Rb, Rc and/or Rd" should read -- $R^a$, $R^b$, $R^c$ and/or $R^d$ --.
Col. 391, line 65, "C1-2" should read -- $C_{1-2}$ --.
Col. 391, line 66, "C1-C2 alkyl and/or (d) one of Rc and Rd" should read
-- $C_1$-$C_2$ alkyl and/or (d) one of $R^c$ and $R^d$ --.
Col. 396, line 31, delete "horizontal bar".
Col. 396, line 32, delete "or F.".
Col. 397, lines 1-15, delete "or F. 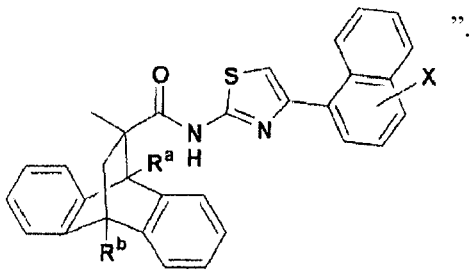 ".

Col. 397, line 16, move "$R^a$  $R^b$  X" to Col. 397, line 28.
Col. 398, lines 1-15, delete "horizontal bar" and "or F. 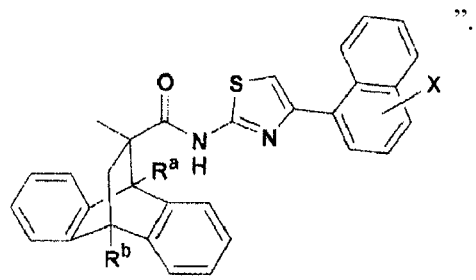 ".

UNITED STATES PATENT AND TRADEMARK OFFICE
CERTIFICATE OF CORRECTION

PATENT NO. : 6,995,181 B2
APPLICATION NO. : 10/621909
DATED : February 7, 2006
INVENTOR(S) : Wayne Vaccaro et al.

It is certified that error appears in the above-identified patent and that said Letters Patent is hereby corrected as shown below:

In the Claims:

Col. 401, delete structure at top of column:

" 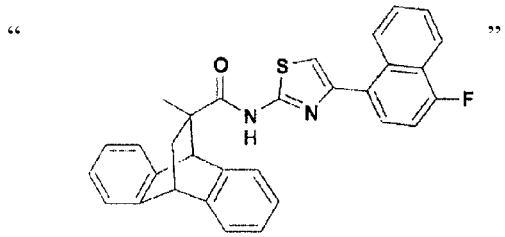 "

and delete horizontal bars before and after said structure.

Col. 403, delete structure at top of column:

" 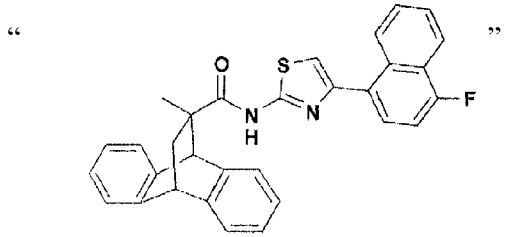 "

and delete horizontal bars before and after said structure.

Col. 405, delete structure at top of column:

" 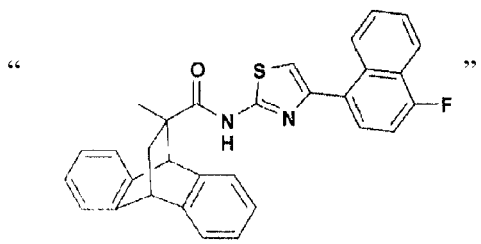 "

and delete horizontal bars before and after said structure.

UNITED STATES PATENT AND TRADEMARK OFFICE
CERTIFICATE OF CORRECTION

PATENT NO. : 6,995,181 B2  Page 3 of 7
APPLICATION NO. : 10/621909
DATED : February 7, 2006
INVENTOR(S) : Wayne Vaccaro et al.

It is certified that error appears in the above-identified patent and that said Letters Patent is hereby corrected as shown below:

In the Claims:

Col. 407, delete structure at top of column:

" 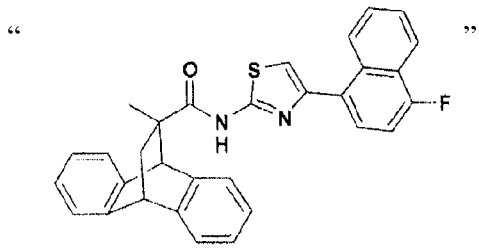 "

and delete horizontal bars before and after said structure.

Col. 409, delete structure at top of column:

" 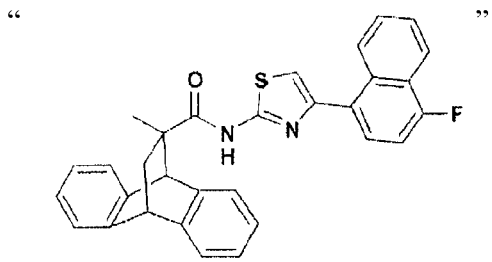 "

and delete horizontal bars before and after said structure.

Col. 411, delete structure at top of column:

" 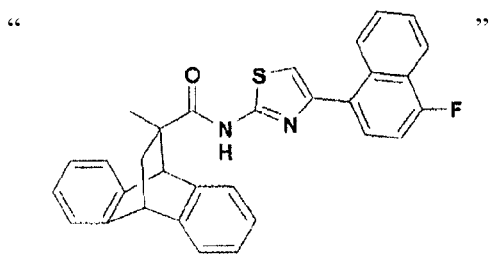 "

and delete horizontal bars before and after said structure.

UNITED STATES PATENT AND TRADEMARK OFFICE
CERTIFICATE OF CORRECTION

PATENT NO. : 6,995,181 B2
APPLICATION NO. : 10/621909
DATED : February 7, 2006
INVENTOR(S) : Wayne Vaccaro et al.

It is certified that error appears in the above-identified patent and that said Letters Patent is hereby corrected as shown below:

In the Claims:

Col. 413, delete structure at top of column:

"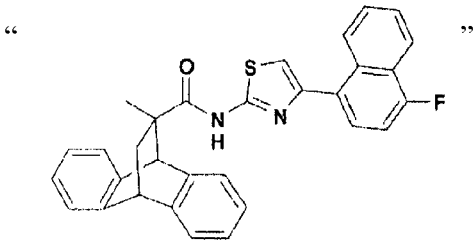"

and delete horizontal bars before and after said structure.

Col. 415, delete structure at top of column:

"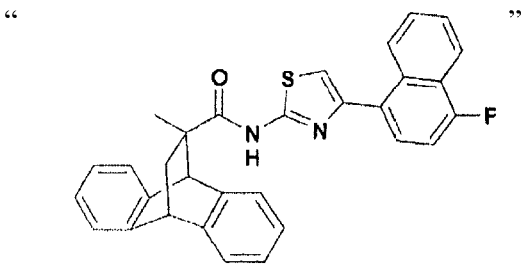"

and delete horizontal bars before and after said structure.

Col. 417, delete structure at top of column:

"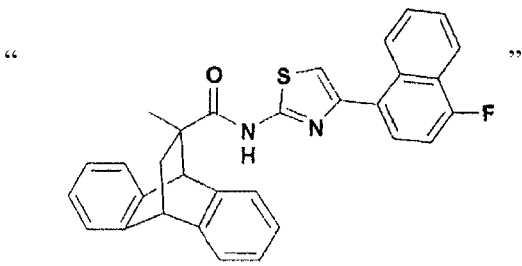"

and delete horizontal bars before and after said structure.

UNITED STATES PATENT AND TRADEMARK OFFICE
CERTIFICATE OF CORRECTION

PATENT NO.       : 6,995,181 B2
APPLICATION NO.  : 10/621909
DATED            : February 7, 2006
INVENTOR(S)      : Wayne Vaccaro et al.

It is certified that error appears in the above-identified patent and that said Letters Patent is hereby corrected as shown below:

In the Claims:

Col. 419, delete structure at top of column:

"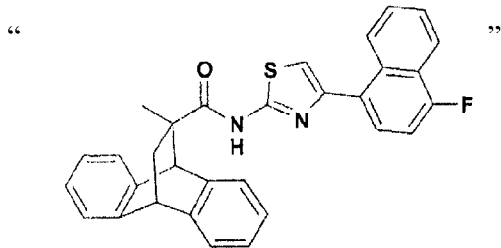"

and delete horizontal bars before and after said structure.

Col. 421, delete structure at top of column:

"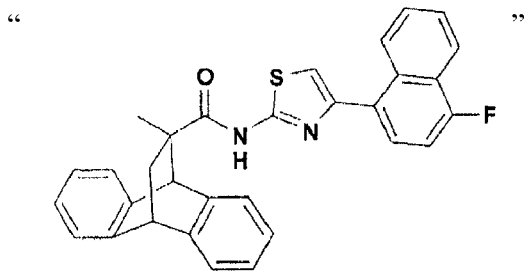"

and delete horizontal bars before and after said structure.

Col. 423, delete structure at top of column:

"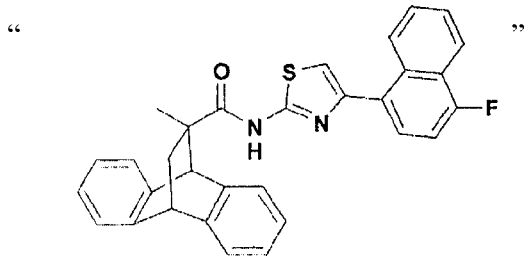"

and delete horizontal bars before and after said structure.

UNITED STATES PATENT AND TRADEMARK OFFICE
CERTIFICATE OF CORRECTION

PATENT NO.         : 6,995,181 B2
APPLICATION NO.    : 10/621909
DATED              : February 7, 2006
INVENTOR(S)        : Wayne Vaccaro et al.

It is certified that error appears in the above-identified patent and that said Letters Patent is hereby corrected as shown below:

In the Claims:

Col. 425, delete structure at top of column:

"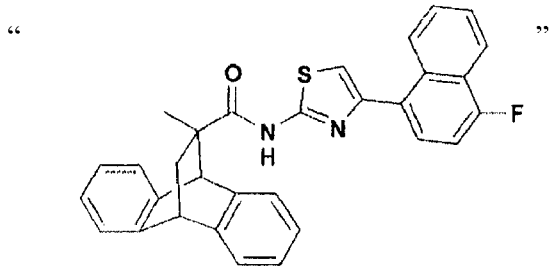"

and delete horizontal bars before and after said structure.

Col. 427, delete structure at top of column:

"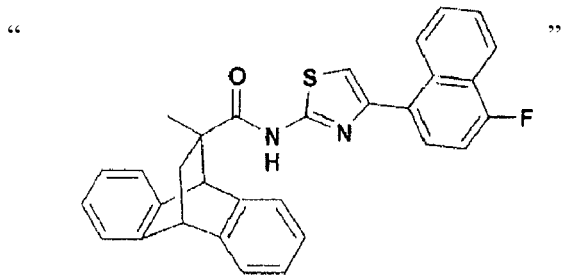"

and delete horizontal bars before and after said structure.

Col. 429, delete structure at top of column:

"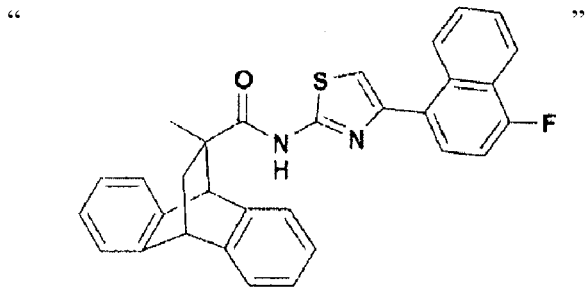"

and delete horizontal bars before and after said structure.

UNITED STATES PATENT AND TRADEMARK OFFICE
CERTIFICATE OF CORRECTION

| | |
|---|---|
| PATENT NO. | : 6,995,181 B2 |
| APPLICATION NO. | : 10/621909 |
| DATED | : February 7, 2006 |
| INVENTOR(S) | : Wayne Vaccaro et al. |

It is certified that error appears in the above-identified patent and that said Letters Patent is hereby corrected as shown below:

In the Claims:

Col. 429, delete the horizontal bars before and after "12. The compound as defined in claim 1 having the structure;".

Signed and Sealed this

Twenty-first Day of October, 2008

JON W. DUDAS
*Director of the United States Patent and Trademark Office*